(12) United States Patent
Brubaker et al.

(10) Patent No.: US 9,394,282 B2
(45) Date of Patent: Jul. 19, 2016

(54) PYRAZOLE CARBOXAMIDES AS JANUS KINASE INHIBITORS

(71) Applicants: Jason Brubaker, Cambridge, MA (US); Joshua Close, Franklin, MA (US); Tony Siu, Brookline, MA (US); Graham Frank Smith, Sudbury, MA (US); Luis E. Torres, Norwood, MA (US); Hyun Chong Woo, Natick, MA (US); Jonathan R. Young, Southborough, MA (US); Zhongyong Wei, Beijing (CN); Feng Shi, Beijing (CN)

(72) Inventors: Jason Brubaker, Cambridge, MA (US); Joshua Close, Franklin, MA (US); Tony Siu, Brookline, MA (US); Graham Frank Smith, Sudbury, MA (US); Luis E. Torres, Norwood, MA (US); Hyun Chong Woo, Natick, MA (US); Jonathan R. Young, Southborough, MA (US); Zhongyong Wei, Beijing (CN); Feng Shi, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 104 days.

(21) Appl. No.: 14/345,982

(22) PCT Filed: Sep. 21, 2012

(86) PCT No.: PCT/CN2012/081723
§ 371 (c)(1),
(2) Date: Mar. 20, 2014

(87) PCT Pub. No.: WO2013/041042
PCT Pub. Date: Mar. 28, 2013

(65) Prior Publication Data
US 2014/0235641 A1    Aug. 21, 2014

Related U.S. Application Data

(60) Provisional application No. 61/537,978, filed on Sep. 22, 2011.

(51) Int. Cl.
| | |
|---|---|
| *C07D 401/04* | (2006.01) |
| *C07D 405/14* | (2006.01) |
| *C07D 409/04* | (2006.01) |
| *C07D 417/14* | (2006.01) |
| *C07D 405/04* | (2006.01) |
| *C07D 413/14* | (2006.01) |
| *C07D 401/14* | (2006.01) |
| *C07D 405/08* | (2006.01) |
| *C07D 403/12* | (2006.01) |
| *C07D 231/38* | (2006.01) |
| *C07D 401/12* | (2006.01) |
| *C07D 403/08* | (2006.01) |
| *C07D 405/12* | (2006.01) |
| *C07D 409/12* | (2006.01) |
| *C07D 413/12* | (2006.01) |
| *C07D 403/04* | (2006.01) |
| *C07D 401/06* | (2006.01) |
| *C07D 403/06* | (2006.01) |
| *C07D 405/06* | (2006.01) |

(52) U.S. Cl.
CPC ............ *C07D 405/08* (2013.01); *C07D 231/38* (2013.01); *C07D 401/04* (2013.01); *C07D 401/06* (2013.01); *C07D 401/12* (2013.01); *C07D 401/14* (2013.01); *C07D 403/04* (2013.01); *C07D 403/06* (2013.01); *C07D 403/08* (2013.01); *C07D 403/12* (2013.01); *C07D 405/04* (2013.01); *C07D 405/06* (2013.01); *C07D 405/12* (2013.01); *C07D 405/14* (2013.01); *C07D 409/04* (2013.01); *C07D 409/12* (2013.01); *C07D 413/12* (2013.01); *C07D 413/14* (2013.01); *C07D 417/14* (2013.01)

(58) Field of Classification Search
None
See application file for complete search history.

(56) References Cited

U.S. PATENT DOCUMENTS

2009/0233903 A1    9/2009  Rodgers et al.

FOREIGN PATENT DOCUMENTS

| WO | 2008132502 A1 | 11/2008 |
| WO | WO2010014453  | * 2/2010 |
| WO | 2010135650 A1 | 11/2010 |
| WO | 2011028685 A1 | 3/2011 |
| WO | 2011075334 A1 | 6/2011 |
| WO | 2011112662 A1 | 9/2011 |

OTHER PUBLICATIONS

Kiss, et al., Informa Healthcare, Recent Developments on JAK2 Inhibitors, Apr. 1, 2010, vol. 20, No. 4, pp. 471-495.
EP Search Report and Written Opinion, Aug. 4, 2015.

* cited by examiner

*Primary Examiner* — Michael Barker
*Assistant Examiner* — Po-Chih Chen
(74) *Attorney, Agent, or Firm* — Patricia A. Shatynski; Catherine D. Fitch

(57) ABSTRACT

The instant invention provides compounds of formula I which are JAK inhibitors, and as such are useful for the treatment of JAK-mediated diseases such as rheumatoid arthritis, asthma, COPD and cancer.

20 Claims, No Drawings

PYRAZOLE CARBOXAMIDES AS JANUS KINASE INHIBITORS

CROSS REFERENCE TO RELATED APPLICATIONS

This application is a U.S. National Phase application under 35 U.S.C. §371 of PCT Application No. PCT/CN2012/081723, filed Sep. 21, 2012, which claims priority under 35 U.S.C. §119(e) from U.S. Provisional Application Ser. No. 61/537,978, filed Sep. 21, 2011.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines. Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoietic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)). However, several adverse events have been reported that may be associated with inhibition of JAK2 signaling such as anemia, neutropenia and thrombocytopenia. Thus new or improved agents that selectively inhibit JAK1 activity but spare JAK2 activity are required for the treatment of several human diseases with an improved therapeutic index.

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts or stereoisomers thereof:

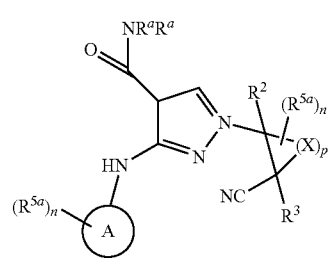

$R^a$ and $R^4$ are each independently chosen from hydrogen and $C_{1-4}$alkyl;
n is 0, 1, 2, 3, or 4;
p is 2, 3, or 4;
X is independently chosen from C, N, S, and O, wherein at least one X is other than carbon;
A is chosen from aryl, and heteroaryl;
$R^2$ and $R^3$ are each independently selected from:
  hydrogen,
  halogen,
  $C_{1-10}$ alkyl,
  $C_{2-10}$ alkenyl,
  $C_{1-10}$ heteroalkyl,
  aryl $C_{0-10}$ alkyl$C_{0-10}$ alkyl,
  $C_{3-8}$ cycloalkyl$C_{0-10}$ alkyl,
  heteroaryl $C_{0-10}$ alkyl,
  $(C_{3-8})$heterocycloalkyl $C_{0-10}$ alkyl, wherein each of $R^2$ and $R^3$ are independently substituted with 0, 1, 2, 3, or 4, substituents $R^{5a}$;
$R^{5a}$ is selected from:
hydrogen,
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
$C_{2-10}$ alkynyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl$(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylamino(oxy)$_{0-1}$carbonyl$C_{0-10}$ alkyl,
$(C_{0-10})$heteroalkylamino(oxy)$_{0-1}$carbonyl$C_{0-10}$ alkyl,
$C_{3-8}$ cycloalkyl$C_{0-10}$ alkylamino(oxy)$_{0-1}$carbonyl$C_{0-10}$ alkyl,
aryl $C_{0-10}$alkylamino(oxy)$_{0-1}$carbonyl$C_{0-10}$ alkyl,
heteroaryl$C_{0-10}$ alkylamino(oxy)$_{0-1}$carbonyl$C_{0-10}$ alkyl,
$(C_{3-8})$heterocycloalkyl$C_{0-10}$alkylamino(oxy)$_{0-1}$ carbonyl $C_{0-10}$ alkyl,
$C_{1-10}$ alkyl(oxy)$_{0-1}$carbonylamino$C_{0-10}$ alkyl,
$C_{1-10}$ heteroalkyl(oxy)$_{0-1}$carbonylamino$C_{0-10}$alkyl,
$C_{3-8}$ cycloalkyl$C_{0-10}$ alkyl(oxy)$_{0-1}$carbonylamino$C_{0-10}$ alkyl,
aryl $C_{0-10}$ alkyl(oxy)$_{0-1}$carbonylamino$C_{0-10}$ alkyl,
heteroaryl $C_{0-10}$ alkyl(oxy)$_{0-1}$carbonylamino$C_{0-10}$ alkyl,
$(C_{3-8})$heterocycloalkyl $C_{0-10}$ alkyl(oxy)$_{0-1}$carbonylamino $C_{0-10}$ alkyl,
—$CO_2(C_{0-10}$ alkyl),
—$(C_{0-10}$ alkyl)$CO_2H$,
Oxo (═O),
$C_{1-10}$ alkylsulfonyl,
$C_{1-10}$ heteroalkylsulfonyl,
$(C_{3-8})$cycloalkylsulfonyl,
$(C_{3-8})$cycloheteroalkylsulfonyl,
heteroarylsulfonyl,
arylsulfonyl,
aminosulfonyl,
—$SO_2N(C_{1-6}$alkyl$)_{1-2}$,
—$SO_2C_{1-6}$alkyl,
—$SO_2CF_3$,
—$SO_2CF_2H$,
$C_{1-10}$ alkylsulfinyl,
amino,
$(C_{0-10}$ alkyl$)_{1-2}$ amino,
$C_{1-4}$acylamino $C_{0-10}$ alkyl,
hydroxy,
$C_{0-10}$ alkylalkoxy,
cyano,
$C_{1-6}$alkylcyano, and
$C_{1-6}$haloalkyl;

wherein $R^{5a}$ is each optionally substituted with 0, 1, 2, 3, or 4 substituents, $R^6$, independently selected from:
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
aryl$(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylamino(oxy)$_{0-1}$carbonyl$C_{0-10}$ alkyl,
$C_{3-8}$ cycloalkyl$C_{0-10}$ alkylamino(oxy)$_{0-1}$carbonyl$C_{0-10}$ alkyl,
aryl $C_{0-10}$ alkylamino(oxy)$_{0-1}$carbonyl$C_{0-10}$ alkyl,
heteroaryl $C_{0-10}$ alkylamino(oxy)$_{0-1}$carbonyl$C_{0-10}$ alkyl,
$(C_{3-8})$heterocycloalkyl $C_{0-10}$ alkylamino(oxy)$_{0-1}$carbonyl $C_{0-10}$ alkyl,
$C_{1-10}$ alkyl(oxy)$_{0-1}$carbonylamino$C_{0-10}$ alkyl,
$C_{3-8}$ cycloalkyl$C_{0-10}$ alkyl(oxy)$_{0-1}$carbonylamino$C_{0-10}$ alkyl,
aryl $C_{0-10}$ alkyl(oxy)$_{0-1}$carbonylamino$C_{0-10}$ alkyl,
heteroaryl $C_{0-10}$ alkyl(oxy)$_{0-1}$carbonylamino$C_{0-10}$ alkyl,
$(C_{3-8})$heterocycloalkyl $C_{0-10}$ alkyl(oxy)$_{0-1}$carbonylamino $C_{0-10}$ alkyl,
—$CO_2(C_{0-10}$ alkyl),
—$(C_{0-10}$ alkyl)$CO_2H$,
Oxo (═O),
$C_{1-10}$ alkylsulfonyl,
$C_{1-10}$ heteroalkylsulfonyl,
$(C_{3-8})$cycloalkylsulfonyl,
$(C_{3-8})$cycloheteroalkylsulfonyl,
heteroarylsulfonyl,
arylsulfonyl,
aminosulfonyl,
—$SO_2N(C_{1-6}$alkyl$)_{1-2}$,
—$SO_2C_{1-6}$alkyl,
—$SO_2CF_3$,
—$SO_2CF_2H$,
$C_{1-10}$ alkylsulfinyl,
—$OSi(C_6H_{15})$
amino,
$(C_{0-10}$ alkyl$)_{1-2}$ amino,
-(oxy)$_{0-1}$(carbonyl)$_{0-1}N(C_{0-10}$ alkyl$)_{1-2}$
$C_{1-4}$ acylamino $C_{0-10}$ alkyl,
hydroxy,
$C_{1-10}$ alkoxy,
cyano, and
$C_{1-6}$haloalkyl; and
$R^6$ is optionally substituted with 0, 1, 2, or 3 substituents independently chosen from hydroxy, $(C_{1-6})$alkoxy, halogen, $CO_2H$, —$(C_{0-6})$alkylCN, —$O(C$═$O)C_1$-$C_6$ alkyl, $NO_2$, trifluoromethoxy, trifluoroethoxy, —N—$C(O)O(C_{0-6})$alkyl, $C_{1-10}$ alkylsulfonyl, $C_{1-10}$ heteroalkylsulfonyl, oxo (O═), $(C_{3-8})$cycloalkylsulfonyl, $(C_{3-8})$cycloheteroalkylsulfonyl, heteroarylsulfonyl, arylsulfonyl, aminosulfonyl, —SO$_2$N$(C_{1-6}$ alkyl$)_{1-2}$, —SO$_2$C$_{1-6}$ alkyl, —SO$_2$CF$_3$, —SO$_2$CF$_2$H, —C$_{1-10}$ alkylsulfinyl, —O—Si, —OSi(C$_6$H$_{15}$), —O$_{(0-1)}$(C$_{1-10}$)haloalkyl, and NH$_2$.

Representative compounds of the instant invention include, but are not limited to, the following compounds, stereoisomers, and pharmaceutically acceptable salts, thereof:

tert-Butyl-4-[4-(aminocarbonyl)-3-anilino-1H-pyrazol-1-yl]-3-cyanopiperidine-1-carboxylate,
tert-Butyl(3R,4S)-4-[4-(aminocarbonyl)-3-anilino-1H-pyrazol-1-yl]-3-cyanopiperidine-1-carboxylate,
tert-Butyl(3S,4R)-4-[4-(aminocarbonyl)-3-anilino-1H-pyrazol-1-yl]-3-cyanopiperidine-1-carboxylate,
tert-butyl(3S,4S)-4-[4-(aminocarbonyl)-3-anilino-1H-pyrazol-1-yl]-3-cyanopiperidine-1-carboxylate,
tert-butyl(3R,4R)-4-[4-(aminocarbonyl)-3-anilino-1H-pyrazol-1-yl]-3-cyanopiperidine-1-carboxylate,
tert-butyl-3-[4-(aminocarbonyl)-3-anilino-1H-pyrazol-1-yl]-4-cyanopiperidine-1-carboxylate,
tert-butyl(3R,4S)-3-[4-(aminocarbonyl)-3-anilino-1H-pyrazol-1-yl]-4-cyanopiperidine-1-carboxylate,
tert-butyl(3S,4R)-3-[4-(aminocarbonyl)-3-anilino-1H-pyrazol-1-yl]-4-cyanopiperidine-1-carboxylate,
tert-butyl-3-{4-carbamoyl-3-[(4-fluorophenyl)amino]-1H-pyrazol-1-yl}-4-cyanopiperidine-1-carboxylate,
tert-butyl(3R,4S)-3-{4-carbamoyl-3-[(4-fluorophenyl)amino]-1H-pyrazol-1-yl}-4-cyanopiperidine-1-carboxylate,
tert-butyl(3S,4R)-3-{4-carbamoyl-3-[(4-fluorophenyl)amino]-1H-pyrazol-1-yl}-4-cyanopiperidine-1-carboxylate,
tert-butyl 4-(4-carbamoyl-3-((4-fluorophenyl)amino)-1H-pyrazol-1-yl)-3-cyanopiperidine-1-carboxylate,
(3R,4S)-tert-butyl 4-(4-carbamoyl-3-((4-fluorophenyl)amino)-1H-pyrazol-1-yl)-3-cyanopiperidine-1-carboxylate,
(3S,4R)-tert-butyl 4-(4-carbamoyl-3-((4-fluorophenyl)amino)-1H-pyrazol-1-yl)-3-cyanopiperidine-1-carboxylate,
1-4-cyanopiperidin-3-yl]-3-[(4-fluorophenyl)amino]-1H-pyrazole-4-carboxamide,
1-[(3R,4S)-4-cyanopiperidin-3-yl]-3-[(4-fluorophenyl)amino]-1H-pyrazole-4-carboxamide,
1-[(3S,4R)-4-cyanopiperidin-3-yl]-3-[(4-fluorophenyl)amino]-1H-pyrazole-4-carboxamide,
1-3-cyanopiperidin-4-yl]-3-[(4-fluorophenyl)amino]-1H-pyrazole-4-carboxamide,
1-[(3R,4R)-3-cyanopiperidin-4-yl]-3-[(4-fluorophenyl)amino]-1H-pyrazole-4-carboxamide,
1-[(3S,4S)-3-cyanopiperidin-4-yl]-3-[(4-fluorophenyl)amino]-1H-pyrazole-4-carboxamide,
3,3-Dimethylbutyl-{4-carbamoyl-3-[(4-fluorophenyl)amino]-1H-pyrazol-1-yl}-4-cyanopiperidine-1-carboxylate,
3,3-Dimethylbutyl(3S,4R)-3-{4-carbamoyl-3-[(4-fluorophenyl)amino]-1H-pyrazol-1-yl}-4-cyanopiperidine-1-carboxylate,
3,3-Dimethylbutyl(3R,4S)-3-{4-carbamoyl-3-[(4-fluorophenyl)amino]-1H-pyrazol-1-yl}-4-cyanopiperidine-1-carboxylate,
2,2,2-Trifluoro-1-methylethyl-4-{4-carbamoyl-3-[(4-fluorophenyl)amino]-1H-pyrazol-1-yl}-3-cyanopiperidine-1-carboxylate,
2,2,2-Trifluoro-1-methylethyl(3R,4R)-4-{4-carbamoyl-3-[(4-fluorophenyl)amino]-1H-pyrazol-1-yl}-3-cyanopiperidine-1-carboxylate,
2,2,2-Trifluoro-1-methylethyl(3S,4S)-4-{4-carbamoyl-3-[(4-fluorophenyl)amino]-1H-pyrazol-1-yl}-3-cyanopiperidine-1-carboxylate,
2-fluoroethyl-4-{4-carbamoyl-3-[(4-fluorophenyl)amino]-1H-pyrazol-1-yl}-3-cyanopiperidine-1-carboxylate,
2-fluoroethyl(3S,4S)-4-{4-carbamoyl-3-[(4-fluorophenyl)amino]-1H-pyrazol-1-yl}-3-cyanopiperidine-1-carboxylate,
2-fluoroethyl(3R,4R)-4-{4-carbamoyl-3-[(4-fluorophenyl)amino]-1H-pyrazol-1-yl}-3-cyanopiperidine-1-carboxylate,
3-phenylpropyl-4-{4-carbamoyl-3-[(4-fluorophenyl)amino]-1H-pyrazol-1-yl}-3-cyanopiperidine-1-carboxylate,
3-phenylpropyl(3R,4R)-4-{4-carbamoyl-3-[(4-fluorophenyl)amino]-1H-pyrazol-1-yl}-3-cyanopiperidine-1-carboxylate,
3-phenylpropyl(3S,4S)-4-{4-carbamoyl-3-[(4-fluorophenyl)amino]-1H-pyrazol-1-yl}-3-cyanopiperidine-1-carboxylate,
2-morpholin-4-ylethyl(3R,4R and 3S,4S)-4-{4-carbamoyl-3-[(4-fluorophenyl)amino]-1H-pyrazol-1-yl}-3-cyanopiperidine-1-carboxylate,
2-morpholin-4-ylethyl(3R,4R and 3S,4S)-4-{4-carbamoyl-3-[(4-fluorophenyl)amino]-1H-pyrazol-1-yl}-3-cyanopiperidine-1-carboxylate,
2-morpholin-4-ylethyl(3R,4R and 3S,4S)-4-{4-carbamoyl-3-[(4-fluorophenyl)amino]-1H-pyrazol-1-yl}-3-cyanopiperidine-1-carboxylate,
oxetan-3-yl-4-{4-carbamoyl-3-[(4-fluorophenyl)amino]-1H-pyrazol-1-yl}-3-cyanopiperidine-1-carboxylate,
oxetan-3-yl(3R,4R)-4-{4-carbamoyl-3-[(4-fluorophenyl)amino]-1H-pyrazol-1-yl}-3-cyanopiperidine-1-carboxylate,
oxetan-3-yl(3S,4S)-4-{4-carbamoyl-3-[(4-fluorophenyl)amino]-1H-pyrazol-1-yl}-3-cyanopiperidine-1-carboxylate,
2-cyano-2-methylpropyl-4-{4-carbamoyl-3-[(4-fluorophenyl)amino]-1H-pyrazol-1-yl}-3-cyanopiperidine-1-carboxylate,
2-cyano-2-methylpropyl(3R,4R)-4-{4-carbamoyl-3-[(4-fluorophenyl)amino]-1H-pyrazol-1-yl}-3-cyanopiperidine-1-carboxylate,
2-cyano-2-methylpropyl(3S,4S)-4-{4-carbamoyl-3-[(4-fluorophenyl)amino]-1H-pyrazol-1-yl}-3-cyanopiperidine-1-carboxylate,
(1-methylpiperidin-4-yl)methyl-4-{4-carbamoyl-3-[(4-fluorophenyl)amino]-1H-pyrazol-1-yl}-3-cyanopiperidine-1-carboxylate,
(1-methylpiperidin-4-yl)methyl(3R,4R)-4-{4-carbamoyl-3-[(4-fluorophenyl)amino]-1H-pyrazol-1-yl}-3-cyanopiperidine-1-carboxylate,
(1-methylpiperidin-4-yl)methyl(3S,4S)-4-{4-carbamoyl-3-[(4-fluorophenyl)amino]-1H-pyrazol-1-yl}-3-cyanopiperidine-1-carboxylate,
(1-aminocyclopropyl)methyl-4-{4-carbamoyl-3-[(4-fluorophenyl)amino]-1H-pyrazol-1-yl}-3-cyanopiperidine-1-carboxylate,
(1-aminocyclopropyl)methyl(3R,4R)-4-{4-carbamoyl-3-[(4-fluorophenyl)amino]-1H-pyrazol-1-yl}-3-cyanopiperidine-1-carboxylate,
(1-aminocyclopropyl)methyl(3S,4S)-4-{4-carbamoyl-3-[(4-fluorophenyl)amino]-1H-pyrazol-1-yl}-3-cyanopiperidine-1-carboxylate, (1-methylcyclopropyl)methyl-4-{4-carbamoyl-3-[(4-fluorophenyl)amino]-1H-pyrazol-1-yl}-3-cyanopiperidine-1-carboxylate,
(1-methylcyclopropyl)methyl(3R,4R)-4-{4-carbamoyl-3-[(4-fluorophenyl)amino]-1H-pyrazol-1-yl}-3-cyanopiperidine-1-carboxylate,
(1-methylcyclopropyl)methyl(3S,4S)-4-{4-carbamoyl-3-[(4-fluorophenyl)amino]-1H-pyrazol-1-yl}-3-cyanopiperidine-1-carboxylate,
2-methylpropyl-4-{4-carbamoyl-3-[(4-fluorophenyl)amino]-1H-pyrazol-1-yl}-3-cyanopiperidine-1-carboxylate,
2-methylpropyl(3R,4R)-4-{4-carbamoyl-3-[(4-fluorophenyl)amino]-1H-pyrazol-1-yl}-3-cyanopiperidine-1-carboxylate,
2-methylpropyl(3S,4S)-4-{4-carbamoyl-3-[(4-fluorophenyl)amino]-1H-pyrazol-1-yl}-3-cyanopiperidine-1-carboxylate,
cyclopentyl-4-{4-carbamoyl-3-[(4-fluorophenyl)amino]-1H-pyrazol-1-yl}-3-cyanopiperidine-1-carboxylate,
cyclopentyl(3S,4S)-4-{4-carbamoyl-3-[(4-fluorophenyl)amino]-1H-pyrazol-1-yl}-3-cyanopiperidine-1-carboxylate,
cyclopentyl(3R,4R)-4-{4-carbamoyl-3-[(4-fluorophenyl)amino]-1H-pyrazol-1-yl}-3-cyanopiperidine-1-carboxylate,
benzyl-4-{4-carbamoyl-3-[(4-fluorophenyl)amino]-1H-pyrazol-1-yl}-3-cyanopiperidine-1-carboxylate,
benzyl(3R,4R)-4-{4-carbamoyl-3-[(4-fluorophenyl)amino]-1H-pyrazol-1-yl}-3-cyanopiperidine-1-carboxylate,
benzyl(3S,4S)-4-{4-carbamoyl-3-[(4-fluorophenyl)amino]-1H-pyrazol-1-yl}-3-cyanopiperidine-1-carboxylate,
tetrahydro-2H-pyran-4-yl-4-{4-carbamoyl-3-[(4-fluorophenyl)amino]-1H-pyrazol-1-yl}-3-cyanopiperidine-1-carboxylate,
tetrahydro-2H-pyran-4-yl(3R,4R)-4-{4-carbamoyl-3-[(4-fluorophenyl)amino]-1H-pyrazol-1-yl}-3-cyanopiperidine-1-carboxylate,
tetrahydro-2H-pyran-4-yl(3S,4S)-4-{4-carbamoyl-3-[(4-fluorophenyl)amino]-1H-pyrazol-1-yl}-3-cyanopiperidine-1-carboxylate,
2-cyclopropylethyl-4-{4-carbamoyl-3-[(4-fluorophenyl)amino]-1H-pyrazol-1-yl}-3-cyanopiperidine-1-carboxylate,
2-cyclopropylethyl(3R,4R)-4-{4-carbamoyl-3-[(4-fluorophenyl)amino]-1H-pyrazol-1-yl}-3-cyanopiperidine-1-carboxylate,
2-cyclopropylethyl(3S,4S)-4-{4-carbamoyl-3-[(4-fluorophenyl)amino]-1H-pyrazol-1-yl}-3-cyanopiperidine-1-carboxylate,
2-(2-oxopyrrolidin-1-yl)ethyl-4-{4-carbamoyl-3-[(4-fluorophenyl)amino]-1H-pyrazol-1-yl}-3-cyanopiperidine-1-carboxylate,
2-(2-oxopyrrolidin-1-yl)ethyl(3R,4R)-4-{4-carbamoyl-3-[(4-fluorophenyl)amino]-1H-pyrazol-1-yl}-3-cyanopiperidine-1-carboxylate,
2-(2-oxopyrrolidin-1-yl)ethyl(3S,4S)-4-{4-carbamoyl-3-[(4-fluorophenyl)amino]-1H-pyrazol-1-yl}-3-cyanopiperidine-1-carboxylate,
2,2-difluoroethyl-4-{4-carbamoyl-3-[(4-fluorophenyl)amino]-1H-pyrazol-1-yl}-3-cyanopiperidine-1-carboxylate,
2,2-difluoroethyl(3S,4S)-4-{4-carbamoyl-3-[(4-fluorophenyl)amino]-1H-pyrazol-1-yl}-3-cyanopiperidine-1-carboxylate,
2,2-difluoroethyl(3R,4R)-4-{4-carbamoyl-3-[(4-fluorophenyl)amino]-1H-pyrazol-1-yl}-3-cyanopiperidine-1-carboxylate,
cyclohexyl-4-{4-carbamoyl-3-[(4-fluorophenyl)amino]-1H-pyrazol-1-yl}-3-cyanopiperidine-1-carboxylate,
cyclohexyl(3R,4R)-4-{4-carbamoyl-3-[(4-fluorophenyl)amino]-1H-pyrazol-1-yl}-3-cyanopiperidine-1-carboxylate,
cyclohexyl(3S,4S)-4-{4-carbamoyl-3-[(4-fluorophenyl)amino]-1H-pyrazol-1-yl}-3-cyanopiperidine-1-carboxylate,
2,2-dimethylpropyl-4-{4-carbamoyl-3-[(4-fluorophenyl)amino]-1H-pyrazol-1-yl}-3-cyanopiperidine-1-carboxylate,
2,2-dimethylpropyl(3R,4R)-4-{4-carbamoyl-3-[(4-fluorophenyl)amino]-1H-pyrazol-1-yl}-3-cyanopiperidine-1-carboxylate,
2,2-dimethylpropyl(3S,4S)-4-{4-carbamoyl-3-[(4-fluorophenyl)amino]-1H-pyrazol-1-yl}-3-cyanopiperidine-1-carboxylate,
2-pyrrolidin-1-ylethyl-4-{4-carbamoyl-3-[(4-fluorophenyl)amino]-1H-pyrazol-1-yl}-3-cyanopiperidine-1-carboxylate,
2-pyrrolidin-1-ylethyl(3R,4R)-4-{4-carbamoyl-3-[(4-fluorophenyl)amino]-1H-pyrazol-1-yl}-3-cyanopiperidine-1-carboxylate,
2-pyrrolidin-1-ylethyl(3S,4S)-4-{4-carbamoyl-3-[(4-fluorophenyl)amino]-1H-pyrazol-1-yl}-3-cyanopiperidine-1-carboxylate,
2,2-difluoro-3-hydroxypropyl-4-{4-carbamoyl-3-[(4-fluorophenyl)amino]-1H-pyrazol-1-yl}-3-cyanopiperidine-1-carboxylate,
2,2-difluoro-3-hydroxypropyl(3R,4R)-4-{4-carbamoyl-3-[(4-fluorophenyl)amino]-1H-pyrazol-1-yl}-3-cyanopiperidine-1-carboxylate,
2,2-difluoro-3-hydroxypropyl(3S,4S)-4-{4-carbamoyl-3-[(4-fluorophenyl)amino]-1H-pyrazol-1-yl}-3-cyanopiperidine-1-carboxylate,
3-(dimethylamino)-2,2-dimethylpropyl-4-{4-carbamoyl-3-[(4-fluorophenyl)amino]-1H-pyrazol-1-yl}-3-cyanopiperidine-1-carboxylate;
3-(dimethylamino)-2,2-dimethylpropyl(3R,4R)-4-{4-carbamoyl-3-[(4-fluorophenyl)amino]-1H-pyrazol-1-yl}-3-cyanopiperidine-1-carboxylate,
3-(dimethylamino)-2,2-dimethylpropyl(3S,4S)-4-{4-carbamoyl-3-[(4-fluorophenyl)amino]-1H-pyrazol-1-yl}-3-cyanopiperidine-1-carboxylate,
2-(dimethylamino)ethyl-4-{4-carbamoyl-3-[(4-fluorophenyl)amino]-1H-pyrazol-1-yl}-3-cyanopiperidine-1-carboxylate,
2-(dimethylamino)ethyl(3R,4R)-4-{4-carbamoyl-3-[(4-fluorophenyl)amino]-1H-pyrazol-1-yl}-3-cyanopiperidine-1-carboxylate,
2-(dimethylamino)ethyl(3S,4S)-4-{4-carbamoyl-3-[(4-fluorophenyl)amino]-1H-pyrazol-1-yl}-3-cyanopiperidine-1-carboxylate,
ethyl-4-{4-carbamoyl-3-[(4-fluorophenyl)amino]-1H-pyrazol-1-yl}-3-cyanopiperidine-1-carboxylate,
ethyl(3R,4R)-4-{4-carbamoyl-3-[(4-fluorophenyl)amino]-1H-pyrazol-1-yl}-3-cyanopiperidine-1-carboxylate,
ethyl(3S,4S)-4-{4-carbamoyl-3-[(4-fluorophenyl)amino]-1H-pyrazol-1-yl}-3-cyanopiperidine-1-carboxylate,
2-(4-methylpiperazin-1-yl)ethyl-4-{4-carbamoyl-3-[(4-fluorophenyl)amino]-1H-pyrazol-1-yl}-3-cyanopiperidine-1-carboxylate, 2-(4-methylpiperazin-1-yl)ethyl(3R,4R)-4-{4-carbamoyl-3-[(4-fluorophenyl)amino]-1H-pyrazol-1-yl}-3-cyanopiperidine-1-carboxylate, 2-(4-methylpiperazin-1-yl)ethyl(3S,4S)-4-{4-carbamoyl-3-[(4-fluorophenyl)amino]-1H-pyrazol-1-yl}-3-cyanopiperidine-1-carboxylate, tetrahydrofuran-3-yl-4-{4-carbamoyl-3-[(4-fluorophenyl)amino]-1H-pyrazol-1-yl}-3-cyanopiperidine-1-carboxylate, tetrahydrofuran-3-yl(3R,4R)-4-{4-carbamoyl-3-[(4-fluorophenyl)amino]-1H-pyrazol-1-yl}-3-cyanopiperidine-1-carboxylate, tetrahydrofuran-3-yl(3S,4S)-4-{4-carbamoyl-3-[(4-fluorophenyl)amino]-1H-pyrazol-1-yl}-3-cyanopiperidine-1-carboxylate, 1-methylpiperidin-4-yl-4-{4-carbamoyl-3-[(4-fluorophenyl)amino]-1H-pyrazol-1-yl}-3-cyanopiperidine-1-carboxylate, 1-methylpiperidin-4-yl(3S,4S)-4-{4-carbamoyl-3-[(4-fluorophenyl)amino]-1H-pyrazol-1-yl}-3-cyanopiperidine-1-carboxylate, 1-methylpiperidin-4-yl(3R,4R)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl(3R,4R)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl(3S,4S)-4-{4-carbamoyl-3-[(4-fluorophenyl)amino]-1H-pyrazol-1-yl}-3-cyanopiperidine-1-carboxylate, 2,2,2-trifluoroethyl-4-{4-carbamoyl-3-[(4-fluorophenyl)amino]-1H-pyrazol-1-yl}-3-cyanopiperidine-1-carboxylate, 2,2,2-trifluoroethyl(3R,4R)-4-{4-carbamoyl-3-[(4-fluorophenyl)amino]-1H-pyrazol-1-yl}-3-cyanopiperidine-1-carboxylate, 2,2,2-trifluoroethyl(3S,4S)-4-{4-carbamoyl-3-[(4-fluorophenyl)amino]-1H-pyrazol-1-yl}-3-cyanopiperidine-1-carboxylate, 2-methoxyethyl-4-{4-carbamoyl-3-[(4-fluorophenyl)amino]-1H-pyrazol-1-yl}-3-cyanopiperidine-1-carboxylate, 2-methoxyethyl(3R,4R)-4-{4-carbamoyl-3-[(4-fluorophenyl)amino]-1H-pyrazol-1-yl}-3-cyanopiperidine-1-carboxylate, 2-methoxyethyl(3S,4S)-4-{4-carbamoyl-3-[(4-fluorophenyl)amino]-1H-pyrazol-1-yl}-3-cyanopiperidine-1-carboxylate, cyclopropylmethyl-4-{4-carbamoyl-3-[(4-fluorophenyl)amino]-1H-pyrazol-1-yl}-3-cyanopiperidine-1-carboxylate, cyclopropylmethyl(3R,4R)-4-{4-carbamoyl-3-[(4-fluorophenyl)amino]-1H-pyrazol-1-yl}-3-cyanopiperidine-1-carboxylate, cyclopropylmethyl(3S,4S)-4-{4-carbamoyl-3-[(4-fluorophenyl)amino]-1H-pyrazol-1-yl}-3-cyanopiperidine-1-carboxylate, 2-fluoro-1-(fluoromethyl)ethyl-4-{4-carbamoyl-3-[(4-fluorophenyl)amino]-1H-pyrazol-1-yl}-3-cyanopiperidine-1-carboxylate, 2-fluoro-1-(fluoromethyl)ethyl(3R,4R)-4-{4-carbamoyl-3-[(4-fluorophenyl)amino]-1H-pyrazol-1-yl}-3-cyanopiperidine-1-carboxylate 2-fluoro-1-(fluoromethyl)ethyl(3S,4S)-4-{4-carbamoyl-3-[(4-fluorophenyl)amino]-1H-pyrazol-1-yl}-3-cyanopiperidine-1-carboxylate, 3-methoxypropyl-4-{4-carbamoyl-3-[(4-fluorophenyl)amino]-1H-pyrazol-1-yl}-3-cyanopiperidine-1-carboxylate, 3-methoxypropyl(3R,4R)-4-{4-carbamoyl-3-[(4-fluorophenyl)amino]-1H-pyrazol-1-yl}-3-cyanopiperidine-1-carboxylate, 3-methoxypropyl(3S,4S)-4-{4-carbamoyl-3-[(4-fluorophenyl)amino]-1H-pyrazol-1-yl}-3-cyanopiperidine-1-carboxylate, (3-methyloxetan-3-yl)methyl-4-{4-carbamoyl-3-[(4-fluorophenyl)amino]-1H-pyrazol-1-yl}-3-cyanopiperidine-1-carboxylate, (3-methyloxetan-3-yl)methyl(3R,4R)-4-{4-carbamoyl-3-[(4-fluorophenyl)amino]-1H-pyrazol-1-yl}-3-cyanopiperidine-1-carboxylate, (3-methyloxetan-3-yl)methyl(3S,4S)-4-{4-carbamoyl-3-[(4-fluorophenyl)amino]-1H-pyrazol-1-yl}-3-cyanopiperidine-1-carboxylate, but-3-yn-1-yl-4-{4-carbamoyl-3-[(4-fluorophenyl)amino]-1H-pyrazol-1-yl}-3-cyanopiperidine-1-carboxylate, but-3-yn-1-yl(3R,4R)-4-{4-carbamoyl-3-[(4-fluorophenyl)amino]-1H-pyrazol-1-yl}-3-cyanopiperidine-1-carboxylate, but-3-yn-1-yl(3S,4S)-4-{4-carbamoyl-3-[(4-fluorophenyl)amino]-1H-pyrazol-1-yl}-3-cyanopiperidine-1-carboxylate, 1-cyclopropylethyl-4-{4-carbamoyl-3-[(4-fluorophenyl)amino]-1H-pyrazol-1-yl}-3-cyanopiperidine-1-carboxylate, 1-cyclopropylethyl(3R,4R)-4-{4-carbamoyl-3-[(4-fluorophenyl)amino]-1H-pyrazol-1-yl}-3-cyanopiperidine-1-carboxylate, 1-cyclopropylethyl(3S,4S)-4-{4-carbamoyl-3-[(4-fluorophenyl)amino]-1H-pyrazol-1-yl}-3-cyanopiperidine-1-carboxylate, 2-phenylethyl-4-{4-carbamoyl-3-[(4-fluorophenyl)amino]-1H-pyrazol-1-yl}-3-cyanopiperidine-1-carboxylate, 2-phenylethyl(3R,4R)-4-{4-carbamoyl-3-[(4-fluorophenyl)amino]-1H-pyrazol-1-yl}-3-cyanopiperidine-1-carboxylate, 2-phenylethyl(3S,4S)-4-{4-carbamoyl-3-[(4-fluorophenyl)amino]-1H-pyrazol-1-yl}-3-cyanopiperidine-1-carboxylate, 2,3-dihydro-1H-inden-2-yl-4-{4-carbamoyl-3-[(4-fluorophenyl)amino]-1H-pyrazol-1-yl}-3-cyanopiperidine-1-carboxylate, 2,3-dihydro-1H-inden-2-yl(3R,4R)-4-{4-carbamoyl-3-[(4-fluorophenyl)amino]-1H-pyrazol-1-yl}-3-cyanopiperidine-1-carboxylate, 2,3-dihydro-1H-inden-2-yl(3S,4S)-4-{4-carbamoyl-3-[(4-fluorophenyl)amino]-1H-pyrazol-1-yl}-3-cyanopiperidine-1-carboxylate, 2-ethoxy-2-oxoethyl-4-{4-carbamoyl-3-[(4-fluorophenyl)amino]-1H-pyrazol-1-yl}-3-cyanopiperidine-1-carboxylate, 2-ethoxy-2-oxoethyl(3S,4S)-4-{4-carbamoyl-3-[(4-fluorophenyl)amino]-1H-pyrazol-1-yl}-3-cyanopiperidine-1-carboxylate, 2-ethoxy-2-oxoethyl(3R,4R)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl-4-{4-carbamoyl-3-[(4-fluorophenyl)amino]-1H-pyrazol-1-yl}-3-cyanopiperidine-1-carboxylate,

[1-(cyanomethyl)cyclopropyl]methyl(3R,4R)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl(3S,4S)-4-{4-carbamoyl-3-[(4-fluorophenyl)amino]-1H-pyrazol-1-yl}-3-cyanopiperidine-1-carboxylate, but-3-yn-1-yl-4-{4-carbamoyl-3-[(4-fluorophenyl)amino]-1H-pyrazol-1-yl}-3-cyanopiperidine-1-carboxylate, but-3-yn-1-yl(3R,4S)-4-{4-carbamoyl-3-[(4-fluorophenyl)amino]-1H-pyrazol-1-yl}-3-cyanopiperidine-1-carboxylate, but-3-yn-1-yl(3S,4R)-4-{4-carbamoyl-3-[(4-fluorophenyl)amino]-1H-pyrazol-1-yl}-3-cyanopiperidine-1-carboxylate, 2-cyclopropylethyl-4-{4-carbamoyl-3-[(4-fluorophenyl)amino]-1H-pyrazol-1-yl}-3-cyanopiperidine-1-carboxylate, 2-cyclopropylethyl(3R,4S)-4-{4-carbamoyl-3-[(4-fluorophenyl)amino]-1H-pyrazol-1-yl}-3-cyanopiperidine-1-carboxylate, 2-cyclopropylethyl(3S,4R)-4-{4-carbamoyl-3-[(4-fluorophenyl)amino]-1H-pyrazol-1-yl}-3-cyanopiperidine-1-carboxylate, 2,3-dihydro-1H-inden-2-yl-4-{4-carbamoyl-3-[(4-fluorophenyl)amino]-1H-pyrazol-1-yl}-3-cyanopiperidine-1-carboxylate, 2,3-dihydro-1H-inden-2-yl(3R,4S)-4-{4-carbamoyl-3-[(4-fluorophenyl)amino]-1H-pyrazol-1-yl}-3-cyanopiperidine-1-carboxylate, 2,3-dihydro-1H-inden-2-yl(3S,4R)-4-{4-carbamoyl-3-[(4-fluorophenyl)amino]-1H-pyrazol-1-yl}-3-cyanopiperidine-1-carboxylate, 2,2,2-trifluoro-1-methylethyl-4-{4-carbamoyl-3-[(4-fluorophenyl)amino]-1H-pyrazol-1-yl}-3-cyanopiperidine-1-carboxylate, 2,2,2-trifluoro-1-methylethyl(3R,4S)-4-{4-carbamoyl-3-[(4-fluorophenyl)amino]-1H-pyrazol-1-yl}-3-cyanopiperidine-1-carboxylate, 2,2,2-trifluoro-1-methylethyl(3S,4R)-4-{4-carbamoyl-3-[(4-fluorophenyl)amino]-1H-pyrazol-1-yl}-3-cyanopiperidine-1-carboxylate, ethyl-4-{4-carbamoyl-3-[(4-fluorophenyl)amino]-1H-pyrazol-1-yl}-3-cyanopiperidine-1-carboxylate, ethyl(3S,4R)-4-{4-carbamoyl-3-[(4-fluorophenyl)amino]-1H-pyrazol-1-yl}-3-cyanopiperidine-1-carboxylate, ethyl(3R,4S)-4-{4-carbamoyl-3-[(4-fluorophenyl)amino]-1H-pyrazol-1-yl}-3-cyanopiperidine-1-carboxylate, (3-methyloxetan-3-yl)methyl-4-{4-carbamoyl-3-[(4-fluorophenyl)amino]-1H-pyrazol-1-yl}-3-cyanopiperidine-1-carboxylate, (3-methyloxetan-3-yl)methyl(3R,4S)-4-{4-carbamoyl-3-[(4-fluorophenyl)amino]-1H-pyrazol-1-yl}-3-cyanopiperidine-1-carboxylate, (3-methyloxetan-3-yl)methyl(3S,4R)-4-{4-carbamoyl-3-[(4-fluorophenyl)amino]-1H-pyrazol-1-yl}-3-cyanopiperidine-1-carboxylate, cyclopropylmethyl-4-{4-carbamoyl-3-[(4-fluorophenyl)amino]-1H-pyrazol-1-yl}-3-cyanopiperidine-1-carboxylate, cyclopropylmethyl(3R,4S)-4-{4-carbamoyl-3-[(4-fluorophenyl)amino]-1H-pyrazol-1-yl}-3-cyanopiperidine-1-carboxylate, cyclopropylmethyl(3S,4R)-4-{4-carbamoyl-3-[(4-fluorophenyl)amino]-1H-pyrazol-1-yl}-3-cyanopiperidine-1-carboxylate, 2-fluoro-1-(fluoromethyl)ethyl-4-{4-carbamoyl-3-[(4-fluorophenyl)amino]-1H-pyrazol-1-yl}-3-cyanopiperidine-1-carboxylate, 2-fluoro-1-(fluoromethyl)ethyl(3R,4S)-4-{4-carbamoyl-3-[(4-fluorophenyl)amino]-1H-pyrazol-1-yl}-3-cyanopiperidine-1-carboxylate, 2-fluoro-1-(fluoromethyl)ethyl(3S,4R)-4-{4-carbamoyl-3-[(4-fluorophenyl)amino]-1H-pyrazol-1-yl}-3-cyanopiperidine-1-carboxylate, 2-phenylethyl-4-{4-carbamoyl-3-[(4-fluorophenyl)amino]-1H-pyrazol-1-yl}-3-cyanopiperidine-1-carboxylate, 2-phenylethyl(3R,4S)-4-{4-carbamoyl-3-[(4-fluorophenyl)amino]-1H-pyrazol-1-yl}-3-cyanopiperidine-1-carboxylate, 2-phenylethyl(3S,4R)-4-{4-carbamoyl-3-[(4-fluorophenyl)amino]-1H-pyrazol-1-yl}-3-cyanopiperidine-1-carboxylate, cyclopentyl-4-{4-carbamoyl-3-[(4-fluorophenyl)amino]-1H-pyrazol-1-yl}-3-cyanopiperidine-1-carboxylate, cyclopentyl(3R,4S)-4-{4-carbamoyl-3-[(4-fluorophenyl)amino]-1H-pyrazol-1-yl}-3-cyanopiperidine-1-carboxylate, cyclopentyl(3S,4R)-4-{4-carbamoyl-3-[(4-fluorophenyl)amino]-1H-pyrazol-1-yl}-3-cyanopiperidine-1-carboxylate, 2,2-dimethylpropyl-4-{4-carbamoyl-3-[(4-fluorophenyl)amino]-1H-pyrazol-1-yl}-3-cyanopiperidine-1-carboxylate, 2,2-dimethylpropyl(3R,4S)-4-{4-carbamoyl-3-[(4-fluorophenyl)amino]-1H-pyrazol-1-yl}-3-cyanopiperidine-1-carboxylate, 2,2-dimethylpropyl(3S,4R)-4-{4-carbamoyl-3-[(4-fluorophenyl)amino]-1H-pyrazol-1-yl}-3-cyanopiperidine-1-carboxylate, tetrahydrofuran-3-yl-4-{4-carbamoyl-3-[(4-fluorophenyl)amino]-1H-pyrazol-1-yl}-3-cyanopiperidine-1-carboxylate, tetrahydrofuran-3-yl(3R,4S)-4-{4-carbamoyl-3-[(4-fluorophenyl)amino]-1H-pyrazol-1-yl}-3-cyanopiperidine-1-carboxylate, tetrahydrofuran-3-yl(3S,4R)-4-{4-carbamoyl-3-[(4-fluorophenyl)amino]-1H-pyrazol-1-yl}-3-cyanopiperidine-1-carboxylate, benzyl-4-{4-carbamoyl-3-[(4-fluorophenyl)amino]-1H-pyrazol-1-yl}-3-cyanopiperidine-1-carboxylate, benzyl(3R,4S)-4-{4-carbamoyl-3-[(4-fluorophenyl)amino]-1H-pyrazol-1-yl}-3-cyanopiperidine-1-carboxylate, benzyl(3S,4R)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl(3R,4S)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl(3S,4R)-4-{4-carbamoyl-3-[(4-fluorophenyl)amino]-1H-pyrazol-1-yl}-3-cyanopiperidine-1-carboxylate, 2-methoxyethyl-4-{4-carbamoyl-3-[(4-fluorophenyl)amino]-1H-pyrazol-1-yl}-3-cyanopiperidine-1-carboxylate, 2-methoxyethyl(3R,4S)-4-{4-carbamoyl-3-[(4-fluorophenyl)amino]-1H-pyrazol-1-yl}-3-cyanopiperidine-1-carboxylate, 2-methoxyethyl(3S,4R)-4-{4-carbamoyl-3-[(4-fluorophenyl)amino]-1H-pyrazol-1-yl}-3-cyanopiperidine-1-carboxylate, 3-phenylpropyl-4-{4-carbamoyl-3-[(4-fluorophenyl)amino]-1H-pyrazol-1-yl}-3-cyanopiperidine-1-carboxylate, 3-phenylpropyl(3R,4S)-4-{4-carbamoyl-3-[(4-fluorophenyl)amino]-1H-pyrazol-1-yl}-3-cyanopiperidine-1-carboxylate, 3-phenylpropyl(3S,4R)-4-{4-carbamoyl-3-[(4-fluorophenyl)amino]-1H-pyrazol-1-yl}-3-cyanopiperidine-1-carboxylate, 2-methylpropyl-4-{4-carbamoyl-3-[(4-fluorophenyl)amino]-1H-pyrazol-1-yl}-3-cyanopiperidine-1-carboxylate, 2-methylpropyl(3R,4S)-4-{4-carbamoyl-3-[(4-fluorophenyl)amino]-1H-pyrazol-1-yl}-3-cyanopiperidine-1-carboxylate, 2-methylpropyl(3S,4R)-4-{4-carbamoyl-3-[(4-fluorophenyl)amino]-1H-pyrazol-1-yl}-3-cyanopiperidine-1-carboxylate, oxetan-3-yl-4-{4-carbamoyl-3-[(4-fluorophenyl)amino]-1H-pyrazol-1-yl}-3-cyanopiperidine-1-carboxylate, oxetan-3-yl(3R,4S)-4-{4-carbamoyl-3-[(4-fluorophenyl)amino]-1H-pyrazol-1-yl}-3-cyanopiperidine-1-carboxylate, oxetan-3-yl(3S,4R)-4-{4-carbamoyl-3-[(4-fluorophenyl)amino]-1H-pyrazol-1-yl}-3-cyanopiperidine-1-carboxylate, 2-fluoroethyl-4-{4-carbamoyl-3-[(4-fluorophenyl)amino]-1H-pyrazol-1-yl}-3-cyanopiperidine-1-carboxylate, 2-fluoroethyl(3R,4S)-4-{4-carbamoyl-3-[(4-fluorophenyl)amino]-1H-pyrazol-1-yl}-3-cyanopiperidine-1-carboxylate, 2-fluoroethyl(3S,4R)-4-{4-carbamoyl-3-[(4-fluorophenyl)amino]-1H-pyrazol-1-yl}-3-cyanopiperidine-1-carboxylate, 2-ethoxy-2-oxoethyl-4-{4-carbamoyl-3-[(4-fluorophenyl)amino]-1H-pyrazol-1-yl}-3-cyanopiperidine-1-carboxylate, 2-ethoxy-2-oxoethyl(3R,4S)-4-{4-carbamoyl-3-[(4-fluorophenyl)amino]-1H-pyrazol-1-yl}-3-cyanopiperidine-1-carboxylate, 2-ethoxy-2-oxoethyl(3S,4R)-4-{4-carbamoyl-3-[(4-fluorophenyl)amino]-1H-pyrazol-1-yl}-3-cyanopiperidine-1-carboxylate, tetrahydro-2H-pyran-4-yl-4-{4-carbamoyl-3-[(4-fluorophenyl)amino]-1H-pyrazol-1-yl}-3-cyanopiperidine-1-carboxylate, tetrahydro-2H-pyran-4-yl(3R,4S)-4-{4-carbamoyl-3-[(4-fluorophenyl)amino]-1H-pyrazol-1-yl}-3-cyanopiperidine-1-carboxylate, tetrahydro-2H-pyran-4-yl(3S,4R)-4-{4-carbamoyl-3-[(4-fluorophenyl)amino]-1H-pyrazol-1-yl}-3-cyanopiperidine-1-carboxylate, cyclohexyl-4-{4-carbamoyl-3-[(4-fluorophenyl)amino]-1H-pyrazol-1-yl}-3-cyanopiperidine-1-carboxylate, cyclohexyl(3R,4S)-4-{4-carbamoyl-3-[(4-fluorophenyl)amino]-1H-pyrazol-1-yl}-3-cyanopiperidine-1-carboxylate, cyclohexyl(3S,4R)-4-{4-carbamoyl-3-[(4-fluorophenyl)amino]-1H-pyrazol-1-yl}-3-cyanopiperidine-1-carboxylate, (1-methylcyclopropyl)methyl-4-{4-carbamoyl-3-[(4-fluorophenyl)amino]-1H-pyrazol-1-yl}-3-cyanopiperidine-1-carboxylate, (1-methylcyclopropyl)methyl(3R,4S)-4-{4-carbamoyl-3-[(4-fluorophenyl)amino]-1H-pyrazol-1-yl}-3-cyanopiperidine-1-carboxylate, (1-methylcyclopropyl)methyl(3S,4R)-4-{4-carbamoyl-3-[(4-fluorophenyl)amino]-1H-pyrazol-1-yl}-3-cyanopiperidine-1-carboxylate, 3-methoxypropyl-4-{4-carbamoyl-3-[(4-fluorophenyl)amino]-1H-pyrazol-1-yl}-3-cyanopiperidine-1-carboxylate, 3-methoxypropyl(3R,4S)-4-{4-carbamoyl-3-[(4-fluorophenyl)amino]-1H-pyrazol-1-yl}-3-cyanopiperidine-1-carboxylate, 3-methoxypropyl(3S,4R)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl-4-{4-carbamoyl-3-[(4-fluorophenyl)amino]-1H-pyrazol-1-yl}-3-cyanopiperidine-1-carboxylate,

[1-(cyanomethyl)cyclopropyl]methyl(3R,4S)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl(3S,4R)-4-{4-carbamoyl-3-[(4-fluorophenyl)amino]-1H-pyrazol-1-yl}-3-cyanopiperidine-1-carboxylate, 2,2-difluoroethyl-4-{4-carbamoyl-3-[(4-fluorophenyl)amino]-1H-pyrazol-1-yl}-3-cyanopiperidine-1-carboxylate, 2,2-difluoroethyl(3R,4S)-4-{4-carbamoyl-3-[(4-fluorophenyl)amino]-1H-pyrazol-1-yl}-3-cyanopiperidine-1-carboxylate, 2,2-difluoroethyl(3S,4R)-4-{4-carbamoyl-3-[(4-fluorophenyl)amino]-1H-pyrazol-1-yl}-3-cyanopiperidine-1-carboxylate, 2,2,2-trifluoroethyl-4-{4-carbamoyl-3-[(4-fluorophenyl)amino]-1H-pyrazol-1-yl}-3-cyanopiperidine-1-carboxylate, 2,2,2-trifluoroethyl(3R,4S)-4-{4-carbamoyl-3-[(4-fluorophenyl)amino]-1H-pyrazol-1-yl}-3-cyanopiperidine-1-carboxylate, 2,2,2-trifluoroethyl(3S,4R)-4-{4-carbamoyl-3-[(4-fluorophenyl)amino]-1H-pyrazol-1-yl}-3-cyanopiperidine-1-carboxylate, 2,2-difluoro-3-hydroxypropyl-4-{4-carbamoyl-3-[(4-fluorophenyl)amino]-1H-pyrazol-1-yl}-3-cyanopiperidine-1-carboxylate, 2,2-difluoro-3-hydroxypropyl(3R,4S)-4-{4-carbamoyl-3-[(4-fluorophenyl)amino]-1H-pyrazol-1-yl}-3-cyanopiperidine-1-carboxylate, 2,2-difluoro-3-hydroxypropyl(3S,4R)-4-{4-carbamoyl-3-[(4-fluorophenyl)amino]-1H-pyrazol-1-yl}-3-cyanopiperidine-1-carboxylate, 1-cyclopropylethyl-4-{4-carbamoyl-3-[(4-fluorophenyl)amino]-1H-pyrazol-1-yl}-3-cyanopiperidine-1-carboxylate, 1-cyclopropylethyl(3R,4S)-4-{4-carbamoyl-3-[(4-fluorophenyl)amino]-1H-pyrazol-1-yl}-3-cyanopiperidine-1-carboxylate, 1-cyclopropylethyl(3S,4R)-4-{4-carbamoyl-3-[(4-fluorophenyl)amino]-1H-pyrazol-1-yl}-3-cyanopiperidine-1-carboxylate, 2-Cyano-2-methylpropyl-3-{4-carbamoyl-3-[(4-fluorophenyl)amino]-1H-pyrazol-1-yl}-4-cyanopiperidine-1-carboxylate, 2-Cyano-2-methylpropyl(3S,4R)-3-{4-carbamoyl-3-[(4-fluorophenyl)amino]-1H-pyrazol-1-yl}-4-cyanopiperidine-1-carboxylate, 2-Cyano-2-methylpropyl(3R,4S)-3-{4-carbamoyl-3-[(4-fluorophenyl)amino]-1H-pyrazol-1-yl}-4-cyanopiperidine-1-carboxylate, 2,2,2-trifluoro-1-methylethyl-3-{4-carbamoyl-3-[(4-fluorophenyl)amino]-1H-pyrazol-1-yl}-4-cyanopiperidine-1-carboxylate,
2,2,2-trifluoro-1-methylethyl(3S,4R)-3-{4-carbamoyl-3-[(4-fluorophenyl)amino]-1H-pyrazol-1-yl}-4-cyanopiperidine-1-carboxylate,
2,2,2-trifluoro-1-methylethyl(3R,4S)-3-{4-carbamoyl-3-[(4-fluorophenyl)amino]-1H-pyrazol-1-yl}-4-cyanopiperidine-1-carboxylate,
2-fluoro-1-(fluoromethyl)ethyl-3-{4-carbamoyl-3-[(4-fluorophenyl)amino]-1H-pyrazol-1-yl}-4-cyanopiperidine-1-carboxylate,
2-fluoro-1-(fluoromethyl)ethyl(3S,4R)-3-{4-carbamoyl-3-[(4-fluorophenyl)amino]-1H-pyrazol-1-yl}-4-cyanopiperidine-1-carboxylate,
2-fluoro-1-(fluoromethyl)ethyl(3R,4S)-3-{4-carbamoyl-3-[(4-fluorophenyl)amino]-1H-pyrazol-1-yl}-4-cyanopiperidine-1-carboxylate,
(1-methylcyclopropyl)methyl-3-{4-carbamoyl-3-[(4-fluorophenyl)amino]-1H-pyrazol-1-yl}-4-cyanopiperidine-1-carboxylate,
(1-methylcyclopropyl)methyl(3R,4S)-3-{4-carbamoyl-3-[(4-fluorophenyl)amino]-1H-pyrazol-1-yl}-4-cyanopiperidine-1-carboxylate,
(1-methylcyclopropyl)methyl(3S,4R)-3-{4-carbamoyl-3-[(4-fluorophenyl)amino]-1H-pyrazol-1-yl}-4-cyanopiperidine-1-carboxylate,
1-cyclopropylethyl-3-{4-carbamoyl-3-[(4-fluorophenyl)amino]-1H-pyrazol-1-yl}-4-cyanopiperidine-1-carboxylate,
1-cyclopropylethyl(3S,4R)-3-{4-carbamoyl-3-[(4-fluorophenyl)amino]-1H-pyrazol-1-yl}-4-cyanopiperidine-1-carboxylate,
1-cyclopropylethyl(3R,4S)-3-{4-carbamoyl-3-[(4-fluorophenyl)amino]-1H-pyrazol-1-yl}-4-cyanopiperidine-1-carboxylate,
2,2-difluoro-3-hydroxypropyl-3-{4-carbamoyl-3-[(4-fluorophenyl)amino]-1H-pyrazol-1-yl}-4-cyanopiperidine-1-carboxylate,
2,2-difluoro-3-hydroxypropyl(3S,4R)-3-{4-carbamoyl-3-[(4-fluorophenyl)amino]-1H-pyrazol-1-yl}-4-cyanopiperidine-1-carboxylate,
2,2-difluoro-3-hydroxypropyl(3R,4S)-3-{4-carbamoyl-3-[(4-fluorophenyl)amino]-1H-pyrazol-1-yl}-4-cyanopiperidine-1-carboxylate,
3-(dimethylamino)-2,2-dimethylpropyl-3-{4-carbamoyl-3-[(4-fluorophenyl)amino]-1H-pyrazol-1-yl}-4-cyanopiperidine-1-carboxylate,
3-(dimethylamino)-2,2-dimethylpropyl(3S,4R)-3-{4-carbamoyl-3-[(4-fluorophenyl)amino]-1H-pyrazol-1-yl}-4-cyanopiperidine-1-carboxylate,
3-(dimethylamino)-2,2-dimethylpropyl(3R,4S)-3-{4-carbamoyl-3-[(4-fluorophenyl)amino]-1H-pyrazol-1-yl}-4-cyanopiperidine-1-carboxylate,
ethyl-3-{4-carbamoyl-3-[(4-fluorophenyl)amino]-1H-pyrazol-1-yl}-4-cyanopiperidine-1-carboxylate,
ethyl(3S,4R)-3-{4-carbamoyl-3-[(4-fluorophenyl)amino]-1H-pyrazol-1-yl}-4-cyanopiperidine-1-carboxylate,
ethyl(3R,4S)-3-{4-carbamoyl-3-[(4-fluorophenyl)amino]-1H-pyrazol-1-yl}-4-cyanopiperidine-1-carboxylate,
2-methylpropyl-3-{4-carbamoyl-3-[(4-fluorophenyl)amino]-1H-pyrazol-1-yl}-4-cyanopiperidine-1-carboxylate,
2-methylpropyl(3S,4R)-3-{4-carbamoyl-3-[(4-fluorophenyl)amino]-1H-pyrazol-1-yl}-4-cyanopiperidine-1-carboxylate,
2-methylpropyl(3R,4S)-3-{4-carbamoyl-3-[(4-fluorophenyl)amino]-1H-pyrazol-1-yl}-4-cyanopiperidine-1-carboxylate,
2,2,2-trifluoroethyl-3-{4-carbamoyl-3-[(4-fluorophenyl)amino]-1H-pyrazol-1-yl}-4-cyanopiperidine-1-carboxylate,
2,2,2-trifluoroethyl(3S,4R)-3-{4-carbamoyl-3-[(4-fluorophenyl)amino]-1H-pyrazol-1-yl}-4-cyanopiperidine-1-carboxylate,
2,2,2-trifluoroethyl(3R,4S)-3-{4-carbamoyl-3-[(4-fluorophenyl)amino]-1H-pyrazol-1-yl}-4-cyanopiperidine-1-carboxylate,
2-fluoroethyl-3-{4-carbamoyl-3-[(4-fluorophenyl)amino]-1H-pyrazol-1-yl}-4-cyanopiperidine-1-carboxylate,
2-fluoroethyl(3S,4R)-3-{4-carbamoyl-3-[(4-fluorophenyl)amino]-1H-pyrazol-1-yl}-4-cyanopiperidine-1-carboxylate,
2-fluoroethyl(3R,4S)-3-{4-carbamoyl-3-[(4-fluorophenyl)amino]-1H-pyrazol-1-yl}-4-cyanopiperidine-1-carboxylate,
2,2-dimethylpropyl-3-{4-carbamoyl-3-[(4-fluorophenyl)amino]-1H-pyrazol-1-yl}-4-cyanopiperidine-1-carboxylate,
2,2-dimethylpropyl(3S,4R)-3-{4-carbamoyl-3-[(4-fluorophenyl)amino]-1H-pyrazol-1-yl}-4-cyanopiperidine-1-carboxylate,
2,2-dimethylpropyl(3R,4S)-3-{4-carbamoyl-3-[(4-fluorophenyl)amino]-1H-pyrazol-1-yl}-4-cyanopiperidine-1-carboxylate,
cyclopropylmethyl-3-{4-carbamoyl-3-[(4-fluorophenyl)amino]-1H-pyrazol-1-yl}-4-cyanopiperidine-1-carboxylate,
cyclopropylmethyl(3S,4R)-3-{4-carbamoyl-3-[(4-fluorophenyl)amino]-1H-pyrazol-1-yl}-4-cyanopiperidine-1-carboxylate,
cyclopropylmethyl(3R,4S)-3-{4-carbamoyl-3-[(4-fluorophenyl)amino]-1H-pyrazol-1-yl}-4-cyanopiperidine-1-carboxylate,
benzyl-3-{4-carbamoyl-3-[(4-fluorophenyl)amino]-1H-pyrazol-1-yl}-4-cyanopiperidine-1-carboxylate,
benzyl(3S,4R)-3-{4-carbamoyl-3-[(4-fluorophenyl)amino]-1H-pyrazol-1-yl}-4-cyanopiperidine-1-carboxylate,
benzyl(3R,4S)-3-{4-carbamoyl-3-[(4-fluorophenyl)amino]-1H-pyrazol-1-yl}-4-cyanopiperidine-1-carboxylate,
2-methoxyethyl-3-{4-carbamoyl-3-[(4-fluorophenyl)amino]-1H-pyrazol-1-yl}-4-cyanopiperidine-1-carboxylate,
2-methoxyethyl(3S,4R)-3-{4-carbamoyl-3-[(4-fluorophenyl)amino]-1H-pyrazol-1-yl}-4-cyanopiperidine-1-carboxylate,
2-methoxyethyl(3R,4S)-3-{4-carbamoyl-3-[(4-fluorophenyl)amino]-1H-pyrazol-1-yl}-4-cyanopiperidine-1-carboxylate,
2-ethoxy-2-oxoethyl-3-{4-carbamoyl-3-[(4-fluorophenyl)amino]-1H-pyrazol-1-yl}-4-cyanopiperidine-1-carboxylate,
2-ethoxy-2-oxoethyl(3S,4R)-3-{4-carbamoyl-3-[(4-fluorophenyl)amino]-1H-pyrazol-1-yl}-4-cyanopiperidine-1-carboxylate,
2-ethoxy-2-oxoethyl(3R,4S)-3-{4-carbamoyl-3-[(4-fluorophenyl)amino]-1H-pyrazol-1-yl}-4-cyanopiperidine-1-carboxylate,
tetrahydro-2H-pyran-4-yl-3-{4-carbamoyl-3-[(4-fluorophenyl)amino]-1H-pyrazol-1-yl}-4-cyanopiperidine-1-carboxylate, tetrahydro-2H-pyran-4-yl(3S,4R)-3-{4-carbamoyl-3-[(4-fluorophenyl)amino]-1H-pyrazol-1-yl}-4-cyanopiperidine-1-carboxylate,
tetrahydro-2H-pyran-4-yl(3R,4S)-3-{4-carbamoyl-3-[(4-fluorophenyl)amino]-1H-pyrazol-1-yl}-4-cyanopiperidine-1-carboxylate,
2-(dimethylamino)ethyl-3-{4-carbamoyl-3-[(4-fluorophenyl)amino]-1H-pyrazol-1-yl}-4-cyanopiperidine-1-carboxylate,
2-(dimethylamino)ethyl(3S,4R)-3-{4-carbamoyl-3-[(4-fluorophenyl)amino]-1H-pyrazol-1-yl}-4-cyanopiperidine-1-carboxylate,
2-(dimethylamino)ethyl(3R,4S)-3-{4-carbamoyl-3-[(4-fluorophenyl)amino]-1H-pyrazol-1-yl}-4-cyanopiperidine-1-carboxylate,
2-morpholin-4-ylethyl-3-{4-carbamoyl-3-[(4-fluorophenyl)amino]-1H-pyrazol-1-yl}-4-cyanopiperidine-1-carboxylate,
2-morpholin-4-ylethyl(3S,4R)-3-{4-carbamoyl-3-[(4-fluorophenyl)amino]-1H-pyrazol-1-yl}-4-cyanopiperidine-1-carboxylate,
2-morpholin-4-ylethyl(3R,4S)-3-{4-carbamoyl-3-[(4-fluorophenyl)amino]-1H-pyrazol-1-yl}-4-cyanopiperidine-1-carboxylate,
[1-(cyanomethyl)cyclopropyl]methyl-3-{4-carbamoyl-3-[(4-fluorophenyl)amino]-1H-pyrazol-1-yl}-4-cyanopiperidine-1-carboxylate,
[1-(cyanomethyl)cyclopropyl]methyl(3S,4R)-3-{4-carbamoyl-3-[(4-fluorophenyl)amino]-1H-pyrazol-1-yl}-4-cyanopiperidine-1-carboxylate,
[1-(cyanomethyl)cyclopropyl]methyl(3R,4S)-3-{4-carbamoyl-3-[(4-fluorophenyl)amino]-1H-pyrazol-1-yl}-4-cyanopiperidine-1-carboxylate,
oxetan-3-yl-3-{4-carbamoyl-3-[(4-fluorophenyl)amino]-1H-pyrazol-1-yl}-4-cyanopiperidine-1-carboxylate,
oxetan-3-yl(3S,4R)-3-{4-carbamoyl-3-[(4-fluorophenyl)amino]-1H-pyrazol-1-yl}-4-cyanopiperidine-1-carboxylate,
oxetan-3-yl(3R,4S)-3-{4-carbamoyl-3-[(4-fluorophenyl)amino]-1H-pyrazol-1-yl}-4-cyanopiperidine-1-carboxylate,
(3-methyloxetan-3-yl)methyl-3-{4-carbamoyl-3-[(4-fluorophenyl)amino]-1H-pyrazol-1-yl}-4-cyanopiperidine-1-carboxylate,
(3-methyloxetan-3-yl)methyl(3S,4R)-3-{4-carbamoyl-3-[(4-fluorophenyl)amino]-1H-pyrazol-1-yl}-4-cyanopiperidine-1-carboxylate,
(3-methyloxetan-3-yl)methyl(3R,4S)-3-{4-carbamoyl-3-[(4-fluorophenyl)amino]-1H-pyrazol-1-yl}-4-cyanopiperidine-1-carboxylate,
2-cyclopropylethyl-3-{4-carbamoyl-3-[(4-fluorophenyl)amino]-1H-pyrazol-1-yl}-4-cyanopiperidine-1-carboxylate,
2-cyclopropylethyl(3S,4R)-3-{4-carbamoyl-3-[(4-fluorophenyl)amino]-1H-pyrazol-1-yl}-4-cyanopiperidine-1-carboxylate,
2-cyclopropylethyl(3R,4S)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl(3S,4R)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl(3R,4S)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl(3S,4R)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl(3R,4S)-3-{4-carbamoyl-3-[(4-fluorophenyl)amino]-1H-pyrazol-1-yl}-4-cyanopiperidine-1-carboxylate,
2,2-difluoro-3-hydroxypropyl-3-{4-carbamoyl-3-[(4-fluorophenyl)amino]-1H-pyrazol-1-yl}-4-cyanopiperidine-1-carboxylate,
2,2-difluoro-3-hydroxypropyl(3S,4R)-3-{4-carbamoyl-3-[(4-fluorophenyl)amino]-1H-pyrazol-1-yl}-4-cyanopiperidine-1-carboxylate,
2,2-difluoro-3-hydroxypropyl(3R,4S)-3-{4-carbamoyl-3-[(4-fluorophenyl)amino]-1H-pyrazol-1-yl}-4-cyanopiperidine-1-carboxylate,
2,2,2-trifluoro-1-methylethyl-4-{4-carbamoyl-3-[(4-fluorophenyl)amino]-1H-pyrazol-1-yl}-3-cyanopiperidine-1-carboxylate,
2,2,2-trifluoro-1-methylethyl(3R,4R)-4-{4-carbamoyl-3-[(4-fluorophenyl)amino]-1H-pyrazol-1-yl}-3-cyanopiperidine-1-carboxylate,
2,2,2-trifluoro-1-methylethyl(3S,4S)-4-{4-carbamoyl-3-[(4-fluorophenyl)amino]-1H-pyrazol-1-yl}-3-cyanopiperidine-1-carboxylate,
1-[4-cyano-1-(pyridazin-3-ylmethyl)piperidin-3-yl]-3-[(4-fluorophenyl)amino]-1H-pyrazole-4-carboxamide,
1-[(3S,4R)-4-cyano-1-(pyridazin-3-ylmethyl)piperidin-3-yl]-3-[(4-fluorophenyl)amino]-1H-pyrazole-4-carboxamide,
1-[(3R,4S)-4-cyano-1-(pyridazin-3-ylmethyl)piperidin-3-yl]-3-[(4-fluorophenyl)amino]-1H-pyrazole-4-carboxamide,
1-[4-cyano-1-(pyrazin-2-ylmethyl)piperidin-3-yl]-3-[(4-fluorophenyl)amino]-1H-pyrazole-4-carboxamide,
1-[(3S,4R)-4-cyano-1-(pyrazin-2-ylmethyl)piperidin-3-yl]-3-[(4-fluorophenyl)amino]-1H-pyrazole-4-carboxamide,
1-[(3R,4S)-4-cyano-1-(pyrazin-2-ylmethyl)piperidin-3-yl]-3-[(4-fluorophenyl)amino]-1H-pyrazole-4-carboxamide,
1-[4-cyano-1-(isoxazol-3-ylmethyl)piperidin-3-yl]-3-[(4-fluorophenyl)amino]-1H-pyrazole-4-carboxamide,
1-[(3S,4R)-4-cyano-1-(isoxazol-3-ylmethyl)piperidin-3-yl]-3-[(4-fluorophenyl)amino]-1H-pyrazole-4-carboxamide,
1-[(3R,4S)-4-cyano-1-(isoxazol-3-ylmethyl)piperidin-3-yl]-3-[(4-fluorophenyl)amino]-1H-pyrazole-4-carboxamide,
1-[4-cyano-1-(1,3-oxazol-4-ylmethyl)piperidin-3-yl]-3-[(4-fluorophenyl)amino]-1H-pyrazole-4-carboxamide,
1-[(3S,4R)-4-cyano-1-(1,3-oxazol-4-ylmethyl)piperidin-3-yl]-3-[(4-fluorophenyl)amino]-1H-pyrazole-4-carboxamide,
1-[(3R,4S)-4-cyano-1-(1,3-oxazol-4-ylmethyl)piperidin-3-yl]-3-[(4-fluorophenyl)amino]-1H-pyrazole-4-carboxamide,
1-{4-cyano-1-[(1-methyl-1H-pyrazol-3-yl)methyl]piperidin-3-yl}-3-[(4-fluorophenyl)amino]-1H-pyrazole-4-carboxamide,
1-{(3S,4R)-4-cyano-1-[(1-methyl-1H-pyrazol-3-yl)methyl]piperidin-3-yl}-3-[(4-fluorophenyl)amino]-1H-pyrazole-4-carboxamide,
1-{(3R,4S)-4-cyano-1-[(1-methyl-1H-pyrazol-3-yl)methyl]piperidin-3-yl}-3-[(4-fluorophenyl)amino]-1H-pyrazole-4-carboxamide, 1-[4-cyano-1-(1,3-thiazol-4-ylmethyl)piperidin-3-yl]-3-[(4-fluorophenyl)amino]-1H-pyrazole-4-carboxamide,
1-{(3S,4R)-4-cyano-1-(1,3-thiazol-4-ylmethyl)piperidin-3-yl]-3-[(4-fluorophenyl)amino]-1H-pyrazole-4-carboxamide,
1-[(3R,4S)-4-cyano-1-(1,3-thiazol-4-ylmethyl)piperidin-3-yl]-3-[(4-fluorophenyl)amino]-1H-pyrazole-4-carboxamide,
1-{4-cyano-1-[(4-fluoropyridin-2-yl)methyl]piperidin-3-yl}-3-[(4-fluorophenyl)amino]-1H-pyrazole-4-carboxamide,
1-{(3S,4R)-4-cyano-1-[(4-fluoropyridin-2-yl)methyl]piperidin-3-yl}-3-[(4-fluorophenyl)amino]-1H-pyrazole-4-carboxamide,
1-{(3R,4S)-4-cyano-1-[(4-fluoropyridin-2-yl)methyl]piperidin-3-yl}-3-[(4-fluorophenyl)amino]-1H-pyrazole-4-carboxamide,
1-[4-cyano-1-(1,3-oxazol-2-ylmethyl)piperidin-3-yl]-3-[(4-fluorophenyl)amino]-1H-pyrazole-4-carboxamide,
1-[(3S,4R)-4-cyano-1-(1,3-oxazol-2-ylmethyl)piperidin-3-yl]-3-[(4-fluorophenyl)amino]-1H-pyrazole-4-carboxamide,
1-[(3R,4S)-4-cyano-1-(1,3-oxazol-2-ylmethyl)piperidin-3-yl]-3-[(4-fluorophenyl)amino]-1H-pyrazole-4-carboxamide,
1-{4-cyano-1-[(3-methoxycyclobutyp methyl]piperidin-3-yl}-3-[(4-fluorophenyl)amino]-1H-pyrazole-4-carboxamide,
1-{(3S,4R)-4-cyano-1-[(3-methoxycyclobutyl)methyl]piperidin-3-yl}-3-[(4-fluorophenyl)amino]-1H-pyrazole-4-carboxamide,
1-{(3R,4S)-4-cyano-1-[(3-methoxycyclobutyl)methyl]piperidin-3-yl}-3-[(4-fluorophenyl)amino]-1H-pyrazole-4-carboxamide,
1-{4-cyano-1-[2-(tetrahydro-2H-pyran-4-yl)ethyl]piperidin-3-yl}-3-[(4-fluorophenyl)amino]-1H-pyrazole-4-carboxamide,
1-{(3S,4R)-4-cyano-1-[2-(tetrahydro-2H-pyran-4-yl)ethyl]piperidin-3-yl}-3-[(4-fluorophenyl)amino]-1H-pyrazole-4-carboxamide,
1-{(3R,4S)-4-cyano-1-[2-(tetrahydro-2H-pyran-4-yl)ethyl]piperidin-3-yl}-3-[(4-fluorophenyl)amino]-1H-pyrazole-4-carboxamide,
1-[4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[(3S,4R)-4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[(3R,4S)-4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[4-cyano-1-(cyclobutylmethyl)piperidin-3-yl]-3-[(4-fluorophenyl)amino]-1H-pyrazole-4-carboxamide,
1-[(3S,4R)-4-cyano-1-(cyclobutylmethyl)piperidin-3-yl]-3-[(4-fluorophenyl)amino]-1H-pyrazole-4-carboxamide,
1-[(3R,4S)-4-cyano-1-(cyclobutylmethyl)piperidin-3-yl]-3-[(4-fluorophenyl)amino]-1H-pyrazole-4-carboxamide,
1-{(4-cyano-1-[(1-methyl-1H-pyrazol-5-yl)methyl]piperidin-3-yl}-3-[(4-fluorophenyl)amino]-1H-pyrazole-4-carboxamide,
1-{(3S,4R)-4-cyano-1-[(1-methyl-1H-pyrazol-5-yl)methyl]piperidin-3-yl}-3-[(4-fluorophenyl)amino]-1H-pyrazole-4-carboxamide,
1-{(3R,4S)-4-cyano-1-[(1-methyl-1H-pyrazol-5-yl)methyl]piperidin-3-yl}-3-[(4-fluorophenyl)amino]-1H-pyrazole-4-carboxamide,
1-{(4-cyano-1-[(5-methylisoxazol-3-yl)methyl]piperidin-3-yl}-3-[(4-fluorophenyl)amino]-1H-pyrazole-4-carboxamide,
1-{(3S,4R)-4-cyano-1-[(5-methylisoxazol-3-yl)methyl]piperidin-3-yl}-3-[(4-fluorophenyl)amino]-1H-pyrazole-4-carboxamide,
1-{(3R,4S)-4-cyano-1-[(5-methylisoxazol-3-yl)methyl]piperidin-3-yl}-3-[(4-fluorophenyl)amino]-1H-pyrazole-4-carboxamide,
1-{4-cyano-1-[(1,5-dimethyl-1H-pyrazol-4-yl)methyl]piperidin-3-yl}-3-[(4-fluorophenyl)amino]-1H-pyrazole-4-carboxamide,
1-{(3S,4R)-4-cyano-1-[(1,5-dimethyl-1H-pyrazol-4-yl)methyl]piperidin-3-yl}-3-[(4-fluorophenyl)amino]-1H-pyrazole-4-carboxamide,
1-{(3R,4S)-4-cyano-1-[(1,5-dimethyl-1H-pyrazol-4-yl)methyl]piperidin-3-yl}-3-[(4-fluorophenyl)amino]-1H-pyrazole-4-carboxamide,
1-{4-cyano-1-[(5-fluoropyridin-2-yl)methyl]piperidin-3-yl}-3-[(4-fluorophenyl)amino]-1H-pyrazole-4-carboxamide,
1-{(3S,4R)-4-cyano-1-[(5-fluoropyridin-2-yl)methyl]piperidin-3-yl}-3-[(4-fluorophenyl)amino]-1H-pyrazole-4-carboxamide,
1-{(3R,4S)-4-cyano-1-[(5-fluoropyridin-2-yl)methyl]piperidin-3-yl}-3-[(4-fluorophenyl)amino]-1H-pyrazole-4-carboxamide,
1-{4-cyano-1-[(2-fluoropyridin-3-yl)methyl]piperidin-3-yl}-3-[(4-fluorophenyl)amino]-1H-pyrazole-4-carboxamide,
1-{(3S,4R)-4-cyano-1-[(2-fluoropyridin-3-yl)methyl]piperidin-3-yl}-3-[(4-fluorophenyl)amino]-1H-pyrazole-4-carboxamide,
1-{(3R,4S)-4-cyano-1-[(2-fluoropyridin-3-yl)methyl]piperidin-3-yl}-3-[(4-fluorophenyl)amino]-1H-pyrazole-4-carboxamide,
1-{(3S,4R and 3R,4S)-4-cyano-1-[(2-methyl-1,3-thiazol-5-yl)methyl]piperidin-3-yl}-3-[(4-fluorophenyl)amino]-1H-pyrazole-4-carboxamide,
1-{(3S,4R and 3R,4S)-4-cyano-1-[(2-methyl-1,3-thiazol-5-yl)methyl]piperidin-3-yl}-3-[(4-fluorophenyl)amino]-1H-pyrazole-4-carboxamide,
1-{(3S,4R and 3R,4S)-4-cyano-1-[(2-methyl-1,3-thiazol-5-yl)methyl]piperidin-3-yl}-3-[(4-fluorophenyl)amino]-1H-pyrazole-4-carboxamide,
1-{4-cyano-1-[(1-ethyl-1H-imidazol-2-yl)methyl]piperidin-3-yl}-3-[(4-fluorophenyl)amino]-1H-pyrazole-4-carboxamide,
1-{(3S,4R)-4-cyano-1-[(1-ethyl-1H-imidazol-2-yl)methyl]piperidin-3-yl}-3-[(4-fluorophenyl)amino]-1H-pyrazole-4-carboxamide,
1-{(3R,4S)-4-cyano-1-[(1-ethyl-1H-imidazol-2-yl)methyl]piperidin-3-yl}-3-[(4-fluorophenyl)amino]-1H-pyrazole-4-carboxamide,
1-{4-cyano-1-[(3-methyl-4,5-dihydroisoxazol-5-yl)methyl]piperidin-3-yl}-3-[(4-fluorophenyl)amino]-1H-pyrazole-4-carboxamide,
1-{(3S,4R)-4-cyano-1-[(3-methyl-4,5-dihydroisoxazol-5-yl)methyl]piperidin-3-yl}-3-[(4-fluorophenyl)amino]-1H-pyrazole-4-carboxamide,
1-{(3R,4S)-4-cyano-1-[(3-methyl-4,5-dihydroisoxazol-5-yl)methyl]piperidin-3-yl}-3-[(4-fluorophenyl)amino]-1H-pyrazole-4-carboxamide,
1-[4-cyano-1-(tetrahydrofuran-3-ylmethyl)piperidin-3-yl]-3-[(4-fluorophenyl)amino]-1H-pyrazole-4-carboxamide, 1-[(3S,4R)-4-cyano-1-(tetrahydrofuran-3-ylmethyl)piperidin-3-yl]-3-[(4-fluorophenyl)amino]-1H-pyrazole-4-carboxamide,
1-[(3R,4S)-4-cyano-1-(tetrahydrofuran-3-ylmethyl)piperidin-3-yl]-3-[(4-fluorophenyl)amino]-1H-pyrazole-4-carboxamide,
1-[3-cyano-1-(pyridazin-3-ylmethyl)piperidin-4-yl]-3-[(4-fluorophenyl)amino]-1H-pyrazole-4-carboxamide,
1-[(3R,4R)-3-cyano-1-(pyridazin-3-ylmethyl)piperidin-4-yl]-3-[(4-fluorophenyl)amino]-1H-pyrazole-4-carboxamide,
1-[(3S,4S)-3-cyano-1-(pyridazin-3-ylmethyl)piperidin-4-yl]-3-[(4-fluorophenyl)amino]-1H-pyrazole-4-carboxamide,
1-[3-cyano-1-(pyrazin-2-ylmethyl)piperidin-4-yl]-3-[(4-fluorophenyl)amino]-1H-pyrazole-4-carboxamide,
1-[(3R,4R)-3-cyano-1-(pyrazin-2-ylmethyl)piperidin-4-yl]-3-[(4-fluorophenyl)amino]-1H-pyrazole-4-carboxamide,
1-[(3S,4S)-3-cyano-1-(pyrazin-2-ylmethyl)piperidin-4-yl]-3-[(4-fluorophenyl)amino]-1H-pyrazole-4-carboxamide,
1-[3-cyano-1-(isoxazol-3-ylmethyl)piperidin-4-yl]-3-[(4-fluorophenyl)amino]-1H-pyrazole-4-carboxamide,
1-[(3R,4R)-3-cyano-1-(isoxazol-3-ylmethyl)piperidin-4-yl]-3-[(4-fluorophenyl)amino]-1H-pyrazole-4-carboxamide,
1-[(3S,4S)-3-cyano-1-(isoxazol-3-ylmethyl)piperidin-4-yl]-3-[(4-fluorophenyl)amino]-1H-pyrazole-4-carboxamide,
1-[3-cyano-1-(1,3-oxazol-4-ylmethyl)piperidin-4-yl]-3-[(4-fluorophenyl)amino]-1H-pyrazole-4-carboxamide,
1-[(3R,4R)-3-cyano-1-(1,3-oxazol-4-ylmethyl)piperidin-4-yl]-3-[(4-fluorophenyl)amino]-1H-pyrazole-4-carboxamide,
1-[(3S,4S)-3-cyano-1-(1,3-oxazol-4-ylmethyl)piperidin-4-yl]-3-[(4-fluorophenyl)amino]-1H-pyrazole-4-carboxamide,
1-{3-cyano-1-[(1-methyl-1H-pyrazol-3-yl)methyl]piperidin-4-yl}-3-[(4-fluorophenyl)amino]-1H-pyrazole-4-carboxamide,
1-{(3R,4R)-3-cyano-1-[(1-methyl-1H-pyrazol-3-yl)methyl]piperidin-4-yl}-3-[(4-fluorophenyl)amino]-1H-pyrazole-4-carboxamide,
1-{(3S,4S)-3-cyano-1-[(1-methyl-1H-pyrazol-3-yl)methyl]piperidin-4-yl}-3-[(4-fluorophenyl)amino]-1H-pyrazole-4-carboxamide,
1-[3-cyano-1-(1,3-thiazol-4-ylmethyl)piperidin-4-yl]-3-[(4-fluorophenyl)amino]-1H-pyrazole-4-carboxamide,
1-[(3R,4R)-3-cyano-1-(1,3-thiazol-4-ylmethyl)piperidin-4-yl]-3-[(4-fluorophenyl)amino]-1H-pyrazole-4-carboxamide,
1-[(3S,4S)-3-cyano-1-(1,3-thiazol-4-ylmethyl)piperidin-4-yl]-3-[(4-fluorophenyl)amino]-1H-pyrazole-4-carboxamide,
1-{3-cyano-1-[(5-fluoropyridin-3-yl)methyl]piperidin-4-yl}-3-[(4-fluorophenyl)amino]-1H-pyrazole-4-carboxamide,
1-{(3R,4R)-3-cyano-1-[(5-fluoropyridin-3-yl)methyl]piperidin-4-yl}-3-[(4-fluorophenyl)amino]-1H-pyrazole-4-carboxamide,
1-{(3S,4S)-3-cyano-1-[(5-fluoropyridin-3-yl)methyl]piperidin-4-yl}-3-[(4-fluorophenyl)amino]-1H-pyrazole-4-carboxamide,
1-[3-cyano-1-(1,3-oxazol-2-ylmethyl)piperidin-4-yl]-3-[(4-fluorophenyl)amino]-1H-pyrazole-4-carboxamide,
1-[(3R,4R)-3-cyano-1-(1,3-oxazol-2-ylmethyl)piperidin-4-yl]-3-[(4-fluorophenyl)amino]-1H-pyrazole-4-carboxamide,
1-[(3S,4S)-3-cyano-1-(1,3-oxazol-2-ylmethyl)piperidin-4-yl]-3-[(4-fluorophenyl)amino]-1H-pyrazole-4-carboxamide,
1-{3-cyano-1-[(3-methoxycyclobutyl)methyl]piperidin-4-yl}-3-[(4-fluorophenyl)amino]-1H-pyrazole-4-carboxamide,
1-{(3R,4R)-3-cyano-1-[(3-methoxycyclobutyl)methyl]piperidin-4-yl}-3-[(4-fluorophenyl)amino]-1H-pyrazole-4-carboxamide,
1-{(3S,4S)-3-cyano-1-[(3-methoxycyclobutyl)methyl]piperidin-4-yl}-3-[(4-fluorophenyl)amino]-1H-pyrazole-4-carboxamide,
1-{3-cyano-1-[2-(tetrahydro-2H-pyran-4-yl)ethyl]piperidin-4-yl}-3-[(4-fluorophenyl)amino]-1H-pyrazole-4-carboxamide,
1-{(3R,4R)-3-cyano-1-[2-(tetrahydro-2H-pyran-4-yl)ethyl]piperidin-4-yl}-3-[(4-fluorophenyl)amino]-1H-pyrazole-4-carboxamide,
1-{(3S,4S)-3-cyano-1-[2-(tetrahydro-2H-pyran-4-yl)ethyl]piperidin-4-yl}-3-[(4-fluorophenyl)amino]-1H-pyrazole-4-carboxamide,
1-{3-cyano-1-[(1-methyl-1H-pyrazol-5-yl)methyl]piperidin-4-yl}-3-[(4-fluorophenyl)amino]-1H-pyrazole-4-carboxamide,
1-{(3R,4R)-3-cyano-1-[(1-methyl-1H-pyrazol-5-yl)methyl]piperidin-4-yl}-3-[(4-fluorophenyl)amino]-1H-pyrazole-4-carboxamide,
1-{(3S,4S)-3-cyano-1-[(1-methyl-1H-pyrazol-5-yl)methyl]piperidin-4-yl}-3-[(4-fluorophenyl)amino]-1H-pyrazole-4-carboxamide,
1-{3-cyano-1-[(5-methylisoxazol-3-yl)methyl]piperidin-4-yl}-3-[(4-fluorophenyl)amino]-1H-pyrazole-4-carboxamide,
1-{(3R,4R)-3-cyano-1-[(5-methylisoxazol-3-yl)methyl]piperidin-4-yl}-3-[(4-fluorophenyl)amino]-1H-pyrazole-4-carboxamide,
1-{(3S,4S)-3-cyano-1-[(5-methylisoxazol-3-yl)methyl]piperidin-4-yl}-3-[(4-fluorophenyl)amino]-1H-pyrazole-4-carboxamide,
1-{3-cyano-1-[(1,5-dimethyl-1H-pyrazol-4-yl)methyl]piperidin-4-yl}-3-[(4-fluorophenyl)amino]-1H-pyrazole-4-carboxamide,
1-{(3R,4R)-3-cyano-1-[(1,5-dimethyl-1H-pyrazol-4-yl)methyl]piperidin-4-yl}-3-[(4-fluorophenyl)amino]-1H-pyrazole-4-carboxamide,
1-{(3S,4S)-3-cyano-1-[(1,5-dimethyl-1H-pyrazol-4-yl)methyl]piperidin-4-yl}-3-[(4-fluorophenyl)amino]-1H-pyrazole-4-carboxamide,
1-{3-cyano-1-[(2-fluoropyridin-3-yl)methyl]piperidin-4-yl}-3-[(4-fluorophenyl)amino]-1H-pyrazole-4-carboxamide,
1-{(3R,4R)-3-cyano-1-[(2-fluoropyridin-3-yl)methyl]piperidin-4-yl}-3-[(4-fluorophenyl)amino]-1H-pyrazole-4-carboxamide,
1-{(3S,4S)-3-cyano-1-[(2-fluoropyridin-3-yl)methyl]piperidin-4-yl}-3-[(4-fluorophenyl)amino]-1H-pyrazole-4-carboxamide,
1-{3-cyano-1-[(6-fluoropyridin-2-yl)methyl]piperidin-4-yl}-3-[(4-fluorophenyl)amino]-1H-pyrazole-4-carboxamide,
1-{(3S,4S)-3-cyano-1-[(6-fluoropyridin-2-yl)methyl]piperidin-4-yl}-3-[(4-fluorophenyl)amino]-1H-pyrazole-4-carboxamide,
1-{(3R,4R)-3-cyano-1-[(6-fluoropyridin-2-yl)methyl]piperidin-4-yl}-3-[(4-fluorophenyl)amino]-1H-pyrazole-4-carboxamide, 1-{3-cyano-1-[(2-methyl-1,3-thiazol-5-yl)methyl]piperidin-4-yl}-3-[(4-fluorophenyl)amino]-1H-pyrazole-4-carboxamide,
1-{(3R,4R)-3-cyano-1-[(2-methyl-1,3-thiazol-5-yl)methyl]piperidin-4-yl}-3-[(4-fluorophenyl)amino]-1H-pyrazole-4-carboxamide,
1-{(3S,4S)-3-cyano-1-[(2-methyl-1,3-thiazol-5-yl)methyl]piperidin-4-yl}-3-[(4-fluorophenyl)amino]-1H-pyrazole-4-carboxamide,
1-{3-cyano-1-[(1-ethyl-1H-imidazol-2-yl)methyl]piperidin-4-yl}-3-[(4-fluorophenyl)amino]-1H-pyrazole-4-carboxamide,
1-{(3R,4R)-3-cyano-1-[(1-ethyl-1H-imidazol-2-yl)methyl]piperidin-4-yl}-3-[(4-fluorophenyl)amino]-1H-pyrazole-4-carboxamide,
1-{(3S,4S)-3-cyano-1-[(1-ethyl-1H-imidazol-2-yl)methyl]piperidin-4-yl}-3-[(4-fluorophenyl)amino]-1H-pyrazole-4-carboxamide,
1-{3-cyano-1-[(3-methyl-4,5-dihydroisoxazol-5-yl)methyl]piperidin-4-yl}-3-[(4-fluorophenyl)amino]-1H-pyrazole-4-carboxamide,
1-{(3R,4R)-3-cyano-1-[(3-methyl-4,5-dihydroisoxazol-5-yl)methyl]piperidin-4-yl}-3-[(4-fluorophenyl)amino]-1H-pyrazole-4-carboxamide,
1-{(3S,4S)-3-cyano-1-[(3-methyl-4,5-dihydroisoxazol-5-yl)methyl]piperidin-4-yl}-3-[(4-fluorophenyl)amino]-1H-pyrazole-4-carboxamide,
1-[3-cyano-1-(cyclobutylmethyl)piperidin-4-yl]-3-[(4-fluorophenyl)amino]-1H-pyrazole-4-carboxamide,
1-[(3R,4R)-3-cyano-1-(cyclobutylmethyl)piperidin-4-yl]-3-[(4-fluorophenyl)amino]-1H-pyrazole-4-carboxamide,
1-[4-cyano-1-(1,3-thiazol-5-ylmethyl)piperidin-3-yl]-3-[(4-fluorophenyl)amino]-1H-pyrazole-4-carboxamide,
1-[(3S,4R)-4-cyano-1-(1,3-thiazol-5-ylmethyl)piperidin-3-yl]-3-[(4-fluorophenyl)amino]-1H-pyrazole-4-carboxamide,
1-[(3R,4S)-4-cyano-1-(1,3-thiazol-5-ylmethyl)piperidin-3-yl]-3-[(4-fluorophenyl)amino]-1H-pyrazole-4-carboxamide,
1-{4-cyano-1-[(4-methyl-1,3-oxazol-5-yl)methyl]piperidin-3-yl}-3-[(4-fluorophenyl)amino]-1H-pyrazole-4-carboxamide,
1-{(3S,4R)-4-cyano-1-[(4-methyl-1,3-oxazol-5-yl)methyl]piperidin-3-yl}-3-[(4-fluorophenyl)amino]-1H-pyrazole-4-carboxamide,
1-{(3S,4R,3R,4S)-4-cyano-1-[(4-methyl-1,3-oxazol-5-yl)methyl]piperidin-3-yl}-3-[(4-fluorophenyl)amino]-1H-pyrazole-4-carboxamide,
1-(3-cyano-1,1-dioxidotetrahydro-2H-thiopyran-4-yl)-3-((4-fluorophenyl)amino)-1H-pyrazole-4-carboxamide,
1-((3R,4S)-3-cyano-1,1-dioxidotetrahydro-2H-thiopyran-4-yl)-3-((4-fluorophenyl)amino)-1H-pyrazole-4-carboxamide,
1-((3S,4R)-3-cyano-1,1-dioxidotetrahydro-2H-thiopyran-4-yl)-3-((4-fluorophenyl)amino)-1H-pyrazole-4-carboxamide,
1-(3-cyano-1,1-dioxidotetrahydro-2H-thiopyran-4-yl)-3-((4-fluorophenyl)amino)-1H-pyrazole-4-carboxamide,
1-((3R,4S)-3-cyano-1,1-dioxidotetrahydro-2H-thiopyran-4-yl)-3-((4-fluorophenyl)amino)-1H-pyrazole-4-carboxamide,
1-((3S,4R)-3-cyano-1,1-dioxidotetrahydro-2H-thiopyran-4-yl)-3-((4-fluorophenyl)amino)-1H-pyrazole-4-carboxamide,
1-(3-cyano-1,1-dioxidotetrahydro-2H-thiopyran-4-yl)-3-((4-(trifluoromethyl)phenyl)amino)-1H-pyrazole-4-carboxamide,
1-((3R,4R)-3-cyano-1,1-dioxidotetrahydro-2H-thiopyran-4-yl)-3-((4-(trifluoromethyl)phenyl)amino)-1H-pyrazole-4-carboxamide,
1-((3S,4S)-3-cyano-1,1-dioxidotetrahydro-2H-thiopyran-4-yl)-3-((4-(trifluoromethyl)phenyl)amino)-1H-pyrazole-4-carboxamide,
1-(3-cyano-1,1-dioxidotetrahydro-2H-thiopyran-4-yl)-3-((4-(trifluoromethyl)phenyl)amino)-1H-pyrazole-4-carboxamide,
1-((3R,4S)-3-cyano-1,1-dioxidotetrahydro-2H-thiopyran-4-yl)-3-((4-(trifluoromethyl)phenyl)amino)-1H-pyrazole-4-carboxamide,
1-((3S,4R)-3-cyano-1,1-dioxidotetrahydro-2H-thiopyran-4-yl)-3-((4-(trifluoromethyl)phenyl)amino)-1H-pyrazole-4-carboxamide,
1-(4-cyano-1,1-dioxidotetrahydrothiophen-3-yl)-3-((4-fluorophenyl)amino)-1H-pyrazole-4-carboxamide,
1-((3S,4S)-4-cyano-1,1-dioxidotetrahydrothiophen-3-yl)-3-((4-fluorophenyl)amino)-1H-pyrazole-4-carboxamide,
1-((3R,4R)-4-cyano-1,1-dioxidotetrahydrothiophen-3-yl)-3-((4-fluorophenyl)amino)-1H-pyrazole-4-carboxamide,
1-(4-cyano-1,1-dioxidotetrahydrothiophen-3-yl)-3-((4-fluorophenyl)amino)-1H-pyrazole-4-carboxamide,
1-((3S,4R)-4-cyano-1,1-dioxidotetrahydrothiophen-3-yl)-3-((4-fluorophenyl)amino)-1H-pyrazole-4-carboxamide,
1-((3R,4S)-4-cyano-1,1-dioxidotetrahydrothiophen-3-yl)-3-((4-fluorophenyl)amino)-1H-pyrazole-4-carboxamide,
1-(4-cyano-1,1-dioxidotetrahydrothiophen-3-yl)-3-((4-((trifluoromethyl)sulfonyl)phenyl)amino)-1H-pyrazole-4-carboxamide,
1-((3S,4R)-4-cyano-1,1-dioxidotetrahydrothiophen-3-yl)-3-((4-((trifluoromethyl)sulfonyl)phenyl)amino)-1H-pyrazole-4-carboxamide,
1-((3R,4S)-4-cyano-1,1-dioxidotetrahydrothiophen-3-yl)-3-((4-((trifluoromethyl)sulfonyl)phenyl)amino)-1H-pyrazole-4-carboxamide,
1-(4-cyano-1,1-dioxidotetrahydrothiophen-3-yl)-3-((2-fluoropyridin-4-yl)amino)-1H-pyrazole-4-carboxamide,
1-((3S,4S)-4-cyano-1,1-dioxidotetrahydrothiophen-3-yl)-3-((2-fluoropyridin-4-yl)amino)-1H-pyrazole-4-carboxamide,
1-((3R,4R)-4-cyano-1,1-dioxidotetrahydrothiophen-3-yl)-3-((2-fluoropyridin-4-yl)amino)-1H-pyrazole-4-carboxamide,
1-(4-cyano-4-methyl-1,1-dioxidotetrahydrothiophen-3-yl)-3-((4-fluorophenyl)amino)-1H-pyrazole-4-carboxamide,
1-((3S,4R)-4-cyano-4-methyl-1,1-dioxidotetrahydrothiophen-3-yl)-3-((4-fluorophenyl)amino)-1H-pyrazole-4-carboxamide,
1-((3R,4S)-4-cyano-4-methyl-1,1-dioxidotetrahydrothiophen-3-yl)-3-((4-fluorophenyl)amino)-1H-pyrazole-4-carboxamide,
1-(4-cyano-4-methyl-1,1-dioxidotetrahydrothiophen-3-yl)-3-((4-fluorophenyl)amino)-1H-pyrazole-4-carboxamide,
1-((3S,4S)-4-cyano-4-methyl-1,1-dioxidotetrahydrothiophen-3-yl)-3-((4-fluorophenyl)amino)-1H-pyrazole-4-carboxamide,
1-((3R,4R)-4-cyano-4-methyl-1,1-dioxidotetrahydrothiophen-3-yl)-3-((4-fluorophenyl)amino)-1H-pyrazole-4-carboxamide,
1-(4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-((3S,4R)-4-cyano-tetrahydro-2H-pyran-3-yl)-3-(2-fluoropyridin-4-ylamino)-1H-pyrazole-4-carboxamide, 1-(4-cyano-tetrahydro-2H-pyran-3-yl)-3-(2-fluoropyridin-4-ylamino)-1H-pyrazole-4-carboxamide,
1-((3S,4R)-4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-(4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-((3S,4R)-4-cyano-tetrahydro-2H-pyran-3-yl)-3-(2-fluoropyridin-4-ylamino)-1H-pyrazole-4-carboxamide,
1-(4-cyanotetrahydro-2H-pyran-3-yl)-3-((4-(trifluoromethoxy)phenyl)amino)-1H-pyrazole-4-carboxamide,
1-((3R,4S)-4-cyanotetrahydro-2H-pyran-3-yl)-3-((4-(trifluoromethoxy)phenyl)amino)-1H-pyrazole-4-carboxamide,
1-((3S,4R)-4-cyanotetrahydro-2H-pyran-3-yl)-3-((4-(trifluoromethoxy)phenyl)amino)-1H-pyrazole-4-carboxamide,
3-[(4-chlorophenyl)amino]-1-[4-cyanotetrahydro-2H-pyran-3-yl]-1H-pyrazole-4-carboxamide,
3-[(4-chlorophenyl)amino]-1-[(3R,4S)-4-cyanotetrahydro-2H-pyran-3-yl]-1H-pyrazole-4-carboxamide,
3-[(4-chlorophenyl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-[(2-fluoropyridin-4-yl)amino]-1H-pyrazole-4-carboxamide,
1-[(3S,4R)-4-cyanotetrahydro-2H-pyran-3-yl]-3-[(2-fluoropyridin-4-yl)amino]-1H-pyrazole-4-carboxamide,
1-[(3R,4S)-4-cyanotetrahydro-2H-pyran-3-yl]-3-[(2-fluoropyridin-4-yl)amino]-1H-pyrazole-4-carboxamide,
1-[4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[(3R,4S)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[4-cyanotetrahydro-2H-pyran-3-yl]-3-({4-[2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1S)-2,2,2-trifluoro-1-hydroxyethyl]phenyl}amino)-1H-pyrazole-4-carboxamide,
1-[(3R,4S)-4-cyanotetrahydro-2H-pyran-3-yl]-3-({4-[(1S)-2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1R)-2,2,2-trifluoro-1-hydroxyethyl]phenyl}amino)-1H-pyrazole-4-carboxamide,
1-[(3R,4S)-4-cyanotetrahydro-2H-pyran-3-yl]-3-({4-[(1R)-2,2,2-trifluoro-1-hydroxyethyl]phenyl}amino)-1H-pyrazole-4-carboxamide,
1-[(4-cyanotetrahydro-2H-pyran-3-yl]-3-[(3,4-dichlorophenyl)amino]-1H-pyrazole-4-carboxamide,
1-[(3S,4R)-4-cyanotetrahydro-2H-pyran-3-yl]-3-[(3,4-dichlorophenyl)amino]-1H-pyrazole-4-carboxamide,
1-[(3R,4S)-4-cyanotetrahydro-2H-pyran-3-yl]-3-[(3,4-dichlorophenyl)amino]-1H-pyrazole-4-carboxamide,
3-[(4-chloro-3-fluorophenyl)amino]-1-[(4-cyanotetrahydro-2H-pyran-3-yl]-1H-pyrazole-4-carboxamide,
3-[(4-chloro-3-fluorophenyl)amino]-1-[(3S,4R)-4-cyanotetrahydro-2H-pyran-3-yl]-1H-pyrazole-4-carboxamide,
3-[(4-chloro-3-fluorophenyl)amino]-1-[(3R,4S)-4-cyanotetrahydro-2H-pyran-3-yl]-1H-pyrazole-4-carboxamide,
1-[4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[4-cyanotetrahydro-2H-pyran-3-yl]-3-({4-[2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(4-cyanotetrahydro-2H-pyran-3-yl]-3-{[4-(trifluoromethoxy)phenyl]amino}-1H-pyrazole-4-carboxamide,
1-[(3R,4S)-4-cyanotetrahydro-2H-pyran-3-yl]-3-{[4-(trifluoromethoxy)phenyl]amino}-1H-pyrazole-4-carboxamide,
1-[(3S,4R)-4-cyanotetrahydro-2H-pyran-3-yl]-3-{[4-(trifluoromethoxy)phenyl]amino}-1H-pyrazole-4-carboxamide,
3-[(7-chloroquinolin-3-yl)amino]-1-[4-cyanotetrahydro-2H-pyran-3-yl]-1H-pyrazole-4-carboxamide,
3-[(7-chloroquinolin-3-yl)amino]-1-[(3R,4S)-4-cyanotetrahydro-2H-pyran-3-yl]-1H-pyrazole-4-carboxamide,
3-[(7-chloroquinolin-3-yl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-{[4-(trifluoromethoxy)phenyl]amino}-1H-pyrazole-4-carboxamide,
1-[(3S,4R)-4-cyanotetrahydro-2H-pyran-3-yl]-3-{[4-(trifluoromethoxy)phenyl]amino}-1H-pyrazole-4-carboxamide,
1-[(3R,4S)-4-cyanotetrahydro-2H-pyran-3-yl]-3-{[4-(trifluoromethoxy)phenyl]amino}-1H-pyrazole-4-carboxamide,
3-[(4-chloro-3-fluorophenyl)amino]-1-[4-cyanotetrahydro-2H-pyran-3-yl]-1H-pyrazole-4-carboxamide,
3-[(4-chloro-3-fluorophenyl)amino]-1-[(3R,4S)-4-cyanotetrahydro-2H-pyran-3-yl]-1H-pyrazole-4-carboxamide,
3-[(4-chloro-3-fluorophenyl)amino]-1-[(3S,4R)-4-cyanotetrahydro-2H-pyran-3-yl]-1H-pyrazole-4-carboxamide,
1-[(4-cyanotetrahydro-2H-pyran-3-yl]-3-{[4-(1-methoxy-1-methylethyl)phenyl]amino}-1H-pyrazole-4-carboxamide,
1-[(3R,4S)-4-cyanotetrahydro-2H-pyran-3-yl]-3-{[4-(3-methyloxetan-3-yl)phenyl]amino}-1H-pyrazole-4-carboxamide,
1-[(3S,4R)-4-cyanotetrahydro-2H-pyran-3-yl]-3-{[4-(3-methyloxetan-3-yl)phenyl]amino}-1H-pyrazole-4-carboxamide,
1-[4-cyanotetrahydro-2H-pyran-3-yl]-3-{[4-(1-methoxy-1-methylethyl)phenyl]amino}-1H-pyrazole-4-carboxamide, 1-[(3S,4R)-4-cyanotetrahydro-2H-pyran-3-yl]-3-{[4-(3-methyloxetan-3-yl)phenyl]amino}-1H-pyrazole-4-carboxamide,
1-[(3R,4R)-4-cyanotetrahydro-2H-pyran-3-yl]-3-{[4-(1-methoxy-1-methylethyl)phenyl]amino}-1H-pyrazole-4-carboxamide,
1-[(3R,4S)-4-cyanotetrahydro-2H-pyran-3-yl]-3-{[4-(3-methyloxetan-3-yl)phenyl]amino}-1H-pyrazole-4-carboxamide,
3-[(6-chloropyridin-3-yl)amino]-1-[(4-cyanotetrahydro-2H-pyran-3-yl]-1H-pyrazole-4-carboxamide,
3-[(6-chloropyridin-3-yl)amino]-1-[(3S,4R)-4-cyanotetrahydro-2H-pyran-3-yl]-1H-pyrazole-4-carboxamide,
3-[(6-chloropyridin-3-yl)amino]-1-[(3R,4S)-4-cyanotetrahydro-2H-pyran-3-yl]-1H-pyrazole-4-carboxamide,
1-[(4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[(4-cyanotetrahydro-2H-pyran-3-yl]-3-[(6-fluoropyridin-3-yl)amino]-1H-pyrazole-4-carboxamide,
1-[(3R,4S)-4-cyanotetrahydro-2H-pyran-3-yl]-3-[(6-fluoropyridin-3-yl)amino]-1H-pyrazole-4-carboxamide,
1-[(3S,4R)-4-cyanotetrahydro-2H-pyran-3-yl]-3-[(6-fluoropyridin-3-yl)amino]-1H-pyrazole-4-carboxamide,
1-[(4-cyanotetrahydro-2H-pyran-3-yl]-3-[(5-fluoropyridin-3-yl)amino]-1H-pyrazole-4-carboxamide,
1-[(3S,4R)-4-cyanotetrahydro-2H-pyran-3-yl]-3-[(5-fluoropyridin-3-yl)amino]-1H-pyrazole-4-carboxamide,
1-[(3R,4S)-4-cyanotetrahydro-2H-pyran-3-yl]-3-[(5-fluoropyridin-3-yl)amino]-1H-pyrazole-4-carboxamide,
1-[4-cyanotetrahydro-2H-pyran-3-yl]-3-{[6-(difluoromethyl)pyridin-3-yl]amino}-1H-pyrazole-4-carboxamide,
1-[(3S,4R)-4-cyanotetrahydro-2H-pyran-3-yl]-3-{[6-(difluoromethyl)pyridin-3-yl]amino}-1H-pyrazole-4-carboxamide,
1-[(3R,4S)-4-cyanotetrahydro-2H-pyran-3-yl]-3-{[6-(difluoromethyl)pyridin-3-yl]amino}-1H-pyrazole-4-carboxamide,
1-[4-cyanotetrahydro-2H-pyran-3-yl]-3-{[4-(dimethylcarbamoyl)phenyl]amino}-1H-pyrazole-4-carboxamide,
1-[(3R,4S)-4-cyanotetrahydro-2H-pyran-3-yl]-3-{[4-(dimethylcarbamoyl)phenyl]amino}-1H-pyrazole-4-carboxamide,
1-[(3S,4R)-4-cyanotetrahydro-2H-pyran-3-yl]-3-{[4-(dimethylcarbamoyl)phenyl]amino}-1H-pyrazole-4-carboxamide,
3-[(4-cyanophenyl)amino]-1-[4-cyanotetrahydro-2H-pyran-3-yl]-1H-pyrazole-4-carboxamide,
3-[(4-cyanophenyl)amino]-1-[(3R,4S)-4-cyanotetrahydro-2H-pyran-3-yl]-1H-pyrazole-4-carboxamide,
3-[(4-cyanophenyl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-{[6-(2,2,2-trifluoroethoxy)pyridin-3-yl]amino}-1H-pyrazole-4-carboxamide,
1-[(3R,4S)-4-cyanotetrahydro-2H-pyran-3-yl]-3-{[6-(2,2,2-trifluoroethoxy)pyridin-3-yl]amino}-1H-pyrazole-4-carboxamide,
1-[(3S,4R)-4-cyanotetrahydro-2H-pyran-3-yl]-3-{[6-(2,2,2-trifluoroethoxy)pyridin-3-yl]amino}-1H-pyrazole-4-carboxamide,
1-[4-cyanotetrahydro-2H-pyran-3-yl]-3-(phenylamino)-1H-pyrazole-4-carboxamide,
1-[(3R,4S)-4-cyanotetrahydro-2H-pyran-3-yl]-3-(phenylamino)-1H-pyrazole-4-carboxamide,
1-[(3S,4R)-4-cyanotetrahydro-2H-pyran-3-yl]-3-(phenylamino)-1H-pyrazole-4-carboxamide,
1-[4-cyanotetrahydro-2H-pyran-3-yl]-3-[(2-fluoropyridin-4-yl)amino]-1H-pyrazole-4-carboxamide,
1-[(3R,4S)-4-cyanotetrahydro-2H-pyran-3-yl]-3-[(2-fluoropyridin-4-yl)amino]-1H-pyrazole-4-carboxamide,
1-[(3S,4R)-4-cyanotetrahydro-2H-pyran-3-yl]-3-[(2-fluoropyridin-4-yl)amino]-1H-pyrazole-4-carboxamide,
1-[4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[4-cyanotetrahydro-2H-pyran-3-yl]-3-({4-[2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-(4-Cyano-6-methyltetrahydro-2H-pyran-3-yl)-3-((2-fluoropyridin-4-yl)amino)-1H-pyrazole-4-carboxamide,
1-((3R,4S,6R)-4-Cyano-6-methyltetrahydro-2H-pyran-3-yl)-3-((2-fluoropyridin-4-yl)amino)-1H-pyrazole-4-carboxamide,
1-((3R,4R,6R)-4-Cyano-6-methyltetrahydro-2H-pyran-3-yl)-3-((2-fluoropyridin-4-yl)amino)-1H-pyrazole-4-carboxamide,
1-((3R,4R,6S)-4-Cyano-6-methyltetrahydro-2H-pyran-3-yl)-3-((2-fluoropyridin-4-yl)amino)-1H-pyrazole-4-carboxamide,
1-((3R,4S,6S)-4-Cyano-6-methyltetrahydro-2H-pyran-3-yl)-3-((2-fluoropyridin-4-yl)amino)-1H-pyrazole-4-carboxamide,
1-((3S,4S,6R)-4-Cyano-6-methyltetrahydro-2H-pyran-3-yl)-3-((2-fluoropyridin-4-yl)amino)-1H-pyrazole-4-carboxamide,
1-((3S,4S,6S)-4-Cyano-6-methyltetrahydro-2H-pyran-3-yl)-3-((2-fluoropyridin-4-yl)amino)-1H-pyrazole-4-carboxamide,
1-((3S,4R,6R)-4-Cyano-6-methyltetrahydro-2H-pyran-3-yl)-3-((2-fluoropyridin-4-yl)amino)-1H-pyrazole-4-carboxamide,
1-((3S,4R,6S)-4-Cyano-6-methyltetrahydro-2H-pyran-3-yl)-3-((2-fluoropyridin-4-yl)amino)-1H-pyrazole-4-carboxamide,
1-(3-cyano-tetrahydro-2H-pyran-4-yl)-3-(2-fluoropyridin-4-ylamino)-1H-pyrazole-4-carboxamide,
1-((3R,4R)-3-cyano-tetrahydro-2H-pyran-4-yl)-3-(2-fluoropyridin-4-ylamino)-1H-pyrazole-4-carboxamide,
1-((3S,4S)-3-cyano-tetrahydro-2H-pyran-4-yl)-3-(2-fluoropyridin-4-ylamino)-1H-pyrazole-4-carboxamide, 1-(3-cyano-1,1-dioxidotetrahydro-2H-thiopyran-4-yl)-3-((4-fluorophenyl)amino)-1H-pyrazole-4-carboxamide,
1-((3R,4R)-3-cyano-1,1-dioxidotetrahydro-2H-thiopyran-4-yl)-3-((4-fluorophenyl)amino)-1H-pyrazole-4-carboxamide,
1-((3S,4S)-3-cyano-1,1-dioxidotetrahydro-2H-thiopyran-4-yl)-3-((4-fluorophenyl)amino)-1H-pyrazole-4-carboxamide,
1-((3-cyano-1,1-dioxidotetrahydro-2H-thiopyran-4-yl)-3-((4-(trifluoromethyl)phenyl)amino)-1H-pyrazole-4-carboxamide,
1-((3R,4S)-3-cyano-1,1-dioxidotetrahydro-2H-thiopyran-4-yl)-3-((4-(trifluoromethyl)phenyl)amino)-1H-pyrazole-4-carboxamide,
1-((3S,4R)-3-cyano-1,1-dioxidotetrahydro-2H-thiopyran-4-yl)-3-((4-(trifluoromethyl)phenyl)amino)-1H-pyrazole-4-carboxamide,
1-(4-cyano-4-methyl-1,1-dioxidotetrahydrothiophen-3-yl)-3-((4-fluorophenyl)amino)-1H-pyrazole-4-carboxamide,
1-((3S,4R)-4-cyano-4-methyl-1,1-dioxidotetrahydrothiophen-3-yl)-3-((4-fluorophenyl)amino)-1H-pyrazole-4-carboxamide,
1-((3R4S)-4-cyano-4-methyl-1,1-dioxidotetrahydrothiophen-3-yl)-3-((4-fluorophenyl)amino)-1H-pyrazole-4-carboxamide,
1-(4-Cyano-4-methyl-1,1-dioxidotetrahydrothiophen-3-yl)-3-((4-fluorophenyl)amino)-1H-pyrazole-4-carboxamide,
1-((3R,4R)-4-Cyano-4-methyl-1,1-dioxidotetrahydrothiophen-3-yl)-3-((4-fluorophenyl)amino)-1H-pyrazole-4-carboxamide, and
1-((3S,4S)-4-Cyano-4-methyl-1,1-dioxidotetrahydrothiophen-3-yl)-3-((4-fluorophenyl)amino)-1H-pyrazole-4-carboxamide.

The invention also encompasses pharmaceutical compositions containing a compound of formula I, and methods for treatment or prevention of JAK mediated diseases using compounds of formula I.

The invention is described using the following definitions unless otherwise indicated.

"Acyl" means a —C(O)R radical Where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B. The term "alkoxy" represents a linear or branched alkyl group of indicated number of carbon atoms attached through an oxygen bridge.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$ alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

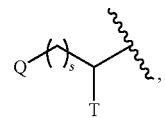

wherein s is an integer equal to zero, 1 or 2, the structure is

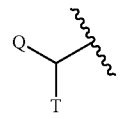

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

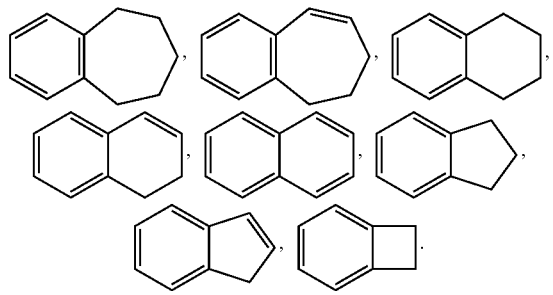

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$haloalkyl, for example, includes $—CF_3$, $—CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl(or tetrahydrofuranyl)

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsaturated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl(or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-c]pyridinyl, imidazo[1,2-c]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 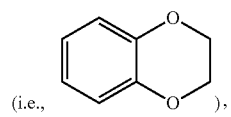 ), imidazo(2,1-b)(1,3)thiazole, (i.e., 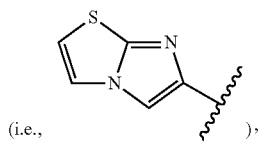 [SMILES: *c1cn2ccsc2n1] ), and benzo-1,3-dioxolyl (i.e., 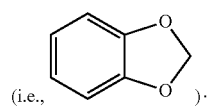 ).

In certain contexts herein,

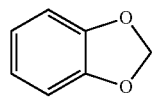

is alternatively referred to as phenyl having as a substituent methylenedioxy attached to two adjacent carbon atoms.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

Structural representations of compounds having substituents terminating with a methyl group may display the terminal methyl group either using the characters "$CH_3$", e.g. "—$CH_3$" or using a straight line representing the presence of the methyl group, e.g. "-", i.e.,

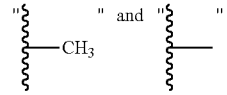

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

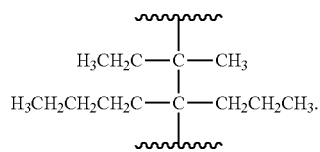

In one embodiment of the invention, $R^a$ is hydrogen, ethyl, propyl, butyl, pentyl, or methyl. In a variant of this embodiment, $R^a$ is hydrogen or methyl. In another variant, $R^a$ is hydrogen.

In one embodiment of the invention $R^4$ is hydrogen, ethyl, propyl, butyl, pentyl, or methyl. In a variant of this embodiment, $R^4$ is hydrogen. In another variant, $R^4$ is methyl or propyl.

In one embodiment, A is aryl or heteroaryl, wherein A is substituted with 0, 1, 2, 3, or 4, substituents, $R^{5a}$.

In one embodiment A is chosen from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine, thienopyridine, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl, imidazo(2,1-b)(1,3)thiazole, and benzo-1,3-dioxolyl, phenyl, indenyl, and naphthalenyl.

In another embodiment, A' is chosen from: phenyl, 1,3-dihydro-2H-isoindole, pyridinyl, quinolinyl, isoquinolinyl, 2,3-dihydro-1-benzofuranyl, dihydro-1H-indenyl, 2,3-dihydro-1,4-benzodioxinyl, 2,3dihydro-1H-isoindolyl, and benzo[b]thiophene, wherein $R^5$ is substituted with 0, 1, 2, 3, or 4, substituents, $R^{5a}$.

In another embodiment, A is chosen from: phenyl, pyridinyl, quinolinyl, and isoquinolinyl, wherein A is substituted with 0, 1, 2, 3, or 4, substituents, $R^{5a}$.

In one embodiment, $R^2$ and $R^3$ are each independently selected from hydrogen, $C_{1-10}$ alkyl, halogen, $C_{2-10}$ alkenyl, aryl $C_{0-10}$ alkyl$C_{0-10}$ alkyl, $(C_{3-8})$heterocycloalkyl $C_{0-10}$ alkyl, $C_{3-8}$ cycloalkyl$C_{0-10}$ alkyl, and heteroaryl $C_{0-10}$ alkyl, wherein each of $R^2$ and $R^3$ are independently substituted with 0, 1, 2, 3, or 4, substituents $R^{5a}$.

In another embodiment, $R^2$ and $R^3$ are selected from hydrogen, $C_{1-10}$ alkyl, $(C_{3-8})$heterocycloalkyl $C_{0-10}$ alkyl, and $C_{3-8}$ cycloalkyl$C_{0-10}$ alkyl, wherein each of $R^2$ and $R^3$ are independently substituted with 0, 1, 2, 3, or 4, substituents $R^{5a}$.

In another embodiment, $R^2$ and $R^3$ are selected from hydrogen, and $C_{1-10}$ alkyl, wherein each of $R^2$ and $R^3$ are independently substituted with 0, 1, 2, 3, or 4, substituents $R^{5a}$.

In another embodiment of the invention, $R^2$ and $R^3$ are independently selected from hydrogen, methyl, ethyl, propyl, tert-butyl, isopropyl, dimethylpropyl, dimethylbutyl, and tertbutylmethyl, and cyclobutyl. In a variant of this embodiment, $R^2$ and $R^3$ are independently selected from hydrogen and methyl.

In one embodiment, $R^{5a}$ is independently selected from: hydrogen, halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkynyl(oxy)$_{0-1}$(carbonyl)$_{0-1}C_{0-10}$ alkyl, $C_{2-10}$ alkenyl (oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, aryl $C_{2-10}$ alkenyl(oxy)$_{0-1}$(carbonyl)$_{0-1}C_{0-10}$ alkyl, aryl $C_{2-10}$ alkynyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl (oxy)$_{0-1}$(carbonyl)$_{0-1}C_{0-10}$ alkyl, $C_{1-10}$ alkyl(carbonyl)$_{0-1}$oxy$C_{0-10}$ alkyl, $((C_{0-10})$alkyl$)_{1-2}$aminocarbonyloxy, $C_{1-10}$ alkylamino(oxy)$_{0-1}$carbonyl$C_{0-10}$ alkyl, $C_{1-10}$ alkyl (oxy)$_{0-1}$carbonylamino$C_{0-10}$ alkyl, —$CO_2(C_{0-10}$ alkyl), —$(C_{0-10}$ alkyl$)CO_2H$, Oxo (═O), $C_{0-10}$ alkylsulfonyl, $C_{1-10}$ heteroalkylsulfonyl, $C_{3-8}$ cycloalkylsulfonyl, $C_{3-8}$ cyclohetroalkylsulfonyl, heteroarylsulfonyl, arylsulfonyl, aminosulfonyl, —$SO_2N(C_{1-6}$ alkyl$)_{1-2}$, —$SO_2C_{1-6}$ alkyl, —$SO_2CF_3$, —$SO_2CF_2H$, $C_{1-10}$ alkylsulfinyl, amino, $(C_{0-10}$ alkyl$)_{1-2}$ amino, hydroxy, $C_{0-10}$ alkylalkoxy, cyano, $C_{1-6}$ alkylcyano, and $C_{1-6}$ haloalkyl; wherein $R^{5a}$ is each optionally substituted with 0, 1, 2, 3, or 4 substituent, $R^6$.

In one embodiment, $R^{5a}$ is independently selected from: hydrogen, halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkynyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkylamino (oxy)$_{0-1}$carbonyl$C_{0-10}$ alkyl, Oxo (═O), $C_{0-10}$ alkylsulfonyl, —$SO_2N(C_{1-6}$alkyl$)_{1-2}$, —$SO_2CF_3$, amino, $(C_{0-10}$ alkyl$)_{1-2}$ amino, $C_{0-10}$ alkylalkoxy, cyano, $C_{1-6}$alkylcyano, and $C_{1-6}$ haloalkyl; wherein $R^{5a}$ is each optionally substituted with 0, 1, 2, 3, or 4 substituent, $R^6$.

In one embodiment, $R^{5a}$ is independently selected from: hydrogen, halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, $C_{2-10}$ alkynyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkylamino (oxy)$_{0-1}$carbonyl$C_{0-10}$ alkyl, Oxo (═O), $C_{0-10}$ alkylsulfonyl, —$SO_2CF_3$, amino, $C_{0-10}$ alkylalkoxy, cyano, and $C_{1-6}$ haloalkyl; wherein $R^{5a}$ is each optionally substituted with 0, 1, 2, 3, or 4 substituent, $R^6$.

In one embodiment of the invention, $R^{5a}$ is independently selected from: hydrogen, butynyloxycarbonyl, tert-butyloxycarbonyl, 3,3dimethylbutyloxycarbonyl, methylethyloxycarbonyl, Ethyloxycarbonyl, phenylpropyloxycarbonyl, morpholinylethyloxycarbonyl, oxetanyloxycarbonyl, methylpropyloxycarbonyl, piperidinylmethyloxycarbonyl, cyclopropylmethyloxycarbonyl, cyclopentyloxycarbonyl, benzyloxycarbonyl, tetrahydro-2H-pyranyloxycarbonyl, cyclopropylethyloxycarbonyl, pyrrolidinylethyloxycarbonyl, cyclohexyloxycarbonyl, dimethylpropyloxycarbonyl, propyloxycarbonyl, piprazininylethyloxycarbonyl, tetrahydrofuranyloxycarbonyl, piperidinyloxycarbonyl, pyrazolylethyloxycarbonyl, methyloxycarbonyl, oxetanylmethyloxycarbonyl, phenylethyloxycarbonyl, 2,3-dihydro-1H-indenyloxycarbonyl, methyloxycarbonyl, methylpropyloxycarbonyl, pyrazinylmethyl, isoxazolylmethyl, 1,3-oxazolylmethyl, pyrazolylmethyl, 1,3-thiazolylmethyl, pyridinylmethyl, cyclobutylmethyl, tetrahydro-2H-pyranylethyl, imidazolylmethyl, 4,5-dihydroisoxazolylmethyl, tetrhydrofuranylmethyl, pyridazinylmethyl, 4,5-dihydroisoxazolylmethyl, Oxo, methyl, halogen, trifluoromethyl, sulfonyl, (trifluoromethyl)sulfonyl, methoxy, hydroxyethyl, rifluroethyl, methylethyl, (difluoromethyl)ethyl, tetrahydro-2-H-pyranyl, difluoromethyl, dimethylaminocarbonyl, cyano, and ethoxy, wherein $R^{5a}$ is independently substituted with 0, 1, 2, 3, or 4, substituents $R^6$.

In one embodiment of the invention, $R^6$, is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-8})$heterocycloalkyl $C_{0-10}$ alkyl(oxy)$_{0-1}$(carbonyl)$_{0-1}C_{0-10}$ alkyl, $C_{1-10}$ alkyl (oxy)$_{0-1}$carbonylamino$C_{0-10}$ alkyl, $C_{3-8}$ cycloalkyl $C_{0-10}$ alkyl(oxy)$_{0-1}$carbonylamino$C_{0-10}$ alkyl, aryl $C_{0-10}$ alkyl (oxy)$_{0-1}$carbonylamino$C_{0-10}$ alkyl, heteroaryl $C_{0-10}$ alkyl (oxy)$_{0-1}$carbonylamino$C_{0-10}$ alkyl, $(C_{3-8})$heterocycloalkyl $C_{0-10}$ alkyl(oxy)$_{0-1}$carbonylamino$C_{0-10}$ alkyl, —$CO_2(C_{0-10}$ alkyl), Oxo, $C_{1-10}$ alkylsulfonyl, $C_{1-10}$ heteroalkylsulfonyl, $(C_{3-8})$cycloalkylsulfonyl, $(C_{3-8})$cyclohetroalkylsulfonyl, heteroarylsulfonyl, arylsulfonyl, aminosulfonyl, —$SO_2C_{1-6}$ alkyl, amino, $(C_{0-10}$ alkyl$)_{1-2}$ amino, hydroxy, $C_{1-10}$ alkoxy, cyano, and $C_{1-6}$ haloalkyl; wherein $R^6$ is optionally substituted.

In one embodiment of the invention, $R^6$, is independently selected from: halogen, $C_{1-10}$ alkyl(oxy)$_{0-1}$(carbonyl)$_{0-1}C_{0-10}$ alkyl, $C_{3-8}$ cycloalkyl $C_{0-10}$ alkyl(oxy)$_{0-1}$(carbonyl)$_{0-1}C_{0-10}$ alkyl, Oxo, amino, $(C_{0-10}$ alkyl$)_{1-2}$ amino, hydroxy, $C_{1-10}$ alkoxy, cyano, and $C_{1-6}$haloalkyl; wherein $R^6$ is optionally substituted.

In another embodiment, $R^6$ is independently selected from: methyl, fluoro, trifluoromethyl, cyano, amino, dimethylamino, oxo, hydroxyl, methoxy, cyclopropyl, ethyoxycarbonyl, cyano, fluoromethyl, methyethylhydroxy, ethyl, and difluoromethyl, wherein $R^6$ is optionally substituted with 1, 2, or 3 substituents chosen from hydrogen, hydroxy, $(C_{1-6})$alkoxy, halogen, $CO_2H$, —$(C_{0-6})$alkylCN, —$O(C=O)C_1-C_6$ alkyl, $NO_2$, trifluoromethoxy, trifluoroethoxy, —N=C(O)O(C$_{0-6}$) alkyl, $C_{1-10}$ alkylsulfonyl, $C_{1-10}$ heteroalkylsulfonyl, oxo (O=), $(C_{3-8})$cycloalkylsulfonyl, $(C_{3-8})$cycloheteroalkylsulfonyl, heteroarylsulfonyl, arylsulfonyl, aminosulfonyl, —$SO_2N(C_{1-6}$ alkyl$)_{1-2}$, —$SO_2C_{1-6}$ alkyl, —$SO_2CF_3$, —$SO_2CF_2H$, —$C_{1-10}$ alkylsulfinyl, —O—Si, —$OSi(C_6H_{15})$, —$O_{(0-1)}(C_{1-10})$haloalkyl, and $NH_2$.

In one embodiment, the compounds of the instant invention are selective JAK1 inhibitors relative to JAK2 and JAK3. The determination of relative selectivity for a given compound of JAK1 inhibition is defined as the relative ratio of the (JAK2 $IC_{50}$ value/JAK1 $IC_{50}$ value) is at least 2. Also, the relative ratio of the (JAK3 $IC_{50}$ value/JAK1 $IC_{50}$ value) is at least 2.

In yet another embodiment, for a given compound, the relative ratios of the (JAK2 $IC_{50}$ value/JAK1 $IC_{50}$ value) is at least 5. In another embodiment, the relative ratio of the (JAK3 $IC_{50}$ value/JAK1 $IC_{50}$ value) is at least 5.

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group —$(CR^3R^3)_2$—, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, 1-(2S,3S and 2R,3R)-3-cyclobutan-2-yl]-3-(phenylamino)-1H-pyrazole-4-carboxamide, the "and" indicates a racemic mixture of the enantiomers. That is, the individual enantiomers were not individually isolated.

When the stereomeric nomenclature includes "or", for example, 1-(2S,3S or 2R,3R)-3-cyclobutan-2-yl]-3-(phenylamino)-1H-pyrazole-4-carboxamide, the "or" indicates that chiral resolution of racemate into individual enantiomers was accomplished but the actual optical activity of the specific enantiomer was not determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic, Id and Ie, subsets thereof, embodiments thereof, as well as specific compounds are meant to also include the pharmaceutically acceptable salts.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compound of formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2 or JAK3. Such conditions and diseases include, but are not limited to: (1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of formula I. In one embodiment such diseases include asthma and rheumatoid arthritis.

Another aspect of the present invention provides for the use of a compound of formula I in the manufacture of a medicament for the treatment or prevention of a JAK-mediated diseases or disorder.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 μm to about 10 μm; however, for effective delivery to the distal lung, at least 95 percent of the active agent particles are 5 μm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of formula I may be co-administered with other therapeutic agents. Thus in another aspect the present invention provides pharmaceutical compositions for treating JAK mediated diseases comprising a therapeutically effective amount of a compound of formula I and one or more other therapeutic agents. In particular, for the treatment of the inflammatory diseases rheumatoid arthritis, psoriasis, inflammatory bowel disease, COPD, asthma and allergic rhinitis a compound of formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

Methods of Synthesis

Schemes and Examples

The abbreviations used herein have the following tabulated meanings Abbreviations not tabulated below have their meanings as commonly used unless specifically stated otherwise.

| | |
|---|---|
| ACN | acetonitrile |
| MeCN | acetonitrile |
| BAST | bis(2-methoxyethyl)aminosulfur trifluoride |
| Chiral SFC | chiral super critical fluid chromatography |
| $CO_2$ | carbon dioxide |
| $Cs_2CO_3$ | cesium carbonate |

-continued

| | |
|---|---|
| DBU | 1,8-diazabicyclo[5.4.0]undec-7-ene |
| DCE | 1,2-dichloroethane |
| DCM | dichloromethane |
| DIPEA | N,N-diisopropylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LRMS | low resolution mass spectrometry |
| MeI | iodomethane |
| Me-THF | 2-methyltetrahydrofuran |
| MgSO4 | magnesium sulfate |
| MP-(OAc)$_3$BH | solid supported (macro porous) triacetoxyborohydride |
| MPLC | medium pressure liquid chromatography |
| NaH | sodium hydride |
| Na$_2$SO$_4$ | sodium sulfate |
| NaBH$_4$ | sodium borohydride |
| NaHCO$_3$ | sodium bicarbonate |
| NaOMe | sodium methoxide |
| Pd$_2$(dba)$_3$ | tris(dibenzylideneacetone)dipalladium(0) |
| POCl$_3$ | phosphorus (V) oxychloride |
| PyBOP | (7-azabenzotriazol-1-yloxy)tripyrrolidinophosphonium hexafluorophosphate |
| SEM-Cl | 2-(trimethylsilyl)ethoxymethyl chloride |
| SiliaCat® DPP-Pd | silica bound diphenylphosphine palladium (II) |
| TBAF | tetra-n-butylammonium fluoride |
| TBS-Cl | tert-butyldimethylsilyl chloride |
| t-BuOH | tert-butanol |
| TEA | triethylamine |
| TFA | trifluoroacetic acid |
| THF | tetrahydrofuran |
| X-Phos | 2-dicyclohexylphosphino-2',4',6'-triisopropylbiphenyl |
| Me$_4$-$^t$Bu-X-Phos | di-tert-butyl[3,4,5,6-tetramethyl-2',4',6'-tri(propan-2-yl)biphenyl-2-yl]phosphane |
| NMO | 4-methylmorpholine N-oxide |
| TPAP | tetra-n-propylammonium perruthenate (VII) |
| HCOOH | formic acid |
| K$^t$OBu | potassium tert-butoxide |
| Na$_2$S$_2$O$_5$ | sodium metabisulfite |
| NMR | nuclear magnetic resonance |
| TLC | thin layer chromatography |
| (EtO)$_2$P(O)CH$_2$CN | diethyl (cyanomethyl)phosphonate |
| MsCl | methanesulfonyl chloride |
| TsOH | p-toluenesulfonic acid |
| KCN | potassium cyanide |
| Si-DMT | silica supported Dimercaptotriazine |
| TMS | trimethylsilane |
| CF$_3$TMS | (trifluoromethyl)trimethylsilane |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All temperatures are degrees Celsius (° C.) unless otherwise noted.

Ambient temperature is 15-25° C.

Most compounds were purified by reverse-phase preparative HPLC, MPLC on silica gel, recrystallization and/or swish (suspension in a solvent followed by filtration of the solid). The course of the reactions was followed by thin layer chromatography (TLC) and/or LCMS and/or NMR and reaction times are given for illustration only.

All end products were analyzed by NMR and LCMS. Intermediates were analyzed by NMR and/or TLC and/or LCMS.

Method 1

General procedures to prepare intermediates of the instant invention are described in Scheme 1. Alkyl Grignard reagents are reacted with appropriately substituted (hetero)aryl carboxylates 1A at or around 0° C. in an appropriate solvent, such as THF, to afford intermediates 1B used in the synthesis of examples of the instant invention.

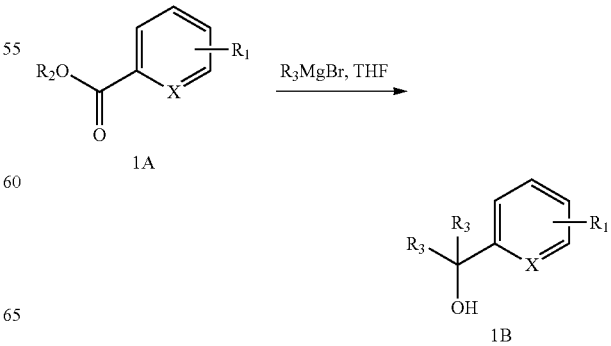

Scheme 1

Method 2

General procedures to prepare intermediates of the instant invention are described in Scheme 2. A trifluoromethyl anion equivalent, such as CF$_3$TMS, is reacted with TBAF and an appropriately substituted (hetero)aryl aldehyde 2A in an appropriate solvent, such as THF, to yield intermediates 2B used in the synthesis of examples of the instant invention.

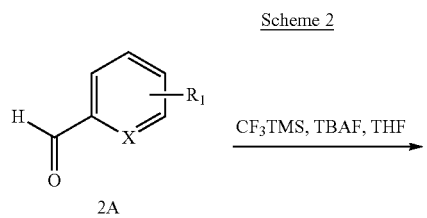

Method 3

General procedures to prepare intermediates of the instant invention are described in Scheme 3. Appropriately substituted thiophenols 3A are reacted with a suitable base, such as sodium hydride, and a trifluoromethylating agent, such as 5-(trifluoromethyl)dibenzo[b,d]thiophenium trifluoromethanesulfonate at ambient temperature in an appropriate solvent, such as DMF. The resulting intermediate is oxidized to the corresponding sulfone 3B with a suitable oxidant, such as m-CPBA, to afford an intermediate used in the synthesis of examples of the instant invention.

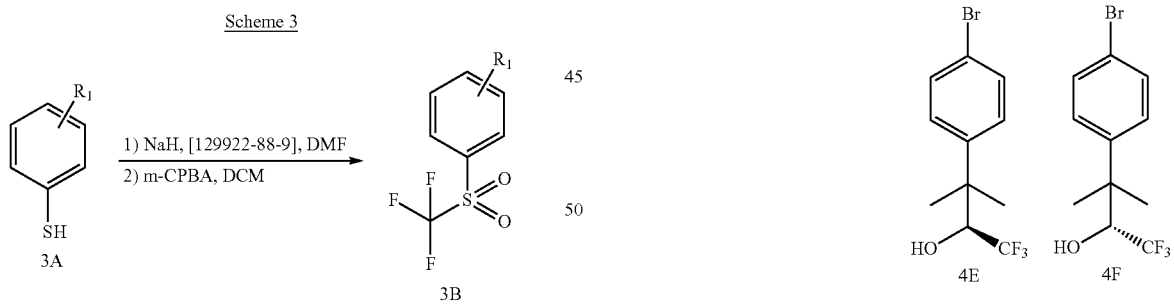

Method 4

General procedures to prepare intermediates of the instant invention are described in Scheme 4. Appropriately substituted phenylacetic esters 4A are reacted with a suitable base, such as sodium hydride, and methylating agent, such as methyliodide at an appropriate temperature in solvent, such as THF to provide 4B. The resulting intermediate is reduced to alcohol 4C with a suitable reducing agent, such as LiAlH$_4$, which was subsequently oxidized to aldehyde 4D with an oxidant such as PCC. Treatment of 4D with CF$_3$ anion followed by resolution of enantiomers using chiral stationary phase chromatography afford intermediates 4E and 4F used in the synthesis of examples of the instant invention.

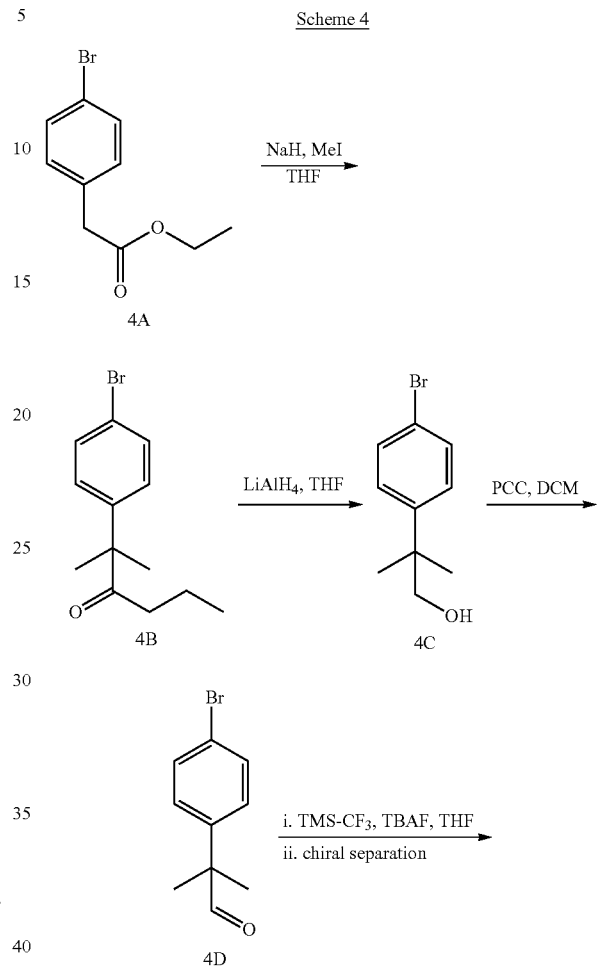

Method 5

General procedures to prepare intermediates of the instant invention are described in Scheme 5. Appropriately substituted benzylbromides 5A are reacted with sodium nitrile in an appropriate solvent, such as aqueous ethanol to provide 5B. The resulting intermediate is reacted with a suitable base, such as sodium hydride, and methylating agent, such as methyliodide at an appropriate temperature in solvent, such as THF to provide 5C which is subsequently reduced to aldehyde 5D with a suitable reducing agent, such as DIBAL-H, in a suitable solvent such as THF. Treatment of 5D with a CF$_3$ anion afforded intermediate 5E used in the synthesis of examples of the instant invention.

Scheme 5

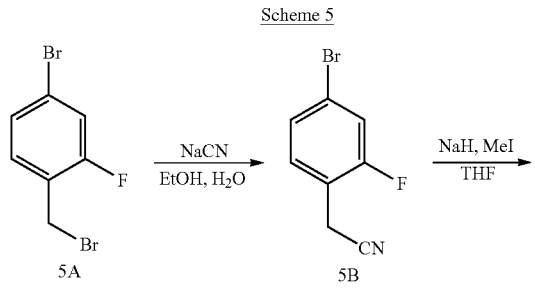

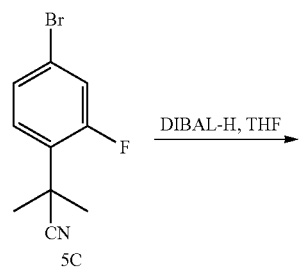

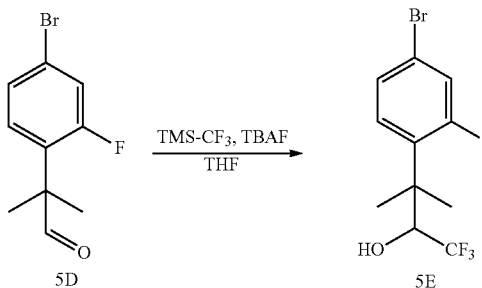

Method 6

General procedures to prepare intermediates of the instant invention are described in Scheme 6. 2-Cyanopropane is reacted with a suitable base, such as NaHMDS, in an appropriate solvent, such as toluene and reacted with 2,5-dibromopyridine 6A to provide 6B which is subsequently reduced to aldehyde 6C with a suitable reducing agent, such as DIBAL-H, in a suitable solvent such as THF. Treatment of 6C with CF$_3$ anion afforded intermediate 6D used in the synthesis of examples of the instant invention.

Scheme 6

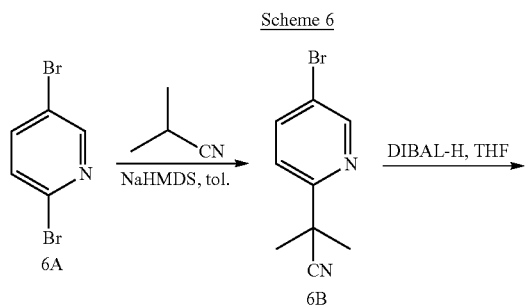

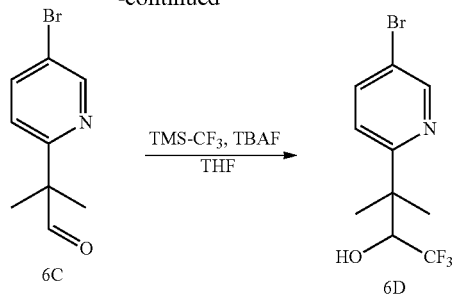

Method 7

General procedures to prepare intermediates of the instant invention are described in Scheme 7. Difluoroacetate is reacted with a suitable base, such as n-BuLi, in an appropriate solvent, such as toluene and reacted with 2,5-dibromopyridine 7A to provide 7B. Ketone 7B is subsequently reduced to alcohol 7C (R$_1$ is hydrogen) with a suitable reducing agent, such as NaBH$_4$, in a suitable solvent such as methanol. Alternatively, ketone 7B is reacted with a Grignard reagent to afford alcohol 7C (R$_1$ is alkyl) used in the synthesis of examples of the instant invention.

Scheme 7

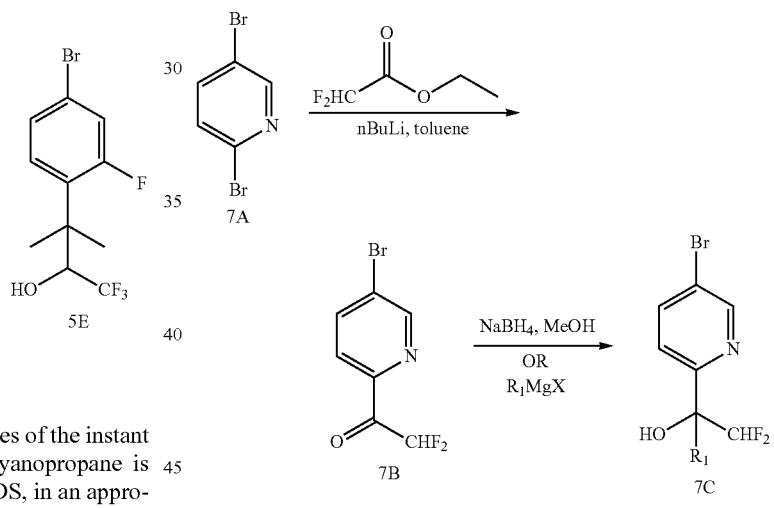

Method 8

General procedures to prepare intermediates of the instant invention are described in Scheme 8. Alcohol 8A is reacted with a nucleophillic fluoride source such as DAST to afford 8B used in the synthesis of examples of the instant invention.

Scheme 8

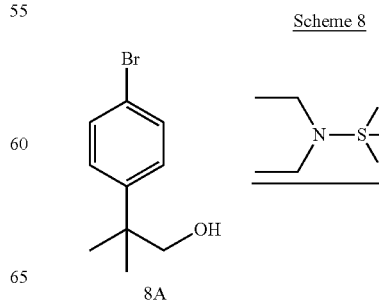

Method 9

General procedures to prepare intermediates of the instant invention are described in Scheme 9. Ketone 9A is subsequently reduced to a racemic mixture of alcohols with a suitable reducing agent, such as NaBH$_4$, in a suitable solvent such as methanol followed by enantiomeric separation on a chiral stationary phase column to afford intermediates 9B and 9C used in the synthesis of examples of the instant invention. Alternatively, ketone 9A is reacted with a Grignard reagent in a suitable solvent such as THF, followed by enantiomeric separation on a chiral stationary phase column to afford intermediates (R$_1$ is alkyl) 9D and 9E used in the synthesis of examples of the instant invention.

Scheme 9

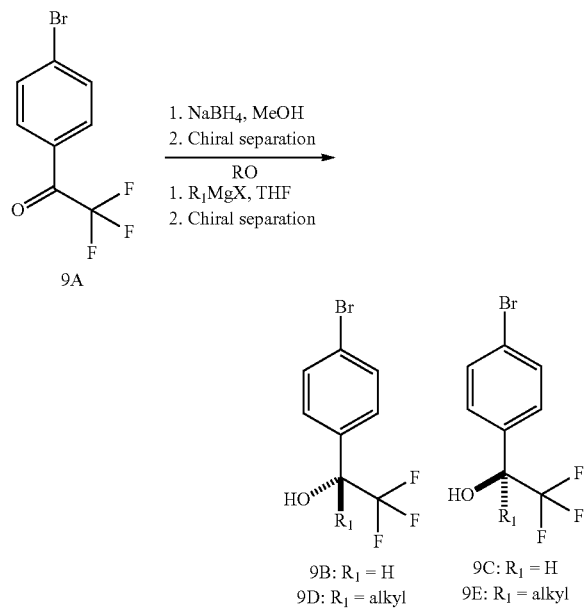

Method 10

General procedures to prepare intermediates of the instant invention are described in Scheme 10. Appropriately substituted thiophenols 10A are reacted with a suitable base, such as potassium hydroxide, and a difluoromethylating agent, such as diethyl [bromo(difluoro)methyl]phosphonate, in an appropriate solvent or solvent mixture, such as 1:1 v:v MeCN:water. The resulting intermediate is oxidized to the corresponding sulfone 10B with a suitable oxidant, such as m-CPBA, to afford an intermediate used in the synthesis of examples of the instant invention.

Scheme 10

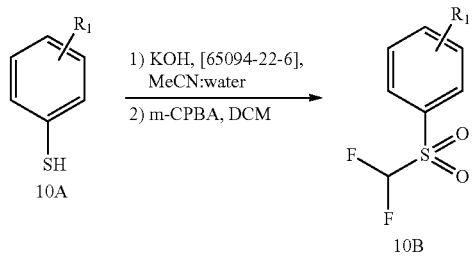

Method 11

General procedures to prepare intermediates of the instant invention are described in Scheme 11. Appropriately substituted aryl sulfoxides 11A are reacted with a lewis acid, such as zinc iodide, and a suitable nucleophilic fluorine source, such as BAST, in a solvent, such as 1,2-DCE, at or around 40° C. The resulting intermediate is oxidized to the corresponding sulfone 11B with a suitable oxidant, such as m-CPBA, to afford an intermediate used in the synthesis of examples of the instant invention.

Scheme 11

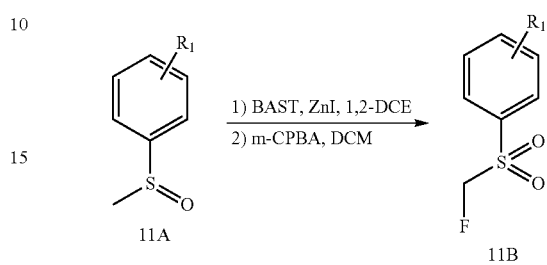

Method 12

General procedures to prepare intermediates of the instant invention are described in Scheme 12. Optionally substituted alkyl aldehydes/ketones 12A are condensed with diethyl (cyanomethyl)phosphonate in the presence of a suitable base, such as potassium tert-butoxide to yield substituted acrylonitriles 12B used as intermediates in the synthesis of examples of the instant invention.

Scheme 12

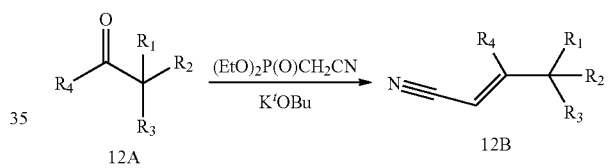

Method 13

General procedures to prepare intermediates of the instant invention are described in Scheme 13. Cyanohydrins 13B of optionally substituted (hetero)cyclic ketones 13A are prepared using aqueous sodium metabisulfite, followed by the addition of a suitable cyanide source, such as potassium cyanide. Hydroxyl group activation with a suitable agent, such as mesyl chloride or POCl$_3$, followed by elimination under appropriate conditions, such as refluxing pyridine, yields substituted acrylonitriles 13C used as intermediates in the synthesis of examples of the instant invention.

Scheme 13

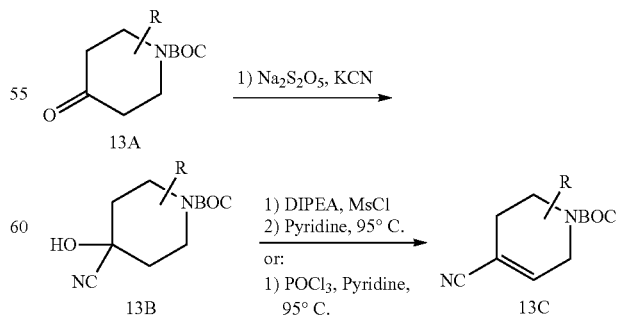

Method 14

General procedures to prepare intermediates of the instant invention are described in Scheme 14. Optionally substituted (hetero)cyclic ketones 14A are enolized with an appropriate base, such as LDA, and reacted with a suitable triflating agent, such as N-(5-chloropyridin-2-yl)-1,1,1-trifluoro-N-(trifluoromethylsulfonyl)methanesulfonamide. The resulting vinyl triflate 14B is reacted with a suitable palladium complex, such as tetrakis(triphenylphosphine) palladium (0), and an appropriate cyanide source, such as zinc cyanide, to afford substituted acrylonitriles 14C used as intermediates in the synthesis of examples of the instant invention.

Scheme 14

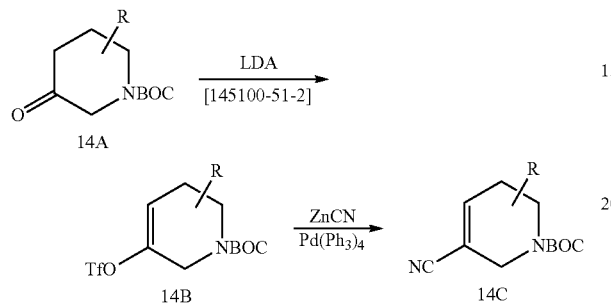

Method 15

General procedures to prepare intermediates of the instant invention are described in Scheme 15. Unsaturated aldehyde 15A was condensed with hydroxylamine hydrochloride in the presence of a base such as sodium hydroxide and in a solvent such as water to afford oxime 15B which was dehydrated under the action of tripropylphosphonic anhydride in the presence of a suitable base such as triethylamine and in a suitable solvent such as THF to afford 15D as an intermediate in the synthesis of examples of the instant invention.

Scheme 15

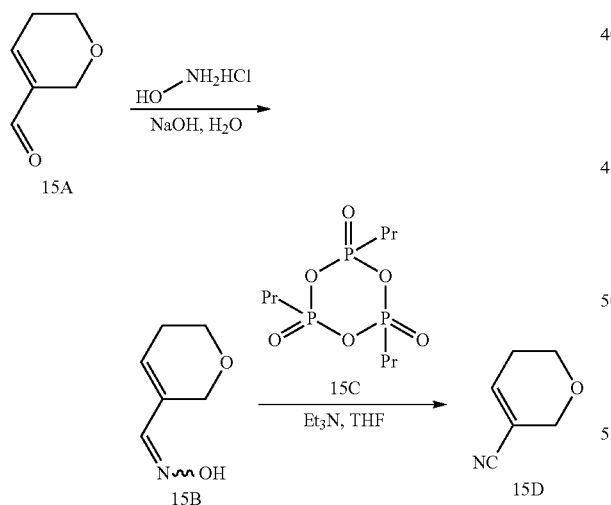

Method 16

General procedures to prepare intermediates of the instant invention are described in Scheme 26. 3-Amino pyrazole carboxamide 16A is cross coupled to (hetero)aryl halides 16B using a catalytic palladium-ligand system, such as Pd$_2$(dba)$_3$, and Me$_4$-$^t$Bu-X-Phos, with a suitable base, such as K$_3$PO$_4$ or KOAc, in an appropriate solvent, such as 2-propanol, to yield pyrazole intermediates 16C.

Scheme 16

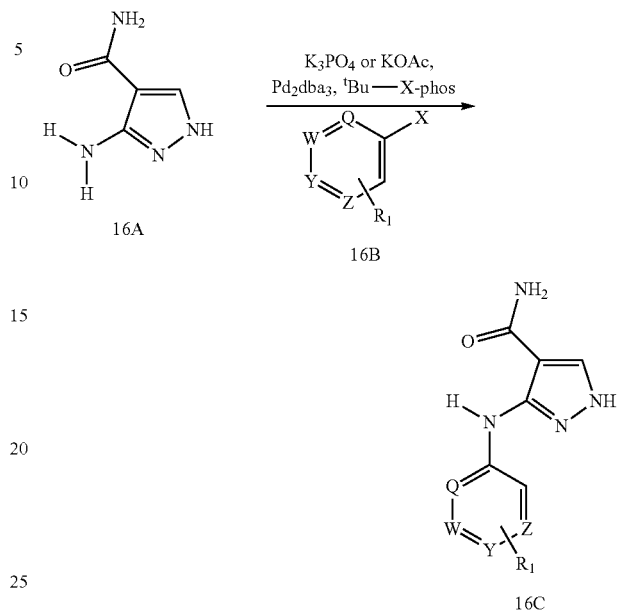

Method 17

General procedures to prepare intermediates of the instant invention are described in Scheme 17. 3-Amino-1H-pyrazole-4-carbonitrile 17A is reacted with a suitable base, such as sodium hydride, and SEM-Cl to yield a mixture of 3-amino pyrazoles 17B and 17C, which are arylated with an appropriately substituted halogenated (hetero)aromatic 17D using a suitable catalytic palladium-ligand system, such as Pd$_2$(dba)$_3$ and X-Phos, an appropriate base, such as K$_3$PO$_4$, in a suitable solvent, such as dioxane. The intermediate nitriles 17E and 17F are oxidized to the corresponding amides using an appropriate oxidant, such as hydrogen peroxide mixed with sodium hydroxide, and the SEM group is then removed by acid hydrolysis to yield pyrazole 17G, an intermediate in the synthesis of examples of the instant invention.

Scheme 17

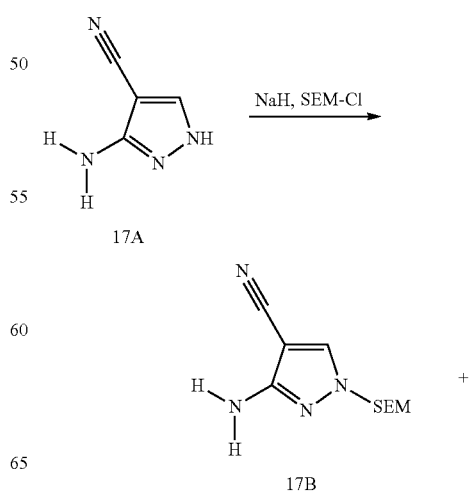

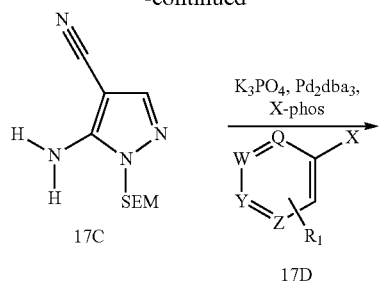

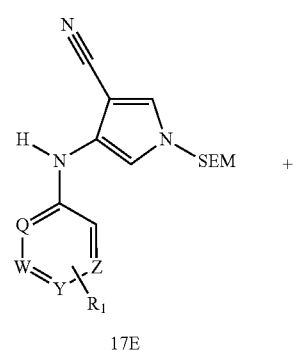

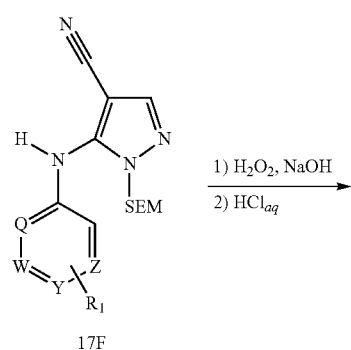

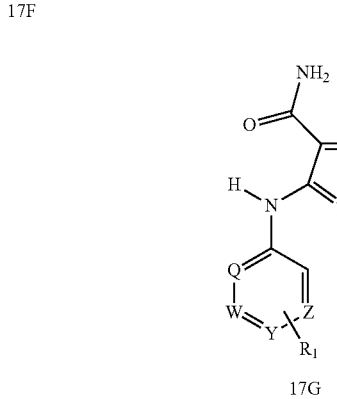

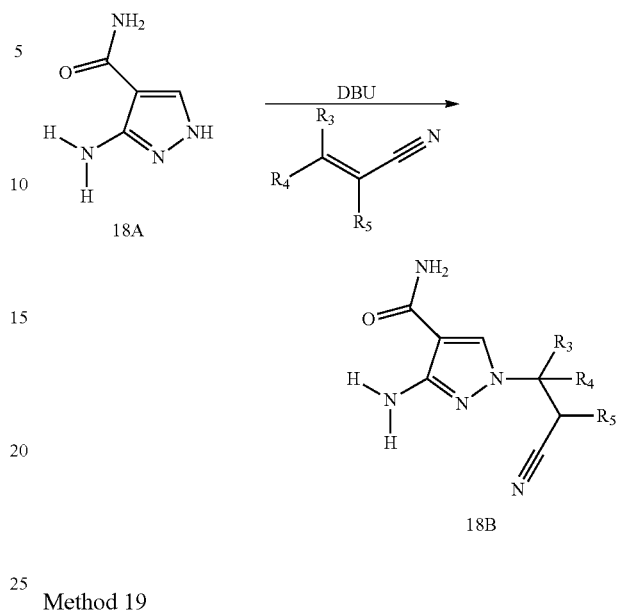

Scheme 18

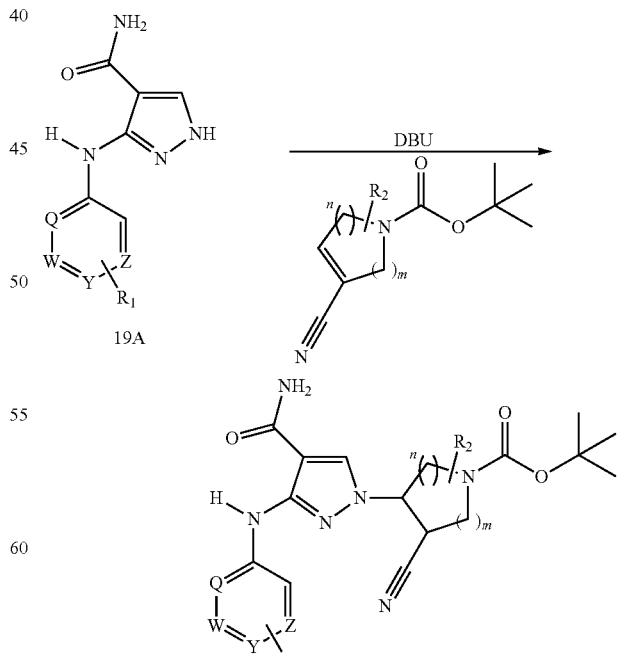

Scheme 19

Method 19

General procedures to prepare intermediates of the instant invention are described in Scheme 19. Using an appropriate base, such as DBU, in a suitable solvent, such as MeCN, EtOH, or tert-BuOH, 3-amino pyrazole carboxamide 19A is conjugatively added to optionally substituted acrylonitriles, including but not limited to those illustrated in Schemes #12-15 and Schemes 25-29 to yield alkylated pyrazole carboxamide 19B, an intermediate in the synthesis of examples of the instant invention.

Method 18

General procedures to prepare intermediates of the instant invention are described in Scheme 18. Using an appropriate base, such as DBU, in a suitable solvent, such as MeCN, EtOH, or tert-BuOH, 3-amino pyrazole carboxamide 18A is conjugatively added to optionally substituted acrylonitriles, including but not limited to those illustrated in Schemes #12-15 and Schemes 25-29 to yield alkylated pyrazole carboxamide 18B, an intermediate in the synthesis of examples of the instant invention.

Method 20

General procedures to prepare examples of the instant invention are described in Scheme 20. Methyl 5-amino-1H-pyrazole-4-carboxylate 20A is conjugatively added to substituted acrylonitriles including but not limited to those illustrated in Schemes #12-15 and Schemes #25-29 in the presence of a suitable base, such as catalytic sodium methoxide. The resulting intermediates 20B are cross coupled to (hetero)aryl halides 20C using an appropriate catalytic palladium-ligand system, such as $Pd_2(dba)_3$ and X-Phos, and an appropriate base, such as $K_3PO_4$. Saponification of 20D using aqueous hydroxide, such as LiOH, followed by amide formation using standard conditions, such as EDC, HOBT, and optionally substituted primary and secondary amines yields examples 20F of the instant invention.

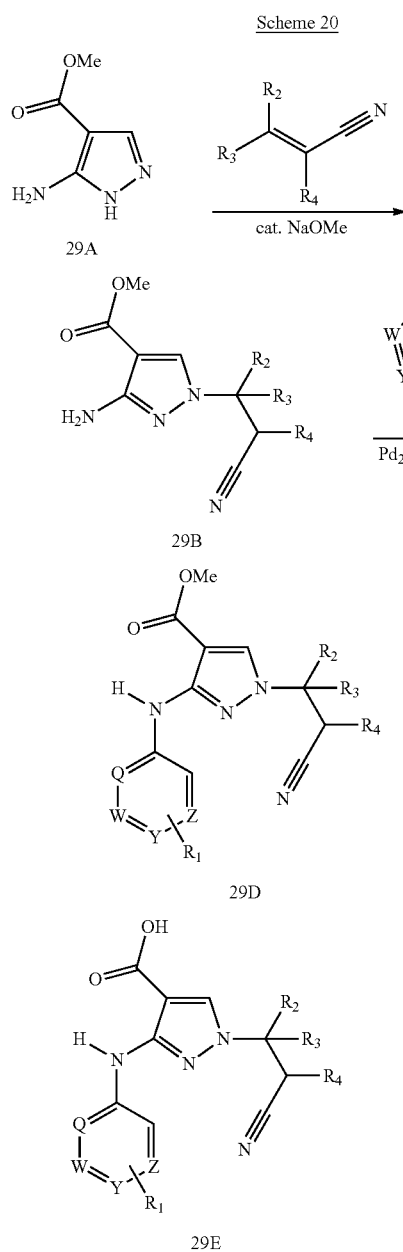

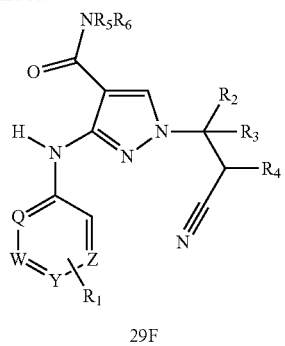

29F

Method 21

General procedures to prepare examples of the instant invention are described in Scheme 21. Using an appropriate base, such as DBU, in a suitable solvent, such as MeCN, EtOH, or tert-BuOH, N-(hetero)arylated pyrazole carboxamides 21A are conjugatively added to optionally substituted acrylonitriles, including but not limited to those illustrated in Schemes #12-15 and Schemes 25-29 to yield examples 21B of the instant invention.

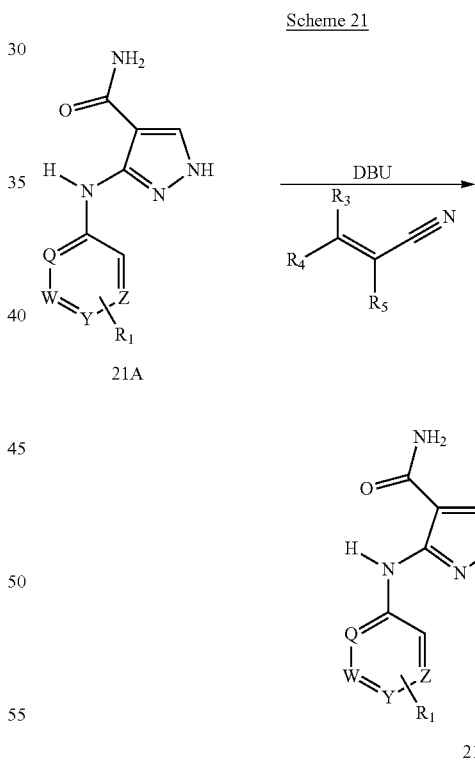

Method 22

General procedures to prepare examples of the instant invention are described in Scheme 22. Alkylated 3-amino pyrazole carboxamides 22A are cross coupled to (hetero)aryl halides 22B using an appropriate catalytic palladium-ligand system, such as $Pd_2(dba)_3$ and X-Phos or $Me_4{}^tBu$-X-Phos, and a suitable base, such as $K_3PO_4$ or KOAc, in solvent, such as dioxane, to yield examples 22C of the instant invention.

Scheme 22

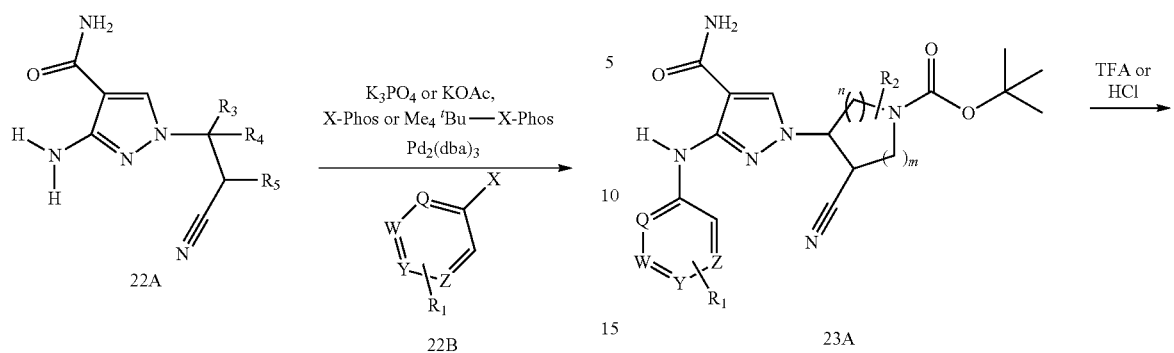

Method 23

General procedures to prepare examples of the instant invention are described in Scheme 23. Optionally substituted, carbamate protected pyrazole carboxamides 23A are deprotected in the presence of acid, such as TFA or HCl, amine derivatives 23B of the instant invention.

Method 24

General procedures to prepare examples of the instant invention are described in Scheme 24. Optionally substituted aminopyrazole carboxamides 24A are reacted with optionally substituted alcohols in the presence of a doubly activated carbonyl group, such as DSC or phosgene, to afford carbamate derivatives 24C of the instant invention. Alternatively, optionally substituted aminopyrazole carboxamides 24A are reacted with substituted aldehydes in the presence of an acid, such as acetic acid, and in the presence of a suitable reducing agent, such as $NaCNBH_3$ or $Na(OAc)_3BH$, to afford tertiary amino derivatives 24B of the instant invention. Alternatively, optionally substituted aminopyrazole carboxamides 24A are reacted with phosgene and alcohols to afford tertiary amino derivatives 24B of the instant invention.

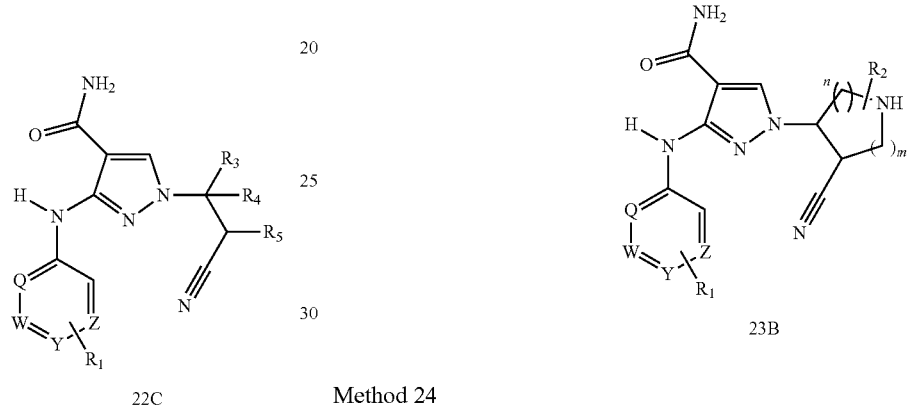

Scheme 24

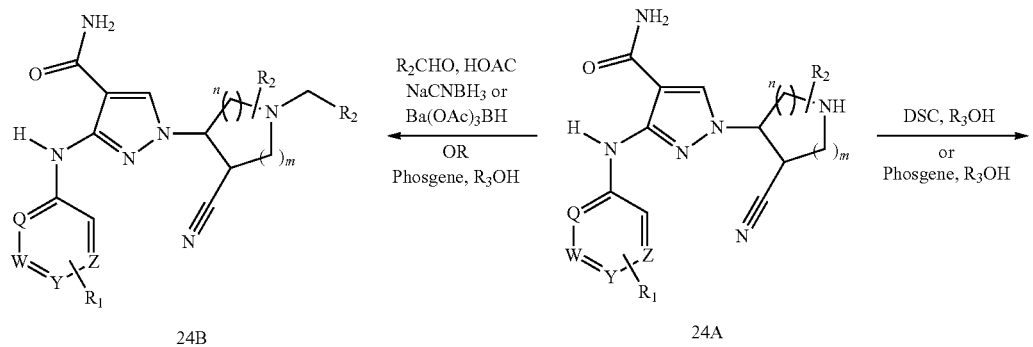

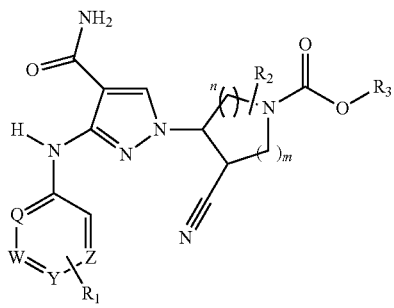

24C

Method 25

General procedures to prepare examples of the instant invention are described in Scheme 25. Ketone 25A was reacted with a reducing agent, such as NaBH$_4$, followed by activation of the alcohol for example with methanesulfonyl chloride in the presence of a suitable base such as DIPEA, followed by elimination in the presence of a suitable base such as DBU to afford 25B. Using an appropriate base, such as DBU, in a suitable solvent, such as MeCN, EtOH, or tert-BuOH, N-(hetero)arylated pyrazole carboxamides 25C are conjugatively added to optionally substituted acrylonitrile 25B followed by oxidation with a suitable oxidant such as mCPBA to yield examples 25D of the instant invention.

Method 26

General procedures to prepare examples of the instant invention are described in Scheme 26. Cyanoketone 26A was reacted with a suitable base, such as potassium carbonate, and an appropriate methylating agent such as methyliodide, followed by treatment with a reducing agent, such as NaBH$_4$, followed by oxidation with a suitable oxidant such as mCPBA to yield 26B. Alcohol 26B was activated, for example with methanesulfonyl chloride in the presence of a suitable base such as DIPEA, followed by elimination in the presence of a suitable base such as DBU to afford 26C. Using an appropriate base, such as DBU, in a suitable solvent, such as MeCN, EtOH, or tert-BuOH, N-(hetero)arylated pyrazole carboxamides 26D are conjugatively added to optionally substituted acrylonitrile 26C to yield examples 26E and 26F of the instant invention.

Scheme 25

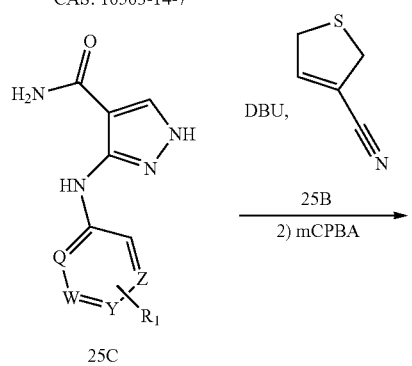

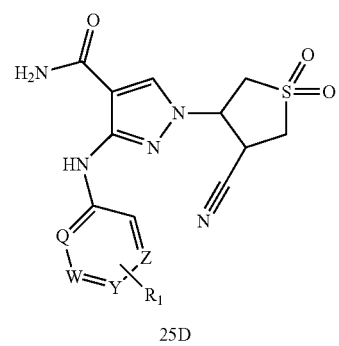

Scheme 26

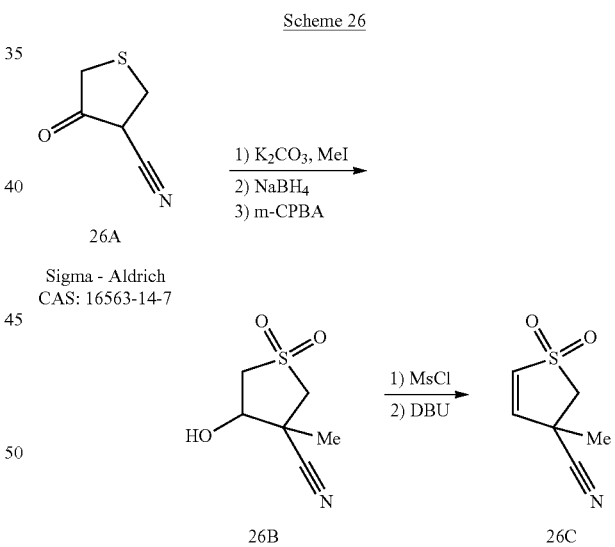

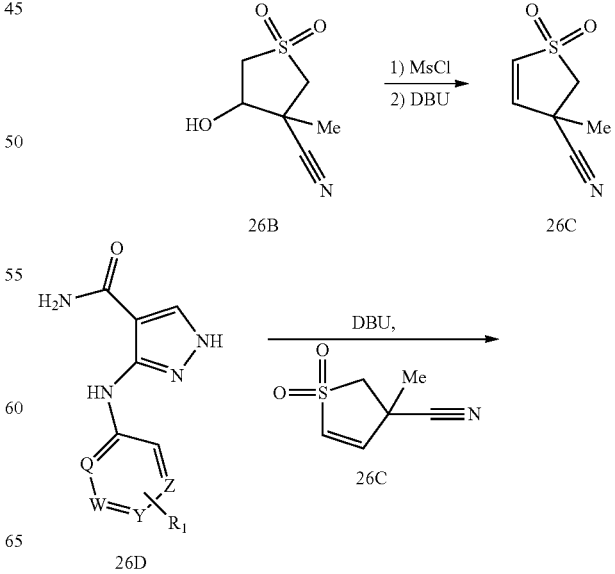

-continued

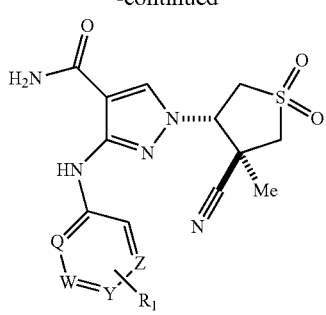

26E

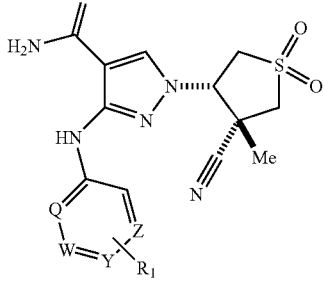

26F

Method 27

General procedures to prepare examples of the instant invention are described in Scheme 27. Ketone 27A was reacted with a reducing agent, such as NaBH$_4$, followed by activation of the alcohol for example with methanesulfonyl chloride in the presence of a suitable base such as DIPEA, followed by elimination in the presence of a suitable base such as DBU to afford 27B. Ester 27B was saponified with a suitable base, such as lithium hydroxide, followed by conversion to the primary amide, for example with activating reagent TBTU and ammonia source HMDS, followed by dehydration, for example with trichloroacetylchloride to afford 27C. Using an appropriate base, such as DBU, in a suitable solvent, such as MeCN, EtOH, or tert-BuOH, N-(hetero)arylated pyrazole carboxamides 27D are conjugatively added to optionally substituted acrylonitrile 27C followed by oxidation with a suitable oxidant such as mCPBA to yield examples 27E of the instant invention.

Scheme 27

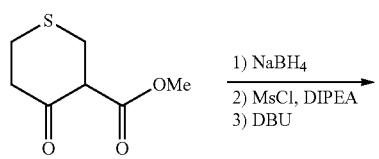

27A

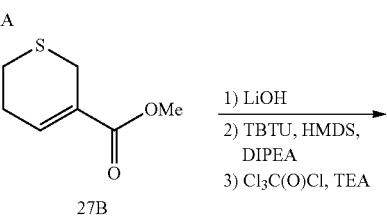

27B

-continued

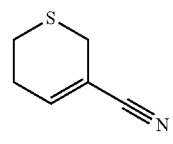

27C

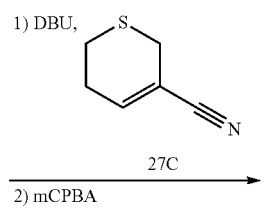

27D

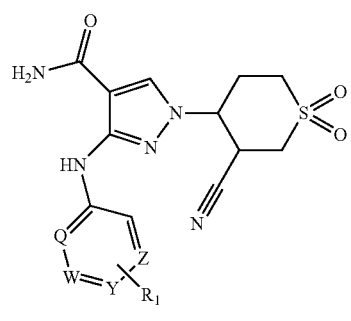

27E

Method 28

General procedures to prepare examples of the instant invention are described in Scheme 28. Using an appropriate base, such as DBU, in a suitable solvent, such as MeCN, EtOH, or tert-BuOH, N-(hetero)arylated pyrazole carboxamides 28C are conjugatively added to optionally substituted acrylonitrile 28B to afford 28D. Alkylated 3-amino pyrazole carboxamides 28D are cross coupled to (hetero)aryl halides 28E using an appropriate catalytic palladium-ligand system, such as Pd$_2$(dba)$_3$ and X-Phos or Me$_4$$^t$Bu-X-Phos, and a suitable base, such as K$_3$PO$_4$ or KOAc, in solvent, such as i-propanol or dioxane, to yield after enantiomeric separation on a chiral stationary column, examples 28F and 28G of the instant invention.

Scheme 28

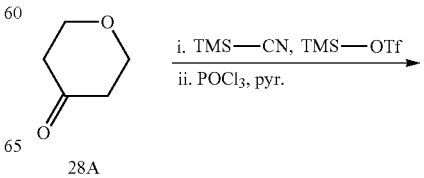

28A

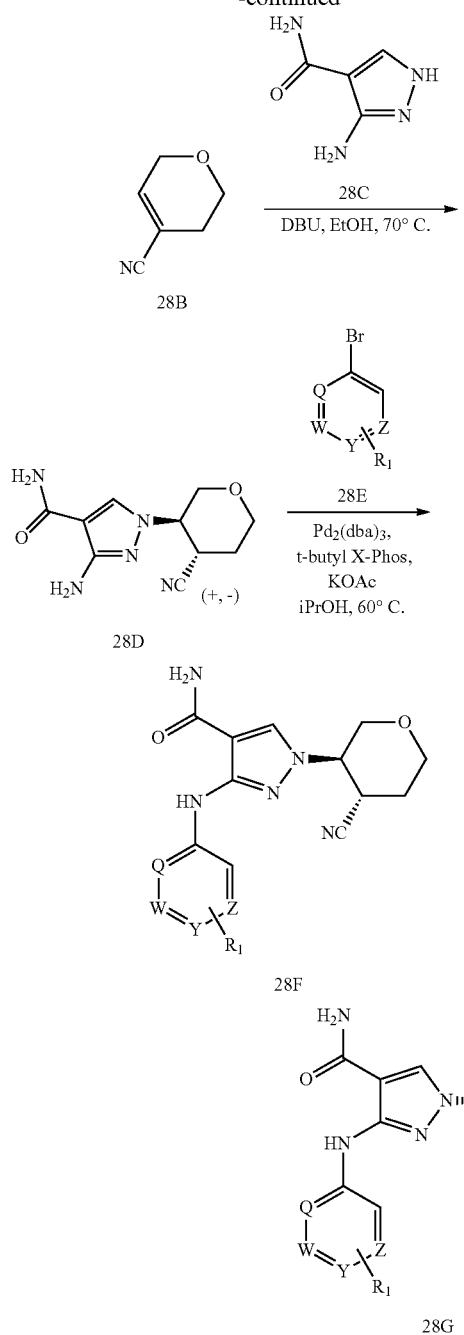

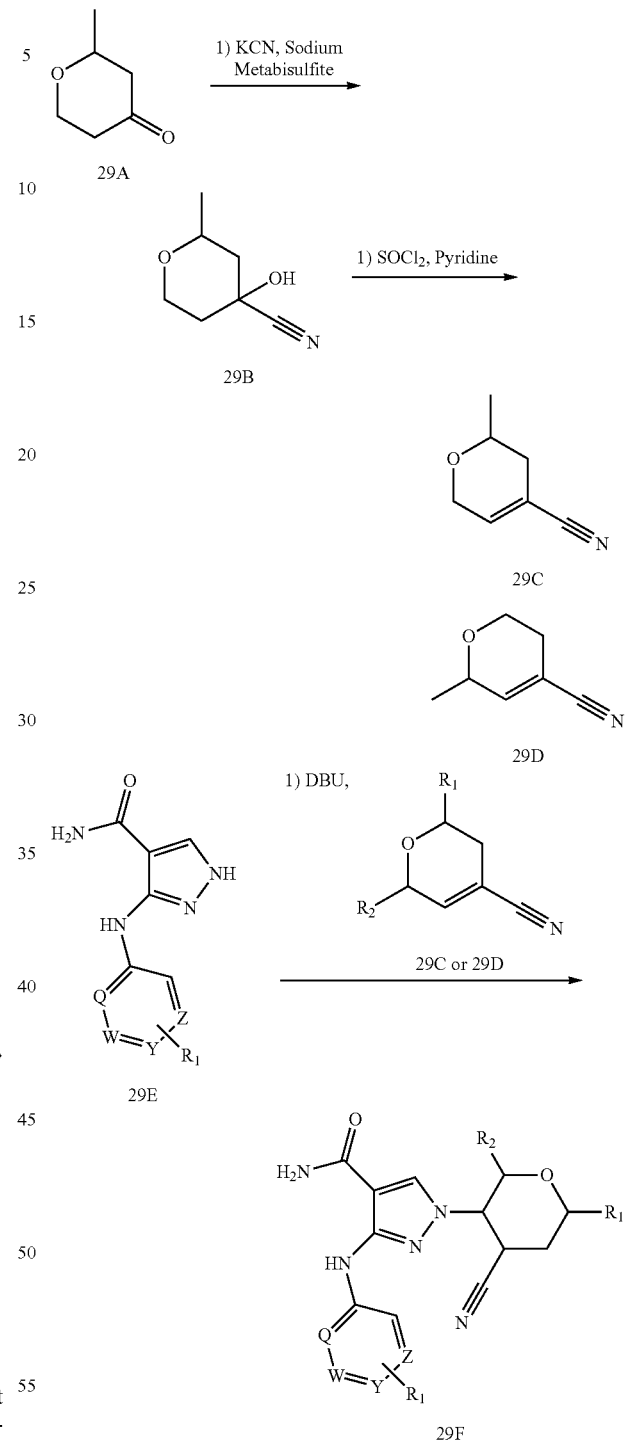

Scheme 29

Method 29

General procedures to prepare examples of the instant invention are described in Scheme 29. Ketone 29A was converted to cyanohydrin 29B under suitable conditions such as potassium cyanide and sodium metabisulfite followed by activation and elimination of the alcohol, for example with thionylchloride in a suitable solvent such as pyridine, to afford intermediates 29C and 29D. Using an appropriate base, such as DBU, in a suitable solvent, such as MeCN, EtOH, or tert-BuOH, N-(hetero)arylated pyrazole carboxamides 29E are conjugatively added to optionally substituted acrylonitrile 29C or 29D to afford 29F of the instant invention.

Commercially Available/Previously Described Materials

The following table lists commercial sources, and previously disclosed synthetic routes for chemical materials employed in the synthesis of intermediates, and Examples of the instant invention. The list is not intended to be exhaustive, exclusive, or limiting in any way.

| Structure | IUPAC Name | Vendor |
|---|---|---|
| 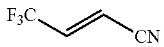 | 4,4,4-trifluorobut-2-enenitrile | Oakwood |
| 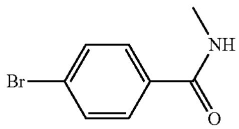 | 4-bromo-N-methylbenzamide | Combi Blocks, Inc. |
| 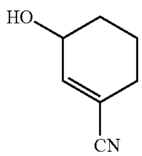 | 3-hydroxycyclohex-1-ene-1-carbonitrile | J. Org. Chem. 2001, 66, 2171-2174. |
| 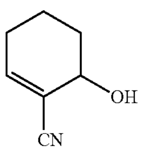 | 6-hydroxycyclohex-1-ene-1-carbonitrile | Tetrahedron Letters 1986, 27, 1577-1578. |
| 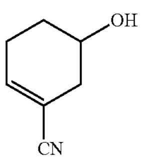 | 5-hydroxycyclohex-1-ene-1-carbonitrile | Canadian Journal of Chemistry 1984, 62, 1093-1098. |
| 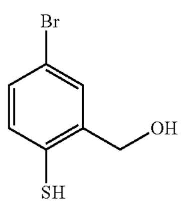 | (5-bromo-2-mercaptophenyl)methanol | Biogene Organics, Inc. |
| 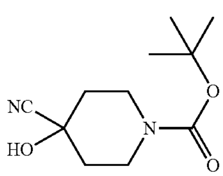 [SMILES: CC(C)(C)OC(=O)N1CCC(O)(C#N)CC1] | tent-butyl 4-cyano-4-hydroxypiperidine-1-carboxylate | Sinova, Inc. |
| 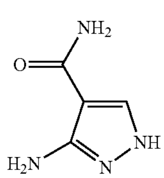 | 3-amino-1H-pyrazole-4-carboxamide | Enamine |
| 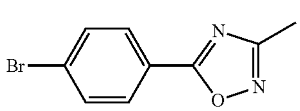 | 5-(4-bromophenyl)-3-methyl-1,2,4-oxadiazole | Maybridge |
| 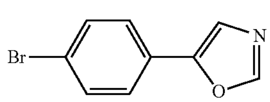 [SMILES: Brc1ccc(-c2cnco2)cc1] | 5-(4-bromophenyl)-1,3-oxazole | Maybridge |
| 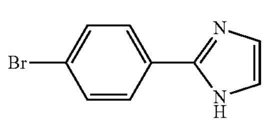 [SMILES: Brc1ccc(-c2ncc[nH]2)cc1] | 2-(4-bromophenyl)-1H-imidazole | J&W Pharmlab LLC |

-continued

| Structure | IUPAC Name | Vendor |
|---|---|---|
| | 3-(4-bromophenyl)-5-methyl-1,2,4-oxadiazole | Maybridge |
| 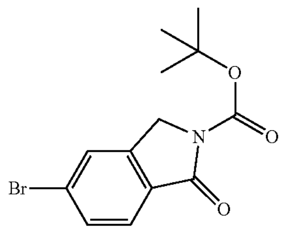 [SMILES: CC(C)(C)OC(=O)N1Cc2cc(Br)ccc2C1=O] | tert-butyl 5-bromo-1-oxo-1,3-dihydro-2H-isoindole-2-carboxylate | Ontario Chemical, Inc. |
| | 5-bromo-2,3-dihydro-1H-isoindol-1-one | Atomole Scientific Co, ltd. |
| 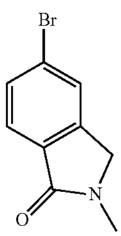 | 5-bromo-2-methyl-2,3-dihydro-1H-isoindol-1-one | J&W Pharmlab LLC |
| 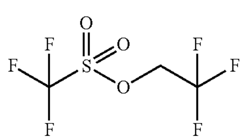 [SMILES: O=S(=O)(OCC(F)(F)F)C(F)(F)F] | 2,2,2-trifluoroethyl trifluoromethanesulfonate | Matrix Scientific |
| 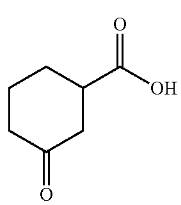 | 3-oxocyclohexanecarboxylic acid | Sigma Aldrich |
| 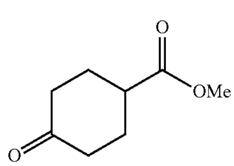 [SMILES: COC(=O)C1CCC(=O)CC1] | methyl 4-oxocyclohexanecarboxylate | Astatech Inc |
| 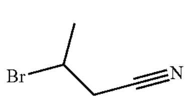 | 3-bromobutyronitrile | TCI America |
| 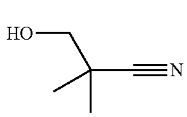 | 3-hydroxy-2,2-dimethylpropanenitrile | Matrix Scientific |

-continued

| Structure | IUPAC Name | Vendor |
|---|---|---|
| (1,1,1-trifluoro-2-propanol structure) | 1,1,1-trifluoro-2-propanol | Sigma Aldrich |
| (1,3-difluoro-2-propanol structure) | 1,3-difluoro-2-propanol | Sigma Aldrich |
| (3-dimethylamino-2,2-dimethyl-1-propanol structure) | 3-dimethylamino-2,2-dimethyl-1-propanol | TCI America |
| (2,2-difluoropropane-1,3-diol structure) | 2,2-difluoropropane-1,3-diol | Chemstep |
| ([1-(hydroxymethyl)cyclopropyl]acetonitrile structure) | [1-(hydroxymethyl)cyclopropyl]acetonitrile | Matrix Scientific |
| (oxetan-3-ol structure) | oxetan-3-ol | Sigma Aldrich |
| ((3-methyloxetan-3-yl)methanol structure) | (3-methyloxetan-3-yl)methanol | Sigma Aldrich |
| (2-cyclopropylethanol structure) | 2-cyclopropylethanol | Sigma Aldrich |
| (Si-DMT structure) | Silica supported Dimercaptotriazine (Si-DMT) | Silicycle Inc. |
| (Silica supported isocyanate structure) | Silica supported Isocyanate | Silicycle Inc. |
| (4-bromo-2-fluoropyridine structure) | 4-bromo-2-fluoropyridine | Synthonix |
| (methyl 5-amino-1H-pyrazole-4-carboxylate structure) | methyl 5-amino-1H-pyrazole-4-carboxylate | Chembridge Corporation |

-continued

| Structure | IUPAC Name | Vendor |
|---|---|---|
| 5-bromo-2-fluoropyridine structure | 5-bromo-2-fluoropyridine | Matrix Scientific |
| 4-bromopyridazine structure | 4-bromopyridazine | Fisher Scientific |
| 4-bromo-N,N-dimethylbenzamide structure | 4-bromo-N,N-dimethylbenzamide | Chembridge Corporation |
| 4-bromobenzenesulfonamide structure | 4-bromobenzenesulfonamide | Sigma Aldrich |
| 1-bromo-4-[(trifluoromethyl)sulfonyl]benzene structure | 1-bromo-4-[(trifluoromethyl)sulfonyl]benzene | Sunshine Chemlab. Inc |
| 1-bromo-4-[(difluoromethyl)sulfonyl]benzene structure | 1-bromo-4-[(difluoromethyl)sulfonyl]benzene | WXAT |
| 5-bromopyridine-2-carbonitrile structure | 5-bromopyridine-2-carbonitrile | Sigma Aldrich |
| methyl(4-bromophenyl)acetate structure | methyl(4-bromophenyl)acetate | Toyobo Co., Ltd. |
| methyl 2-hydroxy-2-methylpropanoate structure | methyl 2-hydroxy-2-methylpropanoate | Sigma Aldrich |
| tert-butyl 3-methyl-4-oxopiperidine-1-carboxylate structure | tert-butyl 3-methyl-4-oxopiperidine-1-carboxylate | Small Molecules Inc. |
| tert-butyl 2-methyl-4-oxopiperidine-1-carboxylate structure | tert-butyl 2-methyl-4-oxopiperidine-1-carboxylate | Small Molecules Inc. |

-continued

| Structure | IUPAC Name | Vendor |
|---|---|---|
| Br-pyridine-CF3 | 4-bromo-2-(trifluoromethyl)pyridine | CombiPhos Catalysts, Inc. |
| N≡C-CH=C(CH3)2 | 3-methylbut-2-enenitrile | BePharm Ltd. |
| cyclobutyl-CHO | cyclobutanecarbaldehyde | Beta Pharma Inc |
| tetrahydropyran-3-CHO | tetrahydro-2H-pyran-3-carbaldehyde | J&W Pharmlab LLC |
| tetrahydropyran-4-CH2CHO | tetrahydro-2H-pyran-4-ylacetaldehyde | Maybridge |
| Boc-piperidine-C(O)CH3 | tert-butyl 4-acetylpiperidine-1-carboxylate | Syntech Development Company |
| Boc-piperidine-4-F-4-CHO | tert-butyl 4-fluoro-4-formylpiperidine-1-carboxylate | Ark Pharm, Inc. |

Intermediates

The following experimental procedures detail the preparation of chemical materials used in the synthesis of Examples of the instant invention. The exemplified procedures are for illustrative purposes only, and are not intended to limit the scope of the instant invention in any way.

Scheme #1

Intermediate #1

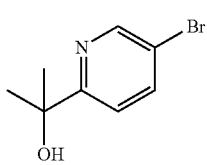

2-(5-Bromopyridin-2-yl)propan-2-ol

Methyl 5-bromopicolinate (500 mg, 2.31 mmol) was dissolved in THF (7.0 mL) and the flask was sealed with a septum and flushed with argon. The mixture was cooled to 0° C. and methylmagnesium bromide (3.1 mL, 9.3 mmol, 3M in THF) was added. The resulting mixture was allowed to stir at 0° C. for 1 hour before the reaction was quenched with saturated aqueous ammonium chloride and extracted with EtOAc. The organic layer was then washed with brine, dried over anhydrous MgSO$_4$, filtered, and concentrated in vacuo to afford the title compound, which was used without further purification. LRMS (ESI) calc'd for C$_8$H$_{10}$BrNO [M+H]$^+$: 216. Found: 216.

Scheme #2

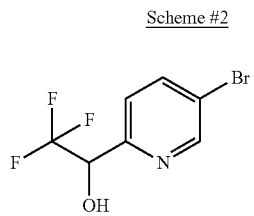

Intermediate #2

1-(5-Bromopyridin-2-yl)-2,2,2-trifluoroethanol

5-Bromopicolinaldehyde (500 mg, 2.70 mmol) was dissolved in THF (9.0 mL) and the flask was then sealed with a septum, flushed with argon, and cooled to 0° C. (Trifluoromethyl)trimethylsilane (0.44 mL, 3.0 mmol) was then added followed by TBAF (2.7 mL, 2.7 mmol, 1M in THF). The resulting mixture was allowed to warm to ambient temperature and was stirred for 2 hours. The reaction was then quenched with water and extracted with DCM (2×). The combined organic extracts were washed with brine, dried over anhydrous MgSO$_4$, and concentrated in vacuo. The residue was purified by MPLC on silica gel (using a gradient elution of 10-20% EtOAc/hexanes) to afford the title compound. LRMS (ESI) calc'd for $C_8H_6BrF_3O$ [M+H]$^+$: 256. Found: 256.

Scheme #8

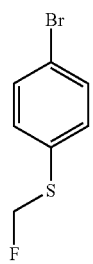

Intermediate #3

1-Bromo-4-[(fluoromethyl)sulfanyl]benzene

1-Bromo-4-(methylsulfinyl)benzene (1.50 g, 6.85 mmol) was dissolved in 1,2-DCE (13.7 mL) and stirred at ambient temperature. BAST (3.79 g, 17.1 mmol) was added dropwise followed by zinc iodide (0.07 g, 0.2 mmol). The reaction vessel was sealed and the mixture was heated to 40° C., allowed to stir for 24 hours, and then allowed to cool to ambient temperature. The mixture was partitioned between EtOAc and water, the layers were separated and the organic layer was dried over anhydrous MgSO$_4$, filtered, and concentrated in vacuo. The residue was purified by MPLC on silica gel (using a gradient elution of 0-20% EtOAc/hexanes). Desired fractions were identified, combined, and concentrated in vacuo to afford the title compound. $^1$H NMR (500 MHz, CDCl$_3$): δ 7.49-7.44 (m, 2H), 7.38-7.33 (m, 2H), 5.69 (d, J=52.8 Hz, 2H).

Scheme #4

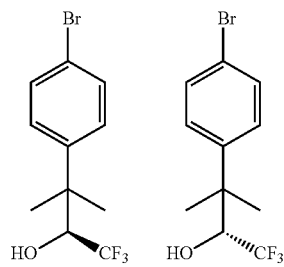

Intermediates #4-1 and 4-2

(S or R)-3-(4-Bromophenyl)-1,1,1-trifluoro-3-methylbutan-2-ol

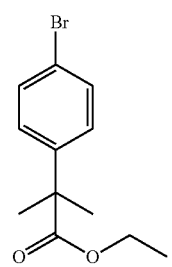

Step A: Ethyl 2-(4-bromophenyl)-2-methylpropanoate

To a stirred solution of ethyl 2-(4-bromophenyl)acetate (10 g, 41 mmol) in tetrahydrofuran (80 mL) under nitrogen was added sodium hydride (4.9 g, 60%, 120 mmol) in portions at 0° C. The resulting solution was stirred at 0° C. for 30 minutes before the addition of iodomethane (17 g, 120 mmol) at 0° C. The resulting mixture was stirred at ambient temperature for an additional 1 hour before the reaction was quenched with saturated aqueous NH$_4$Cl solution (20 mL) at 0° C. The solution was extracted with ethyl acetate (3×100 mL). All the organic solution was dried over sodium sulfate, filtered and concentrated in vacuo. The crude residue was purified by flash column chromatography with 1-2% ethyl acetate in hexane to afford the title compound as a light yellow oil. MS ESI: [M+H]$^+$ m/z 271, 273; $^1$H NMR (400 MHz, CDCl$_3$) δ 7.46 (d, J=6.8 Hz, 2H), 7.24 (d, J=6.8 Hz, 2H), 4.14 (q, J=7.2 Hz, 2H), 1.58 (s, 6H), 1.20 (t, J=7.2 Hz, 3H).

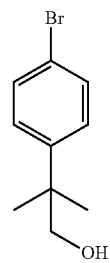

Step B: 2-(4-Bromophenyl)-2-methylpropan-1-ol

To a solution of 2-(4-bromophenyl)-2-methylpropanoate (8.9 g, 33 mmol) in tetrahydrofuran (100 mL) under nitrogen was added LiAlH$_4$ (1.6 g, 43 mmol) in portions at 0° C. The resulting solution was stirred at 0° C. for 1 hour before the addition of saturated aqueous NH$_4$Cl solution (50 mL). The mixture was then extracted with ethyl acetate (3×80 mL). All the organic solution was dried over sodium sulfate, filtered and concentrated in vacuo. The crude residue was purified by flash column chromatography with 2-5% ethyl acetate in hexane to afford the title compound as a colorless oil. MS ESI: [M+H]$^+$ m/z 229, 231; $^1$H NMR (400 MHz, CDCl$_3$) δ 7.47 (d, J=6.8 Hz, 2H), 7.28 (d, J=6.8 Hz, 2H), 3.61 (s, 2H), 1.58 (s, 6H).

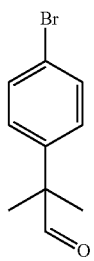

Step C: 2-(4-Bromophenyl)-2-methylpropanal

To a stirred solution of 2-(4-bromophenyl)-2-methylpropan-1-ol (10 g, 44 mmol) in dichloromethane (80 mL) was added PCC (14 g, 65 mmol) in portions at 0° C. The resulting solution was stirred at ambient temperature overnight, and then filtered and concentrated in vacuo. The crude residue was purified by flash column chromatography with 1-2% ethyl acetate in hexane to afford the title compound as an off-white solid. $^1$H NMR (300 MHz, CDCl$_3$) δ 9.49 (s, 1H), 7.52 (d, J=6.3 Hz, 2H), 7.17 (d, J=6.3 Hz, 2H), 1.43 (s, 6H).

Step D: (S or R)-3-(4-Bromophenyl)-1,1,1-trifluoro-3-methylbutan-2-ol

To a solution of 2-(4-bromophenyl)-2-methylpropanal (5.7 g, 25 mmol) and trimethyl(trifluoromethyl)silane (7.1 g, 50 mmol) in tetrahydrofuran (60 mL) under nitrogen was added the solution of TBAF (0.66 g, 2.5 mmol) in tetrahydrofuran (10 mL) dropwise at −30° C. The resulting solution was stirred at −30° C. for 1 hour and at ambient temperature for additional 1 hour before the addition of 1 N hydrochloric acid aqueous solution (20 mL). The mixture was vigorously stirred at ambient temperature for 10 minutes, and then extracted with ethyl acetate (3×100 mL). All the organic solution was dried over sodium sulfate, filtered and concentrated in vacuo. The crude residue was purified by flash column chromatography with 2-4% ethyl acetate in hexane to afford a racemic mixture of (S and R)-3-(4-bromophenyl)-1,1,1-trifluoro-3-methylbutan-2-ol as a light yellow oil. MS GC: [M]$^+$ m/z 295.6, 297.6; $^1$H NMR (300 MHz, CDCl$_3$) δ 7.46-7.41 (m, 2H), 7.28-7.23 (m, 2H), 4.10-3.97 (m, 1H), 2.08 (br, 1H), 1.44 (s, 6H). The constituent enantiomers were separated by preparative chiral HPLC (Column: Chiralpak IA, 2×25 cm; Mobile phase: 5% ethanol in hexane) to afford Intermediate #4-1, (S or R)-3-(4-bromophenyl)-1,1,1-trifluoro-3-methylbutan-2-ol as the first enantiomer to elute, and Intermediate #4-2, (S or R)-3-(4-bromophenyl)-1,1,1-trifluoro-3-methylbutan-2-ol as the second enantiomer to elute.

Scheme #5

Intermediate #5

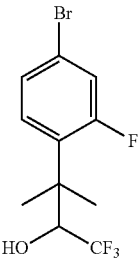

3-(4-bromo-2-fluorophenyl)-1,1,1-trifluoro-3-methylbutan-2-ol

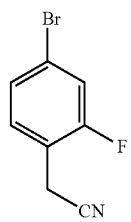

Step A: 2-(4-Bromo-2-fluorophenyl)acetonitrile

The solution of 4-bromo-1-(bromomethyl)-2-fluorobenzene (20 g, 74 mmol) and potassium cyanide (10 g, 153 mmol) in the mixed solvent of ethanol (150 mL) and water (30 mL) was stirred at 70° C. for 1 hour. The resulting solution was diluted with water (50 mL), and then extracted with ethyl acetate (3×200 mL). All the organic solution was dried over sodium sulfate, filtered and concentrated in vacuo. The crude residue was purified by flash column chromatography with 2-5% ethyl acetate in hexane to afford the title compound as a light yellow oil. MS ESI: [M+H]+ m/z 214; $^1$H NMR (400 MHz, CDCl$_3$) δ 7.38-7.22 (m, 3H), 3.74 (s, 2H).

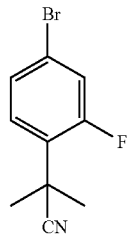

Step B: 2-(4-Bromo-2-fluorophenyl)-2-methylpropanenitrile

To a solution of 2-(4-bromo-2-fluorophenyl)acetonitrile (6.0 g, 28 mmol) in tetrahydrofuran (80 mL) was added sodium hydride (3.4 g, 60%, 140 mmol) in portions at 0° C. The resulting solution was stirred at 0° C. for 30 minutes before the addition of iodomethane (12 g, 83 mmol) at 0° C. The mixture was stirred at ambient temperature for additional 1 hour before the reaction was quenched with saturated aqueous NH₄Cl solution (30 mL) at 0° C. The solution was then extracted with ethyl acetate (3×50 mL). All the organic solution was dried over sodium sulfate, filtered and concentrated in vacuo. The crude residue was purified by flash column chromatography with 1-5% ethyl acetate in hexane to afford the title compound as a yellow oil. MS ESI: [M+H]⁺ m/z 242; ¹H NMR (300 MHz, CDCl₃) δ 7.37-7.23 (m, 3H), 1.75 (s, 6H).

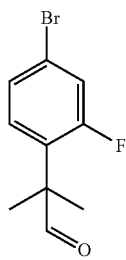

Step C:
2-(4-Bromo-2-fluorophenyl)-2-methylpropanal

To a solution of 2-(4-bromo-2-fluorophenyl)-2-methylpropanenitrile (2.0 g, 8.3 mmol) in tetrahydrofuran (20 mL) under nitrogen was added 1 N solution of DIBAL-H in tetrahydrofuran (19 mL, 19 mmol) dropwise at −30° C. The resulting solution was stirred at ambient temperature for 3 hours before the addition of 2 N hydrochloric acid aqueous solution (10 mL) at 0° C. After stirred at ambient temperature for 10 minutes, the solution was basified with saturated aqueous sodium bicarbonate solution to pH 8-9, and then extracted with ethyl acetate (3×50 mL). All the organic solution was dried over sodium sulfate, filtered and concentrated in vacuo. The crude residue was purified by flash column chromatography with 1-2% ethyl acetate in hexane to afford the title compound as a colorless oil. MS ESI: [M+H]⁺ m/z 245; ¹H NMR (300 MHz, CDCl₃) δ 9.58 (s, 1H), 7.32-7.21 (m, 1H), 7.18-7.03 (m, 2H), 1.41 (s, 6H).

Step D: 3-(4-Bromo-2-fluorophenyl)-1,1,1-trifluoro-3-methylbutan-2-ol

To a solution of 2-(4-bromo-2-fluorophenyl)-2-methylpropanal (2.4 g, 9.8 mmol) and trimethyl(trifluoromethyl)silane (2.8 g, 20 mmol) in tetrahydrofuran (20 mL) under nitrogen was added the solution of TBAF (1.3 g, 4.8 mmol) in tetrahydrofuran (5 mL) dropwise at −30° C. The resulting solution was stirred at −30° C. for 1 hour and at ambient temperature for additional 1 hour before the addition of 1 N hydrochloric acid aqueous solution (10 mL). The mixture was vigorously stirred at ambient temperature for 10 minutes, and then extracted with ethyl acetate (3×30 mL). All the organic solution was dried over sodium sulfate, filtered and concentrated in vacuo. The crude residue was purified by flash column chromatography with 1-3% ethyl acetate in hexane to afford the title compound as a yellow oil. MS ESI: [M+H]⁺ m/z 315; ¹H NMR (300 MHz, CDCl₃) δ 7.25-7.15 (m, 3H), 4.53 (q, J=7.5 Hz, 1H), 2.30 (br, 1H), 1.41 (s, 6H).

Scheme #6

Intermediate #6

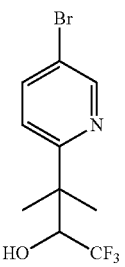

(S and R)-3-(5-Bromopyridin-2-yl)-1,1,1-trifluoro-3-methylbutan-2-ol

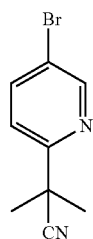

Step A:
2-(5-Bromopyridin-2-yl)-2-methylpropanenitrile

To a solution of 2,5-dibromopyridine (5.0 g, 21 mmol) and 2-methylpropanenitrile (1.6 g, 23 mmol) in toluene (50 mL) under nitrogen was added 2 N solution of NaHMDS in THF (12 mL, 23 mmol) dropwise at 0° C. The resulting solution was stirred at ambient temperature overnight before the addition of saturated aqueous NH₄Cl solution (20 mL). The resulting mixture was extracted with ethyl acetate (3×30 mL). All the organic solution was dried over sodium sulfate, filtered and concentrated in vacuo. The crude residue was purified by flash column chromatography with 1-3% ethyl acetate in hexane to afford the title compound as a light yellow solid. MS ESI [M+H]⁺ m/z 225, 227; ¹H NMR (300 MHz, CDCl₃) δ 8.65 (s, 1H), 7.85 (d, J=8.7 Hz, 1H), 7.51 (d, J=8.7 Hz, 1H), 1.75 (s, 6H).

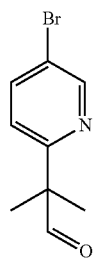

Step B: 2-(5-Bromopyridin-2-yl)-2-methylpropanal

To a solution of 2-(5-bromopyridin-2-yl)-2-methylpropanenitrile (2.0 g, 8.9 mmol) in dichloromethane (20 mL)

under nitrogen was added 1 N solution of DIBAL-H in THF (12.4 mL, 12.4 mmol) dropwise at −30° C. The resulting solution was stirred at ambient temperature for 3 hours before the addition of 2 N hydrochloric acid aqueous solution (10 mL) at 0° C. After stirred at ambient temperature for 10 minutes, the solution was basified with saturated aqueous sodium bicarbonate solution to pH 8-9, and then extracted with ethyl acetate (3×20 mL). All the organic solution was dried over sodium sulfate, filtered and concentrated in vacuo. The crude residue was purified by flash column chromatography with 2-4% ethyl acetate in hexane to afford the title compound as a yellow oil. MS ESI: [M+H]$^+$ m/z 228, 230; $^1$H NMR (300 MHz, CDCl$_3$) δ 9.73 (s, 1H), 8.66 (s, 1H), 7.82 (d, J=8.7 Hz, 1H), 7.17 (d, J=8.7 Hz, 1H), 1.47 (s, 6H).

Step C: 3-(5-Bromopyridin-2-yl)-1,1,1-trifluoro-3-methylbutan-2-ol

To a solution of 2-(5-bromopyridin-2-yl)-2-methylpropanal (1.0 g, 4.4 mmol) and trimethyl(trifluoromethyl)silane (1.1 g, 7.5 mmol) in tetrahydrofuran (10 mL) under nitrogen was added the solution of TBAF (230 mg, 0.88 mmol) in tetrahydrofuran (5 mL) dropwise at −30° C. The resulting solution was stirred at −30° C. for 1 hour and at ambient temperature for an additional 1 hour before the addition of a second batch of TBAF (1.1 g, 4.4 mmol) at ambient temperature. After stirred at ambient temperature for 20 minutes, the reaction solution was diluted with water (10 mL), and then extracted with ethyl acetate (3×15 mL). All the organic solution was dried over sodium sulfate, filtered and concentrated in vacuo. The crude residue was purified by flash column chromatography with 2-5% ethyl acetate in hexane to afford the title compound as a yellow oil. MS ESI: [M+H]$^+$ m/z 298, 300; $^1$H NMR (300 MHz, CDCl$_3$) δ 8.55 (s, 1H), 7.86 (d, J=8.7 Hz, 1H), 7.24 (d, J=8.7 Hz, 1H), 4.01 (q, J=7.8 Hz, 1H), 1.51 (s, 6H).

Step A: 1-(5-Bromopyridin-2-yl)-2,2-difluoroethanone

To a solution of 2,5-dibromopyridine (16 g, 67 mmol) in toluene (150 mL) was added 2.5 N solution of n-BuLi (27 mL, 67 mmol) dropwise at −78° C. The resulting solution was stirred at −78° C. for 1 hour before the addition of 2,2-difluoroacetate (10 g, 80 mmol). After stirred at ambient temperature overnight, the reaction solution was diluted with saturated aqueous NH$_4$Cl solution (80 mL) at 0° C., and then extracted with ethyl acetate (2×100 mL). All the organic solution was dried over sodium sulfate, filtered and concentrated in vacuo. The crude residue was purified by flash column chromatography with 5-10% ethyl acetate in hexane to afford the title compound as a white solid. $^1$H NMR (300 MHz, CDCl$_3$) δ 8.82 (s, 1H), 8.08 (d, J=6.0 Hz, 1H), 8.03 (d, J=6.0 Hz, 1H), 7.05 (t, J=54.4 Hz, 1H).

Step B: (S and R)-1-(5-Bromopyridin-2-yl)-2,2-difluoroethanol

To a solution of 1-(5-bromopyridin-2-yl)-2,2-difluoroethanone (1.0 g, 4.2 mmol) in methanol (10 mL) was added NaBH$_4$ (180 mg, 4.6 mmol) at 0° C. The resulting solution was stirred at ambient temperature for 2 hours before the addition of saturated aqueous NH$_4$Cl solution (5 mL) at 0° C. After methanol was removed in vacuo, the resulting aqueous solution was extracted with ethyl acetate (3×10 mL). All the organic solution was washed with brine, dried over sodium sulfate, filtered and concentrated in vacuo to afford the title compound as an off-white solid, which was used in next step without further purification. $^1$H NMR (400 MHz, CDCl$_3$) δ 8.70 (s, 1H), 7.91 (d, J=6.0 Hz, 1H), 7.52 (d, J=6.0 Hz, 1H), 5.89 (td, J=54.4, 3.9 Hz, 1H), 4.92-4.84 (m, 1H), 4.52 (br, 1H).

Scheme #7

Intermediate #7

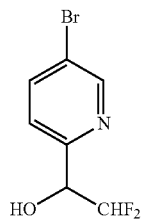

(S and R)-1-(5-Bromopyridin-2-yl)-2,2-difluoroethanol

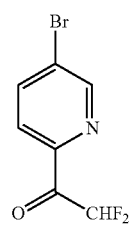

Scheme #7

Intermediate #8

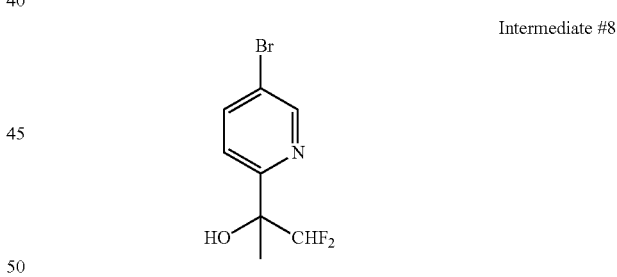

(S and R)-2-(5-Bromopyridin-2-yl)-1,1-difluoropropan-2-ol

To a solution of 1-(5-bromopyridin-2-yl)-2,2-difluoroethanone (1.5 g, 6.4 mmol) in tetrahydrofuran (15 mL) under nitrogen was added 3 N solution of MeMgBr in THF (3.2 mL, 9.6 mmol) dropwise at −15° C. The resulting solution was stirred at ambient temperature for 2 hours before the addition of saturated aqueous NH$_4$Cl solution (10 mL) at 0° C. The resulting mixture was vigorously stirred for 10 minutes, and then extracted with ethyl acetate (3×20 mL). All the organic solution was dried over sodium sulfate, filtered and concentrated in vacuo. The crude residue was purified by flash column chromatography with 1-3% ethyl acetate in hexane to afford the title compound as a yellow oil. $^1$H NMR (400 MHz, CDCl$_3$) δ 8.83 (d, J=2.0 Hz, 1H), 7.92 (dd, J=8.4, 2.0 Hz, 1H), 7.43 (d, J=8.4 Hz, 1H), 5.76 (t, J=56.4 Hz, 1H), 5.22 (br, 1H), 1.60 (s, 3H).

Scheme #8

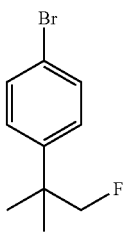

Intermediate #9

1-Bromo-4-(1-fluoro-2-methylpropan-2-yl)benzene 2-(4-Bromophenyl)-2-methylpropan-1-ol (500 mg, 2.182 mmol) was dissolved in Dichloromethane (7.2 mL) in a 20 mL vial. Diethylaminosulfur trifluoride (0.433 mL, 3.27 mmol) was then slowly added To a solution and the resultant mixture was stirred at ambient temperature overnight. At which time, an additional 0.5 eq of DAST was added and stirred for an additional 4 hours. The reaction mixture was purified directly by MPLC on silica gel (eluting with 5% ethyl acetate in hexanes) to afford the title compound. $^1$H NMR (500 MHz, CDCl$_3$) δ 7.43-7.42 (d, 2H), 7.10-7.09 (d, 2H), 2.88 (s, 1H), 2.83 (s, 1H), 1.35 (s, 3H), 1.30 (s, 3H).

Scheme #9

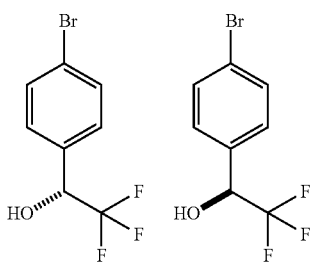

Intermediates #10-1 and 10-2

(R or S)-1-(4-Bromophenyl)-2,2,2-trifluoroethanol

4'-Bromo-2,2,2-trifluoroacetophenone (3.00 mL, 19.8 mmol) was dissolved in MeOH (66 mL) and cooled to 0° C. Sodium borohydride (0.748 g, 19.8 mmol) was added, and the reaction mixture was allowed to warm to ambient temperature where it was maintained for an additional 3 hours. The reaction mixture was quenched with saturated aqueous ammonium chloride and extracted with ethyl acetate. The organic layer was washed with brine, dried over anhydrous MgSO$_4$, filtered, concentrated in vacuo and the crude residue was purified using MPLC on silica gel (eluting with 5% ethyl acetate in hexanes) to afford a racemic mixture of the title compound. The mixture was resolved to the constituent enantiomers by Chiral SFC purification (Chiral Technology OJ-H 2.1×25 cm, 5 uM; mobile phase: 5% isopropyl alcohol/CO$_2$) to afford the title compounds as single enantiomers. Intermediate #10-1: First enantiomer to elute; (R or S)-1-(4-Bromophenyl)-2,2,2-trifluoroethanol; $^1$H NMR (500 MHz, CDCl$_3$) δ 7.56-7.54 (d, 2H), 7.37-7.35 (d, 2H), 5.03-4.98 (m, 1H), 2.79 (bs, 1H). Intermediate #10-2: Second enantiomer to elute; (R or S)-1-(4-Bromophenyl)-2,2,2-trifluoroethanol; $^1$H NMR (500 MHz, CDCl$_3$) δ 7.56-7.54 (d, 2H), 7.37-7.35 (d, 2H), 5.03-4.98 (m, 1H), 2.79 (bs, 1H).

Scheme #9

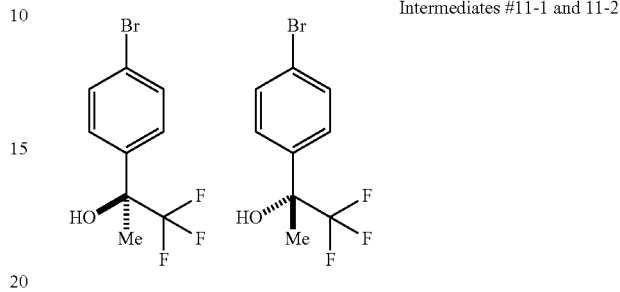

Intermediates #11-1 and 11-2

(S or R)-2-(4-Bromophenyl)-1,1,1-trifluoropropan-2-ol

4'-Bromo-2,2,2-trifluoroacetophenone (1.80 mL, 11.9 mmol) was dissolved in tetrahydrofuran (60 mL), cooled to 0° C., and methylmagnesium bromide (19.8 mL, 59.3 mmol) was added. The reaction mixture was maintained at 0° C. for 1 hour and then allowed to warm to ambient temperature overnight. The reaction was quenched with saturated aqueous ammonium chloride and extracted with ethyl acetate. The organic layer was washed with brine, dried over anhydrous MgSO$_4$, filtered, concentrated in vacuo and the crude residue was purified directly by MPLC on silica gel (using a gradient elution of 0-25% ethyl acetate in hexanes to afford a racemic mixture of the title compound. The mixture was resolved to the constituent enantiomers by Chiral SFC purification (Chiral Technology AZ-H 2.1×25 cm, 5 uM column; mobile phase: 5% methanol/CO$_2$) to afford the title compounds as single enantiomers. Intermediate #11-1: First enantiomer to elute; (S or R)-2-(4-Bromophenyl)-1,1,1-trifluoropropan-2-ol; $^1$H NMR (500 MHz, CDCl$_3$) δ 7.53-7.52 (d, 2H), 7.46-7.45 (d, 2H), 2.64 (bs, 1H), 1.76 (s, 3H). Intermediate #11-2: Second enantiomer to elute; (S or R)-2-(4-Bromophenyl)-1,1,1-trifluoropropan-2-ol; $^1$H NMR (500 MHz, CDCl$_3$) δ 7.53-7.52 (d, 2H), 7.46-7.45 (d, 2H), 2.64 (bs, 1H), 1.76 (s, 3H).

Scheme #13

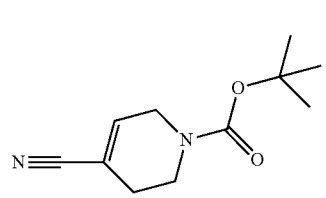

Intermediate #12 tert-Butyl 4-cyano-5,6-dihydropyridine-1(2H)-carboxylate

Methanesulfonyl chloride (0.189 mL, 2.43 mmol) was added to a mixture of tert-butyl 4-cyano-4-hydroxypiperidine-1-carboxylate (500 mg, 2.21 mmol) and N-ethyl-N-isopropylpropan-2-amine (0.579 mL, 3.31 mmol) in chloroform (8.8 mL) at 0° C. The reaction mixture was stirred at 0° C. for 45 minutes, and was then partitioned between dichloromethane and water. The organic layer was dried over anhydrous sodium sulfate, and the dried solution was filtered. The filtrate was concentrated in vacuo, and the residue was dissolved in pyridine (5.5 mL). The reaction mixture was heated to 120° C. for 4 hours, and was then cooled to ambient temperature. The cooled reaction mixture was partitioned between ethyl acetate and water, and the organic layer was washed sequentially with water and saturated aqueous sodium chloride solution. The washed solution was dried over anhydrous sodium sulfate, and the dried solution was filtered. The filtrate was concentrated in vacuo, and the residue was purified by flash-column chromatography (using a gradient elution of 0-100%, ethyl acetate/hexanes) to afford the title compound. ¹H NMR (500 MHz, CDCl₃): δ 6.55 (br s, 1H), 4.05 (m, 2H), 3.55 (t, J=5.6 Hz, 2H), 2.34 (br s, 2H), 1.46 (s, 9H).

Scheme #14

Intermediate #13

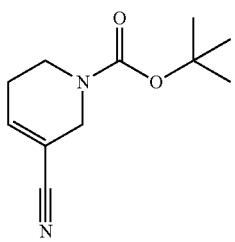

tert-Butyl 5-cyano-3,6-dihydropyridine-1(2H)-carboxylate

A solution of n-butyllithium (2.8 mL, 7.0 mmol, 2.5 M in hexanes) was added to a solution of diisopropylamine (1.0 mL, 7.0 mmol) in THF (10.0 mL) at −78° C. The cooling bath was removed for 15 minutes, and then the reaction mixture was cooled back to −78° C. A solution of tert-butyl 3-oxopiperidine-1-carboxylate (1.0 g, 5.0 mmol) in THF (6 mL) was added to the cooled solution of LDA dropwise over 5 minutes, maintained for 15 minutes, and then N-(5-chloropyridin-2-yl)-1,1,1-trifluoro-N-[(trifluoromethyl)sulfonyl]methanesulfonamide (2.4 g, 6.0 mmol) was added in one portion. The reaction mixture was stirred at 78° C. for 15 minutes, and then the cooling bath was removed. The reaction mixture was stirred for 45 minutes after removal of the cooling bath, and was then partitioned between EtOAc and water. The organic layer was washed with brine, dried over anhydrous Na₂SO₄ and filtered. The filtrate was concentrated in vacuo and the residue was purified by MPLC on silica gel (using a gradient elution of 0-20%, diethyl ether/hexanes) to afford tert-butyl 5-{[(trifluoromethyl)sulfonyl]oxy}-3,6-dihydropyridine-1(2H)-carboxylate as the second regioisomer to elute. A portion of the product (123 mg, 0.371 mmol) was combined with zinc cyanide (52 mg, 0.450 mmol), Pd(PPh₃)₄ (64 mg, 0.056 mmol) and DMF (1.9 mL) in a microwave tube. The reaction mixture was heated in the microwave at 100° C. for 20 minutes. After cooling to ambient temperature, the reaction mixture was partitioned between EtOAc and water. The organic layer was washed with brine, dried over anhydrous Na₂SO₄ and filtered. The filtrate was concentrated in vacuo and the residue was purified by MPLC on silica gel (using a gradient elution of 0-100%, EtOAc/hexanes) to afford the title compound. ¹H NMR (500 MHz, CDCl₃): δ 6.73 (br s, 1H), 4.02 (br s, 2H), 3.49 (t, J=5.6 Hz, 2H), 2.29 (br s, 2H), 1.47 (s, 9H).

Scheme #27

Intermediate #14

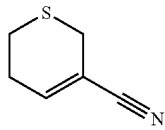

5,6-Dihydro-2H-thiopyran-3-carbonitrile

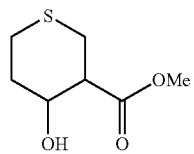 [SMILES: COC(=O)C1CSCCC1O]

Step A: Methyl 4-hydroxytetrahydro-2H-thiopyran-3-carboxylate

A solution of methyl 4-oxotetrahydro-2H-thiopyran-3-carboxylate (3.00 g, 17.2 mmol) in THF (57 mL) was stirred at 0° C. Sodium borohydride (1.30 g, 34.4 mmol) was added and the resulting mixture was stirred at ambient temperature for 4 hours. The mixture was thermally stabilized with a water bath and carefully quenched with 1N aqueous HCl. The reaction mixture was then diluted with water and extracted with EtOAc (2×). The combined organic extracts were washed with water, brine, dried over anhydrous Na₂SO₄, filtered, and concentrated in vacuo to afford the title compound. The residue was carried forward without further purification.

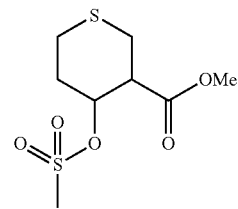

Step B: Methyl 4-((methylsulfonyl)oxy)tetrahydro-2H-thiopyran-3-carboxylate

A solution of methyl 4-hydroxytetrahydro-2H-thiopyran-3-carboxylate (3.00 g, 17.0 mmol) in DCM (170 mL) was stirred at 0° C. DIPEA (5.95 mL, 34.0 mmol) was added followed by the dropwise addition of methanesulfonyl chloride (1.95 g, 17.0 mmol). The resulting mixture was stirred at 0° C. for 30 minutes then warmed to ambient temperature and stirred for an additional 30 minutes. The mixture was carefully diluted with water and extracted with DCM (2×). The combined organic extracts were washed with 1N aqueous HCl, brine, dried over anhydrous Na₂SO₄, filtered, and concentrated in vacuo to afford the title compound. The residue was carried forward without further purification.

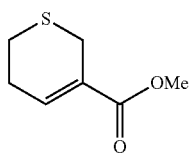

Step C: Methyl 5,6-dihydro-2H-thiopyran-3-carboxylate

To a solution of methyl 4-((methylsulfonyl)oxy)tetrahydro-2H-thiopyran-3-carboxylate (4.33 g, 17.0 mmol) in DCM (170 mL) was added DBU (3.89 g, 25.5 mmol). The resulting mixture was refluxed at 50° C. for 30 minutes. The mixture was cooled to ambient temperature and washed with 1N aqueous HCl. The organic extract was washed with brine, dried over anhydrous $Na_2SO_4$, filtered, and concentrated in vacuo. The crude residue was purified by MPLC on silica gel (using a gradient elution of 0-45% EtOAc/hexanes) to afford the title compound. $^1$H NMR (500 MHz, $CDCl_3$): δ 7.12-7.13 (m, 1H); 3.75 (s, 3H); 3.36 (q, J=2.2 Hz, 2H); 2.68 (t, J=5.8 Hz, 2H); 2.51-2.52 (m, 2H).

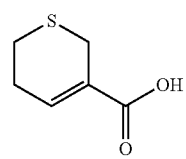

Step D: 5,6-Dihydro-2H-thiopyran-3-carboxylic acid

To a solution of methyl 5,6-dihydro-2H-thiopyran-3-carboxylate (1.0 g, 6.32 mmol) in 10:1 MeOH:THF (16.5 mL) was added lithium hydroxide (0.30 g, 13 mmol) in water (15 mL). The resulting mixture was stirred at ambient temperature for 4 hours. The reaction mixture was carefully acidified with 1N aqueous HCl, and extracted with EtOAc (3×). The combined organic extracts were washed with brine, dried over anhydrous $Na_2SO_4$, filtered, and concentrated in vacuo to afford the title compound. The residue was carried forward without further purification.

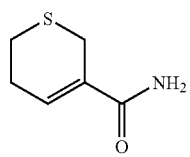

Step E: 5,6-Dihydro-2H-thiopyran-3-carboxamide

To a solution of 5,6-dihydro-2H-thiopyran-3-carboxylic acid (0.84 g, 5.8 mmol) in DMF (29 mL) was added DIPEA (3.4 g, 26 mmol), followed by TBTU (4.1 g, 13 mmol). The resulting mixture was stirred at ambient temperature for 30 minutes, then HMDS (2.1 g, 13 mmol) was added. The mixture was stirred at ambient temperature for 16 hours. The reaction mixture was acidified with 1N aqueous HCl, and extracted with EtOAc (3×). The combined organic extracts were again washed with 1N aqueous HCl, brine, dried over anhydrous $Na_2SO_4$, filtered, and concentrated in vacuo. The crude residue was purified by MPLC on silica gel (using a gradient elution of 0-5% MeOH/DCM). Desired fractions were identified, combined and concentrated in vacuo to afford the title compound. $^1$H NMR (500 MHz, $CDCl_3$): δ 6.68-6.69 (m, 1H); 3.38 (q, J=2.2 Hz, 2H); 2.70 (t, J=5.8 Hz, 2H); 2.50-2.51 (m, 2H).

Step F: 5,6-Dihydro-2H-thiopyran-3-carbonitrile

To a solution of 5,6-dihydro-2H-thiopyran-3-carboxamide (0.40 g, 2.8 mmol) in DCM (6.0 mL) was added TEA (0.56 g, 5.6 mmol). The resulting mixture was stirred at 0° C., then trichloroacetyl chloride (0.56 g, 3.1 mmol) was added. The resulting mixture was stirred at 0° C. for 15 minutes before being treated with ice water and then 1N aqueous NaOH. The mixture was stirred for 10 minutes, then carefully acidified with 1N aqueous HCl, and extracted with EtOAc (3×). The combined organic extracts were washed with brine, dried over anhydrous $Na_2SO_4$, filtered, and concentrated in vacuo. The crude residue was purified by MPLC on silica gel (using a gradient elution of 0-45% EtOAc/hexanes). Desired fractions were identified, combined and concentrated in vacuo to afford the title compound. $^1$H NMR (600 MHz, $CDCl_3$): δ 6.70-6.71 (m, 1H); 3.23 (q, J=2.3 Hz, 3H); 2.71 (t, J=5.8 Hz, 3H); 2.48-2.49 (m, 2H).

Scheme #25

Intermediate #15

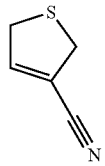

2,5-Dihydrothiophene-3-carbonitrile

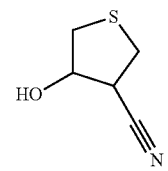

Step A: 4-Hydroxytetrahydrothiophene-3-carbonitrile

A solution of 4-oxotetrahydrothiophene-3-carbonitrile (1.0 g, 7.9 mmol) in EtOH (39 mL) was stirred at 0° C. Sodium borohydride (0.50 g, 12 mmol) was added and the resulting mixture was stirred at ambient temperature for 4 hours. The mixture was thermally stabilized with a water bath and carefully quenched with acetic acid. The reaction mixture was then diluted with water and extracted with EtOAc (2×). The combined organic extracts were washed with water, brine, dried over anhydrous $Na_2SO_4$, filtered, and concentrated in vacuo to afford the title compound. The residue was carried forward without further purification.

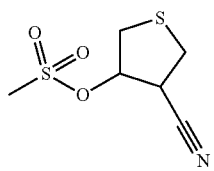

Step B: 4-Cyanotetrahydrothiophen-3-yl methanesulfonate

A solution of 4-hydroxytetrahydrothiophene-3-carbonitrile (1.0 g, 7.7 mmol) in DCM (15 mL) was stirred at 0° C. TEA (4.3 mL, 31 mmol) was added followed by the dropwise addition of methanesulfonyl chloride (1.77 g, 15.5 mmol). The resulting mixture was stirred at 0° C. for 30 minutes then warmed to ambient temperature and stirred for an additional 30 minutes. The mixture was carefully diluted with water and extracted with DCM (2×). The combined organic extracts were washed with 1N aqueous HCl, brine, dried over anhydrous Na$_2$SO$_4$, filtered, and concentrated in vacuo. The crude residue was purified by MPLC on silica gel (using a gradient elution of 0-5% MeOH/DCM) to afford the title compound, which was used without further purification.

Step C: 2,5-Dihydrothiophene-3-carbonitrile

To a solution of 4-cyanotetrahydrothiophen-3-yl methanesulfonate (0.63 g, 3.0 mmol) in DCM (30 mL) was added DBU (0.69 g, 4.6 mmol). The resulting mixture was refluxed at 50° C. for 30 minutes. The mixture was cooled to ambient temperature and washed with 1N aqueous HCl. The organic extract was washed with brine, dried over anhydrous Na$_2$SO$_4$, filtered, and concentrated in vacuo to afford the title compound. $^1$H NMR (500 MHz, CDCl$_3$): δ 6.72 (t, J=2.3 Hz, 1H); 3.88-3.89 (m, 4H).

Scheme #26

Intermediate #16

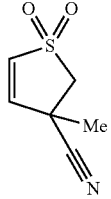

3-Methyl-2,3-dihydrothiophene-3-carbonitrile 1,1-dioxide

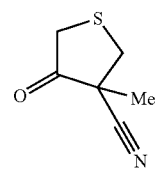

Step A: 3-Methyl-4-oxotetrahydrothiophene-3-carbonitrile

To a solution of 4-oxotetrahydrothiophene-3-carbonitrile (0.50 g, 3.9 mmol) in anhydrous acetone (7.8 mL) was added potassium carbonate (1.63 g, 11.8 mmol), followed by iodomethane (0.56 g, 3.9 mmol). The resulting mixture was stirred at 35° C. for 1 hour. The mixture was cooled to ambient temperature, filtered, and carefully concentrated in vacuo to afford the title compound. The residue was carried forward without further purification.

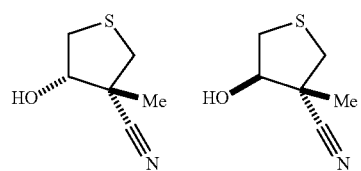 [SMILES: C[C@]1(C#N)CSC[C@H]1O ; C[C@]1(C#N)CSC[C@@H]1O]

Step B: (3R,4S and 3S,4R)-4-Hydroxy-3-methyltetrahydrothiophene-3-carbonitrile and (3R,4R and 3S,4S)-4-hydroxy-3-methyltetrahydrothiophene-3-carbonitrile According to the protocol described for Intermediate 15 step A, 4-hydroxytetrahydrothiophene-3-carbonitrile, the title compounds were prepared.

Intermediate 16-B1: (3R,4S and 3S,4R)-4-hydroxy-3-methyltetrahydrothiophene-3-carbonitrile: $^1$H NMR (500 MHz, CD$_3$OD): δ 4.06-4.08 (m, 1H); 3.19 (d, J=11.0 Hz, 1H); 3.08 (dd, J=11.1, 5.7 Hz, 1H); 2.86-2.87 (m, 2H); 1.43 (d, J=1.3 Hz, 3H).

Intermediate 16-B2: (3S,4S and 3R,4R)-4-hydroxy-3-methyltetrahydrothiophene-3-carbonitrile: $^1$H NMR (500 MHz, CD$_3$OD): δ 4.40 (t, J=4.4 Hz, 1H); 3.25 (dd, J=11.4, 5.0 Hz, 1H); 3.10 (d, J=10.9 Hz, 1H); 2.90 (d, J=10.9 Hz, 1H); 2.81 (dd, J=11.4, 3.8 Hz, 1H); 1.48 (s, 3H).

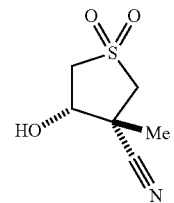 [SMILES: C[C@]1(C#N)CS(=O)(=O)C[C@H]1O]

Step C: (3R,4S and 3S,4R)-4-Hydroxy-3-methyltetrahydrothiophene-3-carbonitrile 1,1-dioxide (3R,4S and 3S,4R)-4-Hydroxy-3-methyltetrahydrothiophene-3-carbonitrile (140 mg, 0.98 mmol) was dissolved in DCM (4.9 mL) and was stirred vigorously at ambient temperature. m-CPBA (340 mg, 2.0 mmol) was added in three portions and the resulting mixture was maintained at ambient temperature for 18 hours. The mixture was then diluted with 1M aqueous sodium thiosulfate and extracted with EtOAc. The organic layer was again washed with 1M aqueous sodium thiosulfate, saturated aqueous NaHCO$_3$, brine, dried over anhydrous MgSO$_4$, filtered, and concentrated in vacuo. The residue was purified by MPLC on silica gel (using a gradient elution of 0-100% EtOAc/hexanes) to afford the title compound. $^1$H NMR (600 MHz, CD$_3$OD): δ 4.40 (t, J=6.5 Hz, 1H); 3.70 (d, J=13.6 Hz, 1H); 3.56 (dd, J=13.8, 6.2 Hz, 1H); 3.29-3.30 (m, 1H); 3.23 (dd, J=13.7, 6.8 Hz, 1H); 1.60 (s, 3H).

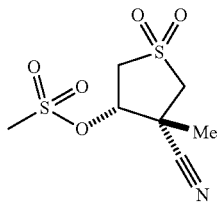

Step D: (3S,4R and 3R,4S)-4-Cyano-4-methyl-1,1-dioxidotetrahydrothiophen-3-yl methanesulfonate According to the protocol described for Intermediate 15 step B, 4-cyanotetrahydrothiophen-3-yl methanesulfonate, the title compound was prepared. $^1$H NMR (500 MHz, CDCl$_3$): δ 5.27-5.28 (m, 1H); 3.74 (d, J=13.6 Hz, 1H); 3.66-3.69 (m, 2H); 3.30 (d, J=13.6 Hz, 1H); 3.24 (s, 3H); 3.14 (s, 3H).

Step E: 3-Methyl-2,3-dihydrothiophene-3-carbonitrile 1,1-dioxide

According to the protocol described for Intermediate 15 step C, 2,5-dihydrothiophene-3-carbonitrile, the title compound was prepared. $^1$H NMR (500 MHz, CDCl$_3$): δ 6.83 (d, J=6.6 Hz, 1H); 6.68 (d, J=6.6 Hz, 1H); 3.71 (d, J=13.7 Hz, 1H); 3.29 (d, J=13.7 Hz, 1H); 1.79 (s, 3H).

Scheme #15

Intermediate #17

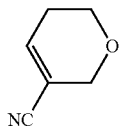

5,6-Dihydro-2H-pyran-3-carbonitrile

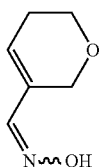

Step A: (E or Z)-5,6-Dihydro-2H-pyran-3-carbaldehyde oxime

To a cooled (0° C.) solution of 5,6-dihydro-2H-pyran-3-carbaldehyde (10 g, 89 mmol) and hydrochloric acid salt of hydroxylamine (12.0 g, 178 mmol) in water (80 mL) was added a solution of sodium hydroxide (6.4 g, 160 mmol) in water (20 mL) dropwise. The cooling bath was removed and the mixture was allowed to stir at ambient temperature for 1 hour, the resulting solution was acidified with 2 N aqueous hydrochloric acid to pH 3-4, and then extracted with ethyl acetate (3×100 mL). All the organic solutions were washed with saturated NaHCO$_3$ aqueous solution (2×50 mL), brine (2×50 mL), dried over anhydrous sodium sulfate, filtered and concentrated in vacuo to afford the title compound as a white solid, which was used in next step without further purification. $^1$H NMR (300 MHz, CD$_3$OD) δ 7.76 (s, 1H), 6.15 (br, 1H), 4.35 (d, J=1.8 Hz, 2H), 3.86 (t, J=5.7 Hz, 2H), 2.32-2.31 (m, 2H).

Step B: 5,6-Dihydro-2H-pyran-3-carbonitrile

To a solution of (E or Z)-5,6-dihydro-2H-pyran-3-carbaldehyde oxime (1.0 g, 7.9 mmol) in tetrahydrofuran (20 mL) were added tripropylphosphonic anhydride (5.0 g, 16 mmol) and triethylamine (4.0 g, 40 mmol) sequentially. The resulting solution was stirred at 50° C. for 1 hour, then acidified with 2 N aqueous hydrochloric acid solution to pH 2-3, and extracted with dichloromethane (3×40 mL). All the organic solutions were dried over anhydrous sodium sulfate, filtered and concentrated in vacuo. The crude residue was purified by flash column chromatography with 2-4% ethyl acetate in hexane to afford the title compound as a yellow oil. $^1$H NMR (400 MHz, CDCl$_3$) δ 6.80-6.78 (m, 1H), 4.22 (d, J=2.0 Hz, 2H), 3.82 (t, J=5.6 Hz, 2H), 2.36-2.31 (m, 2H).

Scheme #28

Intermediate #18

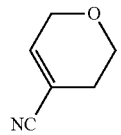

3,6-Dihydro-2H-pyran-4-carbonitrile

To a solution of trimethylsilyl cyanide (28.0 g, 288 mmol) in dichloromethane (100 mL) were sequentially added tetrahydro-4H-pyran-4-one (24 g, 243 mmol) and trimethylsilyl triflate (1.6 g, 7.2 mmol) at 0° C. The resulting solution was stirred at 0° C. for 1 hour before the addition of pyridine (300 mL) and phosphoryl chloride (110 g, 719 mmol). The mixture was refluxed for 12 hours, and then poured into a mixture of 2 N aqueous hydrochloric acid solution (600 mL), crushed ice (180 mL) and ether (600 mL) at 0° C. The mixture was vigorously stirred for 15 minutes, and then extracted with ether (3×1 L). All the organic solution was washed with brine (2×300 mL), dried over anhydrous sodium sulfate, filtered and concentrated in vacuo. The crude residue was purified by flash column chromatography with 1-2% ethyl acetate in hexane to afford the title compound as a yellow oil. $^1$H NMR (300 MHz, CDCl$_3$) δ 6.62-6.59 (m, 1H), 4.29-4.21 (m, 2H), 3.78 (t, J=5.4 Hz, 2H), 2.34-2.30 (m, 2H).

Scheme #29

Intermediates #19-1 and 19-2

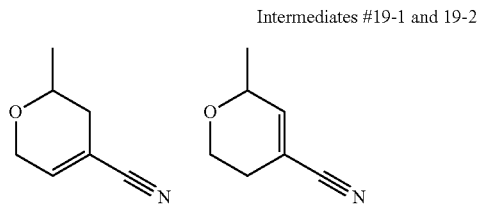

2-Methyl-3,6-dihydro-2H-pyran-4-carbonitrile and
6-Methyl-3,6-dihydro-2H-pyran-4-carbonitrile 2-Methyldihydro-2H-pyran-4(3H)-one (1.0 g, 8.8 mmol) was taken up in 1:1 water:diethyl ether (30 mL) and vigorously stirred at ambient temperature. Sodium metabisulfite (0.97 g, 5.1 mmol) was added and the mixture was allowed to stir for 40 minutes. Potassium cyanide (0.90 g, 14 mmol) was added. The resulting mixture was allowed to stir vigorously for 2 hours before it was partitioned between diethyl ether and water. The organic layer was washed with water, brine, dried over anhydrous MgSO$_4$, filtered, and concentrated in vacuo. The residue, used without further purification, was dissolved in pyridine (6.6 mL) and was stirred at 0° C. Thionyl chloride (0.86 g, 7.3 mmol) was added dropwise and the resulting mixture was stirred for 16 hours. The mixture was poured over ice and extracted with diethyl ether. The organic layer was washed with 1N aqueous HCl (3×), washed with brine, dried over anhydrous Na$_2$SO$_4$, filtered, and concentrated in vacuo to give the title compound as a mixture of regioisomers. The residue was used without further purification.

Intermediate #19-1: 2-Methyl-3,6-dihydro-2H-pyran-4-carbonitrile: $^1$H NMR (500 MHz, CDCl$_3$): δ 6.50 (q, J=1.8 Hz, 1H); 4.23-4.35 (m, 1H); 3.99 (ddd, J=11.7, 5.7, 2.5 Hz, 1H); 3.60-3.65 (m, 1H); 2.40-2.48 (m, 1H); 2.10-2.20 (m, 1H); 1.24-1.28 (m, 3H).

Intermediate #19-2: 6-Methyl-3,6-dihydro-2H-pyran-4-carbonitrile: $^1$H NMR (500 MHz, CDCl$_3$): δ 6.62 (dt, J=3.7, 1.9 Hz, 1H); 4.23-4.35 (m, 1H); 3.99 (ddd, J=11.7, 5.7, 2.5 Hz, 1H); 3.60-3.65 (m, 1H); 2.40-2.48 (m, 1H); 2.10-2.20 (m, 1H); 1.24-1.28 (m, 3H).

Scheme #16

Intermediate #20-1

3-(Phenylamino)-1H-pyrazole-4-carboxamide

3-Amino-1H-pyrazole-4-carboxamide (19.8 g, 157 mmol), K$_3$PO$_4$ (66.7 g, 314 mmol), bromobenzene (23.2 mL, 220 mmol) and 2-propanol (785 mL) were combined in a round bottom flask and purged with a stream of N$_2$ gas for 40 minutes. Pd$_2$(dba)$_3$ (1.80 g, 1.96 mmol) and 2-di-t-butylphosphino-3,4,5,6-tetramethyl-2',4',6'-tri-i-propylbiphenyl(3.77 g, 7.85 mmol) were added and the reaction was purged for an additional 5 minutes. The reaction mixture was then heated to 80° C. and allowed to stir under a N$_2$ atmosphere for 12 hours. The mixture was then allowed to cool to ambient temperature for an additional 16 hours. The reaction mixture was diluted with EtOAc (300 mL) and filtered through celite (slowly). The celite was washed with EtOAc (300 mL) and the combined filtrates were concentrated in vacuo to afford an oil which was purified by MPLC on silica gel (using a gradient elution of 0-10% MeOH/DCM). The major, low rf product, was isolated to afford a reddish-brown oily solid. The brown solid was suspended in 40 mL of warm MeOH, cooled to ambient temperature, and water (40 mL) was added. The mixture was stirred for 30 minutes and filtered. The solid was suction dried for 16 hours to afford the title compound as a peach-colored solid. LRMS (ESI) calc'd for C$_{10}$H$_{10}$N$_4$O [M+H]$^+$: 203. Found: 203.

The following intermediates shown in TABLE 1 were prepared according to Scheme #16 following similar procedures described for Intermediate #20-1, which can be achieved by those of ordinary skill in the art of organic synthesis.

TABLE 1

| Intermediate | Structure | IUPAC Name | Exact Mass [M + H]$^+$ |
|---|---|---|---|
| 20-2 | ![structure] | 3-[(4-bromophenyl)amino]-1H-pyrazole-4-carboxamide | Calc'd 280, Found 280 |

TABLE 1-continued

| Intermediate | Structure | IUPAC Name | Exact Mass [M + H]+ |
| --- | --- | --- | --- |
| 20-3 | 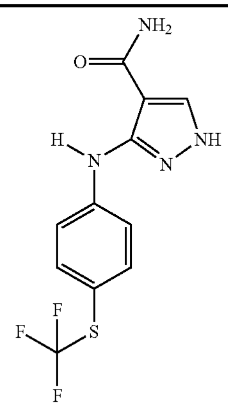 | 3-({4-[(trifluoromethyl)sulfanyl]phenyl}amino)-1H-pyrazole-4-carboxamide | Calc'd 303, Found 303 |
| 20-4 | 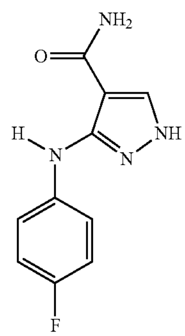 [SMILES: NC(=O)c1c[nH]nc1Nc1ccc(F)cc1] | 3-[(4-fluorophenyl)amino]-1H-pyrazole-4-carboxamide | Calc'd 221, Found 221 |
| 20-5 | 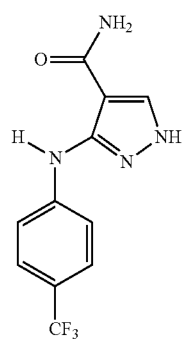 [SMILES: NC(=O)c1c[nH]nc1Nc1ccc(C(F)(F)F)cc1] | 3-((4-(trifluoromethyl)phenyl)amino)-1H-pyrazole-4-carboxamide | Calc'd 271, Found 271 |
| 20-6 | 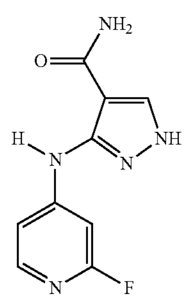 [SMILES: NC(=O)c1c[nH]nc1Nc1ccnc(F)c1] | 3-((2-fluoropyridin-4-yl)amino)-1H-pyrazole-4-carboxamide | Calc'd 222, Found 222 |
| 20-7 | 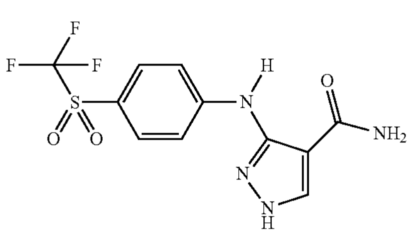 [SMILES: NC(=O)c1c[nH]nc1Nc1ccc(S(=O)(=O)C(F)(F)F)cc1] | 3-({4-[(Trifluoromethyl)sulfonyl]phenyl}amino)-1H-pyrazole-4-carboxamide | Calc'd 335, Found 335 |

Examples of the Instant Invention

The following experimental procedures detail the preparation of specific examples of the instant invention. The examples are for illustrative purposes only and are not intended to limit the scope of the instant invention in any way.

Scheme #19

Examples #1-1 and #1-2

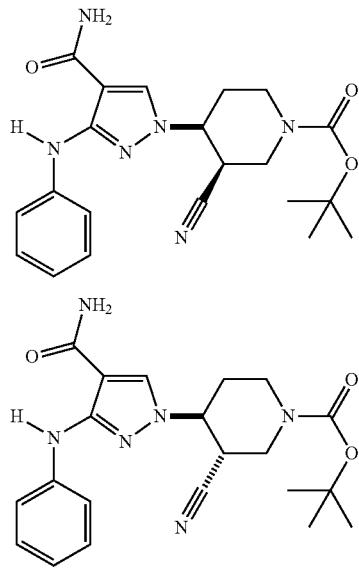

tert-Butyl(3R,4S and 3S,4R)-4-[4-(aminocarbonyl)-3-anilino-1H-pyrazol-1-yl]-3-cyanopiperidine-1-carboxylate and tert-butyl(3S,4S and 3R,4R)-4-[4-(aminocarbonyl)-3-anilino-1H-pyrazol-1-yl]-3-cyanopiperidine-1-carboxylate tert-Butyl 5-cyano-3,6-dihydropyridine-1(2H)-carboxylate (Intermediate #13, 34 mg, 0.16 mmol) was combined with 3-(phenylamino)-1H-pyrazole-4-carboxamide (Intermediate #20-1, 66 mg, 0.33 mmol) and DBU (0.049 mL, 0.33 mmol) in DMF (0.8 mL) and heated to 70° C. for 16 hours. The reaction mixture was cooled to ambient temperature and was purified by reverse-phase preparative HPLC (MeCN/water, with 0.1% v/v TFA modifier) to afford the two title compounds.

Example #1-1: first eluting diastereomer, tert-butyl(3R,4S and 3S,4R)-4-[4-(aminocarbonyl)-3-anilino-1H-pyrazol-1-yl]-3-cyanopiperidine-1-carboxylate. $^1$HNMR (600 MHz, CDCl$_3$): δ 8.76 (s, 1H), 7.69 (s, 1H), 7.51 (d, J=7.8 Hz, 2H), 7.26 (t, J=7.2 Hz, 2H), 6.89 (t, J=7.2 Hz, 1H), 5.54 (s, 2H), 4.68-4.48 (m, 2H), 4.42 (ddd, J=12.0, 4.0, 4.0 Hz, 1H), 3.62-3.58 (m, 1H), 3.17-3.05 (m, 1H), 2.88-2.80 (m, 1H), 2.28-2.20 (m, 1H), 2.13 (d, J=10.8 Hz, 1H), 1.22 (s, 9H). LRMS (ESI) calc'd for $C_{21}H_{27}N_6O_3$ [M+H]$^+$: 411. Found: 411.

Example #1-2: second eluting diastereomer, tert-butyl(3S,4S and 3R,4R)-4-[4-(aminocarbonyl)-3-anilino-1H-pyrazol-1-yl]-3-cyanopiperidine-1-carboxylate. $^1$HNMR (600 MHz, CDCl$_3$): δ 8.74 (s, 1H), 7.67 (s, 1H), 7.50 (d, J=7.2 Hz, 2H), 7.27 (t, J=7.2 Hz, 2H), 6.89 (t, J=7.2 Hz, 1H), 5.58 (br s, 2H), 4.70-4.06 (m, 3H), 3.30 (t, J=9.0 Hz, 1H), 3.10-2.92 (m, 1H), 2.85 (t, J=13.0 Hz, 1H), 2.32-2.25 (m, 1H), 2.04-1.98 (m, 1H), 1.49 (s, 9H). LRMS (ESI) calc'd for $C_{21}H_{27}N_6O_3$ [M+H]$^+$: 411. Found: 411.

The following examples shown in TABLE 2 were prepared according to Scheme #19 following similar procedures described for Examples #1-1 and #1-2, which can be achieved by those of ordinary skill in the art of organic synthesis utilizing but not limited to the intermediates described above.

TABLE 2

| Example | Structure | IUPAC Name | Exact Mass [M + H]$^+$ |
|---|---|---|---|
| 1-3 | 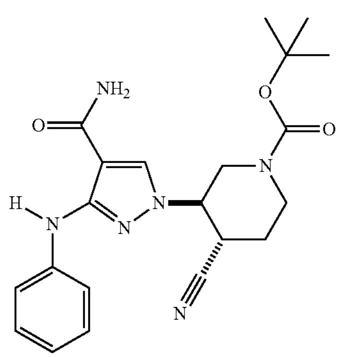 | tert-butyl(3R,4S and 3S,4R)-3-[4-(aminocarbonyl)-3-anilino-1H-pyrazol-1-yl]-4-cyanopiperidine-1-carboxylate | Calc'd 411, Found 411 |

Scheme #19

Example #2-1

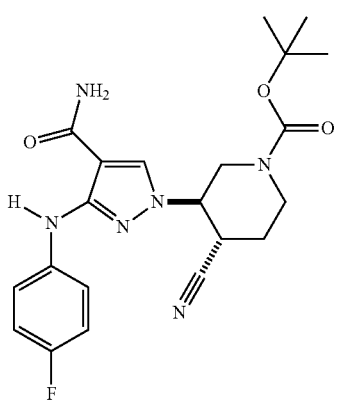

tert-Butyl(3R,4S and 3S,4R)-3-{4-carbamoyl-3-[(4-fluorophenyl)amino]-1H-pyrazol-1-yl}-4-cyanopiperidine-1-carboxylate tert-Butyl 4-cyano-3,6-dihydropyridine-1(2H)-carboxylate (Intermediate #12, 4.9 g, 12 mmol) was combined with DBU (3.6 mL, 24 mmol) and 3-[(4-fluorophenyl)amino]-1H-pyrazole-4-carboxamide (Intermediate 20-4, 2.6 g, 12 mmol) in EtOH (13 mL). The reaction mixture was heated to 75° C. for 18 hours. The mixture was then cooled to ambient temperature and concentrated in vacuo. The residue was purified by MPLC on silica gel (eluting with 100% EtOAc). Desired fractions were identified, combined, and concentrated in vacuo to afford the title compound. $^1$H NMR (600 MHz, DMSO-$d_6$): δ 9.10 (s, 1H), 8.25 (s, 1H), 7.68 (br s, 1H), 7.54-7.48 (m, 2H), 7.15 (br s, 1H), 7.08-7.00 (m, 2H), 4.55-4.45 (m, 1H), 4.15-3.90 (m, 2H), 3.60-3.50 (m, 1H), 3.29-2.75 (m, 2H), 2.20-2.10 (m, 1H), 1.85-1.73 (m, 1H), 1.37 (s, 9H).

The following examples shown in TABLE 3 were prepared according to Scheme #19 following similar procedures described for Examples #2-1, which can be achieved by those of ordinary skill in the art of organic synthesis utilizing but not limited to the intermediates described above.

TABLE 3

| Example | Structure | IUPAC Name | Exact Mass [M + H]$^+$ |
|---|---|---|---|
| 2-2 | 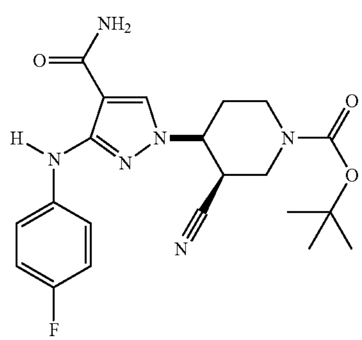 | (3R,4S and 3S,4R)-tert-butyl 4-(4-carbamoyl-3-((4-fluorophenyl)amino)-1H-pyrazol-1-yl)-3-cyanopiperidine-1-carboxylate | Calc'd 429, Found 429 |
| 2-3 | 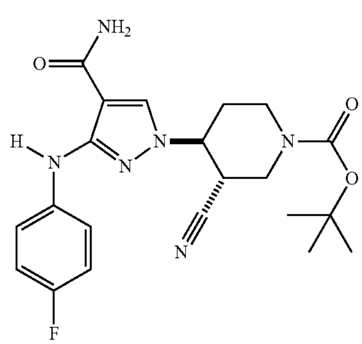 | (3S,4S and 3R,4R)-tert-butyl 4-(4-carbamoyl-3-((4-fluorophenyl)amino)-1H-pyrazol-1-yl)-3-cyanopiperidine-1-carboxylate | Calc'd 429, Found 429 |

Scheme #23

Example #3-1

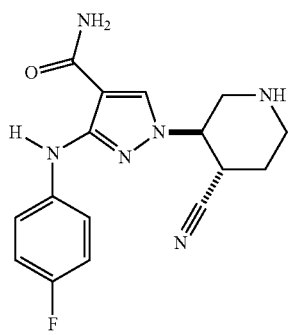

1-[(3R,4S and 3S,4R)-4-cyanopiperidin-3-yl]-3-[(4-fluorophenyl)amino]-1H-pyrazole-4-carboxamide Trifluoroacetic acid (0.360 mL, 4.67 mmol) was added to a solution of tert-butyl (3R,4S and 3S,4R)-3-{4-carbamoyl-3-[(4-fluorophenyl)amino]-1H-pyrazol-1-yl}-4-cyanopiperidine-1-carboxylate (Example #2-1, 100 mg, 0.233 mmol) in DCM (2.26 mL) at ambient temperature. The reaction mixture was allowed to stir for 18 hours. Excess reagent and solvent were removed in vacuo to afford the title compound as a TFA salt. $^1$HNMR (500 MHz, CD$_3$OD): δ 9.22 (br s, 1H), 9.15 (s, 1H), 8.87 (br s, 1H), 8.31 (s, 1H), 7.71 (br s, 1H), 7.54-7.51 (m, 2H), 7.23 (br s, 1H), 7.06-7.03 (m, 2H), 4.66-4.61 (m, 1H), 3.75-3.71 (m, 1H), 3.62-3.59 (m, 1H), 3.38-3.33 (m, 2H), 3.13-3.08 (m, 1H), 2.40-2.34 (m, 1H), 2.07-1.99 (m, 1H). LRMS (ESI) calc'd for C$_{16}$H$_{18}$FN$_6$O [M+H]$^+$: 329. Found: 329.

The following examples shown in TABLE 4 were prepared according to Scheme #23 following similar procedures described for Example #3-1, which can be achieved by those of ordinary skill in the art of organic synthesis utilizing but not limited to the intermediates described above.

TABLE 4

| Example Number | Structure | IUPAC Name | Exact Mass [M + H]+ |
| --- | --- | --- | --- |
| 3-2 | 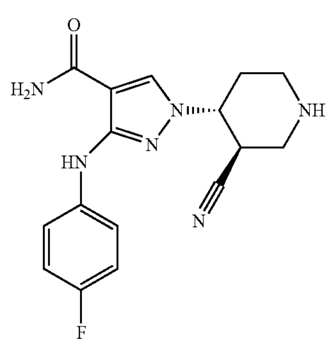 [SMILES: N#C[C@@H]1CNCC[C@H]1n1cc(C(N)=O)c(Nc2ccc(F)cc2)n1] | 1-[(3R,4R and 3S,4S)-3-cyanopiperidin-4-yl]-3-[(4-fluorophenyl)amino]-1H-pyrazole-4-carboxamide | Calc'd 329, found 329 |
| 3-3 | 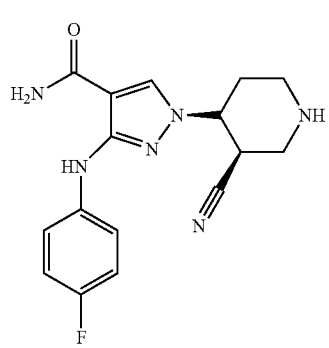 | 1-[(3R,4R and 3S,4S)-3-cyanopiperidin-4-yl]-3-[(4-fluorophenyl)amino]-1H-pyrazole-4-carboxamide | Calc'd 329, found 329 |

Scheme #24

Example #4

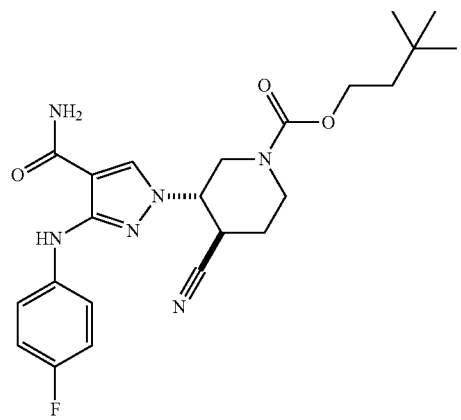

3,3-Dimethylbutyl(3S,4R and 3R,4S)-3-{4-carbamoyl-3-[(4-fluorophenyl)amino]-1H-pyrazol-1-yl}-4-cyanopiperidine-1-carboxylate To a solution of 3,3-dimethyl-1-butanol (10 mg, 0.097 mmol) in THF (0.48 mL) at ambient temperature was added TEA (0.041 mL, 0.29 mmol). To this reaction mixture, phosgene (0.083 mL, 0.15 mmol, 20% in toluene) was quickly added. The reaction mixture was heated to 85° C. and allowed to stir for 15 minutes, then 1-[(3S,4R and 3R,4S)-3-{4-carbamoyl-3-[(4-fluorophenyl)amino]-1H-pyrazol-1-yl}-4-cyanopiperidinium trifluoroacetate (Example #3-1, 30 mg, 0.068 mmol) was added. The mixture was allowed to stir at 85° C. for 18 hours. The mixture was then cooled to ambient temperature and concentrated in vacuo. The residue was dissolved in DMSO and purified by reverse-phase preparative HPLC (MeCN/water, with 0.1% v/v TFA modifier) to afford the title compound. LRMS (ESI) calc'd for $C_{23}H_{29}FN_6O_3$ [M+H]+: 457. Found: 457.

Scheme #24

Example #5-1

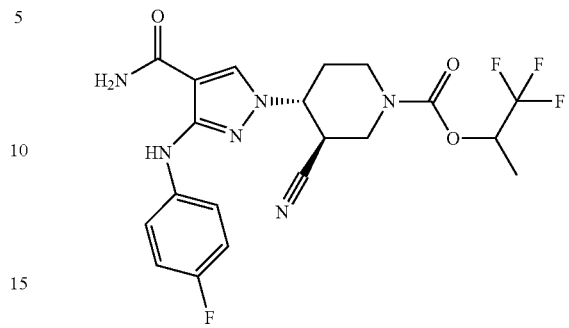

2,2,2-Trifluoro-1-methylethyl(3R,4R and 3S,4S)-4-{4-carbamoyl-3-[(4-fluorophenyl)amino]-1H-pyrazol-1-yl}-3-cyanopiperidine-1-carboxylate Triethylamine (0.10 mL, 0.72 mmol) was added to a solution of 1,1,1-trifluoro-2-propanol (21 mg, 0.18 mmol) and N,N'-dissuccinimidyl carbonate (46 mg, 0.18 mmol) in DMSO (0.45 mL) at ambient temperature. The reaction mixture was stirred at ambient temperature for 8 hours. 1-[(3R,4R and 3S,4S)-3-cyanopiperidin-4-yl]-3-[(4-fluorophenyl)amino]-1H-pyrazole-4-carboxamide (Example 3-2, 56 mg, 0.09 mmol) was added to the reaction mixture and stirred for 15 hours. Samples were diluted to 1 mL of DMSO and purified by mass-triggered reverse phased chromatography to afford the title compound as a TFA salt. $^1$HNMR (500 MHz, CD$_3$OD): δ 9.08 (s, 1H), 8.24 (s, 1H), 7.65 (br s, 1H), 7.51-7.49 (m, 2H), 7.15 (br s, 1H), 7.03 (br m, 2H), 5.36-5.34 (m, 1H), 4.67 (br s, 1H), 4.32 (br s, 1H), 4.03-4.01 (br m, 1H), 3.11 (br s, 1H), 2.51-2.47 (m, 2H), 2.03 (br m, 1H), 1.94 (br m, 1H), 1.37 (d, J=5.5 Hz, 3H). LRMS (ESI) calc'd for $C_{20}H_{21}F_4N_6O_3$ [M+H]+: 469. Found: 469.

The following examples shown in TABLE 5 were prepared according to Scheme #24 following similar procedures described for Example #5-1, which can be achieved by those of ordinary skill in the art of organic synthesis utilizing but not limited to the intermediates described above.

TABLE 5

| Example | Structure | IUPAC Name | Exact Mass [M + H]+ |
|---|---|---|---|
| 5-2 | ![structure] | 2-fluoroethyl (3R,4R and 3S,4S)-4-{4-carbamoyl-3-[(4-fluorophenyl)amino]-1H-pyrazol-1-yl}-3-cyanopiperidine-1-carboxylate | Calc'd 419, found 419 |

TABLE 5-continued

| Example | Structure | IUPAC Name | Exact Mass [M + H]+ |
|---|---|---|---|
| 5-3 | 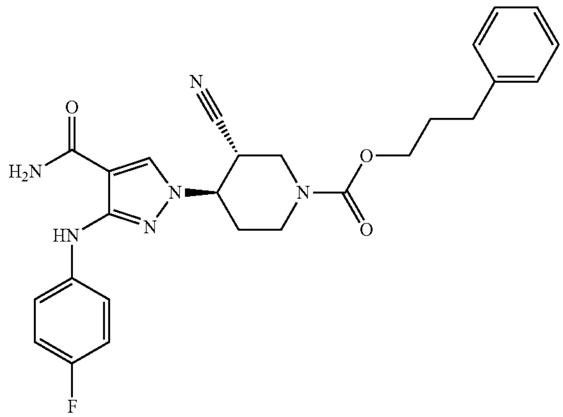 [SMILES: N#C[C@@H]1CN(C(=O)OCCCc2ccccc2)CC[C@H]1n1cc(C(N)=O)c(Nc2ccc(F)cc2)n1] | 3-phenylpropyl (3R,4R and 3S,4S)-4-{4-carbamoyl-3-[(4-fluorophenyl)amino]-1H-pyrazol-1-yl}-3-cyanopiperidine-1-carboxylate | Calc'd 491, found 491 |
| 5-4 | 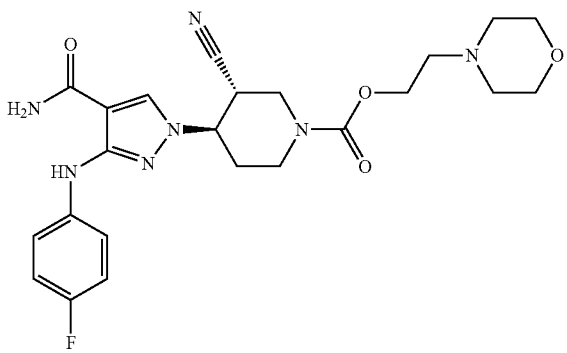 [SMILES: N#C[C@@H]1CN(C(=O)OCCN2CCOCC2)CC[C@H]1n1cc(C(N)=O)c(Nc2ccc(F)cc2)n1] | 2-morpholin-4-ylethyl (3R,4R and 3S,4S)-4-{4-carbamoyl-3-[(4-fluorophenyl)amino]-1H-pyrazol-1-yl}-3-cyanopiperidine-1-carboxylate | Calc'd 486, found 486 |
| 5-5 | 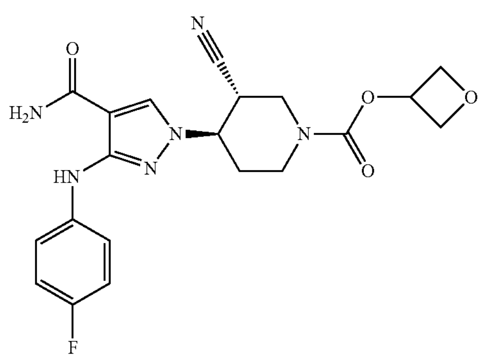 [SMILES: N#C[C@@H]1CN(C(=O)OC2COC2)CC[C@H]1n1cc(C(N)=O)c(Nc2ccc(F)cc2)n1] | oxetan-3-yl (3R,4R and 3S,4S)-4-{4-carbamoyl-3-[(4-fluorophenyl)amino]-1H-pyrazol-1-yl}-3-cyanopiperidine-1-carboxylate | Calc'd 429, found 429 |
| 5-6 | 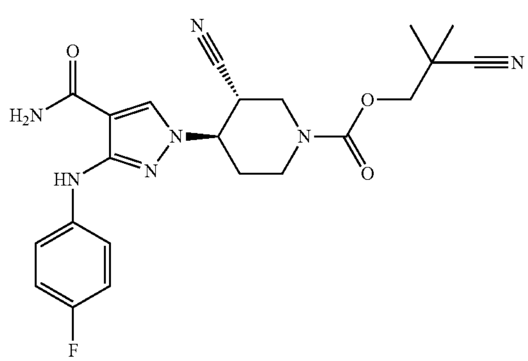 [SMILES: CC(C)(C#N)COC(=O)N1CC[C@@H](n2cc(C(N)=O)c(Nc3ccc(F)cc3)n2)[C@H](C#N)C1] | 2-cyano-2-methylpropyl (3R,4R and 3S,4S)-4-{4-carbamoyl-3-[(4-fluorophenyl)amino]-1H-pyrazol-1-yl}-3-cyanopiperidine-1-carboxylate | Calc'd 454, found 454 |

TABLE 5-continued

| Example | Structure | IUPAC Name | Exact Mass [M + H]+ |
|---|---|---|---|
| 5-7 | 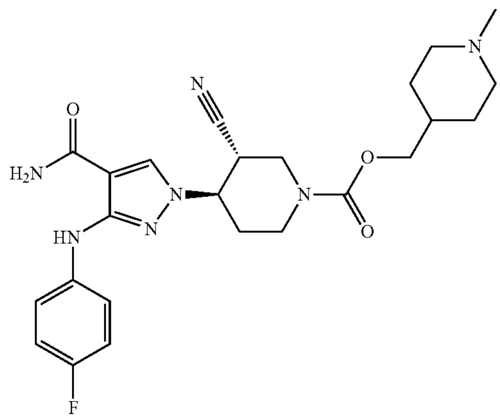 [SMILES: CN1CCC(COC(=O)N2CC[C@@H](n3cc(C(N)=O)c(Nc4ccc(F)cc4)n3)[C@H](C#N)C2)CC1] | (1-methylpiperidin-4-yl)methyl (3R,4R and 3S,4S)-4-{4-carbamoyl-3-[(4-fluorophenyl)amino]-1H-pyrazol-1-yl}-3-cyanopiperidine-1-carboxylate | Calc'd 484, found 484 |
| 5-8 | 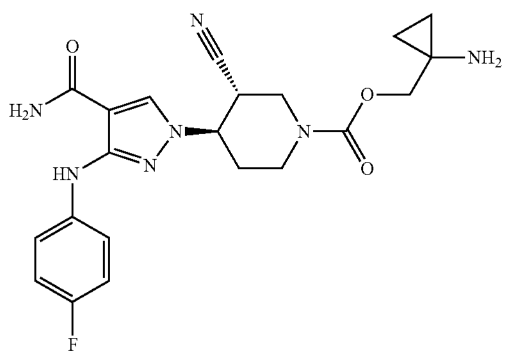 [SMILES: N#C[C@@H]1CN(C(=O)OCC2(N)CC2)CC[C@H]1n1cc(C(N)=O)c(Nc2ccc(F)cc2)n1] | (1-aminocyclopropyl)methyl (3R,4R and 3S,4S)-4-{4-carbamoyl-3-[(4-fluorophenyl)amino]-1H-pyrazol-1-yl}-3-cyanopiperidine-1-carboxylate | Calc'd 442, found 442 |
| 5-9 | 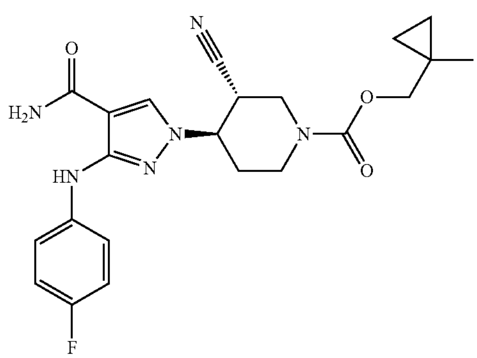 [SMILES: CC1(COC(=O)N2CC[C@@H](n3cc(C(N)=O)c(Nc4ccc(F)cc4)n3)[C@H](C#N)C2)CC1] | (1-methylcyclopropyl)methyl (3R,4R and 3S,4S)-4-{4-carbamoyl-3-[(4-fluorophenyl)amino]-1H-pyrazol-1-yl}-3-cyanopiperidine-1-carboxylate | Calc'd 441, found 441 |
| 5-10 | 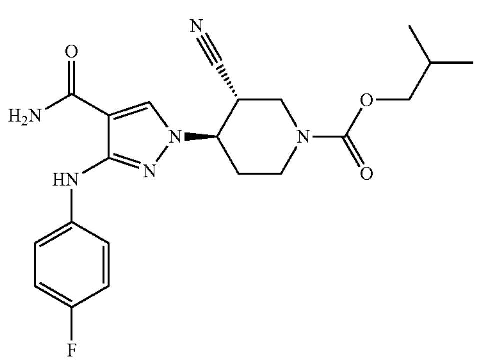 [SMILES: CC(C)COC(=O)N1CC[C@@H](n2cc(C(N)=O)c(Nc3ccc(F)cc3)n2)[C@H](C#N)C1] | 2-methylpropyl (3R,4R and 3S,4S)-4-{4-carbamoyl-3-[(4-fluorophenyl)amino]-1H-pyrazol-1-yl}-3-cyanopiperidine-1-carboxylate | Calc'd 429, found 429 |

TABLE 5-continued

| Example | Structure | IUPAC Name | Exact Mass [M + H]+ |
|---|---|---|---|
| 5-11 | 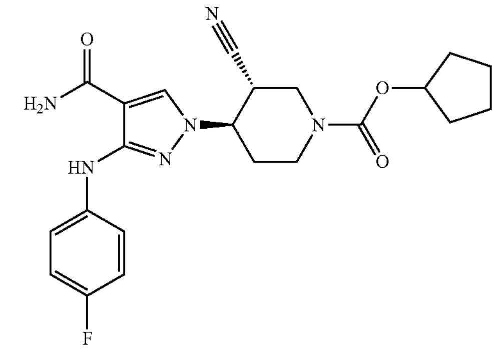 [SMILES: N#C[C@@H]1CN(C(=O)OC2CCCC2)CC[C@H]1n1cc(C(N)=O)c(Nc2ccc(F)cc2)n1] | cyclopentyl (3R,4R and 3S,4S)-4-{4-carbamoyl-3-[(4-fluorophenyl)amino]-1H-pyrazol-1-yl}-3-cyanopiperidine-1-carboxylate | Calc'd 441, found 441 |
| 5-12 | 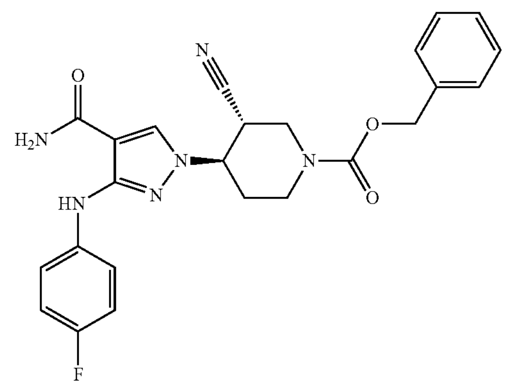 [SMILES: N#C[C@@H]1CN(C(=O)OCc2ccccc2)CC[C@H]1n1cc(C(N)=O)c(Nc2ccc(F)cc2)n1] | benzyl (3R,4R and 3S,4S)-4-{4-carbamoyl-3-[(4-fluorophenyl)amino]-1H-pyrazol-1-yl}-3-cyanopiperidine-1-carboxylate | Calc'd 463, found 463 |
| 5-13 | 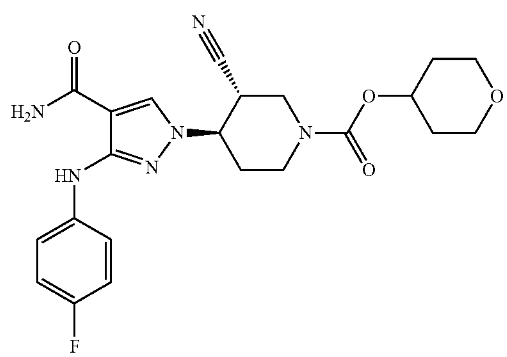 [SMILES: N#C[C@@H]1CN(C(=O)OC2CCOCC2)CC[C@H]1n1cc(C(N)=O)c(Nc2ccc(F)cc2)n1] | tetrahydro-2H-pyran-4-yl (3R,4R and 3S,4S)-4-{4-carbamoyl-3-[(4-fluorophenyl)amino]-1H-pyrazol-1-yl}-3-cyanopiperidine-1-carboxylate | Calc'd 457, found 457 |
| 5-14 | 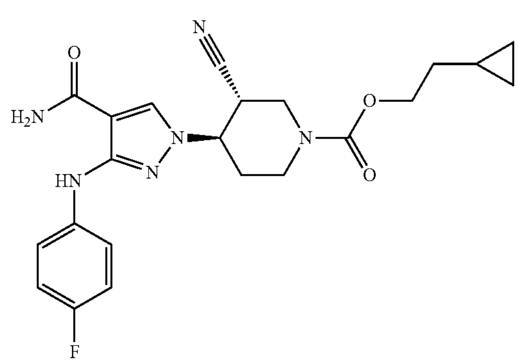 [SMILES: N#C[C@@H]1CN(C(=O)OCCC2CC2)CC[C@H]1n1cc(C(N)=O)c(Nc2ccc(F)cc2)n1] | 2-cyclopropylethyl (3R,4R and 3S,4S)-4-{4-carbamoyl-3-[(4-fluorophenyl)amino]-1H-pyrazol-1-yl}-3-cyanopiperidine-1-carboxylate | Calc'd 441, found 441 |

TABLE 5-continued

| Example | Structure | IUPAC Name | Exact Mass [M + H]+ |
|---|---|---|---|
| 5-15 | 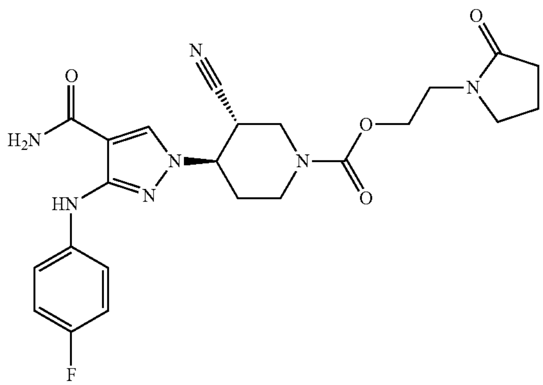 [SMILES: N#C[C@@H]1CN(C(=O)OCCN2CCCC2=O)CC[C@H]1n1cc(C(N)=O)c(Nc2ccc(F)cc2)n1] | 2-(2-oxopyrrolidin-1-yl)ethyl (3R,4R and 3S,4S)-4-{4-carbamoyl-3-[(4-fluorophenyl)amino]-1H-pyrazol-1-yl}-3-cyanopiperidine-1-carboxylate | Calc'd 484, found 484 |
| 5-16 | 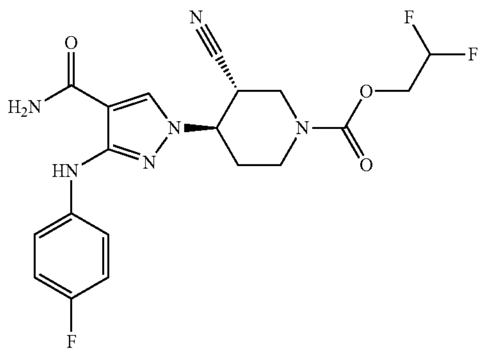 [SMILES: N#C[C@@H]1CN(C(=O)OCC(F)F)CC[C@H]1n1cc(C(N)=O)c(Nc2ccc(F)cc2)n1] | 2,2-difluoroethyl (3R,4R and 3S,4S)-4-{4-carbamoyl-3-[(4-fluorophenyl)amino]-1H-pyrazol-1-yl}-3-cyanopiperidine-1-carboxylate | Calc'd 437, found 437 |
| 5-17 | 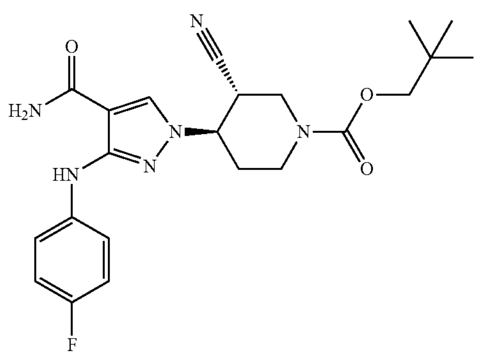 [SMILES: CC(C)(C)COC(=O)N1CC[C@@H](n2cc(C(N)=O)c(Nc3ccc(F)cc3)n2)[C@H](C#N)C1] | cyclohexyl (3R,4R and 3S,4S)-4-{4-carbamoyl-3-[(4-fluorophenyl)amino]-1H-pyrazol-1-yl}-3-cyanopiperidine-1-carboxylate | Calc'd 455, found 455 |
| 5-18 | 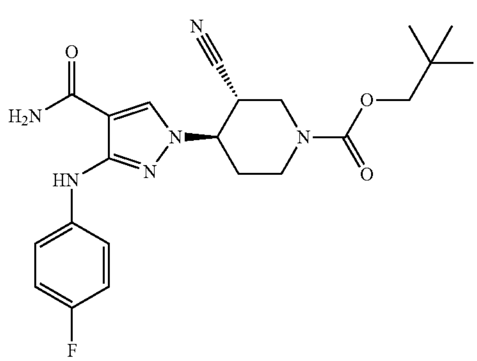 [SMILES: CC(C)(C)COC(=O)N1CC[C@@H](n2cc(C(N)=O)c(Nc3ccc(F)cc3)n2)[C@H](C#N)C1] | 2,2-dimethylpropyl (3R,4R and 3S,4S)-4-{4-carbamoyl-3-[(4-fluorophenyl)amino]-1H-pyrazol-1-yl}-3-cyanopiperidine-1-carboxylate | Calc'd 443, found 443 |

TABLE 5-continued

| Example | Structure | IUPAC Name | Exact Mass [M + H]+ |
|---|---|---|---|
| 5-19 | 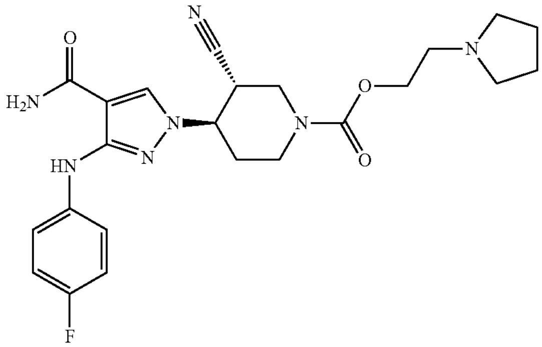 [SMILES: N#C[C@@H]1CN(C(=O)OCCN2CCCC2)CC[C@H]1n1cc(C(N)=O)c(Nc2ccc(F)cc2)n1] | 2-pyrrolidin-1-ylethyl (3R,4R and 3S,4S)-4-{4-carbamoyl-3-[(4-fluorophenyl)amino]-1H-pyrazol-1-yl}-3-cyanopiperidine-1-carboxylate | Calc'd 470, found 470 |
| 5-20 | 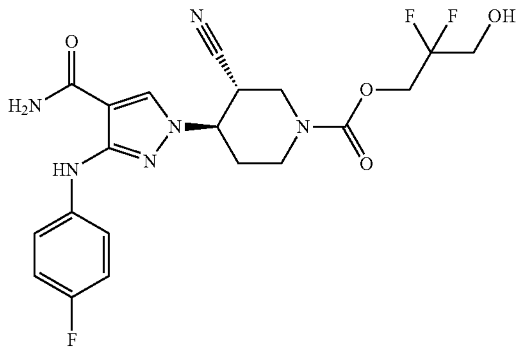 [SMILES: N#C[C@@H]1CN(C(=O)OCC(F)(F)CO)CC[C@H]1n1cc(C(N)=O)c(Nc2ccc(F)cc2)n1] | 2,2-difluoro-3-hydroxypropyl (3R,4R and 3S,4S)-4-{4-carbamoyl-3-[(4-fluorophenyl)amino]-1H-pyrazol-1-yl}-3-cyanopiperidine-1-carboxylate | Calc'd 467, found 467 |
| 5-21 | 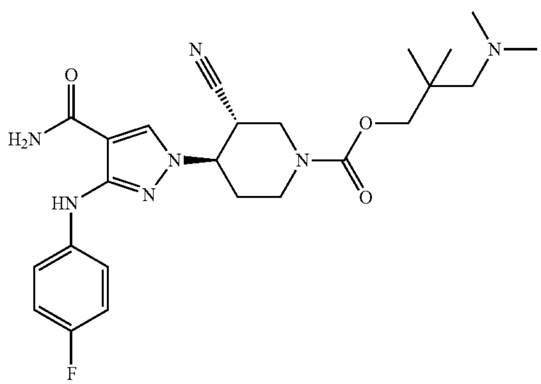 [SMILES: CN(C)CC(C)(C)COC(=O)N1CC[C@@H](n2cc(C(N)=O)c(Nc3ccc(F)cc3)n2)[C@H](C#N)C1] | 3-(dimethylamino)-2,2-dimethylpropyl (3R,4R and 3S,4S)-4-{4-carbamoyl-3-[(4-fluorophenyl)amino]-1H-pyrazol-1-yl}-3-cyanopiperidine-1-carboxylate | Calc'd 486, found 486 |
| 5-22 | 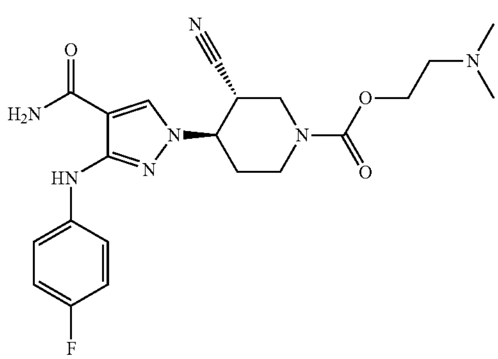 [SMILES: CN(C)CCOC(=O)N1CC[C@@H](n2cc(C(N)=O)c(Nc3ccc(F)cc3)n2)[C@H](C#N)C1] | 2-(dimethylamino)ethyl (3R,4R and 3S,4S)-4-{4-carbamoyl-3-[(4-fluorophenyl)amino]-1H-pyrazol-1-yl}-3-cyanopiperidine-1-carboxylate | Calc'd 444, found 444 |

TABLE 5-continued

| Example | Structure | IUPAC Name | Exact Mass [M + H]+ |
|---|---|---|---|
| 5-23 | 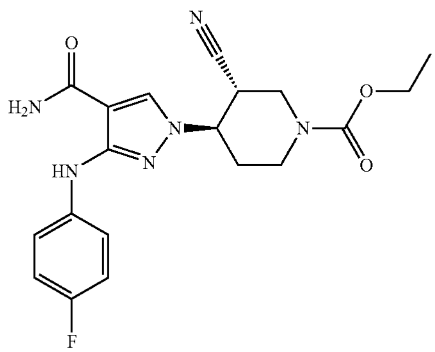 [SMILES: CCOC(=O)N1CC[C@@H](n2cc(C(N)=O)c(Nc3ccc(F)cc3)n2)[C@H](C#N)C1] | ethyl (3R,4R and 3S,4S)-4-{4-carbamoyl-3-[(4-fluorophenyl)amino]-1H-pyrazol-1-yl}-3-cyanopiperidine-1-carboxylate | Calc'd 401, found 401 |
| 5-24 | 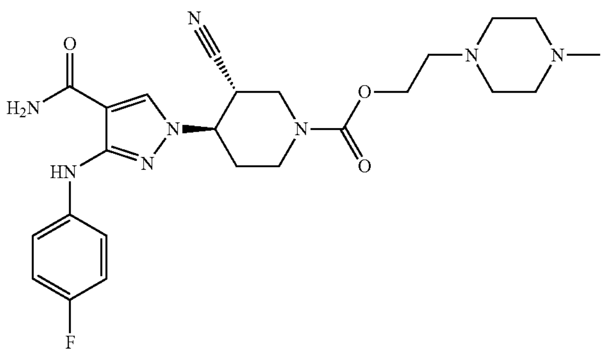 [SMILES: CN1CCN(CCOC(=O)N2CC[C@@H](n3cc(C(N)=O)c(Nc4ccc(F)cc4)n3)[C@H](C#N)C2)CC1] | 2-(4-methylpiperazin-1-yl)ethyl (3R,4R and 3S,4S)-4-{4-carbamoyl-3-[(4-fluorophenyl)amino]-1H-pyrazol-1-yl}-3-cyanopiperidine-1-carboxylate | Calc'd 499, found 499 |
| 5-25 | 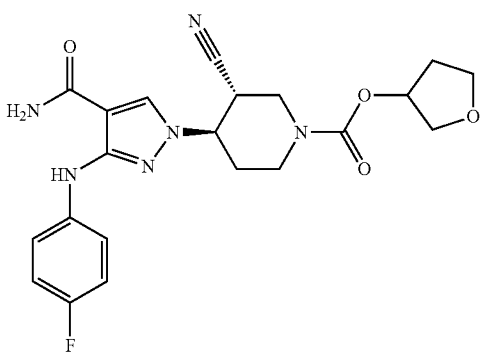 [SMILES: N#C[C@@H]1CN(C(=O)OC2CCOC2)CC[C@H]1n1cc(C(N)=O)c(Nc2ccc(F)cc2)n1] | tetrahydrofuran-3-yl (3R,4R and 3S,4S)-4-{4-carbamoyl-3-[(4-fluorophenyl)amino]-1H-pyrazol-1-yl}-3-cyanopiperidine-1-carboxylate | Calc'd 443, found 443 |
| 5-26 | 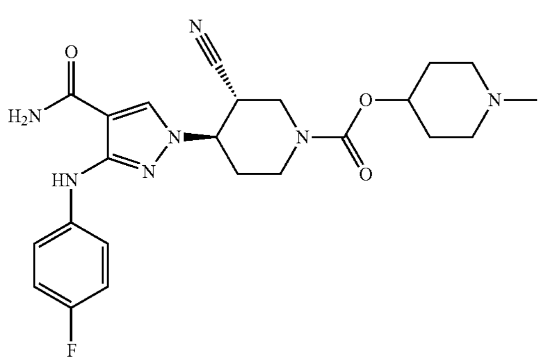 [SMILES: CN1CCC(OC(=O)N2CC[C@@H](n3cc(C(N)=O)c(Nc4ccc(F)cc4)n3)[C@H](C#N)C2)CC1] | 1-methylpiperidin-4-yl (3R,4R and 3S,4S)-4-{4-carbamoyl-3-[(4-fluorophenyl)amino]-1H-pyrazol-1-yl}-3-cyanopiperidine-1-carboxylate | Calc'd 470, found 470 |

TABLE 5-continued

| Example | Structure | IUPAC Name | Exact Mass [M + H]+ |
|---|---|---|---|
| 5-27 | 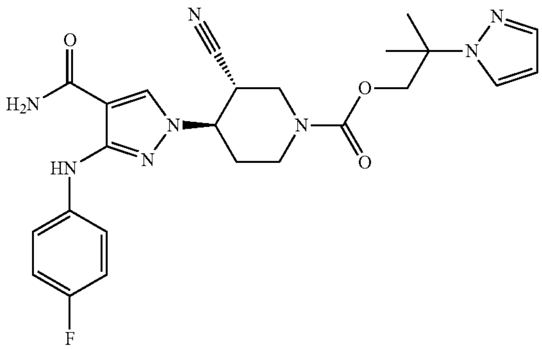 [SMILES: CC(C)(COC(=O)N1CC[C@@H](n2cc(C(N)=O)c(Nc3ccc(F)cc3)n2)[C@H](C#N)C1)n1cccn1] | 2-methyl-2-(1H-pyrazol-1-yl)propyl (3R,4R and 3S,4S)-4-{4-carbamoyl-3-[(4-fluorophenyl)amino]-1H-pyrazol-1-yl}-3-cyanopiperidine-1-carboxylate | Calc'd 495, found 495 |
| 5-28 | 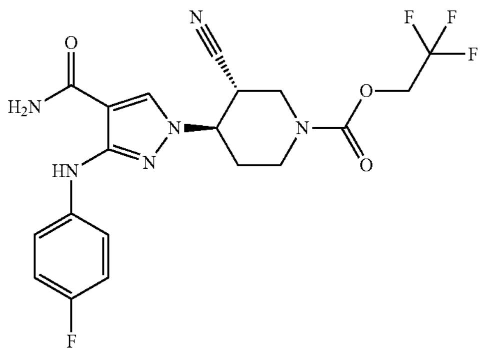 [SMILES: N#C[C@@H]1CN(C(=O)OCC(F)(F)F)CC[C@H]1n1cc(C(N)=O)c(Nc2ccc(F)cc2)n1] | 2,2,2-trifluoroethyl (3R,4R and 3S,4S)-4-{4-carbamoyl-3-[(4-fluorophenyl)amino]-1H-pyrazol-1-yl}-3-cyanopiperidine-1-carboxylate | Calc'd 455, found 455 |
| 5-29 | 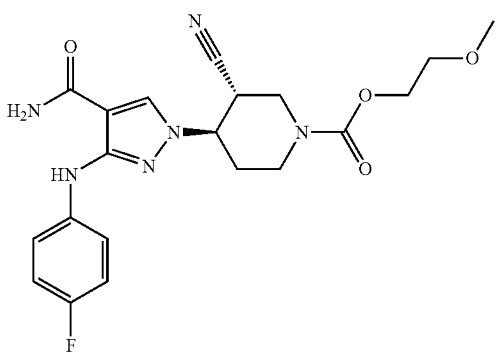 [SMILES: COCCOC(=O)N1CC[C@@H](n2cc(C(N)=O)c(Nc3ccc(F)cc3)n2)[C@H](C#N)C1] | 2-methoxyethyl (3R,4R and 3S,4S)-4-{4-carbamoyl-3-[(4-fluorophenyl)amino]-1H-pyrazol-1-yl}-3-cyanopiperidine-1-carboxylate | Calc'd 431, found 431 |
| 5-30 | 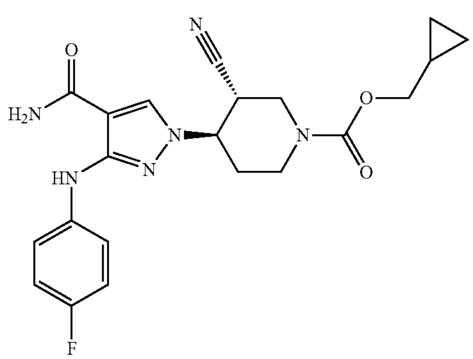 [SMILES: N#C[C@@H]1CN(C(=O)OCC2CC2)CC[C@H]1n1cc(C(N)=O)c(Nc2ccc(F)cc2)n1] | cyclopropylmethyl (3R,4R and 3S,4S)-4-{4-carbamoyl-3-[(4-fluorophenyl)amino]-1H-pyrazol-1-yl}-3-cyanopiperidine-1-carboxylate | Calc'd 427, found 427 |

TABLE 5-continued

| Example | Structure | IUPAC Name | Exact Mass [M + H]+ |
|---|---|---|---|
| 5-31 | 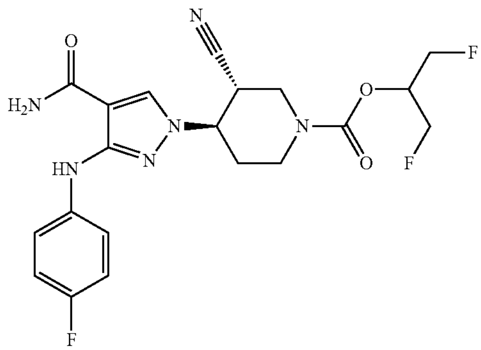 [SMILES: N#C[C@@H]1CN(C(=O)OC(CF)CF)CC[C@H]1n1cc(C(N)=O)c(Nc2ccc(F)cc2)n1] | 2-fluoro-1-(fluoromethyl)ethyl (3R,4R and 3S,4S)-4-{4-carbamoyl-3-[(4-fluorophenyl)amino]-1H-pyrazol-1-yl}-3-cyanopiperidine-1-carboxylate | Calc'd 451, found 451 |
| 5-32 | 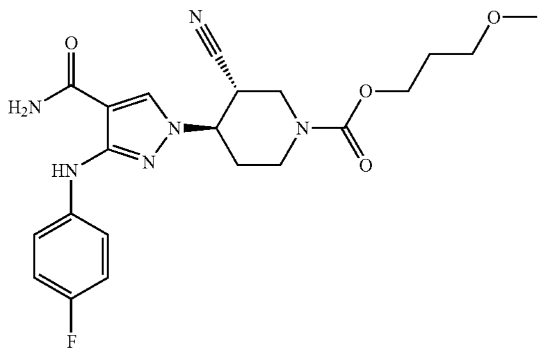 [SMILES: COCCCOC(=O)N1CC[C@@H](n2cc(C(N)=O)c(Nc3ccc(F)cc3)n2)[C@H](C#N)C1] | 3-methoxypropyl (3R,4R and 3S,4S)-4-{4-carbamoyl-3-[(4-fluorophenyl)amino]-1H-pyrazol-1-yl}-3-cyanopiperidine-1-carboxylate | Calc'd 445, found 445 |
| 5-33 | 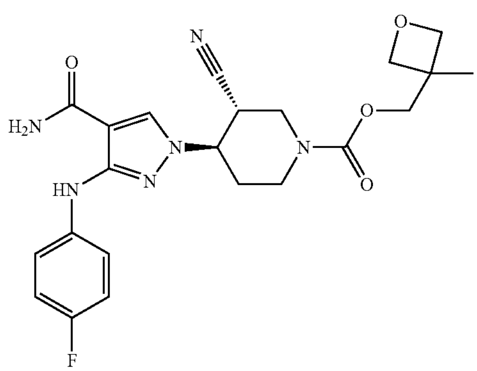 [SMILES: CC1(COC(=O)N2CC[C@@H](n3cc(C(N)=O)c(Nc4ccc(F)cc4)n3)[C@H](C#N)C2)COC1] | (3-methyloxetan-3-yl)methyl (3R,4R and 3S,4S)-4-{4-carbamoyl-3-[(4-fluorophenyl)amino]-1H-pyrazol-1-yl}-3-cyanopiperidine-1-carboxylate | Calc'd 457, found 457 |
| 5-34 | 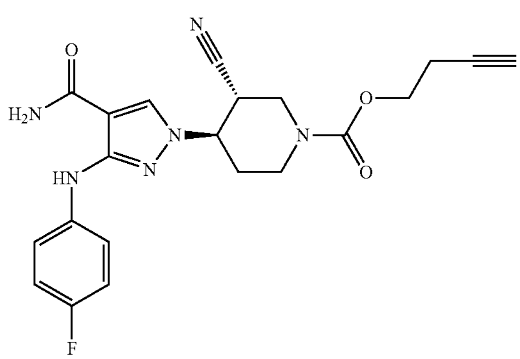 [SMILES: C#CCCOC(=O)N1CC[C@@H](n2cc(C(N)=O)c(Nc3ccc(F)cc3)n2)[C@H](C#N)C1] | but-3-yn-1-yl (3R,4R and 3S,4S)-4-{4-carbamoyl-3-[(4-fluorophenyl)amino]-1H-pyrazol-1-yl}-3-cyanopiperidine-1-carboxylate | Calc'd 425, found 425 |

TABLE 5-continued

| Example | Structure | IUPAC Name | Exact Mass [M + H]+ |
|---|---|---|---|
| 5-35 | 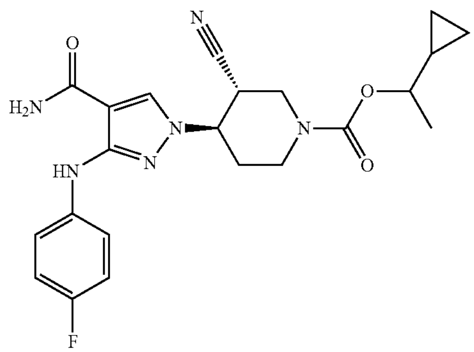 [SMILES: CC(OC(=O)N1CC[C@@H](n2cc(C(N)=O)c(Nc3ccc(F)cc3)n2)[C@H](C#N)C1)C1CC1] | 1-cyclopropylethyl (3R,4R and 3S,4S)-4-{4-carbamoyl-3-[(4-fluorophenyl)amino]-1H-pyrazol-1-yl}-3-cyanopiperidine-1-carboxylate | Calc'd 441, found 441 |
| 5-36 | 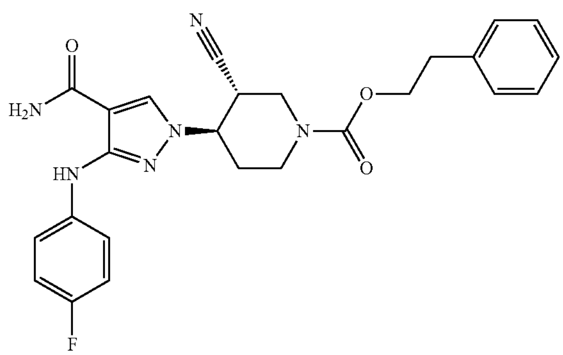 [SMILES: N#C[C@@H]1CN(C(=O)OCCc2ccccc2)CC[C@H]1n1cc(C(N)=O)c(Nc2ccc(F)cc2)n1] | 2-phenylethyl (3R,4R and 3S,4S)-4-{4-carbamoyl-3-[(4-fluorophenyl)amino]-1H-pyrazol-1-yl}-3-cyanopiperidine-1-carboxylate | Calc'd 477, found 477 |
| 5-37 | 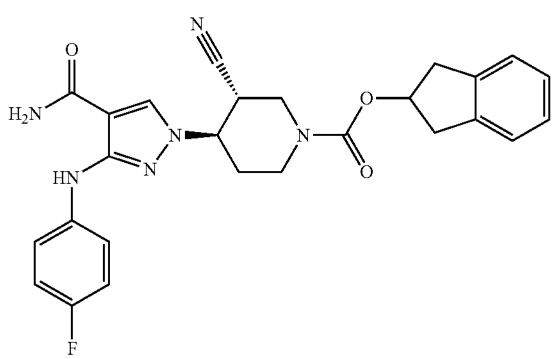 [SMILES: N#C[C@@H]1CN(C(=O)OC2Cc3ccccc3C2)CC[C@H]1n1cc(C(N)=O)c(Nc2ccc(F)cc2)n1] | 2,3-dihydro-1H-inden-2-yl (3R,4R and 3S,4S)-4-{4-carbamoyl-3-[(4-fluorophenyl)amino]-1H-pyrazol-1-yl}-3-cyanopiperidine-1-carboxylate | Calc'd 489, found 489 |
| 5-38 | 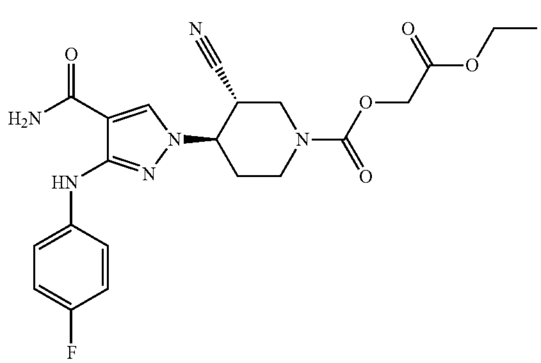 [SMILES: CCOC(=O)COC(=O)N1CC[C@@H](n2cc(C(N)=O)c(Nc3ccc(F)cc3)n2)[C@H](C#N)C1] | 2-ethoxy-2-oxoethyl (3R,4R and 3S,4S)-4-{4-carbamoyl-3-[(4-fluorophenyl)amino]-1H-pyrazol-1-yl}-3-cyanopiperidine-1-carboxylate | Calc'd 459, found 459 |

TABLE 5-continued

| Example | Structure | IUPAC Name | Exact Mass [M + H]+ |
|---|---|---|---|
| 5-39 | 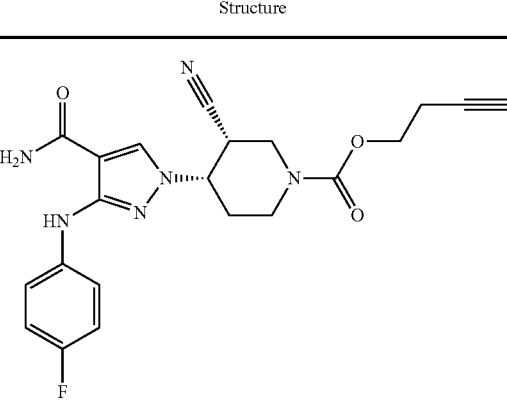 | [1-(cyanomethyl)cyclopropyl]methyl (3R,4R and 3S,4S)-4-{4-carbamoyl-3-[(4-fluorophenyl)amino]-1H-pyrazol-1-yl}-3-cyanopiperidine-1-carboxylate | Calc'd 466, found 466 |

The following examples shown in TABLE 6 were prepared according to Scheme #24 following similar procedures described for Example #5-1, which can be achieved by those of ordinary skill in the art of organic synthesis utilizing but not limited to the intermediates described above.

TABLE 6

| Example | Structure | IUPAC Name | Exact Mass [M + H]+ |
|---|---|---|---|
| 5-40 | 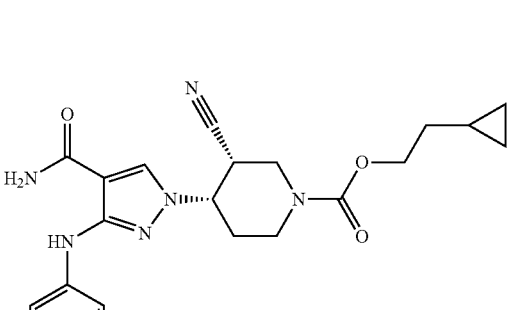 | but-3-yn-1-yl (3R,4S and 3S,4R)-4-{4-carbamoyl-3-[(4-fluorophenyl)amino]-1H-pyrazol-1-yl}-3-cyanopiperidine-1-carboxylate | Calc'd 425, found 425 |
| 5-41 | 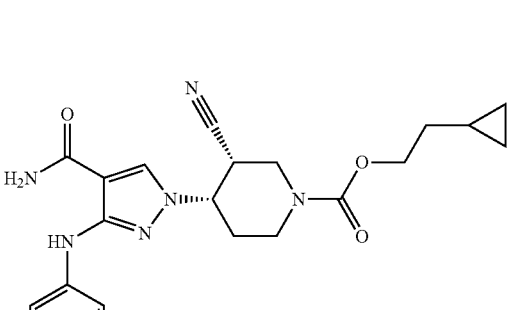 | 2-cyclopropylethyl (3R,4S and 3S,4R)-4-{4-carbamoyl-3-[(4-fluorophenyl)amino]-1H-pyrazol-1-yl}-3-cyanopiperidine-1-carboxylate | Calc'd 441, found 441 |

TABLE 6-continued

| Example | Structure | IUPAC Name | Exact Mass [M + H]+ |
|---|---|---|---|
| 5-42 | 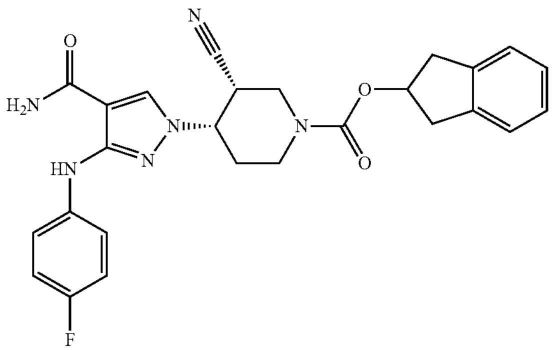 [SMILES: N#C[C@@H]1CN(C(=O)OC2Cc3ccccc3C2)CC[C@@H]1n1cc(C(N)=O)c(Nc2ccc(F)cc2)n1] | 2,3-dihydro-1H-inden-2-yl (3R,4S and 3S,4R)-4-{4-carbamoyl-3-[(4-fluorophenyl)amino]-1H-pyrazol-1-yl}-3-cyanopiperidine-1-carboxylate | Calc'd 489, found 489 |
| 5-43 | 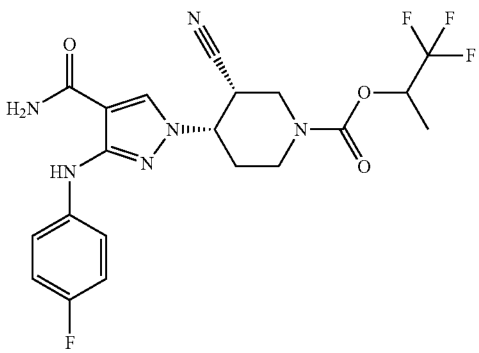 [SMILES: CC(OC(=O)N1CC[C@H](n2cc(C(N)=O)c(Nc3ccc(F)cc3)n2)[C@H](C#N)C1)C(F)(F)F] | 2,2,2-trifluoro-1-methylethyl (3R,4S and 3S,4R)-4-{4-carbamoyl-3-[(4-fluorophenyl)amino]-1H-pyrazol-1-yl}-3-cyanopiperidine-1-carboxylate | Calc'd 469, found 469 |
| 5-44 | 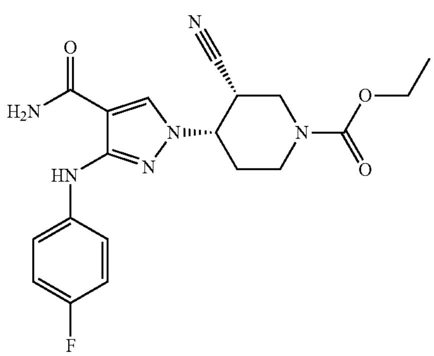 [SMILES: CCOC(=O)N1CC[C@H](n2cc(C(N)=O)c(Nc3ccc(F)cc3)n2)[C@H](C#N)C1] | ethyl (3R,4S and 3S,4R)-4-{4-carbamoyl-3-[(4-fluorophenyl)amino]-1H-pyrazol-1-yl}-3-cyanopiperidine-1-carboxylate | Calc'd 401, found 401 |
| 5-45 | 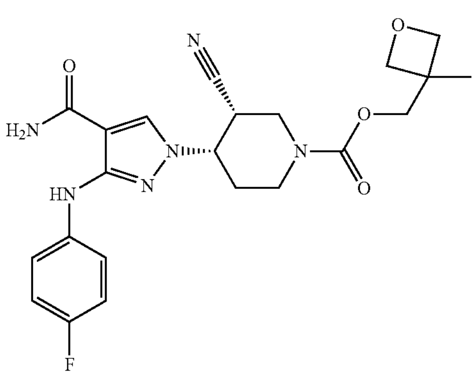 [SMILES: CC1(COC(=O)N2CC[C@H](n3cc(C(N)=O)c(Nc4ccc(F)cc4)n3)[C@H](C#N)C2)COC1] | (3-methyloxetan-3-yl)methyl (3R,4S and 3S,4R)-4-{4-carbamoyl-3-[(4-fluorophenyl)amino]-1H-pyrazol-1-yl}-3-cyanopiperidine-1-carboxylate | Calc'd 457, found 457 |

TABLE 6-continued

| Example | Structure | IUPAC Name | Exact Mass [M + H]+ |
|---|---|---|---|
| 5-46 | 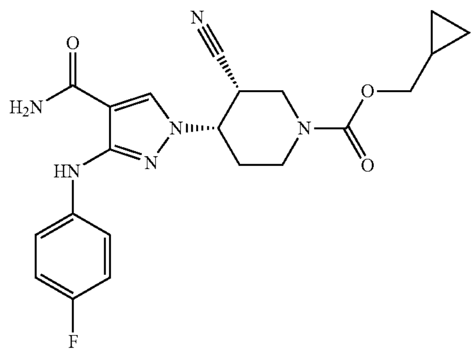 [SMILES: N#C[C@@H]1CN(C(=O)OCC2CC2)CC[C@@H]1n1cc(C(N)=O)c(Nc2ccc(F)cc2)n1] | cyclopropylmethyl (3R,4S and 3S,4R)-4-{4-carbamoyl-3-[(4-fluorophenyl)amino]-1H-pyrazol-1-yl}-3-cyanopiperidine-1-carboxylate | Calc'd 427, found 427 |
| 5-47 | 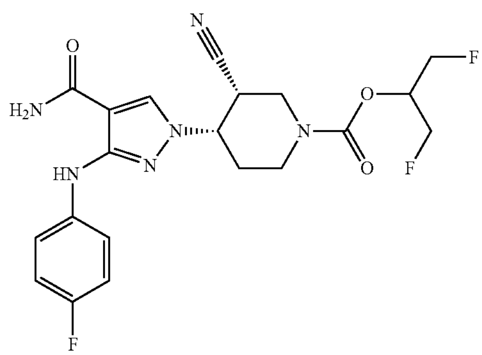 [SMILES: N#C[C@@H]1CN(C(=O)OC(CF)CF)CC[C@@H]1n1cc(C(N)=O)c(Nc2ccc(F)cc2)n1] | 2-fluoro-1-(fluoromethyl)ethyl (3R,4S and 3S,4R)-4-{4-carbamoyl-3-[(4-fluorophenyl)amino]-1H-pyrazol-1-yl}-3-cyanopiperidine-1-carboxylate | Calc'd 451, found 451 |
| 5-48 | 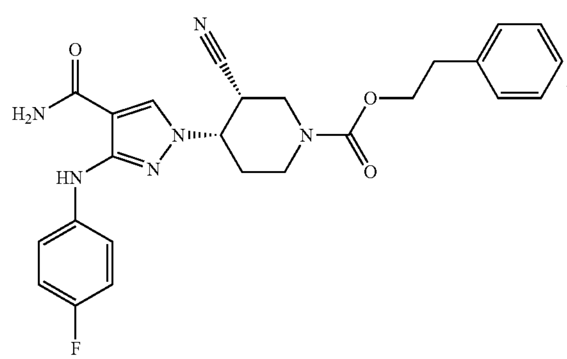 | 2-phenylethyl (3R,4S and 3S,4R)-4-{4-carbamoyl-3-[(4-fluorophenyl)amino]-1H-pyrazol-1-yl}-3-cyanopiperidine-1-carboxylate | Calc'd 477, found 477 |
| 5-49 | 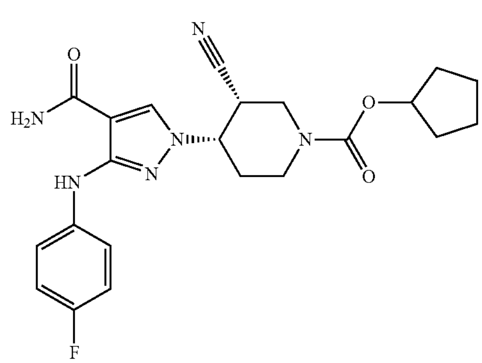 [SMILES: N#C[C@@H]1CN(C(=O)OC2CCCC2)CC[C@@H]1n1cc(C(N)=O)c(Nc2ccc(F)cc2)n1] | cyclopentyl (3R,4S and 3S,4R)-4-{4-carbamoyl-3-[(4-fluorophenyl)amino]-1H-pyrazol-1-yl}-3-cyanopiperidine-1-carboxylate | Calc'd 441, found 441 |

TABLE 6-continued

| Example | Structure | IUPAC Name | Exact Mass [M + H]+ |
|---------|-----------|------------|---------------------|
| 5-50 | 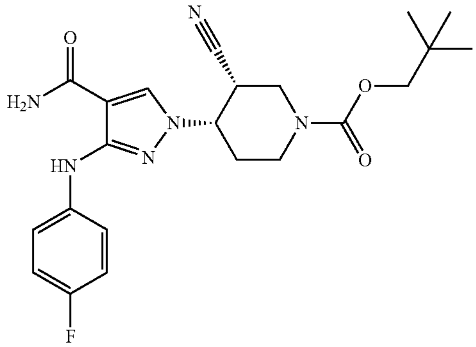 [SMILES: CC(C)(C)COC(=O)N1CC[C@H](n2cc(C(N)=O)c(Nc3ccc(F)cc3)n2)[C@H](C#N)C1] | 2,2-dimethylpropyl (3R,4S and 3S,4R)-4-{4-carbamoyl-3-[(4-fluorophenyl)amino]-1H-pyrazol-1-yl}-3-cyanopiperidine-1-carboxylate | Calc'd 443, found 443 |
| 5-51 | 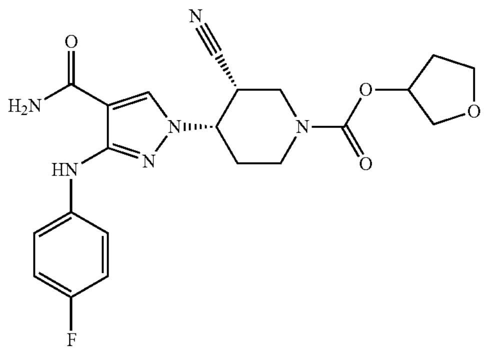 [SMILES: N#C[C@@H]1CN(C(=O)OC2CCOC2)CC[C@@H]1n1cc(C(N)=O)c(Nc2ccc(F)cc2)n1] | tetrahydrofuran-3-yl (3R,4S and 3S,4R)-4-{4-carbamoyl-3-[(4-fluorophenyl)amino]-1H-pyrazol-1-yl}-3-cyanopiperidine-1-carboxylate | Calc'd 443, found 443 |
| 5-52 | 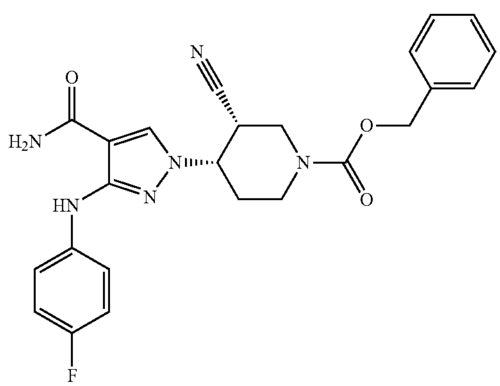 [SMILES: N#C[C@@H]1CN(C(=O)OCc2ccccc2)CC[C@@H]1n1cc(C(N)=O)c(Nc2ccc(F)cc2)n1] | benzyl (3R,4S and 3S,4R)-4-{4-carbamoyl-3-[(4-fluorophenyl)amino]-1H-pyrazol-1-yl}-3-cyanopiperidine-1-carboxylate | Calc'd 463, found 463 |
| 5-53 | 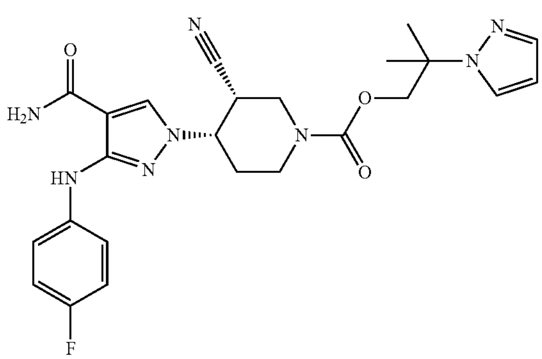 [SMILES: CC(C)(COC(=O)N1CC[C@H](n2cc(C(N)=O)c(Nc3ccc(F)cc3)n2)[C@H](C#N)C1)n1cccn1] | 2-methyl-2-(1H-pyrazol-1-yl)propyl (3R,4S and 3S,4R)-4-{4-carbamoyl-3-[(4-fluorophenyl)amino]-1H-pyrazol-1-yl}-3-cyanopiperidine-1-carboxylate | Calc'd 495, found 495 |

TABLE 6-continued

| Example | Structure | IUPAC Name | Exact Mass [M + H]+ |
|---|---|---|---|
| 5-54 | 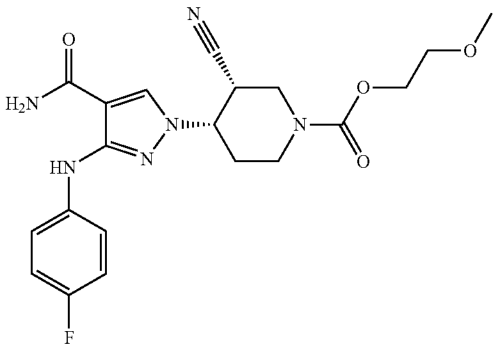 [SMILES: COCCOC(=O)N1CC[C@H](n2cc(C(N)=O)c(Nc3ccc(F)cc3)n2)[C@H](C#N)C1] | 2-methoxyethyl (3R,4S and 3S,4R)-4-{4-carbamoyl-3-[(4-fluorophenyl)amino]-1H-pyrazol-1-yl}-3-cyanopiperidine-1-carboxylate | Calc'd 431, found 431 |
| 5-55 | 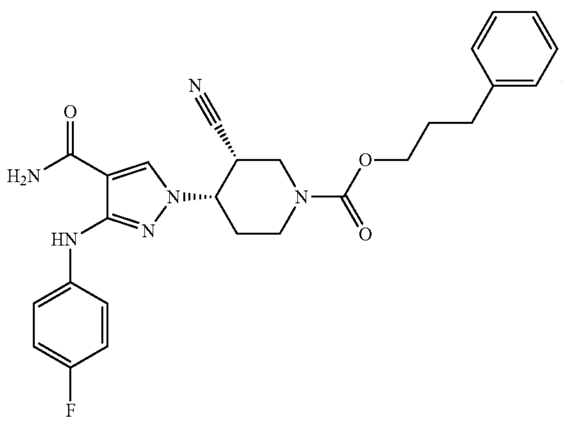 | 3-phenylpropyl (3R,4S and 3S,4R)-4-{4-carbamoyl-3-[(4-fluorophenyl)amino]-1H-pyrazol-1-yl}-3-cyanopiperidine-1-carboxylate | Calc'd 491, found 491 |
| 5-56 | 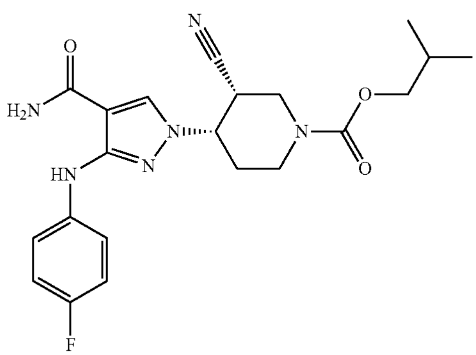 [SMILES: CC(C)COC(=O)N1CC[C@H](n2cc(C(N)=O)c(Nc3ccc(F)cc3)n2)[C@H](C#N)C1] | 2-methylpropyl (3R,4S and 3S,4R)-4-{4-carbamoyl-3-[(4-fluorophenyl)amino]-1H-pyrazol-1-yl}-3-cyanopiperidine-1-carboxylate | Calc'd 429, found 429 |
| 5-57 | 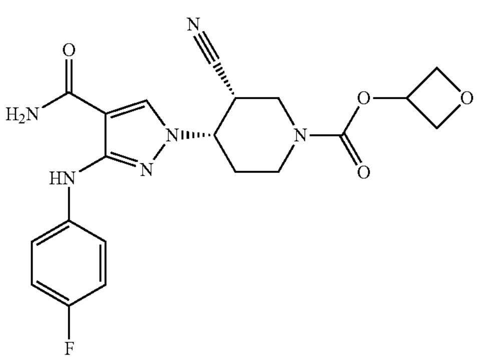 [SMILES: N#C[C@@H]1CN(C(=O)OC2COC2)CC[C@@H]1n1cc(C(N)=O)c(Nc2ccc(F)cc2)n1] | oxetan-3-yl (3R,4S and 3S,4R)-4-{4-carbamoyl-3-[(4-fluorophenyl)amino]-1H-pyrazol-1-yl}-3-cyanopiperidine-1-carboxylate | Calc'd 429, found 429 |

TABLE 6-continued

| Example | Structure | IUPAC Name | Exact Mass [M + H]+ |
|---|---|---|---|
| 5-58 | 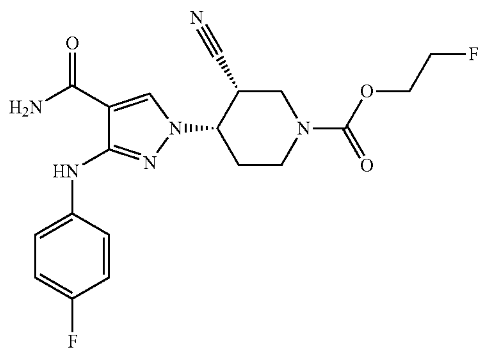 [SMILES: N#C[C@@H]1CN(C(=O)OCCF)CC[C@@H]1n1cc(C(N)=O)c(Nc2ccc(F)cc2)n1] | 2-fluoroethyl (3R,4S and 3S,4R)-4-{4-carbamoyl-3-[(4-fluorophenyl)amino]-1H-pyrazol-1-yl}-3-cyanopiperidine-1-carboxylate | Calc'd 419, found 419 |
| 5-59 | 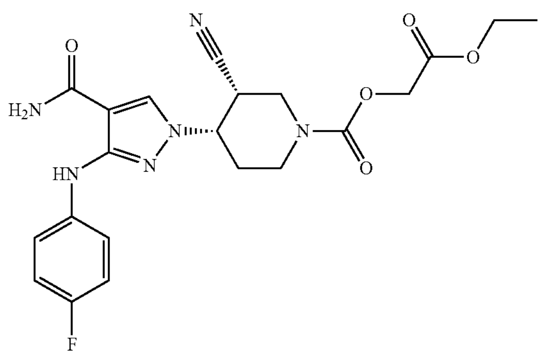 [SMILES: CCOC(=O)COC(=O)N1CC[C@H](n2cc(C(N)=O)c(Nc3ccc(F)cc3)n2)[C@H](C#N)C1] | 2-ethoxy-2-oxoethyl (3R,4S and 3S,4R)-4-{4-carbamoyl-3-[(4-fluorophenyl)amino]-1H-pyrazol-1-yl}-3-cyanopiperidine-1-carboxylate | Calc'd 459, found 459 |
| 5-60 | 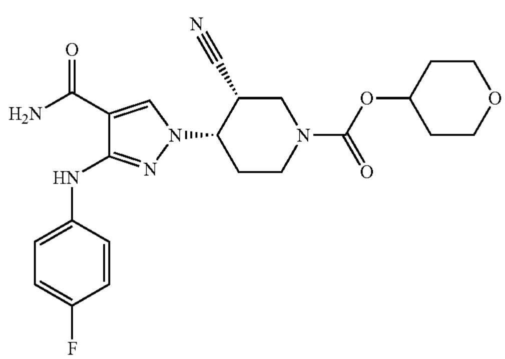 [SMILES: N#C[C@@H]1CN(C(=O)OC2CCOCC2)CC[C@@H]1n1cc(C(N)=O)c(Nc2ccc(F)cc2)n1] | tetrahydro-2H-pyran-4-yl (3R,4S and 3S,4R)-4-{4-carbamoyl-3-[(4-fluorophenyl)amino]-1H-pyrazol-1-yl}-3-cyanopiperidine-1-carboxylate | Calc'd 457, found 457 |
| 5-61 | 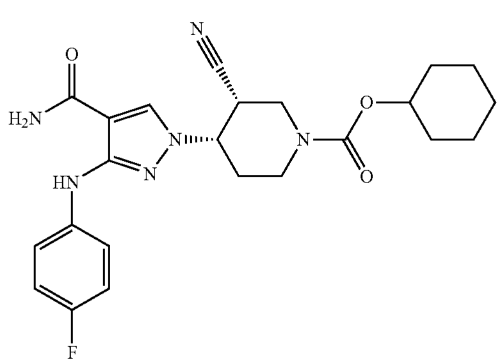 [SMILES: N#C[C@@H]1CN(C(=O)OC2CCCCC2)CC[C@@H]1n1cc(C(N)=O)c(Nc2ccc(F)cc2)n1] | cyclohexyl (3R,4S and 3S,4R)-4-{4-carbamoyl-3-[(4-fluorophenyl)amino]-1H-pyrazol-1-yl}-3-cyanopiperidine-1-carboxylate | Calc'd 455, found 455 |

TABLE 6-continued

| Example | Structure | IUPAC Name | Exact Mass [M + H]+ |
|---|---|---|---|
| 5-62 | 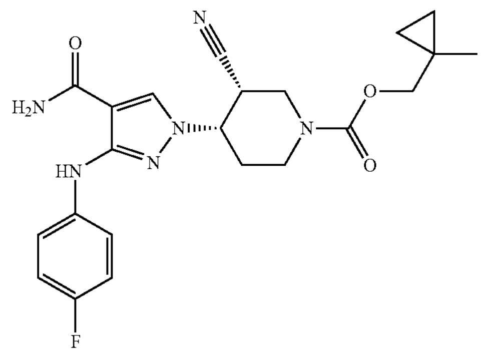 [SMILES: CC1(COC(=O)N2CC[C@H](n3cc(C(N)=O)c(Nc4ccc(F)cc4)n3)[C@H](C#N)C2)CC1] | (1-methylcyclopropyl)methyl (3R,4S and 3S,4R)-4-{4-carbamoyl-3-[(4-fluorophenyl)amino]-1H-pyrazol-1-yl}-3-cyanopiperidine-1-carboxylate | Calc'd 441, found 441 |
| 5-63 | 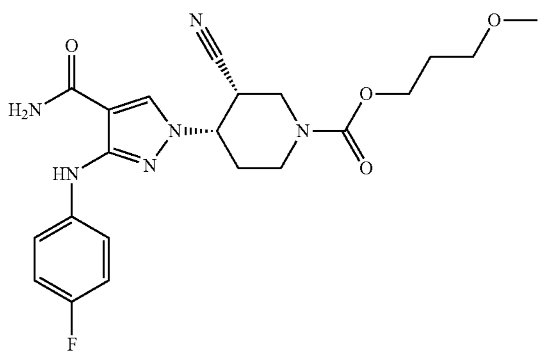 [SMILES: COCCCOC(=O)N1CC[C@H](n2cc(C(N)=O)c(Nc3ccc(F)cc3)n2)[C@H](C#N)C1] | 3-methoxypropyl (3R,4S and 3S,4R)-4-{4-carbamoyl-3-[(4-fluorophenyl)amino]-1H-pyrazol-1-yl}-3-cyanopiperidine-1-carboxylate | Calc'd 445, found 445 |
| 5-64 | 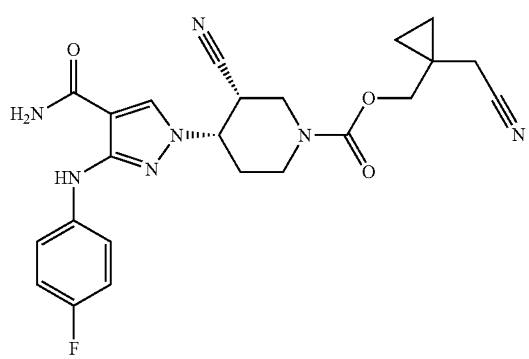 [SMILES: N#CCC1(COC(=O)N2CC[C@H](n3cc(C(N)=O)c(Nc4ccc(F)cc4)n3)[C@H](C#N)C2)CC1] | [1-(cyanomethyl)cyclopropyl]methyl (3R,4S and 3S,4R)-4-{4-carbamoyl-3-[(4-fluorophenyl)amino]-1H-pyrazol-1-yl}-3-cyanopiperidine-1-carboxylate | Calc'd 466, found 466 |
| 5-65 | 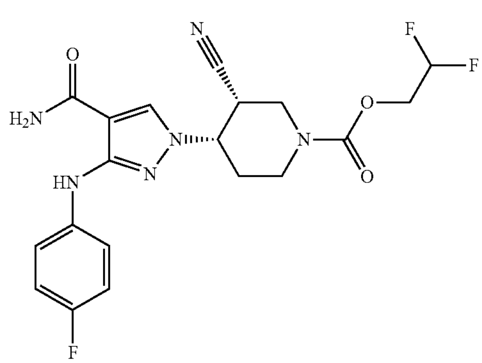 [SMILES: N#C[C@@H]1CN(C(=O)OCC(F)F)CC[C@@H]1n1cc(C(N)=O)c(Nc2ccc(F)cc2)n1] | 2,2-difluoroethyl (3R,4S and 3S,4R)-4-{4-carbamoyl-3-[(4-fluorophenyl)amino]-1H-pyrazol-1-yl}-3-cyanopiperidine-1-carboxylate | Calc'd 437, found 437 |

TABLE 6-continued

| Example | Structure | IUPAC Name | Exact Mass [M + H]+ |
|---|---|---|---|
| 5-66 | 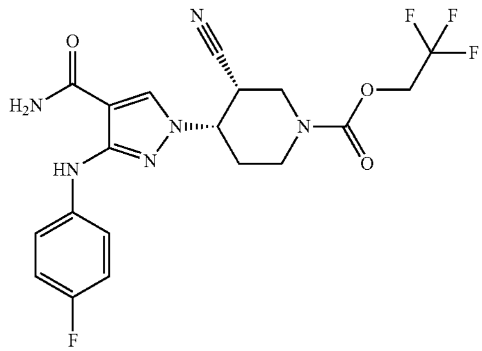 [SMILES: N#C[C@@H]1CN(C(=O)OCC(F)(F)F)CC[C@@H]1n1cc(C(N)=O)c(Nc2ccc(F)cc2)n1] | 2,2,2-trifluoroethyl (3R,4S and 3S,4R)-4-{4-carbamoyl-3-[(4-fluorophenyl)amino]-1H-pyrazol-1-yl}-3-cyanopiperidine-1-carboxylate | Calc'd 455, found 455 |
| 5-67 | 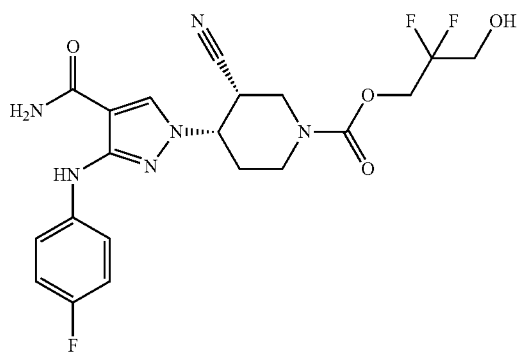 [SMILES: N#C[C@@H]1CN(C(=O)OCC(F)(F)CO)CC[C@@H]1n1cc(C(N)=O)c(Nc2ccc(F)cc2)n1] | 2,2-difluoro-3-hydroxypropyl (3R,4S and 3S,4R)-4-{4-carbamoyl-3-[(4-fluorophenyl)amino]-1H-pyrazol-1-yl}-3-cyanopiperidine-1-carboxylate | Calc'd 467, found 467 |
| 5-68 | 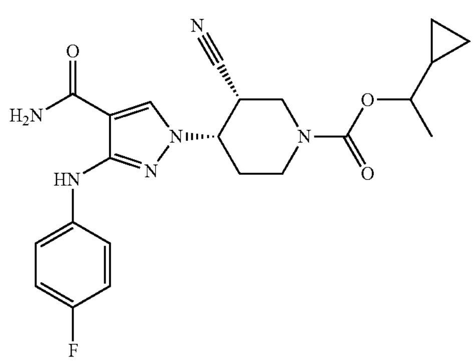 [SMILES: CC(OC(=O)N1CC[C@H](n2cc(C(N)=O)c(Nc3ccc(F)cc3)n2)[C@H](C#N)C1)C1CC1] | 1-cyclopropylethyl (3R,4S and 3S,4R)-4-{4-carbamoyl-3-[(4-fluorophenyl)amino]-1H-pyrazol-1-yl}-3-cyanopiperidine-1-carboxylate | Calc'd 441, found 441 |

The following examples shown in TABLE 7 were prepared according to Scheme #24 following similar procedures described for Example #5-1, which can be achieved by those of ordinary skill in the art of organic synthesis utilizing but not limited to the intermediates described above.

TABLE 7

| Example | Structure | IUPAC Name | Exact Mass [M + H]+ |
|---|---|---|---|
| 5-69 | 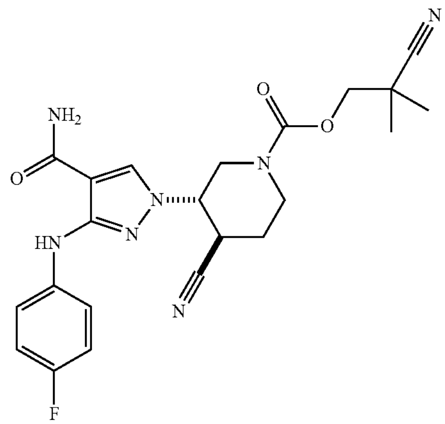 | 2-Cyano-2-methylpropyl (3S,4R and 3R,4S)-3-{4-carbamoyl-3-[(4-fluorophenyl)amino]-1H-pyrazol-1-yl}-4-cyanopiperidine-1-carboxylate | Calc'd 454, Found 454 |
| 5-70 | 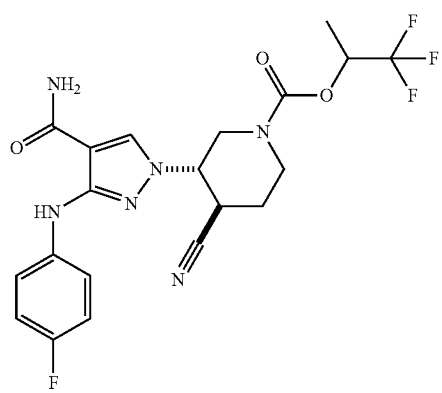 | 2,2,2-trifluoro-1-methylethyl (3S,4R and 3R,4S)-3-{4-carbamoyl-3-[(4-fluorophenyl)amino]-1H-pyrazol-1-yl}-4-cyanopiperidine-1-carboxylate | Calc'd 469, Found 469 |
| 5-71 | 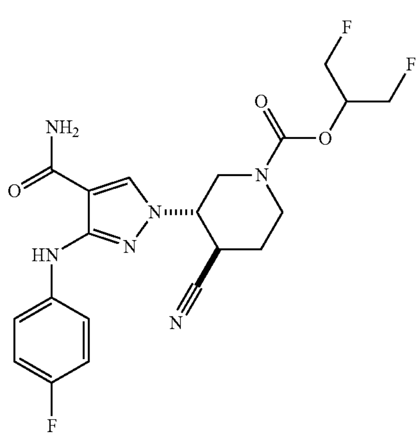 | 2-fluoro-1-(fluoromethyl)ethyl (3S,4R and 3R,4S)-3-{4-carbamoyl-3-[(4-fluorophenyl)amino]-1H-pyrazol-1-yl}-4-cyanopiperidine-1-carboxylate | Calc'd 451, Found 451 |

TABLE 7-continued

| Example | Structure | IUPAC Name | Exact Mass [M + H]+ |
|---|---|---|---|
| 5-72 | 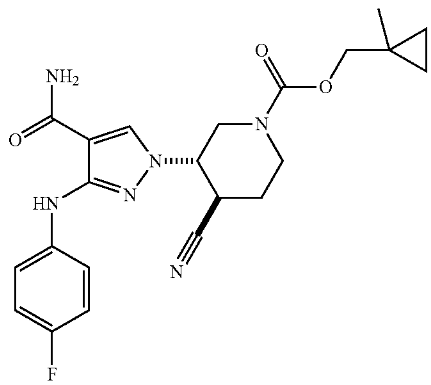 | (1-methylcyclopropyl)methyl (3S,4R and 3R,4S)-3-{4-carbamoyl-3-[(4-fluorophenyl)amino]-1H-pyrazol-1-yl}-4-cyanopiperidine-1-carboxylate | Calc'd 441, Found 441 |
| 5-73 | 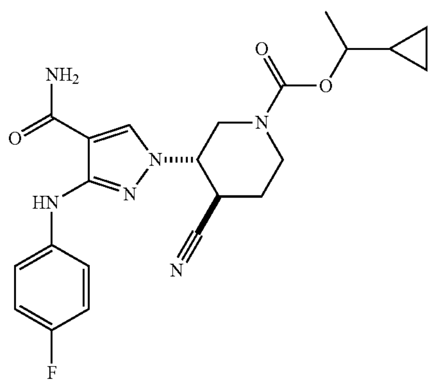 | 1-cyclopropylethyl (3S,4R and 3R,4S)-3-{4-carbamoyl-3-[(4-fluorophenyl)amino]-1H-pyrazol-1-yl}-4-cyanopiperidine-1-carboxylate | Calc'd 441, Found 441 |
| 5-74 | 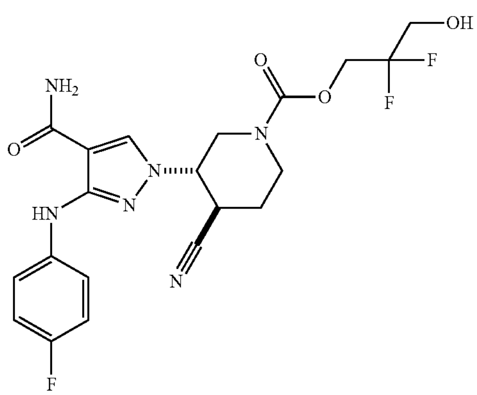 | 2,2-difluoro-3-hydroxypropyl (3S,4R and 3R,4S)-3-{4-carbamoyl-3-[(4-fluorophenyl)amino]-1H-pyrazol-1-yl}-4-cyanopiperidine-1-carboxylate | Calc'd 467, Found 467 |
| 5-75 | 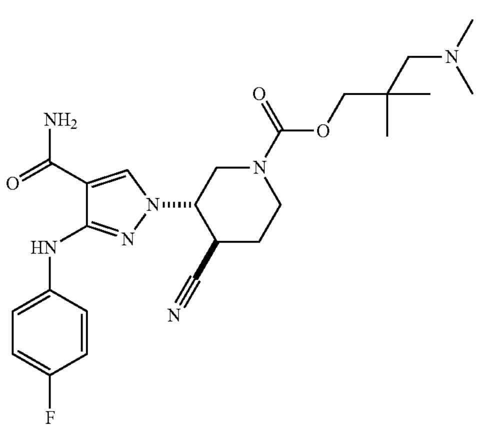 | 3-(dimethylamino)-2,2-dimethylpropyl (3S,4R and 3R,4S)-3-{4-carbamoyl-3-[(4-fluorophenyl)amino]-1H-pyrazol-1-yl}-4-cyanopiperidine-1-carboxylate | Calc'd 486, Found 486 |

TABLE 7-continued

| Example | Structure | IUPAC Name | Exact Mass [M + H]+ |
|---|---|---|---|
| 5-76 | 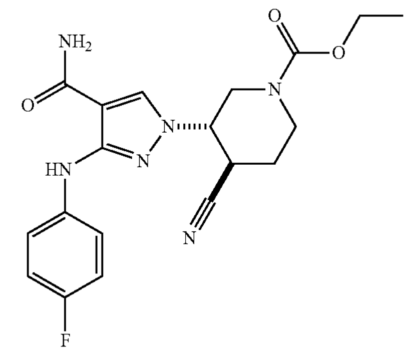 | ethyl (3S,4R and 3R,4S)-3-{4-carbamoyl-3-[(4-fluorophenyl)amino]-1H-pyrazol-1-yl}-4-cyanopiperidine-1-carboxylate | Calc'd 401, Found 401 |
| 5-77 | 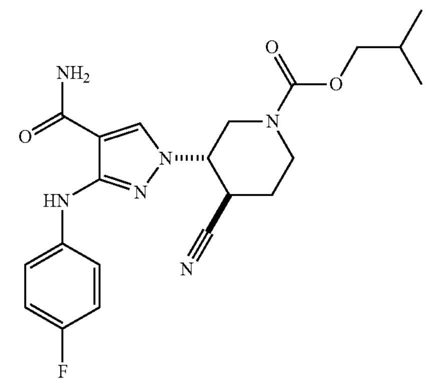 | 2-methylpropyl (3S,4R and 3R,4S)-3-{4-carbamoyl-3-[(4-fluorophenyl)amino]-1H-pyrazol-1-yl}-4-cyanopiperidine-1-carboxylate | Calc'd 429, Found 429 |
| 5-78 | 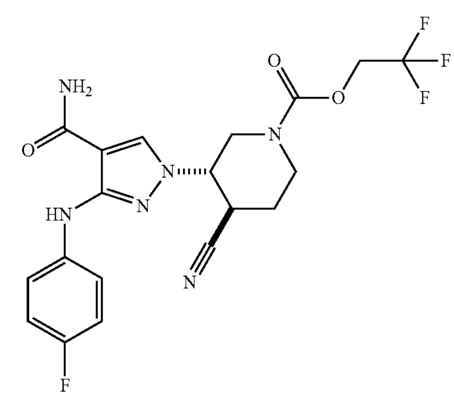 | 2,2,2-trifluoroethyl (3S,4R and 3R,4S)-3-{4-carbamoyl-3-[(4-fluorophenyl)amino]-1H-pyrazol-1-yl}-4-cyanopiperidine-1-carboxylate | Calc'd 455, Found 455 |
| 5-79 | 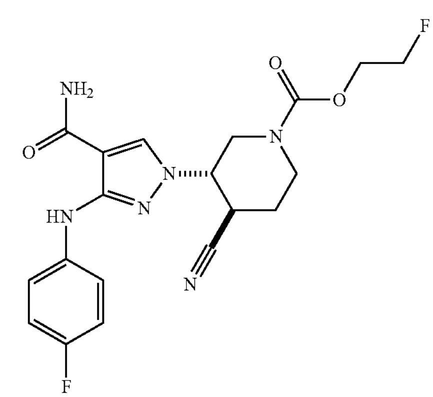 | 2-fluoroethyl (3S,4R and 3R,4S)-3-{4-carbamoyl-3-[(4-fluorophenyl)amino]-1H-pyrazol-1-yl}-4-cyanopiperidine-1-carboxylate | Calc'd 419, Found 419 |

TABLE 7-continued

| Example | Structure | IUPAC Name | Exact Mass [M + H]⁺ |
|---------|-----------|------------|---------------------|
| 5-80 | 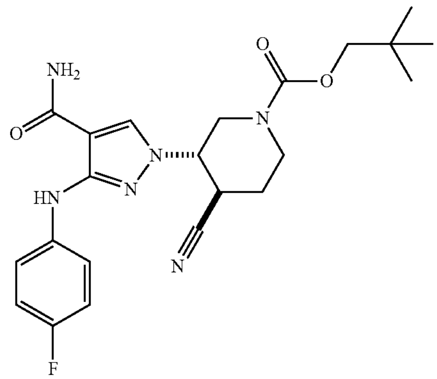 | 2,2-dimethylpropyl (3S,4R and 3R,4S)-3-{4-carbamoyl-3-[(4-fluorophenyl)amino]-1H-pyrazol-1-yl}-4-cyanopiperidine-1-carboxylate | Calc'd 443, Found 443 |
| 5-81 | 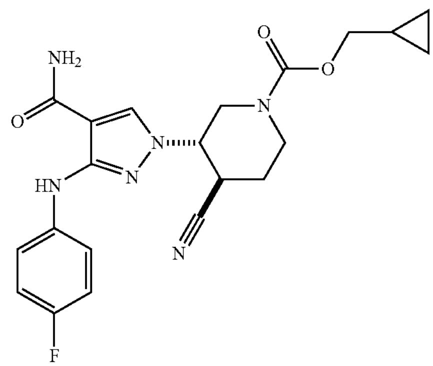 | cyclopropylmethyl (3S,4R and 3R,4S)-3-{4-carbamoyl-3-[(4-fluorophenyl)amino]-1H-pyrazol-1-yl}-4-cyanopiperidine-1-carboxylate | Calc'd 427, Found 427 |
| 5-82 | 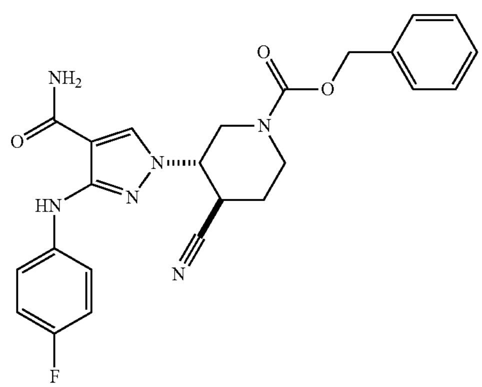 | benzyl (3S,4R and 3R,4S)-3-{4-carbamoyl-3-[(4-fluorophenyl)amino]-1H-pyrazol-1-yl}-4-cyanopiperidine-1-carboxylate | Calc'd 463, Found 463 |
| 5-83 | 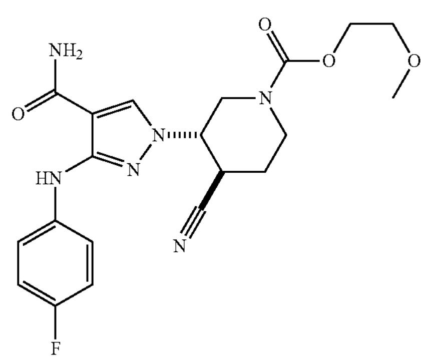 | 2-methoxyethyl (3S,4R and 3R,4S)-3-{4-carbamoyl-3-[(4-fluorophenyl)amino]-1H-pyrazol-1-yl}-4-cyanopiperidine-1-carboxylate | Calc'd 431, Found 431 |

TABLE 7-continued

| Example | Structure | IUPAC Name | Exact Mass [M + H]+ |
|---------|-----------|------------|---------------------|
| 5-84 | 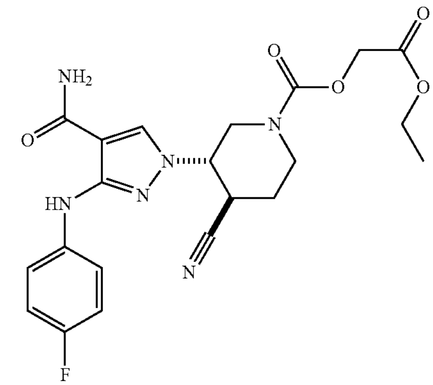 | 2-ethoxy-2-oxoethyl (3S,4R and 3R,4S)-3-{4-carbamoyl-3-[(4-fluorophenyl)amino]-1H-pyrazol-1-yl}-4-cyanopiperidine-1-carboxylate | Calc'd 459, Found 459 |
| 5-85 | 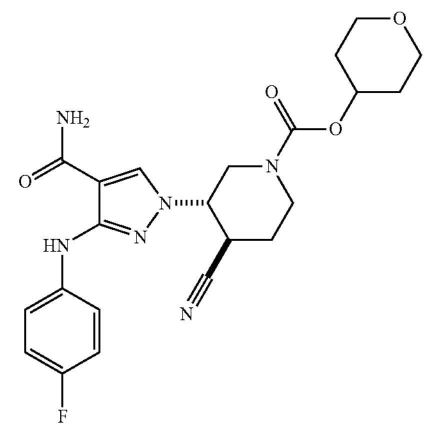 | tetrahydro-2H-pyran-4-yl (3S,4R and 3R,4S)-3-{4-carbamoyl-3-[(4-fluorophenyl)amino]-1H-pyrazol-1-yl}-4-cyanopiperidine-1-carboxylate | Calc'd 457, Found 457 |
| 5-86 | 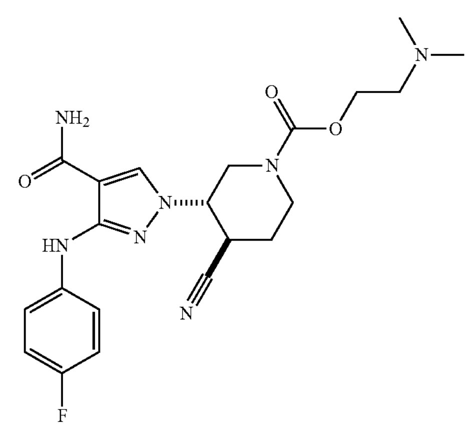 | 2-(dimethylamino)ethyl (3S,4R and 3R,4S)-3-{4-carbamoyl-3-[(4-fluorophenyl)amino]-1H-pyrazol-1-yl}-4-cyanopiperidine-1-carboxylate | Calc'd 444, Found 444 |

TABLE 7-continued

| Example | Structure | IUPAC Name | Exact Mass [M + H]+ |
|---|---|---|---|
| 5-87 | 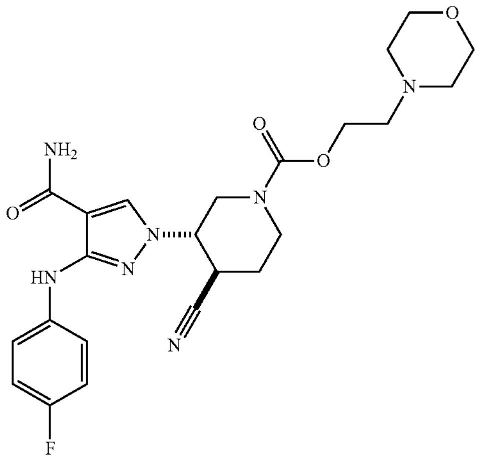 | 2-morpholin-4-ylethyl (3S,4R and 3R,4S)-3-{4-carbamoyl-3-[(4-fluorophenyl)amino]-1H-pyrazol-1-yl}-4-cyanopiperidine-1-carboxylate | Calc'd 486, Found 486 |
| 5-88 | 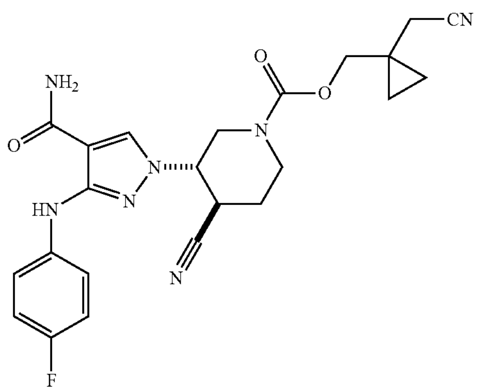 | [1-(cyanomethyl)cyclopropyl]methyl (3S,4R and 3R,4S)-3-{4-carbamoyl-3-[(4-fluorophenyl)amino]-1H-pyrazol-1-yl}-4-cyanopiperidine-1-carboxylate | Calc'd 466, Found 466 |
| 5-89 | 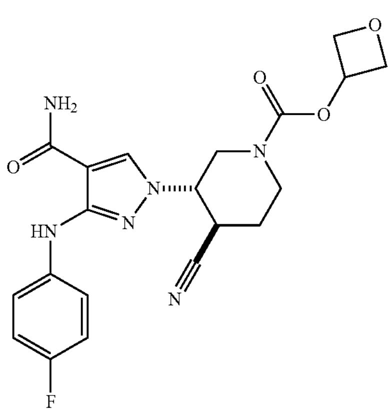 | oxetan-3-yl (3S,4R and 3R,4S)-3-{4-carbamoyl-3-[(4-fluorophenyl)amino]-1H-pyrazol-1-yl}-4-cyanopiperidine-1-carboxylate | Calc'd 429, Found 429 |

TABLE 7-continued

| Example | Structure | IUPAC Name | Exact Mass [M + H]+ |
|---|---|---|---|
| 5-90 | 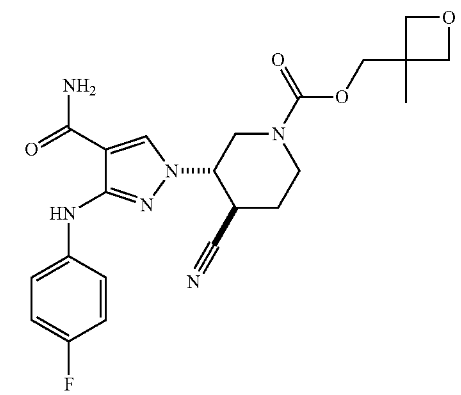 | (3-methyloxetan-3-yl)methyl (3S,4R and 3R,4S)-3-{4-carbamoyl-3-[(4-fluorophenyl)amino]-1H-pyrazol-1-yl}-4-cyanopiperidine-1-carboxylate | Calc'd 457, Found 457 |
| 5-91 | 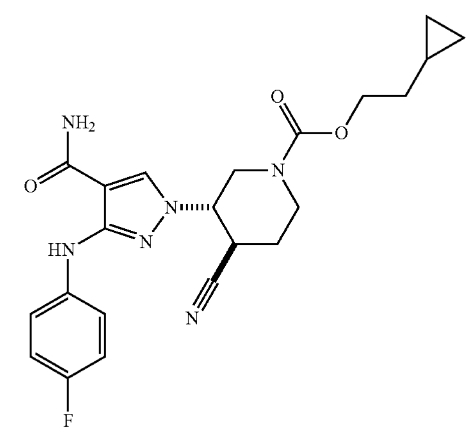 | 2-cyclopropylethyl (3S,4R and 3R,4S)-3-{4-carbamoyl-3-[(4-fluorophenyl)amino]-1H-pyrazol-1-yl}-4-cyanopiperidine-1-carboxylate | Calc'd 441, Found 441 |
| 5-92 | 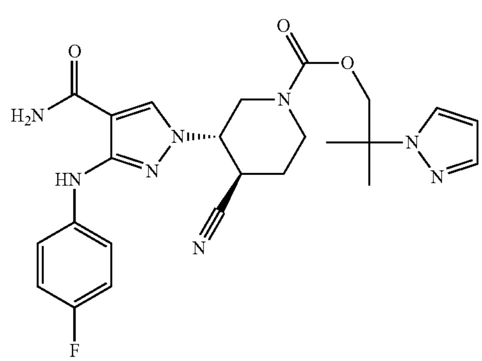 [SMILES: CC(C)(COC(=O)N1CC[C@@H](C#N)[C@H](n2cc(C(N)=O)c(Nc3ccc(F)cc3)n2)C1)n1cccn1] | 2-methyl-2-(1H-pyrazol-1-yl)propyl (3S,4R and 3R, 4S)-3-{4-carbamoyl-3-[(4-fluorophenyl)amino]-1H-pyrazol-1-yl}-4-cyanopiperidine-1-carboxylate | Calc'd 495, found 495 |

Scheme #24

Example #6-1

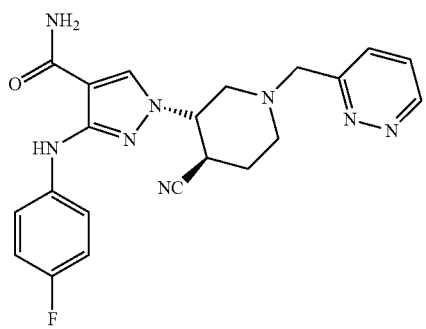

1-[(3S,4R and 3R,4S)-4-Cyano-1-(pyridazin-3-ylmethyl)piperidin-3-yl]-3-[(4-fluorophenyl)amino]-1H-pyrazole-4-carboxamide To a reaction vial was added (3S,4R and 3R,4S)-3-(4-carbamoyl-3-((4-fluorophenyl)amino)-1H-pyrazol-1-yl)-4-cyanopiperidin-1-ium trifluoroacetate (Example 3-1, 20 mg, 0.061 mmol), pyridazine-3-carbaldehyde (7 mg, 0.06 mmol), Na(OAc)$_3$BH (65 mg, 0.31 mmol), TFA (30 mg, 0.020 mL, 0.26 mmol), and DMF (1.0 mL). The reaction vessel was sealed and heated to 50° C. with stirring for 12 hours. The reaction mixture was purified directly by reverse phase preparative HPLC (0-95% acetonitrile:water with 0.1% v/v NH$_4$OH modifier) to afford the title compound. LRMS (ESI) calc'd for C$_{21}$H$_{21}$FN$_8$O [M+H]$^+$: 421. Found: 421.

The following shown in TABLE 8 were prepared according to Scheme #24 following similar procedures described for Example #6-1, which can be achieved by those of ordinary skill in the art of organic synthesis utilizing but not limited to the intermediates described above.

TABLE 8

| Example | Structure | IUPAC Name | Exact Mass [M + H]+ |
|---|---|---|---|
| 6-2 | 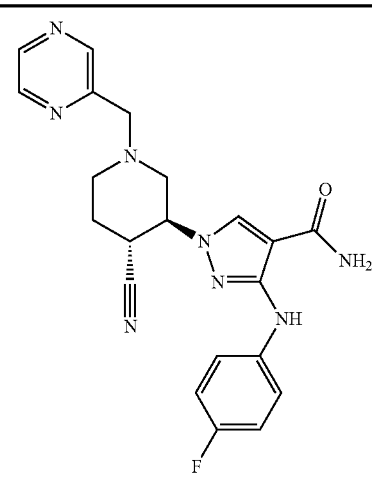 | 1-[(3S,4R and 3R,4S)-4-cyano-1-(pyrazin-2-ylmethyl)piperidin-3-yl]-3-[(4-fluorophenyl)amino]-1H-pyrazole-4-carboxamide | Calc'd 421, found 421 |
| 6-3 | 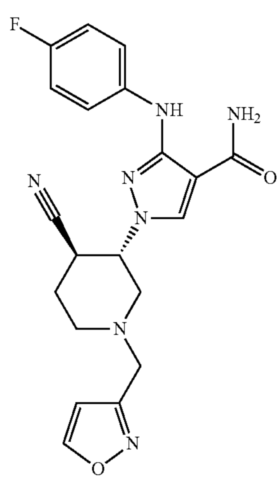 [SMILES: N#C[C@@H]1CCN(Cc2ccon2)C[C@H]1n1cc(C(N)=O)c(Nc2ccc(F)cc2)n1] | 1-[(3S,4R and 3R,4S)-4-cyano-1-(isoxazol-3-ylmethyl)piperidin-3-yl]-3-[(4-fluorophenyl)amino]-1H-pyrazole-4-carboxamide | Calc'd 410, found 410 |

TABLE 8-continued

| Example | Structure | IUPAC Name | Exact Mass [M + H]+ |
|---|---|---|---|
| 6-4 | 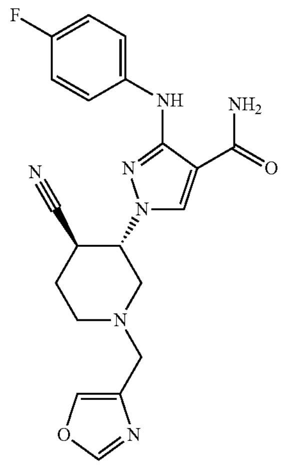 [SMILES: N#C[C@@H]1CCN(Cc2cocn2)C[C@H]1n1cc(C(N)=O)c(Nc2ccc(F)cc2)n1] | 1-[(3S,4R and 3R,4S)-4-cyano-1-(1,3-oxazol-4-ylmethyl)piperidin-3-yl]-3-[(4-fluorophenyl)amino]-1H-pyrazole-4-carboxamide | Calc'd 410, found 410 |
| 6-5 | 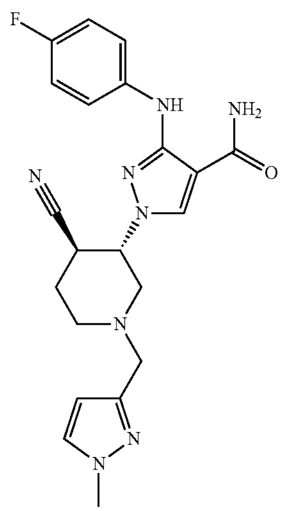 [SMILES: Cn1ccc(CN2CC[C@@H](C#N)[C@H](n3cc(C(N)=O)c(Nc4ccc(F)cc4)n3)C2)n1] | 1-{(3S,4R and 3R,4S)-4-cyano-1-[(1-methyl-1H-pyrazol-3-yl)methyl]piperidin-3-yl}-3-[(4-fluorophenyl)amino]-1H-pyrazole-4-carboxamide | Calc'd 423, found 423 |
| 6-6 | 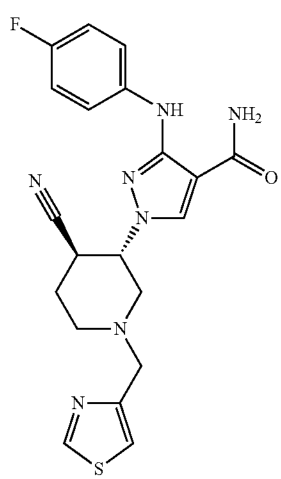 [SMILES: N#C[C@@H]1CCN(Cc2cscn2)C[C@H]1n1cc(C(N)=O)c(Nc2ccc(F)cc2)n1] | 1-[(3S,4R and 3R,4S)-4-cyano-1-(1,3-thiazol-4-ylmethyl)piperidin-3-yl]-3-[(4-fluorophenyl)amino]-1H-pyrazole-4-carboxamide | Calc'd 426, found 426 |

TABLE 8-continued

| Example | Structure | IUPAC Name | Exact Mass [M + H]+ |
|---|---|---|---|
| 6-7 | 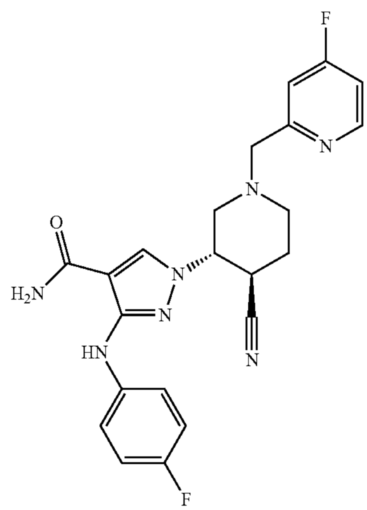 [SMILES: N#C[C@@H]1CCN(Cc2cc(F)ccn2)C[C@H]1n1cc(C(N)=O)c(Nc2ccc(F)cc2)n1] | 1-{(3S,4R and 3R,4S)-4-cyano-1-[(4-fluoropyridin-2-yl)methyl]piperidin-3-yl}-3-[(4-fluorophenyl)amino]-1H-pyrazole-4-carboxamide | Calc'd 438, found 438 |
| 6-8 | 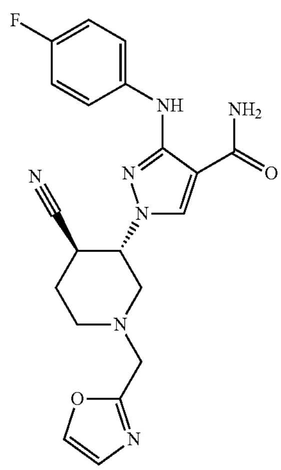 [SMILES: N#C[C@@H]1CCN(Cc2ncco2)C[C@H]1n1cc(C(N)=O)c(Nc2ccc(F)cc2)n1] | 1-[(3S,4R and 3R,4S)-4-cyano-1-(1,3-oxazol-2-ylmethyl)piperidin-3-yl]-3-[(4-fluorophenyl)amino]-1H-pyrazole-4-carboxamide | Calc'd 410, found 410 |
| 6-9 | 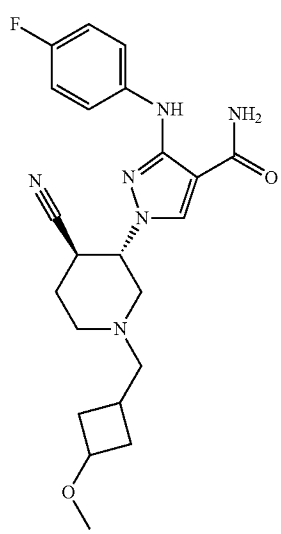 [SMILES: COC1CC(CN2CC[C@@H](C#N)[C@H](n3cc(C(N)=O)c(Nc4ccc(F)cc4)n3)C2)C1] | 1-{(3S,4R and 3R,4S)-4-cyano-1-[(3-methoxycyclobutyl)methyl]piperidin-3-yl}-3-[(4-fluorophenyl)amino]-1H-pyrazole-4-carboxamide | Calc'd 427, found 427 |

TABLE 8-continued

| Example | Structure | IUPAC Name | Exact Mass [M + H]+ |
|---|---|---|---|
| 6-10 | 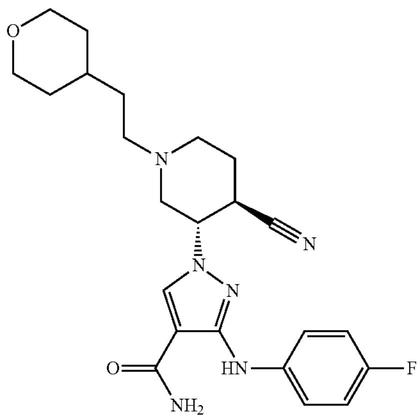 [SMILES: N#C[C@@H]1CCN(CCC2CCOCC2)C[C@H]1n1cc(C(N)=O)c(Nc2ccc(F)cc2)n1] | 1-{(3S,4R and 3R,4S)-4-cyano-1-[2-(tetrahydro-2H-pyran-4-yl)ethyl]piperidin-3-yl}-3-[(4-fluorophenyl)amino]-1H-pyrazole-4-carboxamide | Calc'd 441, found 441 |
| 6-11 | 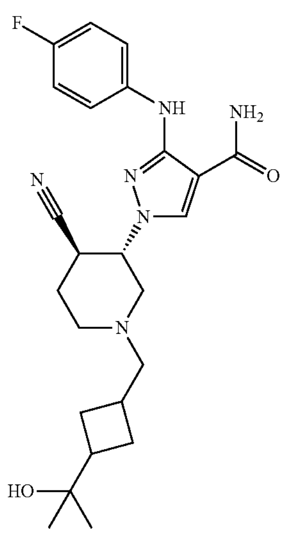 [SMILES: CC(C)(O)C1CC(CN2CC[C@@H](C#N)[C@H](n3cc(C(N)=O)c(Nc4ccc(F)cc4)n3)C2)C1] | 1-[(3S,4R and 3R,4S)-4-cyano-1-{[3-(1-hydroxy-1-methylethyl)cyclobutyl]methyl}piperidin-3-yl]-3-[(4-fluorophenyl)amino]-1H-pyrazole-4-carboxamide | Calc'd 455, found 455 |
| 6-12 | 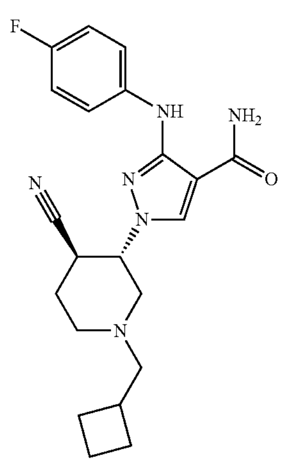 [SMILES: N#C[C@@H]1CCN(CC2CCC2)C[C@H]1n1cc(C(N)=O)c(Nc2ccc(F)cc2)n1] | 1-[(3S,4R and 3R,4S)-4-cyano-1-(cyclobutylmethyl)piperidin-3-yl]-3-[(4-fluorophenyl)amino]-1H-pyrazole-4-carboxamide | Calc'd 397, found 397 |

TABLE 8-continued

| Example | Structure | IUPAC Name | Exact Mass [M + H]+ |
|---|---|---|---|
| 6-13 | 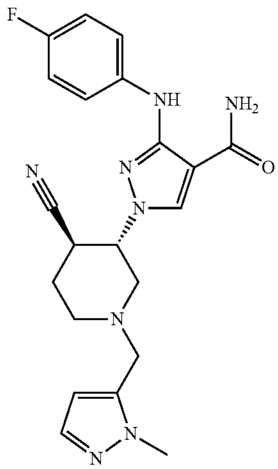 [SMILES: Cn1nccc1CN1CC[C@@H](C#N)[C@H](n2cc(C(N)=O)c(Nc3ccc(F)cc3)n2)C1] | 1-{(3S,4R and 3R,4S)-4-cyano-1-[(1-methyl-1H-pyrazol-5-yl)methyl]piperidin-3-yl}-3-[(4-fluorophenyl)amino]-1H-pyrazole-4-carboxamide | Calc'd 423, found 423 |
| 6-14 | 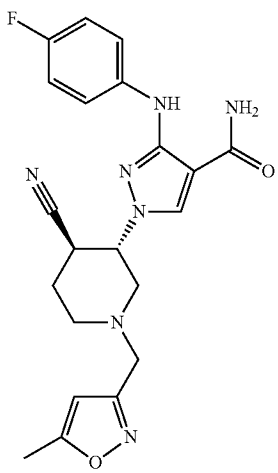 [SMILES: Cc1cc(CN2CC[C@@H](C#N)[C@H](n3cc(C(N)=O)c(Nc4ccc(F)cc4)n3)C2)no1] | 1-{(3S,4R and 3R,4S)-4-cyano-1-[(5-methylisoxazol-3-yl)methyl]piperidin-3-yl}-3-[(4-fluorophenyl)amino]-1H-pyrazole-4-carboxamide | Calc'd 424, found 424 |
| 6-15 | 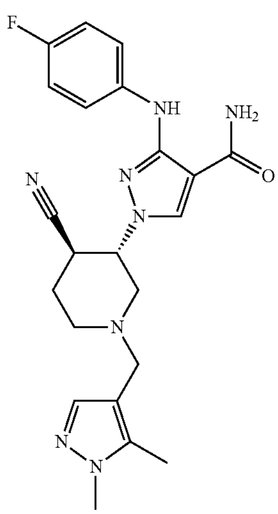 [SMILES: Cc1c(CN2CC[C@@H](C#N)[C@H](n3cc(C(N)=O)c(Nc4ccc(F)cc4)n3)C2)cnn1C] | 1-{(3S,4R and 3R,4S)-4-cyano-1-[(1,5-dimethyl-1H-pyrazol-4-yl)methyl]piperidin-3-yl}-3-[(4-fluorophenyl)amino]-1H-pyrazole-4-carboxamide | Calc'd 437, found 437 |

TABLE 8-continued

| Example | Structure | IUPAC Name | Exact Mass [M + H]+ |
|---|---|---|---|
| 6-16 | 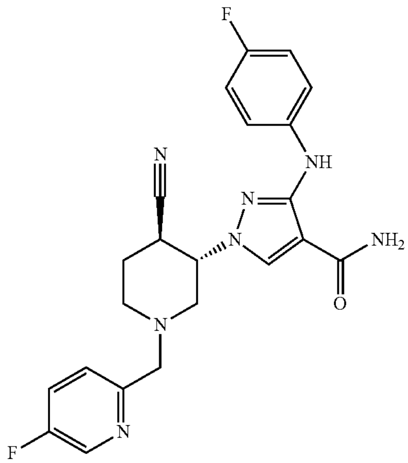 [SMILES: N#C[C@@H]1CCN(Cc2ccc(F)cn2)C[C@H]1n1cc(C(N)=O)c(Nc2ccc(F)cc2)n1] | 1-{(3S,4R and 3R,4S)-4-cyano-1-[(5-fluoropyridin-2-yl)methyl]piperidin-3-yl}-3-[(4-fluorophenyl)amino]-1H-pyrazole-4-carboxamide | Calc'd 438, found 438 |
| 6-17 | 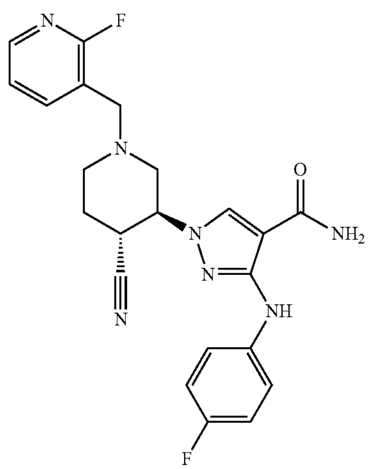 [SMILES: N#C[C@@H]1CCN(Cc2cccnc2F)C[C@H]1n1cc(C(N)=O)c(Nc2ccc(F)cc2)n1] | 1-{(3S,4R and 3R,4S)-4-cyano-1-[(2-fluoropyridin-3-yl)methyl]piperidin-3-yl}-3-[(4-fluorophenyl)amino]-1H-pyrazole-4-carboxamide | Calc'd 438, found 438 |
| 6-18 | 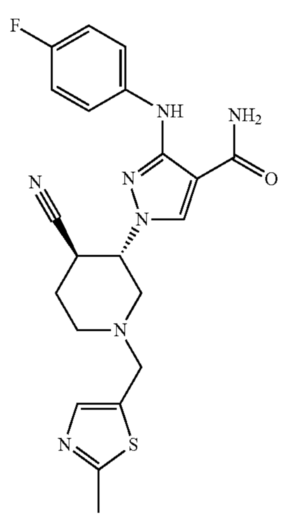 [SMILES: Cc1ncc(CN2CC[C@@H](C#N)[C@H](n3cc(C(N)=O)c(Nc4ccc(F)cc4)n3)C2)s1] | 1-{(3S,4R and 3R,4S)-4-cyano-1-[(2-methyl-1,3-thiazol-5-yl)methyl]piperidin-3-yl}-3-[(4-fluorophenyl)amino]-1H-pyrdzole-4-carboxamide | Calc'd 440, found 440 |

TABLE 8-continued

| Example | Structure | IUPAC Name | Exact Mass [M + H]+ |
|---|---|---|---|
| 6-19 | 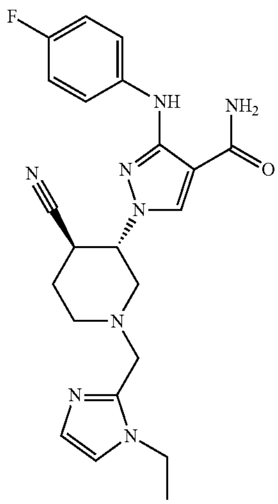 [SMILES: CCn1ccnc1CN1CC[C@@H](C#N)[C@H](n2cc(C(N)=O)c(Nc3ccc(F)cc3)n2)C1] | 1-{(3S,4R and 3R,4S)-4-cyano-1-[(1-ethyl-1H-imidazol-2-yl)methyl]piperidin-3-yl}-3-[(4-fluorophenyl)amino]-1H-pyrazole-4-carboxamide | Calc'd 437, found 437 |
| 6-20 | 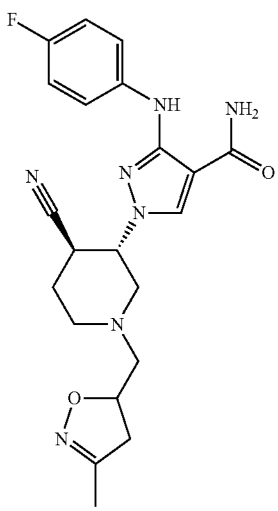 [SMILES: CC1=NOC(CN2CC[C@@H](C#N)[C@H](n3cc(C(N)=O)c(Nc4ccc(F)cc4)n3)C2)C1] | 1-{(3S,4R and 3R,4S)-4-cyano-1-[(3-methyl-4,5-dihydroisoxazol-5-yl)methyl]piperidin-3-yl}-3-[(4-fluorophenyl)amino]-1H-pyrazole-4-carboxamide | Calc'd 426, found 426 |
| 6-21 | 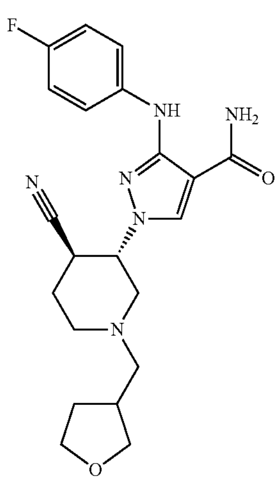 [SMILES: N#C[C@@H]1CCN(CC2CCOC2)C[C@H]1n1cc(C(N)=O)c(Nc2ccc(F)cc2)n1] | 1-[(3S,4R and 3R,4S)-4-cyano-1-(tetrahydrofuran-3-ylmethyl)piperidin-3-yl]-3-[(4-fluorophenyl)amino]-1H-pyrdzole-4-carboxamide | Calc'd 413, found 413 |

TABLE 8-continued

| Example | Structure | IUPAC Name | Exact Mass [M + H]+ |
|---|---|---|---|
| 6-22 | 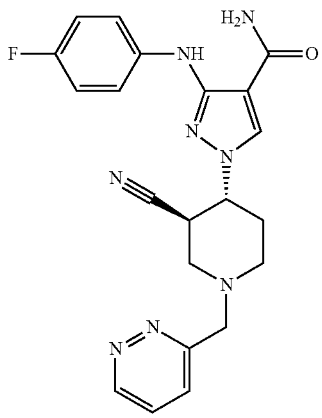 [SMILES: N#C[C@@H]1CN(Cc2cccnn2)CC[C@H]1n1cc(C(N)=O)c(Nc2ccc(F)cc2)n1] | 1-[(3R,4R and 3S,4S)-3-cyano-1-(pyridazin-3-ylmethyl)piperidin-4-yl]-3-[(4-fluorophenyl)amino]-1H-pyrazole-4-carboxamide | Calc'd 421, found 421 |
| 6-23 | 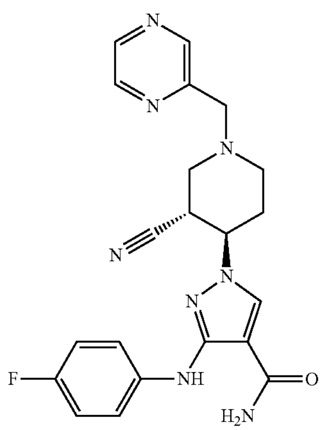 [SMILES: N#C[C@@H]1CN(Cc2cnccn2)CC[C@H]1n1cc(C(N)=O)c(Nc2ccc(F)cc2)n1] | 1-[(3R,4R and 3S,4S)-3-cyano-1-(pyrazin-2-ylmethyl)piperidin-4-yl]-3-[(4-fluorophenyl)amino]-1H-pyrazole-4-carboxamide | Calc'd 421, found 421 |
| 6-24 | 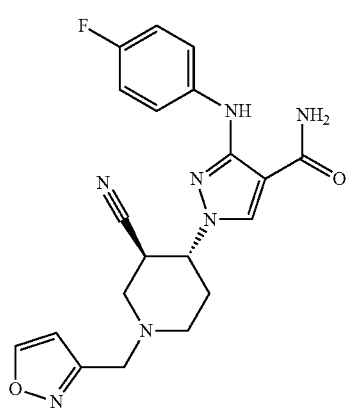 [SMILES: N#C[C@@H]1CN(Cc2ccon2)CC[C@H]1n1cc(C(N)=O)c(Nc2ccc(F)cc2)n1] | 1-[(3R,4R and 3S,4S)-3-cyano-1-(isoxazol-3-ylmethyl)piperidin-4-yl]-3-[(4-fluorophenyl)amino]-1H-pyrazole-4-carboxamide | Calc'd 410, found 410 |

TABLE 8-continued

| Example | Structure | IUPAC Name | Exact Mass [M + H]+ |
|---|---|---|---|
| 6-25 | 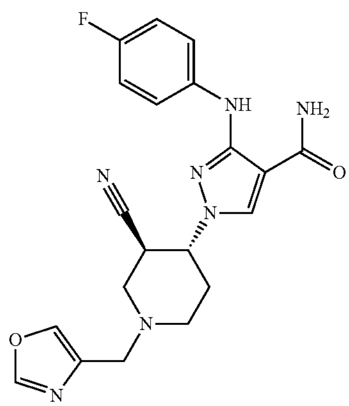 [SMILES: N#C[C@@H]1CN(Cc2cocn2)CC[C@H]1n1cc(C(N)=O)c(Nc2ccc(F)cc2)n1] | 1-[(3R,4R and 3S,4S)-3-cyano-1-(1,3-oxazol-4-ylmethyl)piperidin-4-yl]-3-[(4-fluorophenyl)amino]-1H-pyrazole-4-carboxamide | Calc'd 410, found 410 |
| 6-26 | 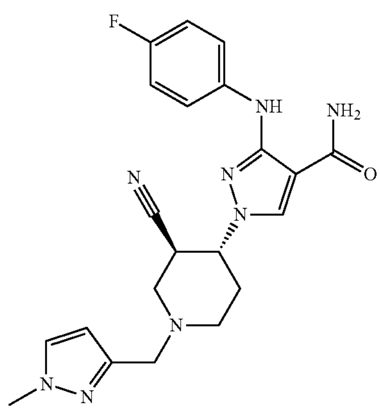 [SMILES: Cn1ccc(CN2CC[C@@H](n3cc(C(N)=O)c(Nc4ccc(F)cc4)n3)[C@H](C#N)C2)n1] | 1-{(3R,4R and 3S,4S)-3-cyano-1-[(1-methyl-1H-pyrazol-3-yl)methyl]piperidin-4-yl}-3-[(4-fluorophenyl)amino]-1H-pyrazole-4-carboxamide | Calc'd 423, found 423 |
| 6-27 | 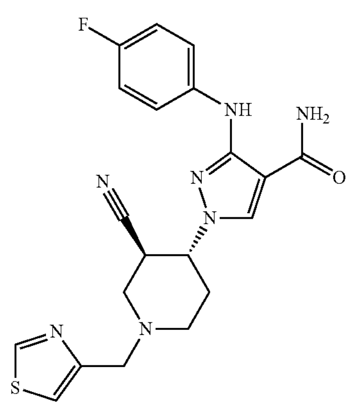 [SMILES: N#C[C@@H]1CN(Cc2cscn2)CC[C@H]1n1cc(C(N)=O)c(Nc2ccc(F)cc2)n1] | 1-[(3R,4R and 3S,4S)-3-cyano-1-(1,3-thiazol-4-ylmethyl)piperidin-4-yl]-3-[(4-fluorophenyl)amino]-1H-pyrazole-4-carboxamide | Calc'd 426, found 426 |

TABLE 8-continued

| Example | Structure | IUPAC Name | Exact Mass [M + H]+ |
|---|---|---|---|
| 6-28 | 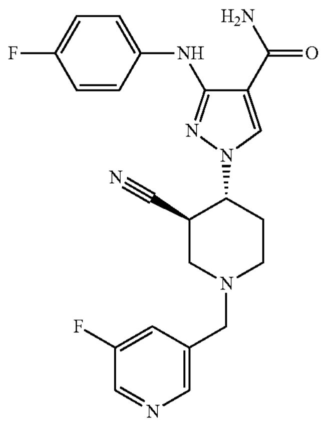 [SMILES: N#C[C@@H]1CN(Cc2cncc(F)c2)CC[C@H]1n1cc(C(N)=O)c(Nc2ccc(F)cc2)n1] | 1-{(3R,4R and 3S,4S)-3-cyano-1-[(5-fluoropyridin-3-yl)methyl]piperidin-4-yl}-3-[(4-fluorophenyl)amino]-1H-pyrazole-4-carboxamide | Calc'd 438, found 438 |
| 6-29 | 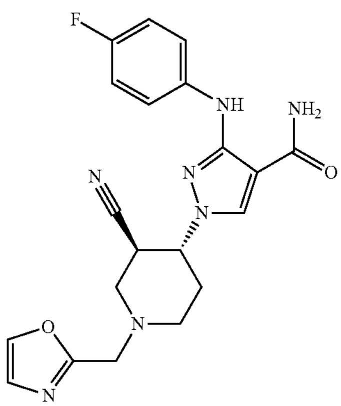 [SMILES: N#C[C@@H]1CN(Cc2ncco2)CC[C@H]1n1cc(C(N)=O)c(Nc2ccc(F)cc2)n1] | 1-[(3R,4R and 3S,4S)-3-cyano-1-(1,3-oxazol-2-ylmethyl)piperidin-4-yl]-3-[(4-fluorophenyl)amino]-1H-pyrazole-4-carboxamide | Calc'd 410, found 410 |
| 6-30 | 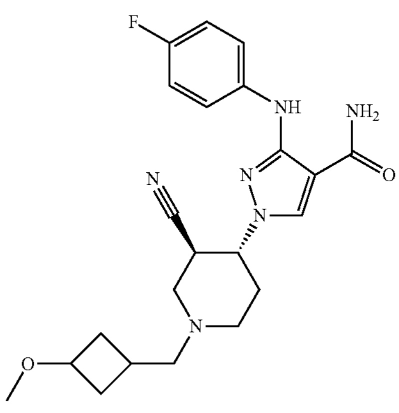 [SMILES: COC1CC(CN2CC[C@@H](n3cc(C(N)=O)c(Nc4ccc(F)cc4)n3)[C@H](C#N)C2)C1] | 1-{(3R,4R and 3S,4S)-3-cyano-1-[(3-methoxycyclobutyl)methyl]piperidin-4-yl}-3-[(4-fluorophenyl)amino]-1H-pyrazole-4-carboxamide | Calc'd 427, found 427 |

TABLE 8-continued

| Example | Structure | IUPAC Name | Exact Mass [M + H]+ |
|---|---|---|---|
| 6-31 | 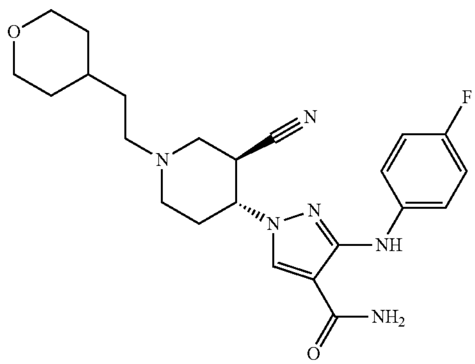 [SMILES: N#C[C@@H]1CN(CCC2CCOCC2)CC[C@H]1n1cc(C(N)=O)c(Nc2ccc(F)cc2)n1] | 1-{(3R,4R and 3S,4S)-3-cyano-1-[2-(tetrahydro-2H-pyran-4-yl)ethyl]piperidin-4-yl}-3-[(4-fluorophenyl)amino]-1H-pyrazole-4-carboxamide | Calc'd 441, found 441 |
| 6-32 | 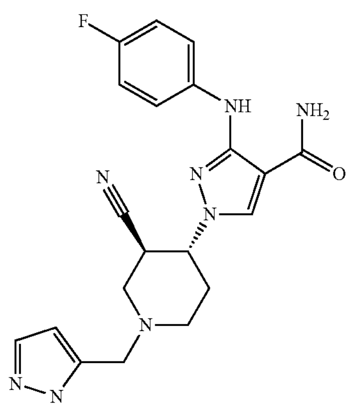 [SMILES: N#C[C@@H]1CN(Cc2ccn[nH]2)CC[C@H]1n1cc(C(N)=O)c(Nc2ccc(F)cc2)n1] | 1-{(3R,4R and 3S,4S)-3-cyano-1-[(1-methyl-1H-pyrazol-5-yl)methyl]piperidin-4-yl}-3-[(4-fluorophenyl)amino]-1H-pyrazole-4-carboxamide | Calc'd 423, found 423 |
| 6-33 | 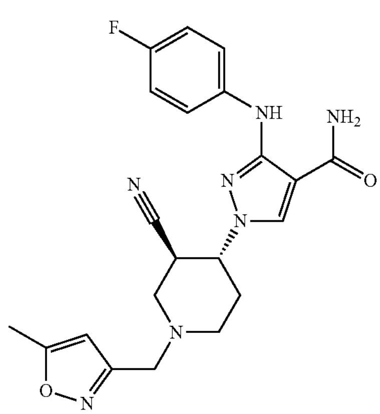 [SMILES: Cc1cc(CN2CC[C@@H](n3cc(C(N)=O)c(Nc4ccc(F)cc4)n3)[C@H](C#N)C2)no1] | 1-{(3R,4R and 3S,4S)-3-cyano-1-[(5-methylisoxazol-3-yl)methyl]piperidin-4-yl}-3-[(4-fluorophenyl)amino]-1H-pyrazole-4-carboxamide | Calc'd 424, found 424 |

| Example | Structure | IUPAC Name | Exact Mass [M + H]+ |
|---|---|---|---|
| 6-34 | 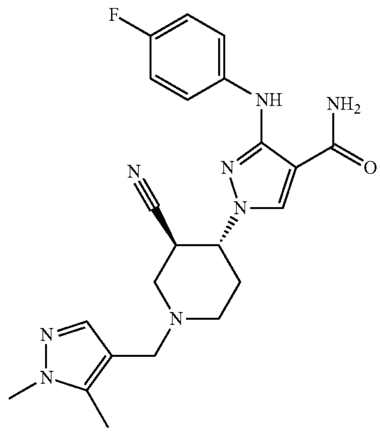 [SMILES: Cc1c(CN2CC[C@@H](n3cc(C(N)=O)c(Nc4ccc(F)cc4)n3)[C@H](C#N)C2)cnn1C] | 1-{(3R,4R and 3S,4S)-3-cyano-1-[(1,5-dimethyl-1H-pyrazol-4-yl)methyl]piperidin-4-yl}-3-[(4-fluorophenyl)amino]-1H-pyrazole-4-carboxamide | Calc'd 437, found 437 |
| 6-35 | 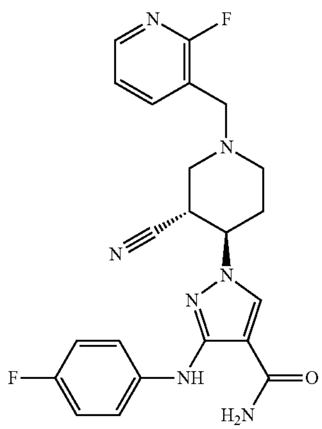 [SMILES: N#C[C@@H]1CN(Cc2cccnc2F)CC[C@H]1n1cc(C(N)=O)c(Nc2ccc(F)cc2)n1] | 1-{(3R,4R and 3S,4S)-3-cyano-1-[(2-fluoropyridin-3-yl)methyl]piperidin-4-yl}-3-[(4-fluorophenyl)amino]-1H-pyrazole-4-carboxamide | Calc'd 438, found 438 |
| 6-36 | 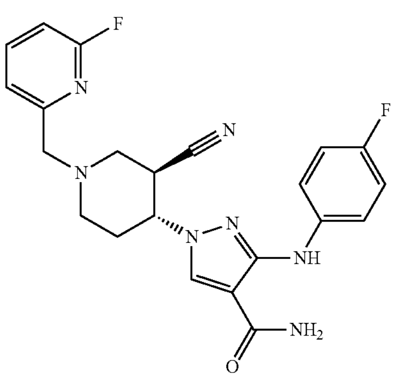 [SMILES: N#C[C@@H]1CN(Cc2cccc(F)n2)CC[C@H]1n1cc(C(N)=O)c(Nc2ccc(F)cc2)n1] | 1-{(3R,4R and 3S,4S)-3-cyano-1-[(6-fluoropyridin-2-yl)methyl]piperidin-4-yl}-3-[(4-fluorophenyl)amino]-1H-pyrazole-4-carboxamide | Calc'd 438, found 438 |

TABLE 8-continued

| Example | Structure | IUPAC Name | Exact Mass [M + H]+ |
|---|---|---|---|
| 6-37 | 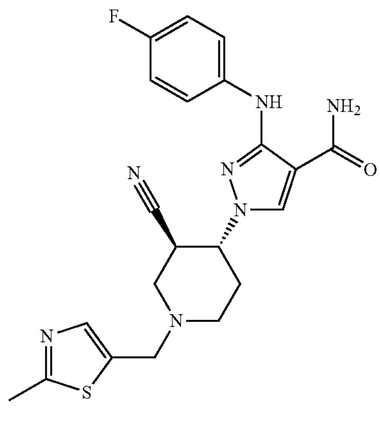 [SMILES: Cc1ncc(CN2CC[C@@H](n3cc(C(N)=O)c(Nc4ccc(F)cc4)n3)[C@H](C#N)C2)s1] | 1-{(3R,4R and 3S,4S)-3-cyano-1-[(2-methyl-1,3-thiazol-5-yl)methyl]piperidin-4-yl}-3-[(4-fluorophenyl)amino]-1H-pyrazole-4-carboxamide | Calc'd 440, found 440 |
| 6-38 | 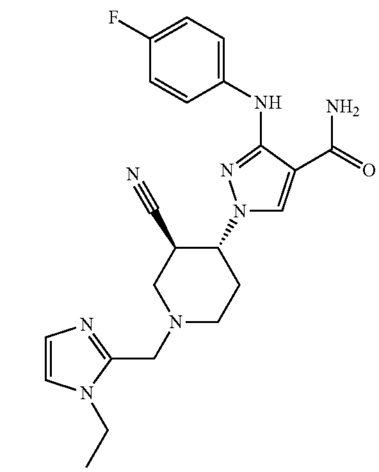 [SMILES: CCn1ccnc1CN1CC[C@@H](n2cc(C(N)=O)c(Nc3ccc(F)cc3)n2)[C@H](C#N)C1] | 1-{(3R,4R and 3S,4S)-3-cyano-1-[(1-ethyl-1H-imidazol-2-yl)methyl]piperidin-4-yl}-3-[(4-fluorophenyl)amino]-1H-pyrdzole-4-carboxamide | Calc'd 437, found 437 |
| 6-39 | 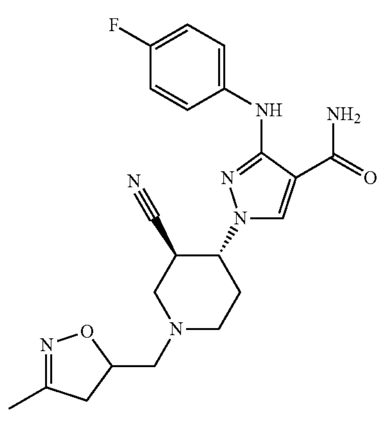 [SMILES: CC1=NOC(CN2CC[C@@H](n3cc(C(N)=O)c(Nc4ccc(F)cc4)n3)[C@H](C#N)C2)C1] | 1-{(3R,4R and 3S,4S)-3-cyano-1-[(3-methyl-4,5-dihydroisoxazol-5-yl)methyl]piperidin-4-yl}-3-[(4-fluorophenyl)amino]-1H-pyrazole-4-carboxamide | Calc'd 426, found 426 |

TABLE 8-continued

| Example | Structure | IUPAC Name | Exact Mass [M + H]+ |
|---|---|---|---|
| 6-40 | 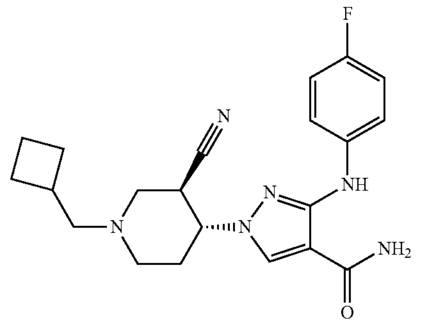 [SMILES: N#C[C@@H]1CN(CC2CCC2)CC[C@H]1n1cc(C(N)=O)c(Nc2ccc(F)cc2)n1] | 1-[(3R,4R)-3-cyano-1-(cyclobutylmethyl)piperidin-4-yl]-3-[(4-fluorophenyl)amino]-1H-pyrazole-4-carboxamide | Calc'd 397, found 397 |

Scheme #24

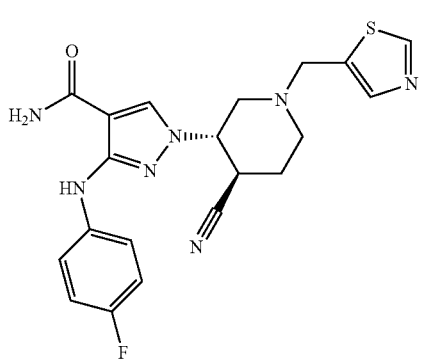

Example #7-1

1-[(3S,4R and 3R,4S)-4-Cyano-1-(1,3-thiazol-5-ylmethyl)piperidin-3-yl]-3-[(4-fluorophenyl)amino]-1H-pyrazole-4-carboxamide A stirred solution of 1,3-thiazol-5-ylmethanol (31 mg, 0.27 mmol) in anhydrous DCM (0.15 mL) was cooled in an ice bath, and a phosgene (20% toluene) (0.31 mL, 0.548 mmol) was slowly added to the solution. The reaction was warmed to ambient temperature and stirred for 18 hours. The solvent was removed in vacuo and the crude reaction mixture was dissolved in dioxane (0.15 mL) and water (0.15 mL), then cesium carbonate (179 mg, 0.548 mmol) and 1-[(3S,4R and 3R,4S)-4-cyanopiperidin-3-yl]-3-[(4-fluorophenyl)amino]-1H-pyrazole-4-carboxamide (Example 3-1, 30 mg, 0.091 mmol) were added at ambient temperature. The reaction mixture was stirred overnight and then heated to 60° C. for 24 hours. Upon cooling to ambient temperature, the crude reaction mixture was diluted to 2 mL of DMSO and purified by mass triggered reverse phased chromatography to afford the title compound. $^1$HNMR (500 MHz, CD$_3$OD): δ 9.10 (s, 1H), 8.24 (s, 1H), 7.87 (s, 1H), 7.67 (br s, 0.5H), 7.51-7.48 (m, 2H), 7.16 (br s, 0.5H), 7.06-7.03 (m, 2H), 4.57 (s, 1H), 4.20 (s, 2H), 3.41 (br s, 2H), 3.26 (br s, 1H), 3.07-3.03 (m, 1H), 2.83 (br s, 1H), 2.35-2.24 (br m, 1H), 1.95-1.93 (br m, 1H). LRMS (ESI) calc'd for C$_{20}$H$_{21}$FN$_7$OS [M+H]$^+$: 426. Found: 426.

The following examples shown in TABLE 9 were prepared according to Scheme #24 following similar procedures described for Example #7-1, which can be achieved by those of ordinary skill in the art of organic synthesis utilizing but not limited to the intermediates described above.

TABLE 9

| Example | Structure | IUPAC Name | Exact Mass [M + H]+ |
|---|---|---|---|
| 7-2 | 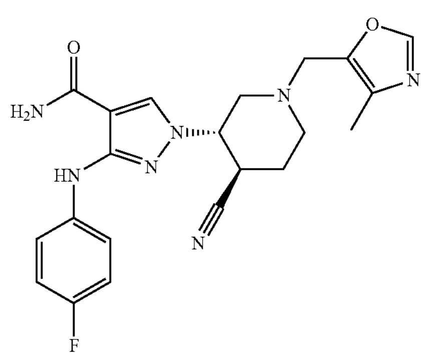 [SMILES: Cc1ncoc1CN1CC[C@@H](C#N)[C@H](n2cc(C(N)=O)c(Nc3ccc(F)cc3)n2)C1] | 1-{(3S,4R, 3R,4S)-4-cyano-1-[(4-methyl-1,3-oxazol-5-yl)methyl]piperidin-3-yl}-3-[(4-fluorophenyl)amino]-1H-pyrazole-4-carboxamide | Calc'd 424, found 424 |

Scheme #27

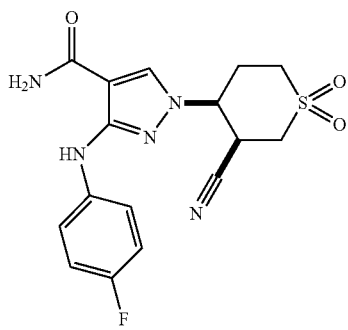

1-((3R,4S and 3S,4R)-3-Cyano-1,1-dioxidotetrahydro-2H-thiopyran-4-yl)-3-((4-fluorophenyl)amino)-1H-pyrazole-4-carboxamide

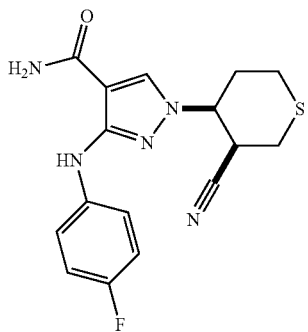

Example #8-1

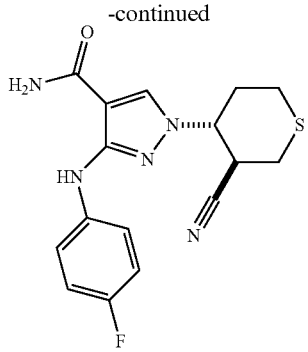

Step A: 1-((3R,4R and 3S,4S)-3-Cyanotetrahydro-2H-thiopyran-4-yl)-3-((4-fluorophenyl)amino)-1H-pyrazole-4-carboxamide and 1-((3R,4S and 3S,4R)-3-cyanotetrahydro-2H-thiopyran-4-yl)-3-((4-fluorophenyl)amino)-1H-pyrazole-4-carboxamide (Intermediates 21-1 and 21-3)

3-((4-Fluorophenyl)amino)-1H-pyrazole-4-carboxamide (Intermediate #20-4, 0.48 g, 2.2 mmol) was combined with 5,6-dihydro-2H-thiopyran-3-carbonitrile (Intermediate #14, 0.25 g, 2.0 mmol) and DBU (0.36 g, 2.4 mmol) in EtOH (10 mL) then heated to 90° C. for 16 hours. The reaction mixture was cooled to ambient temperature and was purified by reverse-phase preparative HPLC (MeCN/water, with 0.1% v/v TFA modifier). Desired fractions were identified, combined, basified with saturated aqueous NaHCO$_3$, and extracted with EtOAc (2×). The combined organic extracts were washed with brine, dried over anhydrous Na$_2$SO$_4$, filtered, and concentrated in vacuo to afford the two title compounds.

Intermediate #21-1: First eluting diastereomer, 1-((3R,4S and 3S,4R)-3-cyanotetrahydro-2H-thiopyran-4-yl)-3-((4-fluorophenyl)amino)-1H-pyrazole-4-carboxamide LRMS (ESI) calc'd for C$_{16}$H$_{16}$FN$_5$OS [M+H]$^+$: 346. Found: 346.

Intermediate #21-2: Second eluting diastereomer, 1-((3R,4R and 3S,4S)-3-cyanotetrahydro-2H-thiopyran-4-yl)-3-((4-fluorophenyl)amino)-1H-pyrazole-4-carboxamide LRMS (ESI) calc'd for C$_{16}$H$_{16}$FN$_5$OS [M+H]$^+$: 346. Found: 346.

The following intermediates shown in TABLE 10 were prepared according to Schemes #25 and 27 following similar procedures described for Intermediates #21-1 and #21-2, which can be achieved by those of ordinary skill in the art of organic synthesis utilizing but not limited to the intermediates described above.

TABLE 10

| Intermediate | Structure | IUPAC Name | Exact Mass [M + H]$^+$ |
|---|---|---|---|
| 21-3 | ![structure] | 1-((3R,4R and 3S,4S)-3-cyanotetrahydro-2H-thiopyran-4-yl)-3-((4-(trifluoromethyl)phenyl)amino)-1H-pyrazole-4-carboxamide | Calc'd 396, Found 396 |

TABLE 10-continued

| Intermediate | Structure | IUPAC Name | Exact Mass [M + H]+ |
|---|---|---|---|
| 21-4 | 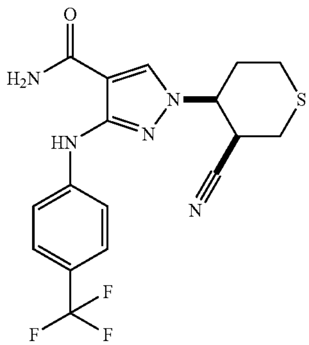 | 1-((3R,4S and 3S,4R)-3-cyanotetrahydro-2H-thiopyran-4-yl)-3-((4-(trifluoromethyl)phenyl)amino)-1H-pyrazole-4-carboxamide | Calc'd 396, found 396 |
| 21-5 | 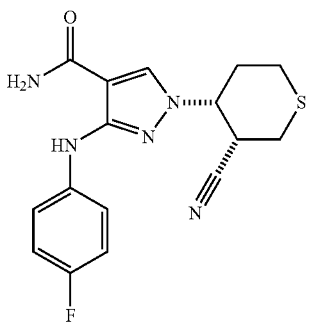 | 1-((3S,4S and 3R,4R)-4-cyanotetrahydrothiophen-3-yl)-3-((4-fluorophenyl)amino)-1H-pyrazole-4-carboxamide | Calc'd 332, Found 332 |
| 21-6 | 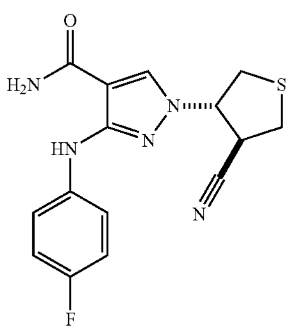 | 1-((3S,4R and 3R,4S)-4-cyanotetrahydrothiophen-3-yl)-3-((4-fluorophenyl)amino)-1H-pyrazole-4-carboxamide | Calc'd 332, Found 332 |
| 21-7 | 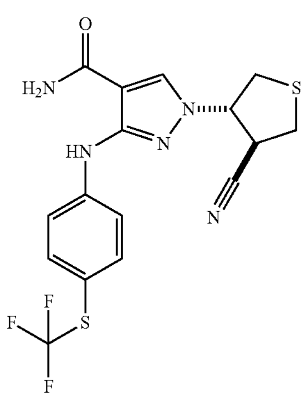 | 1-((3S,4R and 3R,4S)-4-cyanotetrahydrothiophen-3-yl)-3-((4-((trifluoromethyl)thio)phenyl)amino)-1H-pyrazole-4-carboxamide | Calc'd 414, Found 414 |

TABLE 10-continued

| Intermediate | Structure | IUPAC Name | Exact Mass [M + H]+ |
|---|---|---|---|
| 21-8 | 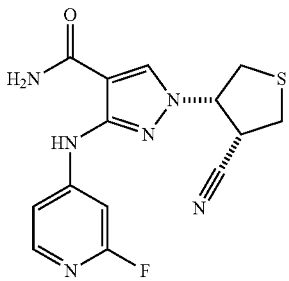 | 1-((3S,4S and 3R,4R)-4-cyanotetrahydrothiophen-3-yl)-3-((2-fluoropyridin-4-yl)amino)-1H-pyrazole-4-carboxamide | Calc'd 333, Found 333 |

Step B: 1-((3R,4S and 3S,4R)-3-cyano-1,1-dioxidotetrahydro-2H-thiopyran-4-yl)-3-((4-fluorophenyl)amino)-1H-pyrazole-4-carboxamide 1-((3R,4S and 3S,4R)-3-Cyanotetrahydro-2H-thiopyran-4-yl)-3-((4-fluorophenyl)amino)-1H-pyrazole-4-carboxamide (82 mg, 0.24 mmol) was dissolved in DCM (2.4 mL) and was stirred vigorously at ambient temperature. m-CPBA (160 mg, 0.71 mmol) was added in three portions and the resulting mixture was maintained at ambient temperature for 3 hours. The mixture was then diluted with 1M aqueous sodium thiosulfate and extracted with EtOAc. The organic layer was again washed with 1M aqueous sodium thiosulfate, saturated aqueous NaHCO₃, brine, dried over anhydrous MgSO₄, filtered, and concentrated in vacuo. The residue was purified by reverse-phase preparative HPLC (MeCN/water, with 0.1% v/v TFA modifier). Desired fractions were identified, combined, basified with saturated aqueous NaHCO₃, and extracted with EtOAc (2×). The combined organic extracts were washed with brine, dried over anhydrous Na₂SO₄, filtered, and concentrated in vacuo to afford the title compound. $^1$H NMR (500 MHz, DMSO-d6): δ 9.10 (s, 1H); 8.36 (s, 1H); 7.64 (s, 1H); 7.53 (t, J=6.2 Hz, 2H); 7.20 (s, 1H); 7.05 (t, J=8.5 Hz, 2H); 4.83 (m, 1H); 4.29 (m, 1H); 3.78-3.85 (m, 1H); 3.62-3.69 (m, 1H); 3.50-3.58 (m, 1H); 3.38-3.48 (m, 1H); 2.52-2.60 (m, 2H). LRMS (ESI) calc'd for $C_{16}H_{16}FN_5O_3S$ [M+H]⁺: 378. Found: 378.

The following intermediates and examples shown in TABLE 11 were prepared according to Schemes #25, 26, and 27 following similar procedures described for Example #8-1, which can be achieved by those of ordinary skill in the art of organic synthesis utilizing but not limited to the intermediates described above.

TABLE 11

| Intermediate or Example | Structure | IUPAC Name | Exact Mass [M + H]+ |
|---|---|---|---|
| 8-2 | 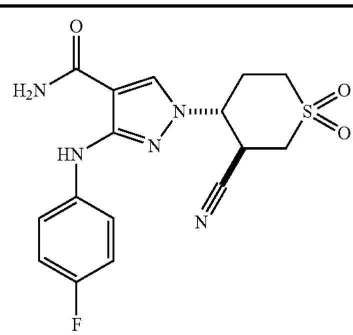 | 1-((3R,4S and 3S, 4R)-3-cyano-1,1-dioxidotetrahydro-2H-thiopyran-4-yl)-3-((4-fluorophenyl)amino)-1H-pyrazole-4-carboxamide | Calc'd 378, Found 378 |
| 8-3 | 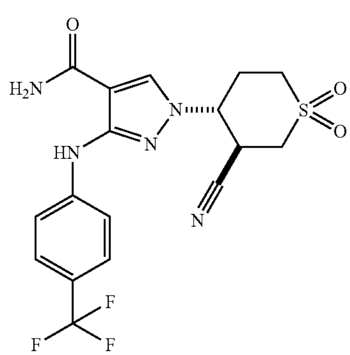 | 1-((3R,4R and 3S,4S)-3-cyano-1,1-dioxidotetrahydro-2H-thiopyran-4-yl)-3-((4-(trifluoromethyl)phenyl)amino)-1H-pyrazole-4-carboxamide | Calc'd 428, Found 428 |

TABLE 11-continued

| Intermediate or Example | Structure | IUPAC Name | Exact Mass [M + H]+ |
|---|---|---|---|
| 8-4 | 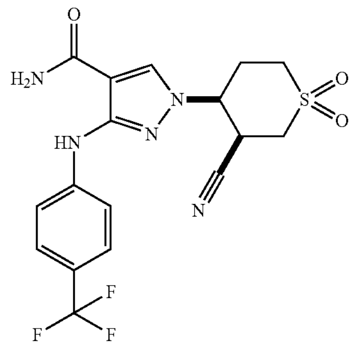 | 1-((3R,4S and 3S,4R)-3-cyano-1,1-dioxidotetrahydro-2H-thiopyran-4-yl)-3-((4-(trifluoromethyl)phenyl)amino)-1H-pyrazole-4-carboxamide | Calc'd 428, Found 428 |
| 8-5 | 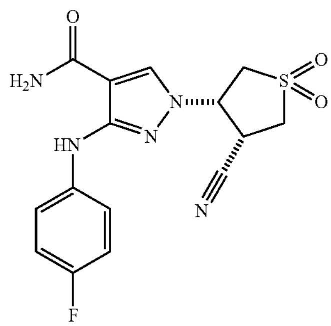 | 1-((3S,4S and 3R,4R)-4-cyano-1,1-dioxidotetrahydrothiophen-3-yl)-3-((4-fluorophenyl)amino)-1H-pyrazole-4-carboxamide | Calc'd 364, Found 364 |
| 8-6 | 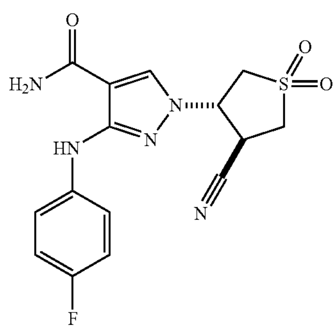 | 1-((3S,4R and 3R,4S)-4-cyano-1,1-dioxidotetrahydrothiophen-3-yl)-3-((4-fluorophenyl)amino)-1H-pyrazole-4-carboxamide | Calc'd 364, Found 364 |
| 8-7 | 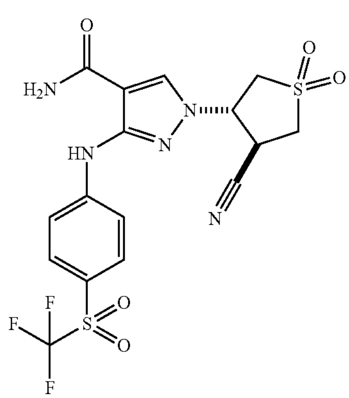 | 1-((3S,4R and 3R,4S)-4-cyano-1,1-dioxidotetrahydrothiophen-3-yl)-3-((4-((trifluoromethyl)sulfonyl)phenyl)amino)-1H-pyrazole-4-carboxamide | Calc'd 478, Found 478 |

TABLE 11-continued

| Intermediate or Example | Structure | IUPAC Name | Exact Mass [M + H]+ |
|---|---|---|---|
| 8-8 | 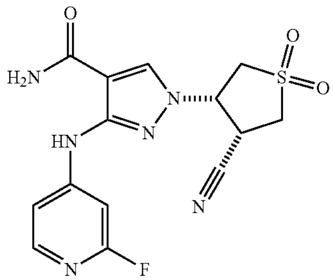 | 1-((3S,4S and 3R,4R)-4-cyano-1,1-dioxidotetrahydrothiophen-3-yl)-3-((2-fluoropyridin-4-yl)amino)-1H-pyrazole-4-carboxamide | Calc'd 365, Found 365 |
| Intermediate 22-1 | 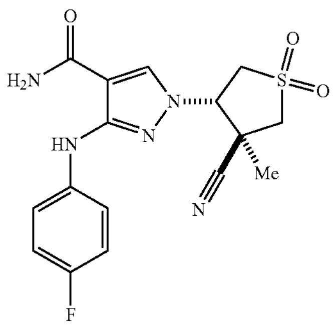 | 1-((3S,4R and 3R,4S)-4-cyano-4-methyl-1,1-dioxidotetrahydrothiophen-3-yl)-3-((4-fluorophenyl)amino)-1H-pyrazole-4-carboxamide | Calc'd 378, Found 378 |
| Intermediate 22-2 | 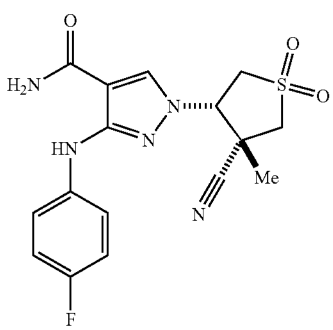 | 1-((3S,4S and 3R,4R)-4-cyano-4-methyl-1,1-dioxidotetrahydrothiophen-3-yl)-3-((4-fluorophenyl)amino)-1H-pyrazole-4-carboxamide | Calc'd 378, Found 378 |

Scheme #28

Examples #9-1 and 9-2

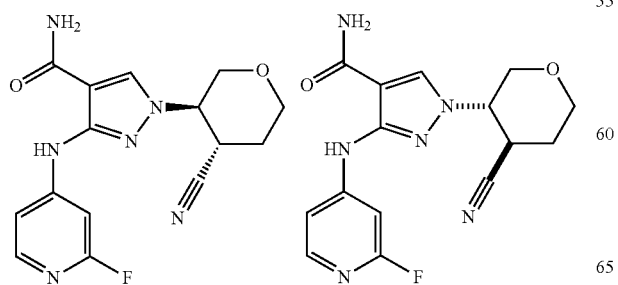

1-((3R,4S or 3S,4R)-4-Cyano-tetrahydro-2H-pyran-3-yl)-3-(2-fluoropyridin-4-ylamino)-1H-pyrazole-4-carboxamide

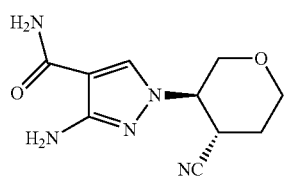 [SMILES: N#C[C@H]1CCOC[C@@H]1n1cc(C(N)=O)c(N)n1]

Step A: 3-Amino-1-((3R,4S and 3S,4R)-4-cyano-tetrahydro-2H-pyran-3-yl)-1H-pyrazole-4-carboxamide A solution of 3-amino-1H-pyrazole-4-carboxamide (500 mg, 4.0 mmol), 3,6-dihydro-2H-pyran-4-carbonitrile (Intermediate 18, 1.2 g, 11 mmol) and DBU (1.4 g, 9.2 mmol) in ethanol (5 mL) was stirred at 70° C. overnight under nitrogen, and then concentrated in vacuo. The crude residue was purified by silica gel flash column chromatography with 2-5% methanol in dichloromethane to afford the title compound as a yellow solid. MS ESI: [M+H]+ m/z 236; $^1$H NMR (500 MHz, CD$_6$SO) δ 8.03 (s, 1H), 7.36 (brs, 1H), 6.80 (brs, 1H), 5.36 (s, 2H), 4.86-4.31 (td, J=10.5, 4.5 Hz, 1H), 3.91-3.88 (dd, J=11.5, 4.5 Hz 1H), 3.86-3.83 (m, 1H), 3.53-3.50 (m, 2H), 3.39-3.33 (td, J=11.5, 2 Hz, 1H), 2.10-2.07 (m, 1H), 1.95-1.87 (m, 1H).

Step B: 1-((3R,4S or 3S,4R)-4-Cyano-tetrahydro-2H-pyran-3-yl)-3-(2-fluoropyridin-4-ylamino)-1H-pyrazole-4-carboxamide The degassed solution of 3-amino-1-((3R,4S and 3S,4R)-4-cyano-tetrahydro-2H-pyran-3-yl)-1H-pyrazole-4-carboxamide (130 mg, 0.55 mmol), 4-bromo-2-fluoropyridine (97 mg, 0.55 mmol), KOAc (160 mg, 1.6 mmol), Pd$_2$(dba)$_3$·CHCl$_3$ (85 mg, 0.090 mmol) and t-Bu XPhos (70 mg, 0.18 mmol) in iso-propanol (10 mL) was stirred at 60° C. for 2 hours under nitrogen, and then concentrated in vacuo. The crude residue was purified by flash column chromatography with 2-4% methanol in dichloromethane to afford the title compound as a racemic mixture, which was then separated by preparative chiral HPLC (Column: Chiralpak AD-H, 2*25 cm; Mobile phase: 15% IPA (0.2% TEA) in hexane (0.2% TEA)) to afford:

Example 9-1: 1-((3R,4S or 3S,4R)-4-cyano-tetrahydro-2H-pyran-3-yl)-3-(2-fluoropyridin-4-ylamino)-1H-pyrazole-4-carboxamide: MS ESI: [M+H]+ m/z 330.8; $^1$H NMR (500 MHz, CD$_6$SO) δ 9.74 (s, 1H), 8.35 (s, 1H), 7.93 (d, J=6 Hz, 1H), 7.84 (s, 1H), 7.33 (m, 3H), 4.65-4.60 (td, J=10.5, 4.5 Hz, 1H), 4.04-4.00 (dd, J=11.5, 4.5, 1H), 3.90-3.88 (m, 1H), 3.73-3.63 (m, 2H), 3.51-3.46 (td, J=11.5, 2 Hz, 1H), 2.15-2.12 (m, 1H), 2.00-1.93 (m, 1H).

Example 9-2: 1-((3R,4S or 3S,4R)-4-cyano-tetrahydro-2H-pyran-3-yl)-3-(2-fluoropyridin-4-ylamino)-1H-pyrazole-4-carboxamide: MS ESI: [M+H]$^1$ m/z 330.8; $^1$H NMR (500 MHz, CD$_6$SO) δ 9.74 (s, 1H), 8.35 (s, 1H), 7.93 (d, J=6 Hz, 1H), 7.84 (s, 1H), 7.33 (m, 3H), 4.65-4.60 (td, J=10.5, 4.5 Hz, 1H), 4.04-4.00 (dd, J=11.5, 4.5, 1H), 3.90-3.88 (m, 1H), 3.73-3.63 (m, 2H), 3.51-3.46 (td, J=11.5, 2 Hz, 1H), 2.15-2.12 (m, 1H), 2.00-1.93 (m, 1H).

The following examples shown in TABLE 12 were prepared according to Scheme #28 following similar procedures described for Examples #9-1 and 9-2, which can be achieved by those of ordinary skill in the art of organic synthesis utilizing but not limited to the intermediates described above.

TABLE 12

| Example | Structure | IUPAC Name | Exact Mass [M + H]+ |
|---------|-----------|------------|---------------------|
| 9-3 | 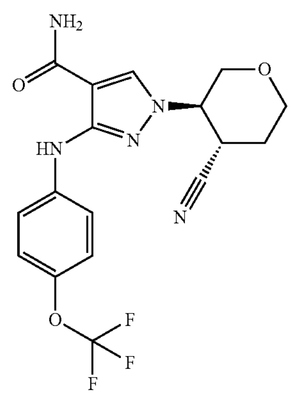 [SMILES: N#C[C@H]1CCOC[C@@H]1n1cc(C(N)=O)c(Nc2ccc(OC(F)(F)F)cc2)n1] | 1-((3R,4S or 3S,4R)-4-cyanotetrahydro-2H-pyran-3-yl)-3-((4-(trifluoromethoxy(phenyl)amino)-1H-pyrazole-4-carboxamide | Calc'd 395, found 395 |
| 9-4 | 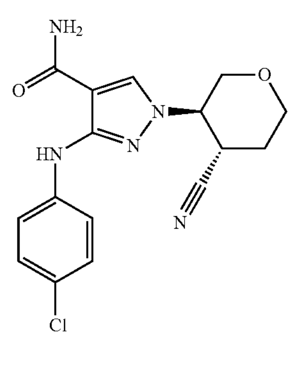 [SMILES: N#C[C@H]1CCOC[C@@H]1n1cc(C(N)=O)c(Nc2ccc(Cl)cc2)n1] | 3-[(4-chlorophenyl)amino]-1-[(3R,4S or 3S,4R)-4-cyanotetrahydro-2H-pyran-3-yl]-1H-pyrazole-4-carboxamide | Calc'd 346, found 346 |

TABLE 12-continued

| Example | Structure | IUPAC Name | Exact Mass [M + H]+ |
|---|---|---|---|
| 9-5 | 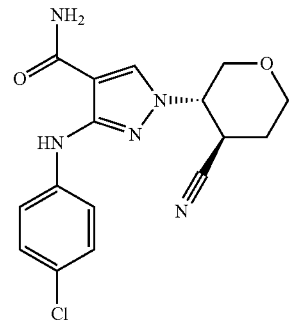 [SMILES: N#C[C@@H]1CCOC[C@H]1n1cc(C(N)=O)c(Nc2ccc(Cl)cc2)n1] | 3-[(4-chlorophenyl)amino]-1-[(3S,4R or 3R,4S)-4-cyanotetrahydro-2H-pyran-3-yl]-1H-pyrazole-4-carboxamide | Calc'd 346, found 346 |
| 9-6 | 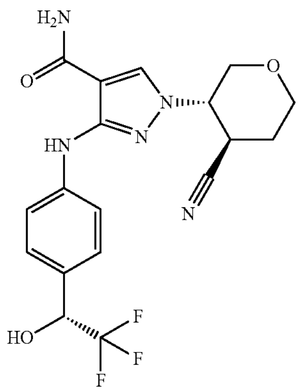 [SMILES: N#C[C@@H]1CCOC[C@H]1n1cc(C(N)=O)c(Nc2ccc([C@@H](O)C(F)(F)F)cc2)n1] | 1-[(3S,4R or 3R,4S)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide | Calc'd 410, found 410 |
| 9-7 | 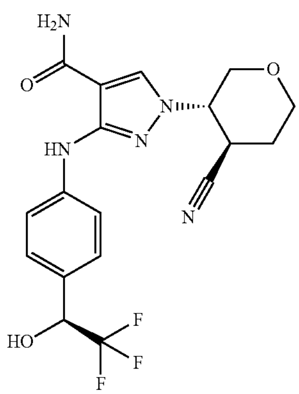 [SMILES: N#C[C@@H]1CCOC[C@H]1n1cc(C(N)=O)c(Nc2ccc([C@H](O)C(F)(F)F)cc2)n1] | 1-[(3S,4R or 3R,4S)-4-cyanotetrahydro-2H-pyran-3-yl]-3-({4-[(1S or 1R)-2,2,2-trifluoro-1-hydroxyethyl]phenyl}amino)-1H-pyrazole-4-carboxamide | Calc'd 410, found 410 |
| 9-8 | 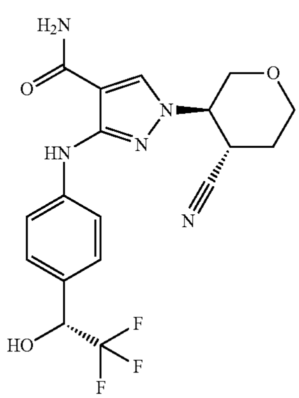 [SMILES: N#C[C@H]1CCOC[C@@H]1n1cc(C(N)=O)c(Nc2ccc([C@@H](O)C(F)(F)F)cc2)n1] | 1-[(3R,4S or 3S,4R)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide | Calc'd 410, found 410 |

TABLE 12-continued

| Example | Structure | IUPAC Name | Exact Mass [M + H]+ |
|---|---|---|---|
| 9-9 | 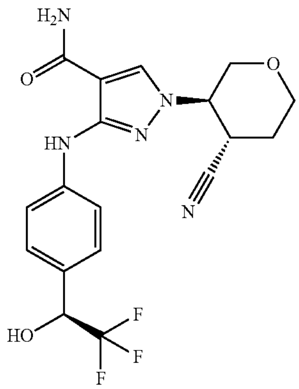 [SMILES: N#C[C@H]1CCOC[C@@H]1n1cc(C(N)=O)c(Nc2ccc([C@H](O)C(F)(F)F)cc2)n1] | 1-[(3R,4S or 3S,4R)-4-cyanotetrahydro-2H-pyran-3-yl]-3-({4-[(1S or 1R)-2,2-trifluoro-1-hydroxyethyl]phenyl}amino)-1H-pyrazole-4-carboxamide | Calc'd 410, found 410 |
| 9-10 | 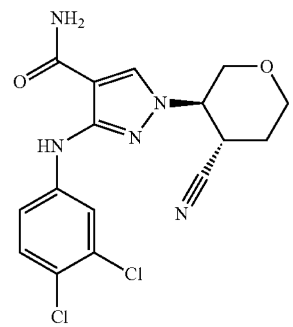 [SMILES: N#C[C@H]1CCOC[C@@H]1n1cc(C(N)=O)c(Nc2ccc(Cl)c(Cl)c2)n1] | 1-[(3R,4S or 3S,4R)-4-cyanotetrahydro-2H-pyran-3-yl]-3-[(3,4-dichlorophenyl)amino]-1H-pyrazole-4-carboxamide | Calc'd 380, found 380 |
| 9-11 | 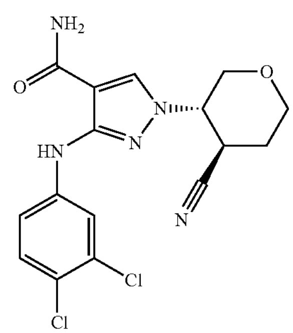 [SMILES: N#C[C@@H]1CCOC[C@H]1n1cc(C(N)=O)c(Nc2ccc(Cl)c(Cl)c2)n1] | 1-[(3S,4R or 3R,4S)-4-cyanotetrahydro-2H-pyran-3-yl]-3-[(3,4-dichlorophenyl)amino]-1H-pyrazole-4-carboxamide | Calc'd 380, found 380 |
| 9-12 | 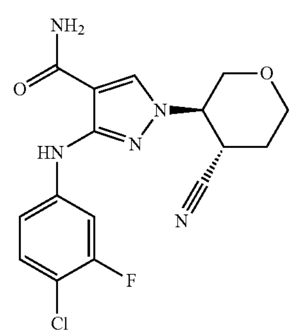 [SMILES: N#C[C@H]1CCOC[C@@H]1n1cc(C(N)=O)c(Nc2ccc(Cl)c(F)c2)n1] | 3-[(4-chloro-3-fluorophenyl)amino]-1-[(3R,4S or 3S,4R)-4-cyanotetrahydro-2H-pyran-3-yl]-1H-pyrazole-4-carboxamide | Calc'd 364, found 364 |

TABLE 12-continued

| Example | Structure | IUPAC Name | Exact Mass [M + H]+ |
|---|---|---|---|
| 9-13 | 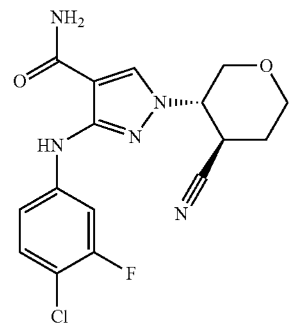 [SMILES: N#C[C@@H]1CCOC[C@H]1n1cc(C(N)=O)c(Nc2ccc(Cl)c(F)c2)n1] | 3-[(4-chloro-3-fluorophenyl)amino]-1-[(3S,4R or 3R,4S)-4-cyanotetrahydro-2H-pyran-3-yl]-1H-pyrazole-4-carboxamide | Calc'd 364, found 364 |
| 9-14 | 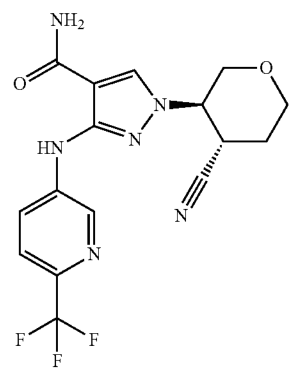 [SMILES: N#C[C@H]1CCOC[C@@H]1n1cc(C(N)=O)c(Nc2ccc(C(F)(F)F)nc2)n1] | 1-[(3R,4S or 3S,4R)-4-cyanotetrahydro-2H-pyran-3-yl]-3-{[6-(trifluoromethyl)pyridin-3-yl]amino}-1H-pyrazole-4-carboxamide | Calc'd 381, found 381 |
| 9-15 | 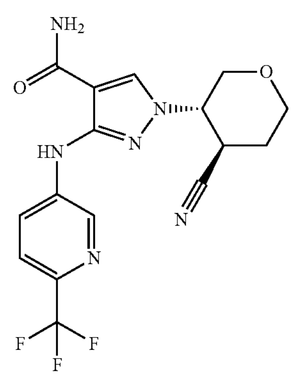 [SMILES: N#C[C@@H]1CCOC[C@H]1n1cc(C(N)=O)c(Nc2ccc(C(F)(F)F)nc2)n1] | 1-[(3S,4R or 3R,4S)-4-cyanotetrahydro-2H-pyran-3-yl]-3-{[6-(trifluoromethyl)pyridin-3-yl]amino}-1H-pyrazole-4-carboxamide | Calc'd 381, found 381 |
| 9-16 | 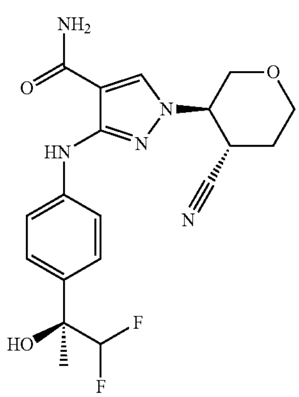 [SMILES: C[C@](O)(c1ccc(Nc2nn([C@H]3COCC[C@@H]3C#N)cc2C(N)=O)cc1)C(F)F] | 1-[(3R,4S or 3S,4R)-4-cyanotetrahydro-2H-pyran-3-yl]-3-({4-[(1S or 1R)-2,2-difluoro-1-hydroxy-1-methylethyl]phenyl}amino)-1H-pyrazole-4-carboxamide | Calc'd 406, found 406 |

TABLE 12-continued

| Example | Structure | IUPAC Name | Exact Mass [M + H]+ |
|---|---|---|---|
| 9-17 | 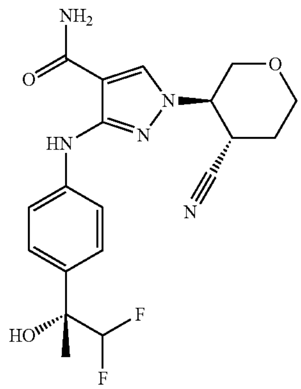 [SMILES: C[C@@](O)(c1ccc(Nc2nn([C@H]3COCC[C@@H]3C#N)cc2C(N)=O)cc1)C(F)F] | 1-[(3R,4S or 3S,4R)-4-cyanotetrahydro-2H-pyran-3-yl]-3-({4-[(1R or 1S)-2,2-difluoro-1-hydroxy-1-methylethyl]phenyl}amino)-1H-pyrazole-4-carboxamide | Calc'd 406, found 406 |
| 9-18 | 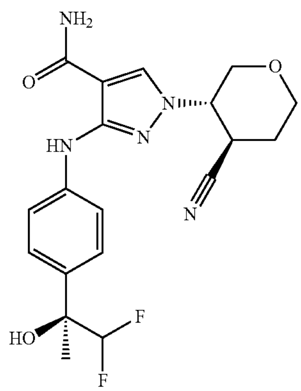 [SMILES: C[C@](O)(c1ccc(Nc2nn([C@@H]3COCC[C@H]3C#N)cc2C(N)=O)cc1)C(F)F] | 1-[(3S,4R or 3R,4S)-4-cyanotetrahydro-2H-pyran-3-yl]-3-({4-[(1S or 1R)-2,2-difluoro-1-hydroxy-1-methylethyl]phenyl}amino)-1H-pyrazole-4-carboxamide | Calc'd 406, found 406 |
| 9-19 | 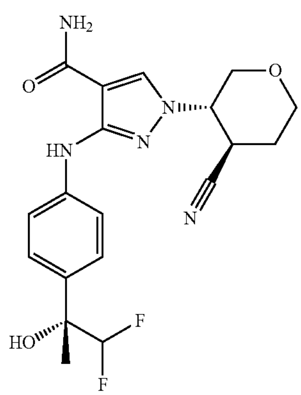 [SMILES: C[C@@](O)(c1ccc(Nc2nn([C@@H]3COCC[C@H]3C#N)cc2C(N)=O)cc1)C(F)F] | 1-[(3S,4R or 3R,4S)-4-cyanotetrahydro-2H-pyran-3-yl]-3-({4-[(1R or 1S)-2,2-difluoro-1-hydroxy-1-methylethyl]phenyl[amino)-1H-pyrazole-4-carboxamide | Calc'd 406, found 406 |
| 9-20 | 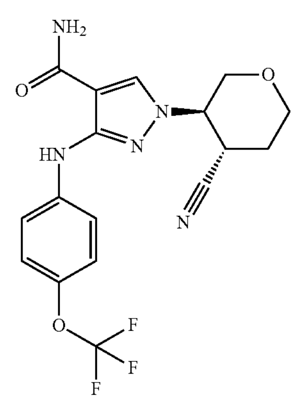 [SMILES: N#C[C@H]1CCOC[C@@H]1n1cc(C(N)=O)c(Nc2ccc(OC(F)(F)F)cc2)n1] | 1-[(3R,4S or 3S,4R)-4-cyanotetrahydro-2H-pyran-3-yl]-3-{[4-(trifluoromethoxy)phenyl]amino}-1H-pyrazole-4-carboxamide | Calc'd 396.0, found 396 |

TABLE 12-continued

| Example | Structure | IUPAC Name | Exact Mass [M + H]+ |
|---|---|---|---|
| 9-21 | 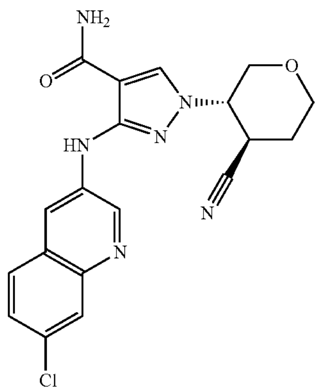 [SMILES: N#C[C@@H]1CCOC[C@H]1n1cc(C(N)=O)c(Nc2cnc3cc(Cl)ccc3c2)n1] | 3-[(7-chloroquinolin-3-yl)amino]-1-[(3S,4R or 3R,4S)-4-cyanotetrahydro-2H-pyran-3-yl]-1H-pyrazole-4-carboxamide | Calc'd 397, found 397 |
| 9-22 | 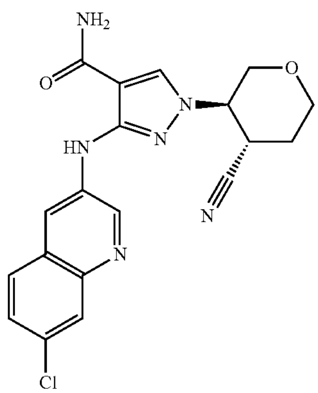 [SMILES: N#C[C@H]1CCOC[C@@H]1n1cc(C(N)=O)c(Nc2cnc3cc(Cl)ccc3c2)n1] | 3-[(7-chloroquinolin-3-yl)amino]-1-[(3R,4S or 3S,4R)-4-cyanotetrahydro-2H-pyran-3-yl]-1H-pyrazole-4-carboxamide | Calc'd 397.0, found 397 |
| 9-23 | 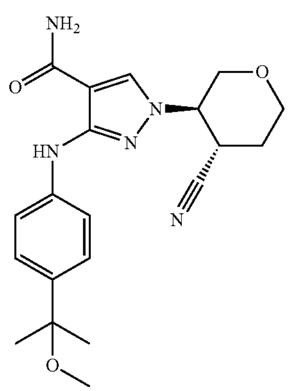 [SMILES: COC(C)(C)c1ccc(Nc2nn([C@H]3COCC[C@@H]3C#N)cc2C(N)=O)cc1] | 1-[(3R,4S or 3S,4R)-4-cyanotetrahydro-2H-pyran-3-yl]-3-{[4-(1-methoxy-1-methylethyl)phenyl]amino}-1H-pyrazole-4-carboxamide | Calc'd 384, found 352 [M − OCH$_3$]$^+$ |
| 9-24 | 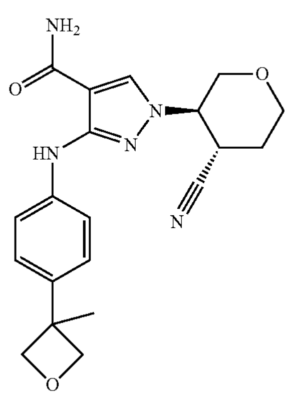 [SMILES: CC1(c2ccc(Nc3nn([C@H]4COCC[C@@H]4C#N)cc3C(N)=O)cc2)COC1] | 1-[(3R,4S or 3S,4R)-4-cyanotetrahydro-2H-pyran-3-yl]-3-{[4-(3-methyloxetan-3-yl)phenyl]amino}-1H-pyrazole-4-carboxamide | Calc'd 382, found 382 |

TABLE 12-continued

| Example | Structure | IUPAC Name | Exact Mass [M + H]+ |
|---|---|---|---|
| 9-25 | 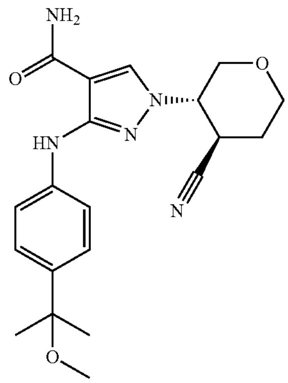 [SMILES: COC(C)(C)c1ccc(Nc2nn([C@@H]3COCC[C@H]3C#N)cc2C(N)=O)cc1] | 1-[(3S,4R or 3R,4R)-4-cyanotetrahydro-2H-pyran-3-yl]-3-{[4-(1-methoxy-1-methylethyl)phenyl]amino}-1H-pyrazole-4-carboxamide | Calc'd 384, found 352 [M − OCH₃]⁺ |
| 9-26 | 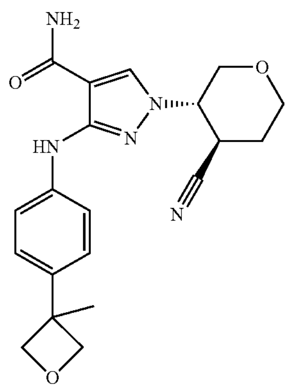 [SMILES: CC1(c2ccc(Nc3nn([C@@H]4COCC[C@H]4C#N)cc3C(N)=O)cc2)COC1] | 1-[(3S,4R or 3R,4S)-4-cyanotetrahydro-2H-pyran-3-yl]-3-{[4-(3-methyloxetan-3-yl)phenyl]amino}1H-pyrazole-4-carboxamide | Calc'd 382, found 382 |
| 9-27 | 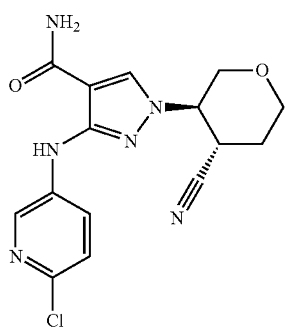 | 3-[(6-chloropyridin-3-yl)amino]-1-[(3R,4S or 3S,4R)-4-cyanotetrahydro-2H-pyran-3-yl]-1H-pyrazole-4-carboxamide | Calc'd 347, found 347 |
| 9-28 | 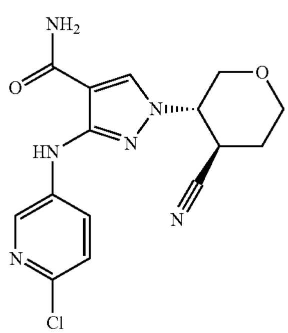 [SMILES: N#C[C@@H]1CCOC[C@H]1n1cc(C(N)=O)c(Nc2ccc(Cl)nc2)n1] | 3-[(6-chloropyridin-3-yl)amino]-1-[(3S,4R or 3R,4S)-4-cyanotetrahydro-2H-pyran-3-yl]-1H-pyrazole-4-carboxamide | Calc'd 347, found 347 |

TABLE 12-continued

| Example | Structure | IUPAC Name | Exact Mass [M + H]+ |
|---|---|---|---|
| 9-29 | 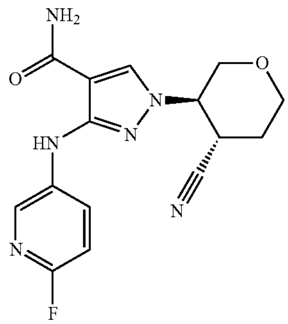 [SMILES: N#C[C@H]1CCOC[C@@H]1n1cc(C(N)=O)c(Nc2ccc(F)nc2)n1] | 1-[(3R,4S or 3S,4R)-4-cyanotetrahydro-2H-pyran-3-yl]-3-[(6-fluoropyridin-3-yl)amino]-1H-pyrazole-4-carboxamide | Calc'd 331, found 331 |
| 9-30 | 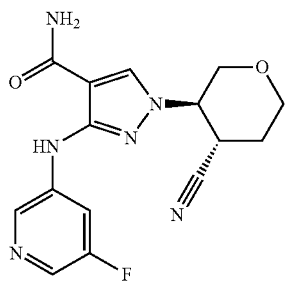 [SMILES: N#C[C@H]1CCOC[C@@H]1n1cc(C(N)=O)c(Nc2cncc(F)c2)n1] | 1-[(3R,4S or 3S,4R)-4-cyanotetrahydro-2H-pyran-3-yl]-3-[(5-fluoropyridin-3-yl)amino]-1H-pyrazole-4-carboxamide | Calc'd 331, found 331 |
| 9-31 | 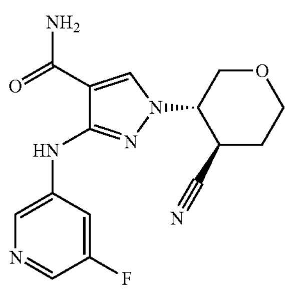 [SMILES: N#C[C@@H]1CCOC[C@H]1n1cc(C(N)=O)c(Nc2cncc(F)c2)n1] | 1-[(3S,4R or 3R,4S)-4-cyanotetrahydro-2H-pyran-3-yl]-3-[(5-fluoropyridin-3-yl)amino]-1H-pyrazole-4-carboxamide | Calc'd 331, found 331 |
| 9-32 | 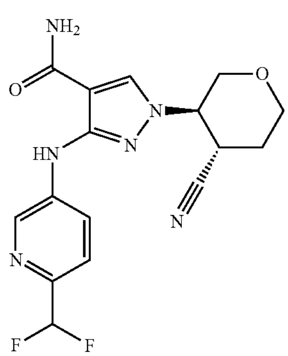 [SMILES: N#C[C@H]1CCOC[C@@H]1n1cc(C(N)=O)c(Nc2ccc(C(F)F)nc2)n1] | 1-[(3R,4S or 3S,4R)-4-cyanotetrahydro-2H-pyran-3-yl]-3-{[6-(difluoromethyl)pyridin-3-yl]amino}-1H-pyrazole-4-carboxamide | Calc'd 363, found 363 |

TABLE 12-continued

| Example | Structure | IUPAC Name | Exact Mass [M + H]+ |
|---|---|---|---|
| 9-33 | 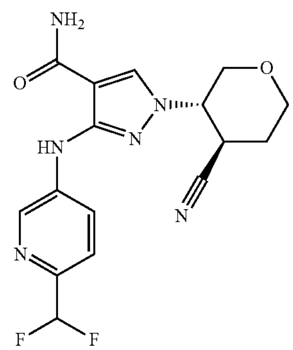 [SMILES: N#C[C@@H]1CCOC[C@H]1n1cc(C(N)=O)c(Nc2ccc(C(F)F)nc2)n1] | 1-[(3S,4R or 3R,4S)-4-cyanotetrahydro-2H-pyran-3-yl]-3-{[6-(difluoromethyl)pyridin-3-yl]amino}-1H-pyrazole-4-carboxamide | Calc'd 363, found 363 |
| 9-34 | 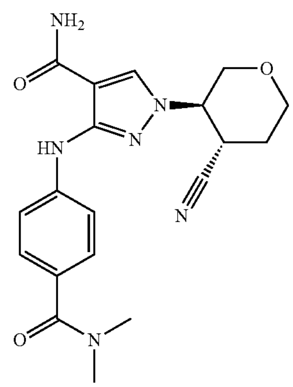 [SMILES: CN(C)C(=O)c1ccc(Nc2nn([C@H]3COCC[C@@H]3C#N)cc2C(N)=O)cc1] | 1-[(3R,4S or 3S,4R)-4-cyanotetrahydro-2H-pyran-3-yl]-3-{[4-(dimethylcarbamoyl)phenyl]amino}-1H-pyrazole-4-carboxamide | Calc'd 383, found 383 |
| 9-35 | 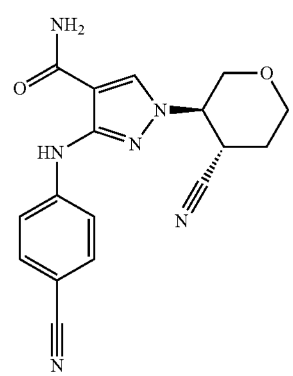 [SMILES: N#Cc1ccc(Nc2nn([C@H]3COCC[C@@H]3C#N)cc2C(N)=O)cc1] | 3-[(4-cyanophenyl)amino]-1-[(3R, 4S or 3S,4R)-4-cyanotetrahydro-2H-pyran-3-yl]-1H-pyrazole-4-carboxamide | Calc'd 337, found 337 |
| 9-36 | 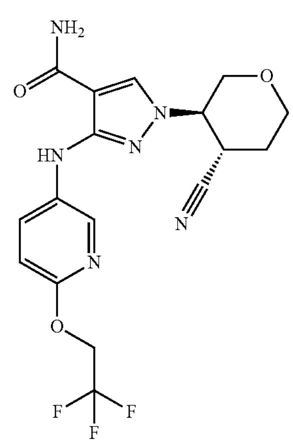 [SMILES: N#C[C@H]1CCOC[C@@H]1n1cc(C(N)=O)c(Nc2ccc(OCC(F)(F)F)nc2)n1] | 1-[(3R,4S or 3S,4R)-4-cyanotetrahydro-2H-pyran-3-yl]-3-{[6-(2,2,2-trifluoroethoxy)pyridin-3-yl]amino}-1H-pyrazole-4-carboxamide | Calc'd 411, found 411 |

TABLE 12-continued

| Example | Structure | IUPAC Name | Exact Mass [M + H]+ |
|---|---|---|---|
| 9-37 | 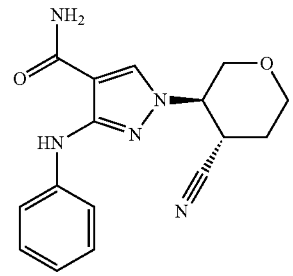 [SMILES: N#C[C@H]1CCOC[C@@H]1n1cc(C(N)=O)c(Nc2ccccc2)n1] | 1-[(3S,4R or 3R,4S)-4-cyanotetrahydro-2H-pyran-3-yl]-3-(phenylamino)-1H-pyrazole-4-carboxamide | Calc'd 312, found 312 |
| 9-38 | 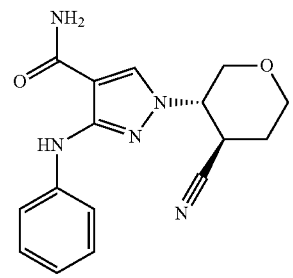 [SMILES: N#C[C@@H]1CCOC[C@H]1n1cc(C(N)=O)c(Nc2ccccc2)n1] | 1-[(3R,4S or 3S,4R)-4-cyanotetrahydro-2H-pyran-3-yl]-3-(phenylamino)-1H-pyrazole-4-carboxamide | Calc'd 312, found 312 |

Scheme #29

Example #10-1 and 10-2

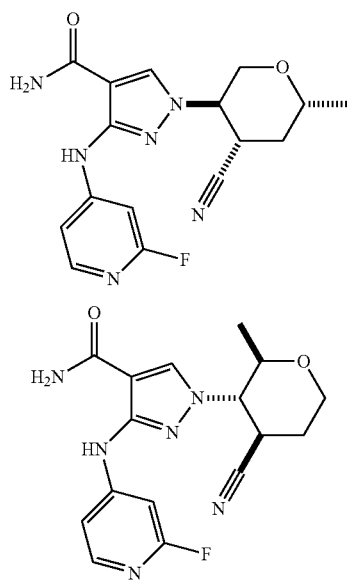

1-((3R,4S,6R and 3S,4R,6S)-4-Cyano-6-methyltetrahydro-2H-pyran-3-yl)-3-((2-fluoropyridin-4-yl)amino)-1H-pyrazole-4-carboxamide and 1-((2S,3R,4S and 2R,3S,4R)-4-cyano-2-methyltetrahydro-2H-pyran-3-yl)-3-((2-fluoropyridin-4-yl)amino)-1H-pyrazole-4-carboxamide 3-((2-Fluoropyridin-4-yl)amino)-1H-pyrazole-4-carboxamide (Intermediate 20-6, 0.10 g, 0.45 mmol) was combined with 2-methyl-3,6-dihydro-2H-pyran-4-carbonitrile (Intermediates 19-1 and 19-2, 0.10 g, 0.41 mmol) and DBU (0.075 g, 0.49 mmol) in EtOH (2.0 mL) and heated to 90° C. for 16 hours. The reaction mixture was cooled to ambient temperature and was purified by reverse-phase preparative HPLC (MeCN/water, with 0.1% v/v TFA modifier). Desired fractions were identified, combined, and lyophilized to afford the title compound.

Example 10-1: 1-((3R,4S,6R and 3S,4R,6S)-4-Cyano-6-methyltetrahydro-2H-pyran-3-yl)-3-((2-fluoropyridin-4-yl)amino)-1H-pyrazole-4-carboxamide: $^1$H NMR (500 MHz, DMSO-d$_6$): δ 9.74 (s, 1H); 8.34 (s, 1H); 7.92 (d, J=5.8 Hz, 1H); 7.84 (s, 1H); 7.28-7.35 (m, 3H); 4.58-4.64 (m, 1H); 4.01 (dd, J=11.1, 4.6 Hz, 1H); 3.60-3.77 (m, 3H); 2.19-2.25 (m, 1H); 1.64-1.76 (m, 1H); 1.15 (d, J=6.1 Hz, 3H). LRMS (ESI) calc'd for $C_{16}H_{17}FN_6O_2$ [M+H]$^+$: 345. Found: 345.

Example 10-2: 1-((2S,3R,4S and 2R,3S,4R)-4-cyano-2-methyltetrahydro-2H-pyran-3-yl)-3-((2-fluoropyridin-4-yl)amino)-1H-pyrazole-4-carboxamide. LRMS (ESI) calc'd for $C_{16}H_{17}FN_6O_2$ [M+H]$^+$: 345. Found: 345.

Scheme 15, 18, and 22

Examples #11-1 and 11-2

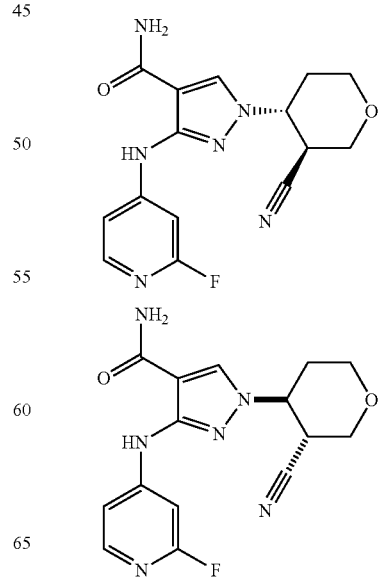

1-[(3S,4S or 3R,4R)-3-Cyanotetrahydro-2H-pyran-4-yl]-3-[(2-fluoropyridin-4-yl)amino]-1H-pyrazole-4-carboxamide

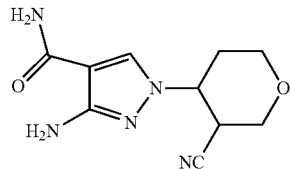 [SMILES: N#CC1COCCC1n1cc(C(N)=O)c(N)n1]

Step A: 3-Amino-1-(3-cyanotetrahydro-2H-pyran-4-yl)-1H-pyrazole-4-carboxamide A solution of 5,6-dihydro-2H-pyran-3-carbonitrile (Intermediate 17, 500 mg, 4.6 mmol), 3-amino-1H-pyrazole-4-carboxamide (1.2 g, 9.1 mmol) and DBU (1.4 g, 9.2 mmol) in ethanol (5 mL) was stirred at 70° C. overnight under nitrogen, and then concentrated in vacuo. The crude residue was purified by flash column chromatography with 2-5% methanol in dichloromethane to afford a mixture of 3-amino-1-(3-cyanotetrahydro-2H-pyran-4-yl)-1H-pyrazole-4-carboxamide diastereomers as a yellow solid. MS ESI: [M+H]$^+$ m/z 236;

Step B: 1-[(3S,4S or 3R,4R)-3-Cyanotetrahydro-2H-pyran-4-yl]-3-[(2-fluoropyridin-4-yl)amino]-1H-pyrazole-4-carboxamide A degassed solution of 3-amino-1-(3-cyanotetrahydro-2H-pyran-4-yl)-1H-pyrazole-4-carboxamide (200 mg, 0.85 mmol), 4-bromo-2-fluoropyridine (118 mg, 0.67 mmol), KOAc (197 mg, 2.0 mmol), Pd$_2$(dba)$_3$CHCl$_3$ (103 mg, 0.10 mmol) and t-Bu XPhos (85 mg, 0.20 mmol) in iso-propanol (10 mL) was stirred at 60° C. for 1 hour under nitrogen, and then concentrated in vacuo. The crude residue was purified by flash column chromatography with 1-2% methanol in dichloromethane followed by preparative reverse-phase HPLC (using a gradient elution of 30-45% MeCN/water with 0.05% NH$_3$.H$_2$O) to afford the title compound as a racemic mixture, which was resolved to the constituent enantiomers by Chiral SFC purification (Chiral Technology ID 2.1×25 cm, 29% MeOH/CO$_2$ with 0.25% dimethyl ethylamine).

Example #11-1: First enantiomer to elute; 1-[(3S,4S or 3R,4R)-3-Cyanotetrahydro-2H-pyran-4-yl]-3-[(2-fluoropyridin-4-yl)amino]-1H-pyrazole-4-carboxamide. MS ESI: [M+H]$^+$ m/z 331; $^1$H NMR (500 MHz, CD$_3$OD) δ 8.24 (s, 1H), 7.91 (d, J=5.5 Hz, 1H), 7.42 (s, 1H), 7.26 (d, J=6 Hz, 1H), 4.65-4.60 (td, J=11.0, 4.0 Hz, 1H), 4.34-4.30 (dd, J=14.5, 4.5 Hz, 1H), 4.17-4.13 (d, J=11.5, 4.5 Hz, 1H), 3.76-3.63 (m, 2H), 3.57-3.50 (td, J=11, 4.5 Hz, 1H), 2.39-2.28 (m, 1H), 2.13-2.05 (m, 1H).

Example #11-2: Second enantiomer to elute; 1-[(3S,4S or 3R,4R)-3-Cyanotetrahydro-2H-pyran-4-yl]-3-[(2-fluoropyridin-4-yl)amino]-1H-pyrazole-4-carboxamide: MS ESI: [M+H]$^+$ m/z 331; $^1$H NMR (500 MHz, CD$_3$OD) δ 8.24 (s, 1H), 7.91 (d, J=5.5 Hz, 1H), 7.42 (s, 1H), 7.26 (d, J=6 Hz, 1H), 4.65-4.60 (td, J=11.0, 4.0 Hz, 1H), 4.34-4.30 (dd, J=14.5, 4.5 Hz, 1H), 4.17-4.13 (d, J=11.5, 4.5 Hz, 1H), 3.76-3.63 (m, 2H), 3.57-3.50 (td, J=11, 4.5 Hz, 1H), 2.39-2.28 (m, 1H), 2.13-2.05 (m, 1H).

Chiral Resolution

The following experimental procedures exemplify the chiral resolution and isolation of enantiopure Examples of the instant invention. The following Examples are for illustrative purposes only and are not intended to limit the scope of the instant invention in any way.

Example #12-1 and 12-2

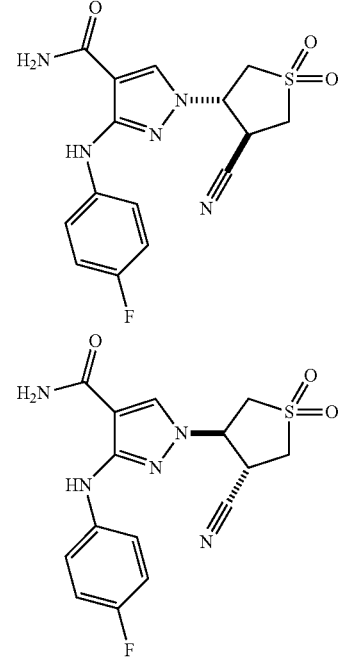

1-((3S,4R or 3R,4S)-4-Cyano-1,1-dioxidotetrahydrothiophen-3-yl)-3-((4-fluorophenyl)amino)-1H-pyrazole-4-carboxamide 1-((3S,4R and 3R,4S)-4-Cyano-1,1-dioxidotetrahydrothiophen-3-yl)-3-((4-fluorophenyl)amino)-1H-pyrazole-4-carboxamide (Example #8-6) was chirally resolved to the constituent enantiomers by chiral SFC (Chiral Technology IB-H, 2.1×25 cm, 35% MeOH/CO$_2$, 70 mL/min). Desired fractions were identified, combined, and concentrated in vacuo to afford enantiomerically pure samples of the title compounds.

Example 12-1: 1-((3R,4R or 3S,4S)-3-cyano-1,1-dioxidotetrahydro-2H-thiopyran-4-yl)-3-((4-fluorophenyl)amino)-1H-pyrazole-4-carboxamide, first enantiomer to elute from column. $^1$H NMR (500 MHz, DMSO-d6): δ 9.19 (s, 1H); 8.33 (s, 1H); 7.74-7.79 (br s, 1H); 7.54 (dd, J=8.8, 4.7 Hz, 2H); 7.19-7.29 (br s, 1H); 7.06 (t, J=8.7 Hz, 2H); 5.54 (d, J=9.0 Hz, 1H); 4.22-4.24 (m, 1H); 3.92-3.94 (m, 2H); 3.76 (t, J=11.9 Hz, 1H); 3.58 (dd, J=13.7, 8.9 Hz, 1H). LRMS (ESI) calc'd for C$_{15}$H$_{14}$FN$_5$O$_3$S [M+H]$^+$: 364. Found: 364.

Example 12-2: 1-((3R,4R or 3S,4S)-3-cyano-1,1-dioxidotetrahydro-2H-thiopyran-4-yl)-3-((4-fluorophenyl)amino)-1H-pyrazole-4-carboxamide, second enantiomer to elute from column. $^1$H NMR (500 MHz, DMSO-d6): δ 9.19 (s, 1H); 8.33 (s, 1H); 7.74-7.79 (br s, 1H); 7.54 (dd, J=8.8, 4.7 Hz, 2H); 7.19-7.29 (br s, 1H); 7.06 (t, J=8.7 Hz, 2H); 5.54 (d, J=9.0 Hz, 1H); 4.22-4.24 (m, 1H); 3.92-3.94 (m, 2H); 3.76 (t, J=11.9

Hz, 1H); 3.58 (dd, J=13.7, 8.9 Hz, 1H). LRMS (ESI) calc'd for $C_{15}H_{14}FN_5O_3S$ [M+H]$^+$: 364. Found: 364.

Examples #13-1 and 13-2

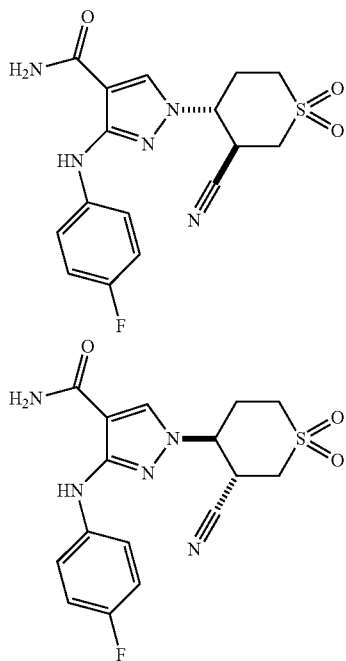

1-((3R,4R or 3S,4S)-3-Cyano-1,1-dioxidotetrahydro-2H-thiopyran-4-yl)-3-((4-fluorophenyl)amino)-1H-pyrazole-4-carboxamide 1-((3R,4S and 3S,4R)-3-Cyano-1,1-dioxidotetrahydro-2H-thiopyran-4-yl)-3-(4-fluorophenyl)amino)-1H-pyrazole-4-carboxamide (Example #8-2) was chirally resolved to the constituent enantiomers by chiral SFC (Chiral Technology OJ-H, 2.1×25 cm, 30% MeOH/CO$_2$, 70 mL/min). Desired fractions were identified, combined, and concentrated in vacuo to afford enantiomerically pure samples of the title compounds.

Example #13-1: 1-((3R,4R or 3S,4S)-3-cyano-1,1-dioxidotetrahydro-2H-thiopyran-4-yl)-3-((4-fluorophenyl)amino)-1H-pyrazole-4-carboxamide, first enantiomer to elute from column. $^1$H NMR (500 MHz, DMSO-d$_6$): δ 9.14 (s, 1H); 8.29 (s, 1H); 7.69 (s, 1H); 7.49-7.50 (m, 2H); 7.22 (s, 1H); 7.09 (t, J=8.8 Hz, 2H); 4.78-4.83 (m, 1H); 4.09 (q, J=5.3 Hz, 1H); 3.88-3.90 (m, 1H); 3.78 (dd, J=10.1, 4.3 Hz, 1H); 3.38-3.48 (m, 1H); 3.15 (d, J=5.2 Hz, 2H); 2.35-2.42 (m, 1H). LRMS (ESI) calc'd for $C_{16}H_{16}FN_5O_3S$ [M+H]$^+$: 378. Found: 378.

Example #13-2: 1-((3R,4R or 3S,4S)-3-cyano-1,1-dioxidotetrahydro-2H-thiopyran-4-yl)-3-((4-fluorophenyl)amino)-1H-pyrazole-4-carboxamide, second enantiomer to elute from column. $^1$H NMR (500 MHz, DMSO-d$_6$): δ 9.14 (s, 1H); 8.29 (s, 1H); 7.69 (s, 1H); 7.49-7.50 (m, 2H); 7.22 (s, 1H); 7.09 (t, J=8.8 Hz, 2H); 4.78-4.83 (m, 1H); 4.09 (q, J=5.3 Hz, 1H); 3.88-3.90 (m, 1H); 3.78 (dd, J=10.1, 4.3 Hz, 1H); 3.38-3.48 (m, 1H); 3.15 (d, J=5.2 Hz, 2H); 2.35-2.42 (m, 1H). LRMS (ESI) calc'd for $C_{16}H_{16}FN_5O_3S$ [M+H]$^+$: 378. Found: 378.

The following examples shown in TABLE 13 were prepared according Examples #13-1 and 13-2, which can be achieved by those of ordinary skill in the art of organic synthesis.

TABLE 13

| Example | Structure | IUPAC Name | Exact Mass [M + H]$^+$ |
|---|---|---|---|
| 13-3 | 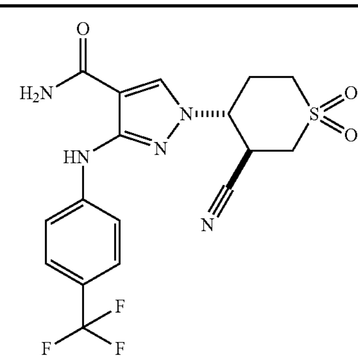 | 1-((3R,4S or 3S,4R)-3-cyano-1,1-dioxidotetrahydro-2H-thiopyrdn-4-yl)-3-((4-(trifluoromethyl)phenyl)amino)-1H-pyrazole-4-carboxamide | Calc'd 428, Found 428 |
| 13-4 | 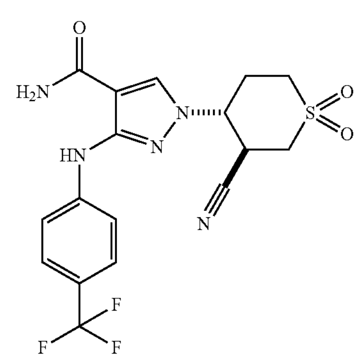 | 1-((3R,4S or 3S,4R)-3-cyano-1,1-dioxidotetrahydro-2H-thiopyran-4-yl)-3-((4-(trifluoromethyl)phenyl)amino)-1H-pyrazole-4-carboxamide | Calc'd 428, Found 428 |

TABLE 13-continued

| Example | Structure | IUPAC Name | Exact Mass [M + H]+ |
|---|---|---|---|
| 13-5 | 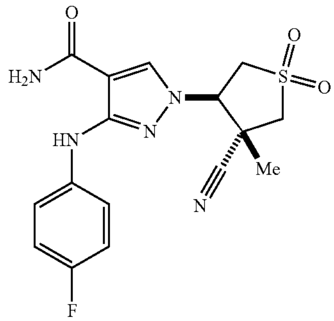 | 1-((3S,4R or 3R4S)-4-cyano-4-methyl-1,1-dioxidotetrahydrothiophen-3-yl)-3-((4-fluorophenyl)amino)-1H-pyrazole-4-carboxamide | Calc'd 378, Found 378 |

Examples 14-1 and 14-2

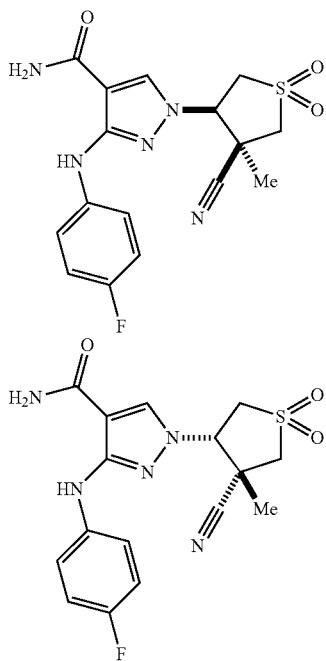

1-((3R,4R or 3S,4S)-4-Cyano-4-methyl-1,1-dioxidotetrahydrothiophen-3-yl)-3-((4-fluorophenyl)amino)-1H-pyrazole-4-carboxamide 1-((3R,4R or 3S,4S)-4-Cyano-4-methyl-1,1-dioxidotetrahydrothiophen-3-yl)-3-((4-fluorophenyl)amino)-1H-pyrazole-4-carboxamide (Example #8-10) was chirally resolved to the constituent enantiomers by chiral SFC (Lux-4 Column, 2.1×25 cm, 25% MeOH/CO$_2$, 70 mL/min). Desired fractions were identified, combined, and concentrated in vacuo to afford enantiomerically pure samples of the title compounds.
Example 14-1: 1-((3R,4R or 3S,4S)-4-Cyano-4-methyl-1,1-dioxidotetrahydrothiophen-3-yl)-3-((4-fluorophenyl)amino)-1H-pyrazole-4-carboxamide, first enantiomer to elute from column. $^1$H NMR (500 MHz, DMSO-d$_6$): δ 9.15 (s, 1H); 8.32 (s, 1H); 7.77 (s, 1H); 7.58-7.59 (m, 2H); 7.24 (s, 1H); 7.03 (t, J=8.8 Hz, 2H); 5.36 (t, J=7.9 Hz, 1H); 4.06-4.07 (m, 2H); 3.84 (dd, J=14.1, 7.9 Hz, 1H); 3.70 (d, J=13.5 Hz, 1H); 1.61 (s, 3H). LRMS (ESI) calc'd for C$_{16}$H$_{16}$FN$_5$O$_5$S [M+H]$^+$: 378. Found: 378.
Example 14-2: 1-((3R,4R or 3S,4S)-4-Cyano-4-methyl-1,1-dioxidotetrahydrothiophen-3-yl)-3-((4-fluorophenyl) amino)-1H-pyrazole-4-carboxamide, second enantiomer to elute from column. $^1$H NMR (500 MHz, DMSO-d$_6$): δ 9.15 (s, 1H); 8.33 (s, 1H); 7.78 (s, 1H); 7.58 (dd, J=8.7, 4.7 Hz, 2H); 7.24 (s, 1H); 7.03 (t, J=8.6 Hz, 2H); 5.37 (t, J=7.9 Hz, 1H); 4.06-4.08 (m, 2H); 3.84 (dd, J=14.5, 8.0 Hz, 1H); 3.69-3.71 (m, 1H); 1.61 (s, 3H). LRMS (ESI) calc'd for C$_{16}$H$_{16}$FN$_5$O$_5$S [M+H]$^+$: 378. Found: 378.

Biological Assays

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDE-PEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 μL of 1.11× enzyme and 1.11× substrate in 1× assay buffer (Invitrogen kinase buffer # PV3189, 2 mM DTT, 0.05% BSA) were added to the wells and shaken and then preincubated for 30 minutes at ambient temperature to allow compound binding to equilibrate. After equilibration, 2 μL of 10×ATP in 1× assay buffer was added to initiate the kinase reaction and the plates were shaken and then incubated at ambient temperature for 120 minutes. At the end of the incubation, 20 μL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at ambient temperature and then read on a Perkin Elmer Envision ($\lambda_{ex}$=337 nm, $\lambda_{em}$=665 and 615 nm, TRF delay time=20 μs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate IC$_5$O values.

Final reaction conditions were:

| Enzyme | [E] (nM) | [S] (μM) | [ATP] (μM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

Biological Data

Examples of the instant invention were evaluated in JAK1 and JAK2 in vitro binding assays as described above. The following table tabulates the JAK1 $IC_{50}$ values and JAK2 $IC_{50}$ values disclosed for the instant invention.

| Example # | JAK1 IC50 (nM) | JAK2 IC50 (nM) |
|---|---|---|
| 1-1 | 108 | 1270 |
| 1-2 | 24 | 496 |
| 1-3 | 5 | 41 |
| 2-1 | 6 | 39 |
| 2-2 | 154 | 841 |
| 2-3 | 27 | 367 |
| 3-1 | 13 | 125 |
| 3-2 | 7 | 81 |
| 3-3 | 102 | 628 |
| 4 | 8 | 117 |
| 5-1 | 15 | 387 |
| 5-2 | 4 | 104 |
| 5-3 | 44 | 1005 |
| 5-4 | 29 | 835 |
| 5-5 | 12 | 185 |
| 5-6 | 15 | 411 |
| 5-7 | 23 | 1089 |
| 5-8 | 13 | 703 |
| 5-9 | 46 | 955 |
| 5-10 | 33 | 755 |
| 5-11 | 29 | 756 |
| 5-12 | 15 | 369 |
| 5-13 | 20 | 432 |
| 5-14 | 38 | 430 |
| 5-15 | 19 | 411 |
| 5-16 | 8 | 132 |
| 5-17 | 97 | 1231 |
| 5-18 | 132 | 1460 |
| 5-19 | 22 | 1101 |
| 5-20 | 5 | 106 |
| 5-21 | 88 | >1496 |
| 5-22 | 25 | 1111 |
| 5-23 | 10 | 158 |
| 5-24 | 38 | 1070 |
| 5-25 | 12 | 255 |
| 5-26 | 58 | >1496 |
| 5-27 | 92 | 1304 |
| 5-28 | 10 | 268 |
| 5-29 | 9 | 202 |
| 5-30 | 12 | 286 |
| 5-31 | 6 | 133 |
| 5-32 | 12 | 275 |
| 5-33 | 28 | 413 |
| 5-34 | 9 | 154 |
| 5-35 | 19 | 468 |
| 5-36 | 86 | 823 |
| 5-37 | 54 | >1496 |
| 5-38 | 3 | 73 |
| 5-39 | 25 | 426 |
| 5-40 | 209 | 1386 |
| 5-41 | 394 | >1496 |
| 5-42 | 652 | >1496 |
| 5-43 | 188 | >1496 |
| 5-44 | 200 | 1196 |
| 5-45 | 624 | >1496 |
| 5-46 | 251 | >1496 |
| 5-47 | 121 | 1337 |
| 5-48 | 403 | >1496 |
| 5-49 | 257 | >1496 |
| 5-50 | 625 | >1496 |
| 5-51 | 212 | >1496 |
| 5-52 | 467 | >1496 |
| 5-53 | 445 | >1496 |
| 5-54 | 529 | >1496 |
| 5-55 | 350 | >1496 |
| 5-56 | 496 | >1496 |
| 5-57 | 295 | 1110 |
| 5-58 | 102 | 1124 |
| 5-59 | 323 | 1395 |
| 5-60 | 358 | >1496 |
| 5-61 | 599 | >1496 |
| 5-62 | 515 | >1496 |
| 5-63 | 727 | >1496 |
| 5-64 | 440 | >1496 |
| 5-65 | 83 | 1084 |
| 5-66 | 84 | 994 |
| 5-67 | 69 | 1204 |
| 5-68 | 434 | >1496 |
| 5-69 | 1 | 41 |
| 5-70 | 8 | 135 |
| 5-71 | 4 | 44 |
| 5-72 | 5 | 69 |
| 5-73 | 6 | 77 |
| 5-74 | 1 | 14 |
| 5-75 | 16 | 444 |
| 5-76 | 5 | 62 |
| 5-77 | 4 | 76 |
| 5-78 | 4 | 61 |
| 5-79 | 6 | 56 |
| 5-80 | 6 | 145 |
| 5-81 | 3 | 52 |
| 5-82 | 2 | 53 |
| 5-83 | 8 | 120 |
| 5-84 | 6 | 187 |
| 5-85 | 6 | 87 |
| 5-86 | 9 | 352 |
| 5-87 | 4 | 85 |
| 5-88 | 0.7 | 15 |
| 5-89 | 3 | 43 |
| 5-90 | 4 | 96 |
| 5-91 | 1 | 76 |
| 5-92 | 27 | 383 |
| 6-1 | 6 | 77 |
| 6-2 | 2 | 26 |
| 6-3 | 2 | 13 |
| 6-4 | 2 | 18 |
| 6-5 | 2 | 14 |
| 6-6 | 2 | 19 |
| 6-7 | 4 | 47 |
| 6-8 | 2 | 22 |
| 6-9 | 16 | 191 |
| 6-10 | 6 | 74 |
| 6-11 | 25 | 533 |
| 6-12 | 5 | 33 |
| 6-13 | 2 | 20 |
| 6-14 | 4 | 42 |
| 6-15 | 1 | 20 |
| 6-16 | 0.7 | 14 |
| 6-17 | 1 | 12 |
| 6-18 | 1 | 19 |
| 6-19 | 2 | 11 |
| 6-20 | 6 | 98 |
| 6-21 | 6 | 63 |
| 6-22 | 19 | 220 |
| 6-23 | 7 | 75 |
| 6-24 | 3 | 34 |
| 6-25 | 6 | 52 |
| 6-26 | 17 | 148 |
| 6-27 | 5 | 37 |
| 6-28 | 6 | 58 |

-continued

| Example # | JAK1 IC50 (nM) | JAK2 IC50 (nM) |
|---|---|---|
| 6-29 | 5 | 47 |
| 6-30 | 16 | 166 |
| 6-31 | 23 | 258 |
| 6-32 | 4 | 35 |
| 6-33 | 7 | 92 |
| 6-34 | 10 | 111 |
| 6-35 | 5 | 79 |
| 6-36 | 2 | 24 |
| 6-37 | 5 | 104 |
| 6-38 | 7 | 82 |
| 6-39 | 4 | 37 |
| 6-40 | 5 | 66 |
| 7-1 | 0.5 | 6 |
| 7-2 | 0.6 | 8 |
| 8-1 | 37 | 112 |
| 8-2 | 6 | 79 |
| 8-3 | 3 | 146 |
| 8-4 | 30 | 371 |
| 8-5 | 1 | 32 |
| 8-6 | 0.8 | 24 |
| 8-7 | 0.5 | 15 |
| 8-8 | 5 | 96 |
| 9-1 | 0.2 | 2 |
| 9-2 | 18 | 111 |
| 9-3 | 0.2 | 1 |
| 9-4 | 0.2 | 3 |
| 9-5 | 5 | 61 |
| 9-6 | 3 | 21 |
| 9-7 | 4 | 27 |
| 9-8 | 0.09 | 0.6 |
| 9-9 | 0.09 | 0.7 |
| 9-10 | 26 | 245 |
| 9-11 | 0.4 | 5 |
| 9-12 | 16 | 121 |
| 9-13 | 0.2 | 4 |
| 9-14 | 0.7 | 4 |
| 9-15 | 46 | 157 |
| 9-16 | 0.03 | 0.2 |
| 9-17 | 0.05 | 0.2 |
| 9-18 | 3 | 12 |
| 9-19 | 2 | 9 |
| 9-20 | 7 | 52 |
| 9-21 | 21 | 118 |
| 9-22 | 0.5 | 5 |
| 9-23 | 3 | 17 |
| 9-24 | 0.1 | 0.6 |
| 9-25 | 0.1 | 0.4 |
| 9-26 | 6 | 21 |
| 9-27 | 31 | 134 |
| 9-28 | 0.5 | 4 |
| 9-29 | 0.8 | 5 |
| 9-30 | 83 | 306 |
| 9-31 | 0.9 | 7 |
| 9-32 | 38 | 134 |
| 9-33 | 0.5 | 3 |
| 9-34 | 0.05 | 0.2 |
| 9-35 | 0.07 | 0.7 |
| 9-36 | 0.6 | 3 |
| 9-37 | 10 | 67 |
| 9-38 | 0.3 | 3 |
| 10-1 | 5 | 25 |
| 10-2 | 29 | 206 |
| 11-1 | 41 | 323 |
| 11-2 | 2 | 14 |
| 12-1 | 179 | >1496 |
| 12-2 | 1 | 16 |
| 13-1 | 163 | >1496 |
| 13-2 | 3 | 60 |
| 13-3 | 71 | 769 |
| 13-4 | 2 | 33 |
| 13-5 | 0.5 | 6 |
| 14-1 | 2 | 18 |
| 14-2 | 84 | 292 |

What is claimed is:

1. A compound of formula I or a pharmaceutically acceptable salt or stereoisomer thereof:

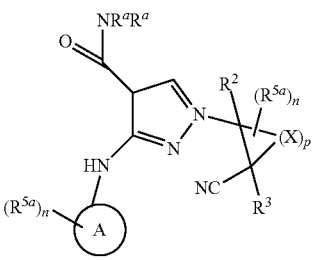

$R^a$ and $R^4$ are each independently chosen from hydrogen and $C_{1-4}$alkyl;
n is 0, 1, 2, 3, or 4;
p is 2, 3, or 4;
X is independently chosen from C, N, S, and O, wherein at least one X is other than carbon;
A is chosen from aryl, and heteroaryl;
$R^2$ and $R^3$ are each independently selected from:
 hydrogen,
 halogen,
 $C_{1-10}$ alkyl,
 $C_{2-10}$ alkenyl,
 $C_{1-10}$ heteroalkyl,
 aryl $C_{0-10}$ alkyl$C_{0-10}$ alkyl,
 $C_{3-8}$ cycloalkyl$C_{0-10}$ alkyl,
 heteroaryl $C_{0-10}$ alkyl,
 $(C_{3-8})$heterocycloalkyl $C_{0-10}$ alkyl,
wherein each of $R^2$ and $R^3$ are independently substituted with 0, 1, 2, 3, or 4, substituents $R^{5a}$;
$R^{5a}$ is selected from:
hydrogen,
halogen,
$C_{1-10}$ alkyl(oxy)$_{0-1}$(carbonyl)$_{0-1}C_{0-10}$ alkyl,
$C_{1-10}$ heteroalkyl(oxy)$_{0-1}$(carbonyl)$_{0-1}C_{0-10}$ alkyl,
$C_{2-10}$ alkenyl(oxy)$_{0-1}$(carbonyl)$_{0-1}C_{0-10}$ alkyl,
$C_{2-10}$ alkynyl(oxy)$_{0-1}$(carbonyl)$_{0-1}C_{0-10}$ alkyl,
aryl $C_{0-10}$ alkyl(oxy)$_{0-1}$(carbonyl)$_{0-1}C_{0-10}$ alkyl,
aryl $C_{2-10}$ alkenyl(oxy)$_{0-1}$(carbonyl)$_{0-1}C_{0-10}$ alkyl,
aryl $C_{2-10}$ alkynyl(oxy)$_{0-1}$(carbonyl)$_{0-1}C_{0-10}$ alkyl,
$C_{3-8}$ cycloalkyl $C_{0-10}$ alkyl(oxy)$_{0-1}$(carbonyl)$_{0-1}C_{0-10}$ alkyl,
heteroaryl $C_{0-10}$ alkyl(oxy)$_{0-1}$(carbonyl)$_{0-1}C_{0-10}$ alkyl,
$(C_{3-8})$heterocycloalkyl $C_{0-10}$ alkyl(oxy)$_{0-1}$(carbonyl)$_{0-1}C_{0-10}$ alkyl,
$C_{1-10}$ alkyl(carbonyl)$_{0-1}$oxy$C_{0-10}$ alkyl,
$C_{1-10}$ heteroalkyl(carbonyl)$_{0-1}$oxy$C_{0-10}$ alkyl,
$C_{2-10}$ alkenyl(carbonyl)$_{0-1}$oxy$C_{0-10}$ alkyl,
$C_{1-10}$ heteroalkyl(carbonyl)$_{0-1}$oxy$C_{0-10}$ alkyl,
aryl $C_{0-10}$ alkyl(carbonyl)$_{0-1}$oxy$C_{0-10}$ alkyl,
$(C_{3-8})$cycloalkyl $C_{0-10}$ alkyl(carbonyl)$_{0-1}$oxy$C_{0-10}$ alkyl,
heteroaryl$C_{0-10}$ alkyl(carbonyl)$_{0-1}$oxy$C_{0-10}$ alkyl,
$(C_{3-8})$heterocycloalkyl $C_{0-10}$ alkyl(carbonyl)$_{0-1}$oxy$C_{0-10}$ alkyl,
$((C_{0-10})$alkyl$)_{1-2}$aminocarbonyloxy,
$(C_{0-10})$heteroalkylaminocarbonyloxy,
aryl $(C_{0-10})$alkylaminocarbonyloxy,
$(C_{3-8})$cycloalkyl$(C_{0-10})$alkylaminocarbonyloxy,
heteroaryl$(C_{0-10})$alkylaminocarbonyloxy,
$(C_{3-8})$heterocycloalkyl$(C_{0-10})$alkylaminocarbonyloxy,
$C_{1-10}$ alkylamino(oxy)$_{0-1}$carbonyl$C_{0-10}$ alkyl,
$(C_{0-10})$heteroalkylamino(oxy)$_{0-1}$carbonyl$C_{0-10}$ alkyl,
$C_{3-8}$ cycloalkyl $C_{0-10}$ alkylamino(oxy)$_{0-1}$carbonyl$C_{0-10}$ alkyl, aryl C$_{0-10}$alkylamino(oxy)$_{0-1}$carbonylC$_{0-10}$ alkyl,
heteroarylC$_{0-10}$alkylamino(oxy)$_{0-1}$carbonylC$_{0-10}$ alkyl,
(C$_{3-8}$)heterocycloalkylC$_{0-10}$alkylamino(oxy)$_{0-1}$carbonylC$_{0-10}$ alkyl,
C$_{1-10}$ alkyl(oxy)$_{0-1}$carbonylaminoC$_{0-10}$ alkyl,
C$_{1-10}$ heteroalkyl(oxy)$_{0-1}$carbonylaminoC$_{0-10}$ alkyl,
C$_{3-8}$ cycloalkyl C$_{0-10}$ alkyl(oxy)$_{0-1}$carbonylaminoC$_{0-10}$ alkyl,
aryl C$_{0-10}$ alkyl(oxy)$_{0-1}$carbonylaminoC$_{0-10}$ alkyl,
heteroaryl C$_{0-10}$ alkyl(oxy)$_{0-1}$carbonylaminoC$_{0-10}$ alkyl,
(C$_{3-8}$)heterocycloalkyl C$_{0-10}$ alkyl(oxy)$_{0-1}$carbonylaminoC$_{0-10}$ alkyl,
—CO$_2$(C$_{0-10}$ alkyl),
—(C$_{0-10}$ alkyl)CO$_2$H,
Oxo (═O),
C$_{1-10}$ alkylsulfonyl,
C$_{1-10}$ heteroalkylsulfonyl,
(C$_{3-8}$) cycloalkylsulfonyl,
(C$_{3-8}$) cycloheteroalkylsulfonyl,
heteroarylsulfonyl,
arylsulfonyl,
aminosulfonyl,
—SO$_2$N(C$_{1-6}$alkyl)$_{1-2}$,
—SO$_2$C$_{1-6}$alkyl,
—SO$_2$CF$_3$,
—SO$_2$CF$_2$H,
C$_{1-10}$ alkylsulfinyl,
amino,
(C$_{0-10}$ alkyl)$_{1-2}$ amino,
C$_{1-4}$acylamino C$_{0-10}$ alkyl,
hydroxy,
C$_{0-10}$ alkylalkoxy,
cyano,
C$_{1-6}$alkylcyano, and
C$_{1-6}$haloalkyl;
wherein R$^{5a}$ is each optionally substituted with 0, 1, 2, 3, or 4 substituents, R$^6$, independently selected from:
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
C$_{2-10}$ alkenyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
aryl C$_{2-10}$ alkenyl(oxy)$_{0-1}$(carbonyl)$_{0-1}$C$_{0-10}$ alkyl,
aryl C$_{2-10}$ alkynyl(oxy)$_{0-1}$(carbonyl)$_{0-1}$C$_{0-10}$ alkyl,
C$_{3-8}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-8}$)heterocycloalkyl C$_{0-10}$ alkyl(oxy)$_{0-1}$(carbonyl)$_{0-1}$C$_{0-10}$ alkyl,
C$_{1-10}$ alkyl(carbonyl)$_{0-1}$oxyC$_{0-10}$ alkyl,
C$_{2-10}$ alkenyl(carbonyl)$_{0-1}$oxyC$_{0-10}$ alkyl,
C$_{1-10}$ heteroalkyl(carbonyl)$_{0-1}$oxyC$_{0-10}$ alkyl,
aryl C$_{0-10}$ alkyl(carbonyl)$_{0-1}$oxyC$_{0-10}$ alkyl,
(C$_{3-8}$)cycloalkyl C$_{0-10}$ alkyl(carbonyl)$_{0-1}$oxyC$_{0-10}$ alkyl,
heteroarylC$_{0-10}$ alkyl(carbonyl)$_{0-1}$oxyC$_{0-10}$ alkyl,
(C$_{3-8}$)heterocycloalkyl C$_{0-10}$ alkyl(carbonyl)$_{0-1}$oxyC$_{0-10}$ alkyl,
((C$_{0-10}$)alkyl)$_{1-2}$aminocarbonyloxy,
aryl (C$_{0-10}$)alkylaminocarbonyloxy,
(C$_{3-8}$)cycloalkyl(C$_{0-10}$)alkylaminocarbonyloxy,
heteroaryl(C$_{0-10}$)alkylaminocarbonyloxy,
(C$_{3-8}$)heterocycloalkyl(C$_{0-10}$)alkylaminocarbonyloxy,
C$_{1-10}$ alkylamino(oxy)$_{0-1}$carbonylC$_{0-10}$ alkyl,
C$_{3-8}$ cycloalkyl C$_{0-10}$ alkylamino(oxy)$_{0-1}$carbonylC$_{0-10}$ alkyl,
aryl C$_{0-10}$ alkylamino(oxy)$_{0-1}$carbonylC$_{0-10}$ alkyl,
heteroaryl C$_{0-10}$ alkylamino(oxy)$_{0-1}$carbonylC$_{0-10}$ alkyl,
(C$_{3-8}$)heterocycloalkyl C$_{0-10}$ alkylamino(oxy)$_{0-1}$carbonylC$_{0-10}$ alkyl,
C$_{1-10}$ alkyl (oxy)$_{0-1}$carbonylaminoC$_{0-10}$ alkyl,
C$_{3-8}$ cycloalkyl C$_{0-10}$ alkyl (oxy)$_{0-1}$carbonylaminoC$_{0-10}$ alkyl,
aryl C$_{0-10}$ alkyl(oxy)$_{0-1}$carbonylaminoC$_{0-10}$ alkyl,
heteroaryl C$_{0-10}$ alkyl(oxy)$_{0-1}$carbonylaminoC$_{0-10}$ alkyl,
(C$_{3-8}$)heterocycloalkyl C$_{0-10}$ alkyl(oxy)$_{0-1}$carbonylaminoC$_{0-10}$ alkyl,
—CO$_2$(C$_{0-10}$ alkyl),
—(C$_{0-10}$ alkyl)CO$_2$H,
Oxo (═O),
C$_{1-10}$ alkylsulfonyl,
C$_{1-10}$ heteroalkylsulfonyl,
(C$_{3-8}$) cycloalkylsulfonyl,
(C$_{3-8}$) cycloheteroalkylsulfonyl,
heteroarylsulfonyl,
arylsulfonyl,
aminosulfonyl,
—SO$_2$N(C$_{1-6}$alkyl)$_{1-2}$,
—SO$_2$C$_{1-6}$alkyl,
—SO$_2$CF$_3$,
—SO$_2$CF$_2$H,
C$_{1-10}$ alkylsulfinyl,
—OSi (C$_6$H$_{15}$)
amino,
(C$_{0-10}$ alkyl)$_{1-2}$ amino,
-(oxy)$_{0-1}$(carbonyl)$_{0-1}$N(C$_{0-10}$ alkyl)$_{1-2}$
C$_{1-4}$acylamino C$_{0-10}$ alkyl,
hydroxy,
C$_{1-10}$ alkoxy,
cyano, and
C$_{1-6}$haloalkyl; and
R$^6$ is optionally substituted with 0, 1, 2, or 3 substituents independently chosen from hydroxy, (C$_{1-6}$)alkoxy, halogen, CO$_2$H, —(C$_{0-6}$)alkylCN, —O(C═O)C$_1$-C$_6$ alkyl, NO$_2$, trifluoromethoxy, trifluoroethoxy, —N—C(O)O (C$_{0-6}$)alkyl, C$_{1-10}$ alkylsulfonyl, C$_{1-10}$ heteroalkylsulfonyl, oxo (O═), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —O—Si, —OSi(C$_6$H$_{15}$), —O$_{(0-1)}$(C$_{1-10}$)haloalkyl, and NH$_2$.

2. A compound according to claim 1, wherein R$^a$ and R$^4$ are each hydrogen.

3. A compound according to claim 2, wherein R$^{5a}$ is independently selected from:
hydrogen,
halogen,
C$_{1-10}$ alkyl(oxy)$_{0-1}$(carbonyl)$_{0-1}$C$_{0-10}$ alkyl,
C$_{1-10}$ heteroalkyl(oxy)$_{0-1}$(carbonyl)$_{0-1}$C$_{0-10}$ alkyl,
C$_{2-10}$ alkynyl(oxy)$_{0-1}$(carbonyl)$_{0-1}$C$_{0-10}$ alkyl,
C$_{2-10}$ alkenyl(oxy)$_{0-1}$(carbonyl)$_{0-1}$C$_{0-10}$ alkyl,
aryl C$_{0-10}$ alkyl(oxy)$_{0-1}$(carbonyl)$_{0-1}$C$_{0-10}$ alkyl,
aryl C$_{2-10}$ alkenyl(oxy)$_{0-1}$(carbonyl)$_{0-1}$C$_{0-10}$ alkyl,
aryl C$_{2-10}$ alkynyl(oxy)$_{0-1}$(carbonyl)$_{0-1}$C$_{0-10}$ alkyl,
C$_{3-8}$ cycloalkyl C$_{0-10}$ alkyl(oxy)$_{0-1}$(carbonyl)$_{0-1}$C$_{0-10}$ alkyl,
heteroaryl C$_{0-10}$ alkyl(oxy)$_{0-1}$(carbonyl)$_{0-1}$C$_{0-10}$ alkyl,
(C$_{3-8}$)heterocycloalkyl C$_{0-10}$ alkyl(oxy)$_{0-1}$(carbonyl)$_{0-1}$C$_{0-10}$ alkyl,
C$_{1-10}$ alkyl(carbonyl)$_{0-1}$oxyC$_{0-10}$ alkyl,
((C$_{0-10}$)alkyl)$_{1-2}$aminocarbonyloxy,
C$_{1-10}$ alkylamino(oxy)$_{0-1}$carbonylC$_{0-10}$ alkyl,
C$_{1-10}$ alkyl(oxy)$_{0-1}$carbonylaminoC$_{0-10}$ alkyl,
—CO$_2$(C$_{0-10}$ alkyl), —(C$_{0-10}$ alkyl)CO$_2$H,
Oxo (=O),
C$_{0-10}$ alkylsulfonyl,
C$_{1-10}$ heteroalkylsulfonyl,
C$_{3-8}$ cycloalkylsulfonyl,
C$_{3-8}$ cyclohetroalkylsulfonyl,
heteroarylsulfonyl,
arylsulfonyl,
aminosulfonyl,
—SO$_2$N(C$_{1-6}$alkyl)$_{1-2}$,
—SO$_2$C$_{1-6}$alkyl,
—SO$_2$CF$_3$,
—SO$_2$CF$_2$H,
C$_{1-10}$ alkylsulfinyl,
amino,
(C$_{0-10}$ alkyl)$_{1-2}$ amino,
hydroxy,
C$_{0-10}$ alkylalkoxy,
cyano,
C$_{1-6}$alkylcyano, and
C$_{1-6}$haloalkyl;
wherein R$^{5a}$ is each optionally substituted with 0, 1, 2, 3, or 4 substituent, R$^6$.

4. A compound according to claim 3, wherein R$^2$ and R$^3$ are selected from hydrogen, C$_{1-10}$ alkyl, (C$_{3-8}$)heterocycloalkyl C$_{0-10}$ alkyl, and C$_{3-8}$ cycloalkylC$_{0-10}$ alkyl, wherein each of R$^2$ and R$^3$ are independently substituted with 0, 1, 2, 3, or 4, substituents R$^{5a}$.

5. A compound according to claim 4, wherein A is chosen from: furanyl, thienyl, pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine, thienopyridine, benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl, imidazo (2,1-b)(1,3)thiazole, and benzo-1,3-dioxolyl, phenyl, indenyl, and naphthalenyl, wherein A is substituted with 0, 1, 2, 3, or 4, substituents, R$^{5a}$.

6. A compound according to claim 1, wherein A is chosen from: phenyl, 1,3-dihydro-2H-isoindole, pyridinyl, quinolinyl, isoquinolinyl, 2,3-dihydro-1-benzofuranyl, dihydro-1H-indenyl, 2,3-dihydro-1,4-benzodioxinyl, 2,3,dihydro-1H-isoindolyl, and benzo[b]thiophene, wherein A is substituted with 0, 1, 2, 3, or 4, substituents, R$^{5a}$.

7. A compound according to claim 6, wherein R$^2$ and R$^3$ are independently selected from hydrogen, methyl, ethyl, propyl, tert-butyl, isopropyl, dimethylpropyl, dimethylbutyl, and tert-butylmethyl, and cyclobutyl.

8. A compound according to claim 7, wherein R$^{5a}$ is independently selected from: hydrogen, butynyloxycarbonyl, tert-butyloxycarbonyl, 3,3dimethylbutyloxycarbonyl, methylethyloxycarbonyl, Ethyloxycarbonyl, phenylpropyloxycarbonyl, morpholinylethyloxycarbonyl, oxetanyloxycarbonyl, methylpropyloxycarbonyl, piperidinylmethyloxycarbonyl, cyclopropylmethyloxycarbonyl, cyclopentyloxycarbonyl, benzyloxycarbonyl, tetrahydro-2H-pyranyloxycarbonyl, cyclopropylethyloxycarbonyl, pyrrolidinylethyloxycarbonyl, cyclohexyloxycarbonyl, dimethylpropyloxycarbonyl, propyloxycarbonyl, piprazininylethyloxycarbonyl, tetrahydrofuranyloxycarbonyl, piperidinyloxycarbonyl, pyrazolylethyloxycarbonyl, methyloxycarbonyl, oxetanylmethyloxycarbonyl, phenylethyloxycarbonyl, 2,3-dihydro-1H-indenyloxycarbonyl, methyloxycarbonyl, methylpropyloxycarbonyl, pyrazinylmethyl, isoxazolylmethyl, 1,3-oxazolylmethyl, pyrazolylmethyl, 1,3-thiazolylmethyl, pyridinylmethyl, cyclobutylmethyl, tetrahydro-2H-pyranylethyl, imidazolylmethyl, 4,5-dihydroisoxazolylmethyl, tetrhydrofuranylmethyl, pyridazinylmethyl, 4,5-dihydroisoxazolylmethyl, Oxo, methyl, halogen, trifluoromethyl, sulfonyl, (trifluoromethyl)sulfonyl, methoxy, hydroxyethyl, rifluroethyl, methylethyl, (difluoromethyl)ethyl, tetrahydro-2-H-pyranyl, difluoromethyl, dimethylaminocarbonyl, cyano, and ethoxy, wherein R$^{5a}$ is independently substituted with 0, 1, 2, 3, or 4, substituents R$^6$.

9. A compound according to claim 8, wherein R$^6$ is independently selected from: methyl, fluoro, trifluoromethyl, cyano, amino, dimethylamino, oxo, hydroxyl, methoxy, cyclopropyl, ethyoxycarbonyl, cyano, fluoromethyl, methyethylhydroxy, ethyl, and difluoromethyl, wherein R$^6$ is optionally substituted with 1, 2, or 3 substituents chosen from hydrogen, hydroxy, (C$_{1-6}$)alkoxy, halogen, CO$_2$H, —(C$_{0-6}$)alkylCN, —O(C=O)C$_1$-C$_6$ alkyl, NO$_2$, trifluoromethoxy, trifluoroethoxy, —N—C(O)O(C$_{0-6}$)alkyl, C$_{1-10}$ alkylsulfonyl, C$_{1-10}$ heteroalkylsulfonyl, oxo (O=), (C$_{3-8}$) cycloalkylsulfonyl, (C$_{3-8}$) cycloheteroalkylsulfonyl, heteroarylsulfonyl, arylsulfonyl, aminosulfonyl, —SO$_2$N(C$_{1-6}$alkyl)$_{1-2}$, —SO$_2$C$_{1-6}$alkyl, —SO$_2$CF$_3$, —SO$_2$CF$_2$H, —C$_{1-10}$ alkylsulfinyl, —O—Si, —OSi(C$_6$H$_{15}$), —O$_{(0-1)}$(C$_{1-10}$)haloalkyl, and NH$_2$.

10. A compound selected from:
tert-Butyl-4-[4-(aminocarbonyl)-3-anilino-1H-pyrazol-1-yl]-3-cyanopiperidine-1-carboxylate,
tert-Butyl (3R,4S)-4-[4-(aminocarbonyl)-3-anilino-1H-pyrazol-1-yl]-3-cyanopiperidine-1-carboxylate,
tert-Butyl (3S,4R)-4-[4-(aminocarbonyl)-3-anilino-1H-pyrazol-1-yl]-3-cyanopiperidine-1-carboxylate,
tert-butyl (3S,4S)-4-[4-(aminocarbonyl)-3-anilino-1H-pyrazol-1-yl]-3-cyanopiperidine-1-carboxylate,
tert-butyl (3R,4R)-4-[4-(aminocarbonyl)-3-anilino-1H-pyrazol-1-yl]-3-cyanopiperidine-1-carboxylate,
tert-butyl-3-[4-(aminocarbonyl)-3-anilino-1H-pyrazol-1-yl]-4-cyanopiperidine-1-carboxylate,
tert-butyl (3R,4S)-3-[4-(aminocarbonyl)-3-anilino-1H-pyrazol-1-yl]-4-cyanopiperidine-1-carboxylate,
tert-butyl (3S,4R)-3-[4-(aminocarbonyl)-3-anilino-1H-pyrazol-1-yl]-4-cyanopiperidine-1-carboxylate,
tert-butyl-3-{4-carbamoyl-3-[(4-fluorophenyl)amino]-1H-pyrazol-1-yl}-4-cyanopiperidine-1-carboxylate,
tert-butyl (3R,4S)-3-{4-carbamoyl-3-[(4-fluorophenyl)amino]-1H-pyrazol-1-yl}-4-cyanopiperidine-1-carboxylate,
tert-butyl (3S,4R)-3-{4-carbamoyl-3-[(4-fluorophenyl)amino]-1H-pyrazol-1-yl}-4-cyanopiperidine-1-carboxylate,
tert-butyl 4-(4-carbamoyl-3-((4-fluorophenyl)amino)-1H-pyrazol-1-yl)-3-cyanopiperidine-1-carboxylate,
(3R,4S)-tert-butyl 4-(4-carbamoyl-3-((4-fluorophenyl)amino)-1H-pyrazol-1-yl)-3-cyanopiperidine-1-carboxylate,
(3S,4R)-tert-butyl 4-(4-carbamoyl-3-((4-fluorophenyl)amino)-1H-pyrazol-1-yl)-3-cyanopiperidine-1-carboxylate, 1-[4-cyanopiperidin-3-yl]-3-[(4-fluorophenyl)amino]-1H-pyrazole-4-carboxamide,
1-[(3R,4S)-4-cyanopiperidin-3-yl]-3-[(4-fluorophenyl)amino]-1H-pyrazole-4-carboxamide,
1-[(3S,4R)-4-cyanopiperidin-3-yl]-3-[(4-fluorophenyl)amino]-1H-pyrazole-4-carboxamide,
1-[3-cyanopiperidin-4-yl]-3-[(4-fluorophenyl)amino]-1H-pyrazole-4-carboxamide,
1-[(3R,4R)-3-cyanopiperidin-4-yl]-3-[(4-fluorophenyl)amino]-1H-pyrazole-4-carboxamide,
1-[(3S,4S)-3-cyanopiperidin-4-yl]-3-[(4-fluorophenyl)amino]-1H-pyrazole-4-carboxamide,
3,3-Dimethylbutyl-3-{4-carbamoyl-3-[(4-fluorophenyl)amino]-1H-pyrazol-1-yl}-4-cyanopiperidine-1-carboxylate,
3,3-Dimethylbutyl (3S,4R)-3-{4-carbamoyl-3-[(4-fluorophenyl)amino]-1H-pyrazol-1-yl}-4-cyanopiperidine-1-carboxylate,
3,3-Dimethylbutyl (3R,4S)-3-{4-carbamoyl-3-[(4-fluorophenyl)amino]-1H-pyrazol-1-yl}-4-cyanopiperidine-1-carboxylate,
2,2,2-Trifluoro-1-methylethyl-4-{4-carbamoyl-3-[(4-fluorophenyl)amino]-1H-pyrazol-1-yl}-3-cyanopiperidine-1-carboxylate,
2,2,2-Trifluoro-1-methylethyl (3R,4R)-4-{4-carbamoyl-3-[(4-fluorophenyl)amino]-1H-pyrazol-1-yl}-3-cyanopiperidine-1-carboxylate,
2,2,2-Trifluoro-1-methylethyl (3S,4S)-4-{4-carbamoyl-3-[(4-fluorophenyl)amino]-1H-pyrazol-1-yl}-3-cyanopiperidine-1-carboxylate,
2-fluoroethyl-4-{4-carbamoyl-3-[(4-fluorophenyl)amino]-1H-pyrazol-yl}-3-cyanopiperidine-1-carboxylate,
2-fluoroethyl (3S,4S)-4-{4-carbamoyl-3-[(4-fluorophenyl)amino]-1H-pyrazol-1-yl}-3-cyanopiperidine-1-carboxylate,
2-fluoroethyl (3R,4R)-4-{4-carbamoyl-3-[(4-fluorophenyl)amino]-1H-pyrazol-1-yl}-3-cyanopiperidine-1-carboxylate,
3-phenylpropyl-4-{4-carbamoyl-3-[(4-fluorophenyl)amino]-1H-pyrazol-1-yl}-3-cyanopiperidine-1-carboxylate,
3-phenylpropyl (3R,4R)-4-{4-carbamoyl-3-[(4-fluorophenyl)amino]-1H-pyrazol-1-yl}-3-cyanopiperidine-1-carboxylate,
3-phenylpropyl (3S,4S)-4-{4-carbamoyl-3-[(4-fluorophenyl)amino]-1H-pyrazol-1-yl}-3-cyanopiperidine-1-carboxylate,
2-morpholin-4-ylethyl-4-{4-carbamoyl-3-[(4-fluorophenyl)amino]-1H-pyrazol-1-yl}-3-cyanopiperidine-1-carboxylate,
2-morpholin-4-ylethyl (3R,4R)-4-{4-carbamoyl-3-[(4-fluorophenyl)amino]-1H-pyrazol-1-yl}-3-cyanopiperidine-1-carboxylate,
2-morpholin-4-ylethyl (3S,4S)-4-{4-carbamoyl-3-[(4-fluorophenyl)amino]-1H-pyrazol-1-yl}-3-cyanopiperidine-1-carboxylate,
oxetan-3-yl-4-{4-carbamoyl-3-[(4-fluorophenyl)amino]-1H-pyrazol-1-yl}-3-cyanopiperidine-1-carboxylate,
oxetan-3-yl (3R,4R)-4-{4-carbamoyl-3-[(4-fluorophenyl)amino]-1H-pyrazol-1-yl}-3-cyanopiperidine-1-carboxylate,
oxetan-3-yl (3S,4S)-4-{4-carbamoyl-3-[(4-fluorophenyl)amino]-1H-pyrazol-1-yl}-3-cyanopiperidine-1-carboxylate,
2-cyano-2-methylpropyl-4-{4-carbamoyl-3-[(4-fluorophenyl)amino]-1H-pyrazol-1-yl}-3-cyanopiperidine-1-carboxylate,
2-cyano-2-methylpropyl (3R,4R)-4-{4-carbamoyl-3-[(4-fluorophenyl)amino]-1H-pyrazol-1-yl}-3-cyanopiperidine-1-carboxylate,
2-cyano-2-methylpropyl (3S,4S)-4-{4-carbamoyl-3-[(4-fluorophenyl)amino]-1H-pyrazol-1-yl}-3-cyanopiperidine-1-carboxylate,
(1-methylpiperidin-4-yl)methyl-4-{4-carbamoyl-3-[(4-fluorophenyl)amino]-1H-pyrazol-1-yl}-3-cyanopiperidine-1-carboxylate,
(1-methylpiperidin-4-yl)methyl (3R,4R)-4-{4-carbamoyl-3-[(4-fluorophenyl)amino]-1H-pyrazol-1-yl}-3-cyanopiperidine-1-carboxylate,
(1-methylpiperidin-4-yl)methyl (3S,4S)-4-{4-carbamoyl-3-[(4-fluorophenyl)amino]-1H-pyrazol-1-yl}-3-cyanopiperidine-1-carboxylate,
(1-aminocyclopropyl)methyl-4-{4-carbamoyl-3-[(4-fluorophenyl)amino]-1H-pyrazol-1-yl}-3-cyanopiperidine-1-carboxylate,
(1-aminocyclopropyl)methyl (3R,4R)-4-{4-carbamoyl-3-[(4-fluorophenyl)amino]-1H-pyrazol-1-yl}-3-cyanopiperidine-1-carboxylate,
(1-aminocyclopropyl)methyl (3S,4S)-4-{4-carbamoyl-3-[(4-fluorophenyl)amino]-1H-pyrazol-1-yl}-3-cyanopiperidine-1-carboxylate,
(1-methylcyclopropyl)methyl-4-{4-carbamoyl-3-[(4-fluorophenyl)amino]-1H-pyrazol-1-yl}-3-cyanopiperidine-1-carboxylate,
(1-methylcyclopropyl)methyl (3R,4R)-4-{4-carbamoyl-3-[(4-fluorophenyl)amino]-1H-pyrazol-1-yl}-3-cyanopiperidine-1-carboxylate,
(1-methylcyclopropyl)methyl (3S,4S)-4-{4-carbamoyl-3-[(4-fluorophenyl)amino]-1H-pyrazol-1-yl}-3-cyanopiperidine-1-carboxylate,
2-methylpropyl-4-{4-carbamoyl-3-[(4-fluorophenyl)amino]-1H-pyrazol-1-yl}-3-cyanopiperidine-1-carboxylate,
2-methylpropyl (3R,4R)-4-{4-carbamoyl-3-[(4-fluorophenyl)amino]-1H-pyrazol-1-yl}-3-cyanopiperidine-1-carboxylate,
2-methylpropyl (3S,4S)-4-{4-carbamoyl-3-[(4-fluorophenyl)amino]-1H-pyrazol-1-yl}-3-cyanopiperidine-1-carboxylate,
cyclopentyl-4-{4-carbamoyl-3-[(4-fluorophenyl)amino]-1H-pyrazol-1-yl}-3-cyanopiperidine-1-carboxylate,
cyclopentyl (3S,4S)-4-{4-carbamoyl-3-[(4-fluorophenyl)amino]-1H-pyrazol-1-yl}-3-cyanopiperidine-1-carboxylate,
cyclopentyl (3R,4R)-4-{4-carbamoyl-3-[(4-fluorophenyl)amino]-1H-pyrazol-1-yl}-3-cyanopiperidine-1-carboxylate,
benzyl-4-{4-carbamoyl-3-[(4-fluorophenyl)amino]-1H-pyrazol-1-yl}-3-cyanopiperidine-1-carboxylate,
benzyl (3R,4R)-4-{4-carbamoyl-3-[(4-fluorophenyl)amino]-1H-pyrazol-1-yl}-3-cyanopiperidine-1-carboxylate,
benzyl (3S,4S)-4-{4-carbamoyl-3-[(4-fluorophenyl)amino]-1H-pyrazol-1-yl}-3-cyanopiperidine-1-carboxylate,
tetrahydro-2H-pyran-4-yl-4-{4-carbamoyl-3-[(4-fluorophenyl)amino]-1H-pyrazol-yl}-3-cyanopiperidine-1-carboxylate,
tetrahydro-2H-pyran-4-yl (3R,4R)-4-{4-carbamoyl-3-[(4-fluorophenyl)amino]-1H-pyrazol-1-yl}-3-cyanopiperidine-1-carboxylate, tetrahydro-2H-pyran-4-yl (3S,4S)-4-{4-carbamoyl-3-[(4-fluorophenyl)amino]-1H-pyrazol-1-yl}-3-cyanopiperidine-1-carboxylate, 2-cyclopropylethyl-4-{4-carbamoyl-3-[(4-fluorophenyl)amino]-1H-pyrazol-1-yl}-3-cyanopiperidine-1-carboxylate, 2-cyclopropylethyl (3R,4R)-4-{4-carbamoyl-3-[(4-fluorophenyl)amino]-1H-pyrazol-1-yl}-3-cyanopiperidine-1-carboxylate, 2-cyclopropylethyl (3S,4S)-4-{4-carbamoyl-3-[(4-fluorophenyl)amino]-1H-pyrazol-1-yl}-3-cyanopiperidine-1-carboxylate, 2-(2-oxopyrrolidin-1-yl)ethyl-4-{4-carbamoyl-3-[(4-fluorophenyl)amino]-1H-pyrazol-1-yl}-3-cyanopiperidine-1-carboxylate, 2-(2-oxopyrrolidin-1-yl)ethyl (3R,4R)-4-{4-carbamoyl-3-[(4-fluorophenyl)amino]-1H-pyrazol-1-yl}-3-cyanopiperidine-1-carboxylate, 2-(2-oxopyrrolidin-1-yl)ethyl (3S,4S)-4-{4-carbamoyl-3-[(4-fluorophenyl)amino]-1H-pyrazol-1-yl}-3-cyanopiperidine-1-carboxylate, 2,2-difluoroethyl-4-{4-carbamoyl-3-[(4-fluorophenyl)amino]-1H-pyrazol-1-yl}-3-cyanopiperidine-1-carboxylate, 2,2-difluoroethyl (3S,4S)-4-{4-carbamoyl-3-[(4-fluorophenyl)amino]-1H-pyrazol-1-yl}-3-cyanopiperidine-1-carboxylate, 2,2-difluoroethyl (3R,4R)-4-{4-carbamoyl-3-[(4-fluorophenyl)amino]-1H-pyrazol-1-yl}-3-cyanopiperidine-1-carboxylate, cyclohexyl-4-{4-carbamoyl-3-[(4-fluorophenyl)amino]-1H-pyrazol-1-yl}-3-cyanopiperidine-1-carboxylate, cyclohexyl (3R,4R)-4-{4-carbamoyl-3-[(4-fluorophenyl)amino]-1H-pyrazol-1-yl}-3-cyanopiperidine-1-carboxylate, cyclohexyl (3S,4S)-4-{4-carbamoyl-3-[(4-fluorophenyl)amino]-1H-pyrazol-1-yl}-3-cyanopiperidine-1-carboxylate, 2,2-dimethylpropyl-4-{4-carbamoyl-3-[(4-fluorophenyl)amino]-1H-pyrazol-1-yl}-3-cyanopiperidine-1-carboxylate, 2,2-dimethylpropyl (3R,4R)-4-{4-carbamoyl-3-[(4-fluorophenyl)amino]-1H-pyrazol-1-yl}-3-cyanopiperidine-1-carboxylate, 2,2-dimethylpropyl (3S,4S)-4-{4-carbamoyl-3-[(4-fluorophenyl)amino]-1H-pyrazol-1-yl}-3-cyanopiperidine-1-carboxylate, 2-pyrrolidin-1-ylethyl-4-{4-carbamoyl-3-[(4-fluorophenyl)amino]-1H-pyrazol-1-yl}-3-cyanopiperidine-1-carboxylate, 2-pyrrolidin-1-ylethyl (3R,4R)-4-{4-carbamoyl-3-[(4-fluorophenyl)amino]-1H-pyrazol-1-yl}-3-cyanopiperidine-1-carboxylate, 2-pyrrolidin-1-ylethyl (3S,4S)-4-{4-carbamoyl-3-[(4-fluorophenyl)amino]-1H-pyrazol-1-yl}-3-cyanopiperidine-1-carboxylate, 2,2-difluoro-3-hydroxypropyl-4-{4-carbamoyl-3-[(4-fluorophenyl)amino]-1H-pyrazol-yl}-3-cyanopiperidine-1-carboxylate, 2,2-difluoro-3-hydroxypropyl (3R,4R)-4-{4-carbamoyl-3-[(4-fluorophenyl)amino]-1H-pyrazol-1-yl}-3-cyanopiperidine-1-carboxylate, 2,2-difluoro-3-hydroxypropyl (3S,4S)-4-{4-carbamoyl-3-[(4-fluorophenyl)amino]-1H-pyrazol-1-yl}-3-cyanopiperidine-1-carboxylate, 3-(dimethylamino)-2,2-dimethylpropyl-4-{4-carbamoyl-3-[(4-fluorophenyl)amino]-1H-pyrazol-1-yl}-3-cyanopiperidine-1-carboxylate;

3-(dimethylamino)-2,2-dimethylpropyl (3R,4R)-4-{4-carbamoyl-3-[(4-fluorophenyl)amino]-1H-pyrazol-1-yl}-3-cyanopiperidine-1-carboxylate, 3-(dimethylamino)-2,2-dimethylpropyl (3S,4S)-4-{4-carbamoyl-3-[(4-fluorophenyl)amino]-1H-pyrazol-1-yl}-3-cyanopiperidine-1-carboxylate, 2-(dimethylamino)ethyl-4-{4-carbamoyl-3-[(4-fluorophenyl)amino]-1H-pyrazol-1-yl}-3-cyanopiperidine-1-carboxylate, 2-(dimethylamino)ethyl (3R,4R)-4-{4-carbamoyl-3-[(4-fluorophenyl)amino]-1H-pyrazol-1-yl}-3-cyanopiperidine-1-carboxylate, 2-(dimethylamino)ethyl (3S,4S)-4-{4-carbamoyl-3-[(4-fluorophenyl)amino]-1H-pyrazol-1-yl}-3-cyanopiperidine-1-carboxylate, ethyl-4-{4-carbamoyl-3-[(4-fluorophenyl)amino]-1H-pyrazol-1-yl}-3-cyanopiperidine-1-carboxylate, ethyl (3R,4R)-4-{4-carbamoyl-3-[(4-fluorophenyl)amino]-1H-pyrazol-1-yl}-3-cyanopiperidine-1-carboxylate, ethyl (3S,4S)-4-{4-carbamoyl-3-[(4-fluorophenyl)amino]-1H-pyrazol-1-yl}-3-cyanopiperidine-1-carboxylate, 2-(4-methylpiperazin-1-yl)ethyl-4-{4-carbamoyl-3-[(4-fluorophenyl)amino]-1H-pyrazol-1-yl}-3-cyanopiperidine-1-carboxylate, 2-(4-methylpiperazin-1-yl)ethyl (3R,4R)-4-{4-carbamoyl-3-[(4-fluorophenyl)amino]-1H-pyrazol-1-yl}-3-cyanopiperidine-1-carboxylate, 2-(4-methylpiperazin-1-yl)ethyl (3S,4S)-4-{4-carbamoyl-3-[(4-fluorophenyl)amino]-1H-pyrazol-1-yl}-3-cyanopiperidine-1-carboxylate, tetrahydrofuran-3-yl-4-{4-carbamoyl-3-[(4-fluorophenyl)amino]-1H-pyrazol-1-yl}-3-cyanopiperidine-1-carboxylate, tetrahydrofuran-3-yl (3R,4R)-4-{4-carbamoyl-3-[(4-fluorophenyl)amino]-1H-pyrazol-1-yl}-3-cyanopiperidine-1-carboxylate, tetrahydrofuran-3-yl (3S,4S)-4-{4-carbamoyl-3-[(4-fluorophenyl)amino]-1H-pyrazol-1-yl}-3-cyanopiperidine-1-carboxylate, 1-methylpiperidin-4-yl-4-{4-carbamoyl-3-[(4-fluorophenyl)amino]-1H-pyrazol-1-yl}-3-cyanopiperidine-1-carboxylate, 1-methylpiperidin-4-yl (3S,4S)-4-{4-carbamoyl-3-[(4-fluorophenyl)amino]-1H-pyrazol-1-yl}-3-cyanopiperidine-1-carboxylate, 1-methylpiperidin-4-yl (3R,4R)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl (3R,4R)-4-{4-carbamoyl-3-[(4-fluorophenyl)amino]-1H-pyrazol-1-yl}-3-cyanopiperidine-1-carboxylate, 2-methyl-2-(1H-pyrazol-1-yl)propyl (3S,4S)-4-{4-carbamoyl-3-[(4-fluorophenyl)amino]-1H-pyrazol-1-yl}-3-cyanopiperidine-1-carboxylate, 2,2,2-trifluoroethyl-4-{4-carbamoyl-3-[(4-fluorophenyl)amino]-1H-pyrazol-1-yl}-3-cyanopiperidine-1-carboxylate, 2,2,2-trifluoroethyl (3R,4R)-4-{4-carbamoyl-3-[(4-fluorophenyl)amino]-1H-pyrazol-1-yl}-3-cyanopiperidine-1-carboxylate, 2,2,2-trifluoroethyl (3S,4S)-4-{4-carbamoyl-3-[(4-fluorophenyl)amino]-1H-pyrazol-1-yl}-3-cyanopiperidine-1-carboxylate, 2-methoxyethyl-4-{4-carbamoyl-3-[(4-fluorophenyl)amino]-1H-pyrazol-1-yl}-3-cyanopiperidine-1-carboxylate, 2-methoxyethyl (3R,4R)-4-{4-carbamoyl-3-[(4-fluorophenyl)amino]-1H-pyrazol-1-yl}-3-cyanopiperidine-1-carboxylate, 2-methoxyethyl (3S,4S)-4-{4-carbamoyl-3-[(4-fluorophenyl)amino]-1H-pyrazol-1-yl}-3-cyanopiperidine-1-carboxylate, cyclopropylmethyl-4-{4-carbamoyl-3-[(4-fluorophenyl)amino]-1H-pyrazol-1-yl}-3-cyanopiperidine-1-carboxylate, cyclopropylmethyl (3R,4R)-4-{4-carbamoyl-3-[(4-fluorophenyl)amino]-1H-pyrazol-1-yl}-3-cyanopiperidine-1-carboxylate, cyclopropylmethyl (3S,4S)-4-{4-carbamoyl-3-[(4-fluorophenyl)amino]-1H-pyrazol-1-yl}-3-cyanopiperidine-1-carboxylate, 2-fluoro-1-(fluoromethyl)ethyl-4-{4-carbamoyl-3-[(4-fluorophenyl)amino]-1H-pyrazol-1-yl}-3-cyanopiperidine-1-carboxylate, 2-fluoro-1-(fluoromethyl)ethyl (3R,4R)-4-{4-carbamoyl-3-[(4-fluorophenyl)amino]-1H-pyrazol-1-yl}-3-cyanopiperidine-1-carboxylate 2-fluoro-1-(fluoromethyl)ethyl (3S,4S)-4-{4-carbamoyl-3-[(4-fluorophenyl)amino]-1H-pyrazol-1-yl}-3-cyanopiperidine-1-carboxylate, 3-methoxypropyl-4-{4-carbamoyl-3-[(4-fluorophenyl)amino]-1H-pyrazol-1-yl}-3-cyanopiperidine-1-carboxylate, 3-methoxypropyl (3R,4R)-4-{4-carbamoyl-3-[(4-fluorophenyl)amino]-1H-pyrazol-1-yl}-3-cyanopiperidine-1-carboxylate, 3-methoxypropyl (3S,4S)-4-{4-carbamoyl-3-[(4-fluorophenyl)amino]-1H-pyrazol-1-yl}-3-cyanopiperidine-1-carboxylate, (3-methyloxetan-3-yl)methyl-4-{4-carbamoyl-3-[(4-fluorophenyl)amino]-1H-pyrazol-1-yl}-3-cyanopiperidine-1-carboxylate, (3-methyloxetan-3-yl)methyl (3R,4R)-4-{4-carbamoyl-3-[(4-fluorophenyl)amino]-1H-pyrazol-1-yl}-3-cyanopiperidine-1-carboxylate, (3-methyloxetan-3-yl)methyl (3S,4S)-4-{4-carbamoyl-3-[(4-fluorophenyl)amino]-1H-pyrazol-1-yl}-3-cyanopiperidine-1-carboxylate, but-3-yn-1-yl-4-{4-carbamoyl-3-[(4-fluorophenyl)amino]-1H-pyrazol-1-yl}-3-cyanopiperidine-1-carboxylate, but-3-yn-1-yl (3R,4R)-4-{4-carbamoyl-3-[(4-fluorophenyl)amino]-1H-pyrazol-1-yl}-3-cyanopiperidine-1-carboxylate, but-3-yn-1-yl (3S,4S)-4-{4-carbamoyl-3-[(4-fluorophenyl)amino]-1H-pyrazol-1-yl}-3-cyanopiperidine-1-carboxylate, 1-cyclopropylethyl-4-{4-carbamoyl-3-[(4-fluorophenyl)amino]-1H-pyrazol-1-yl}-3-cyanopiperidine-1-carboxylate, 1-cyclopropylethyl (3R,4R)-4-{4-carbamoyl-3-[(4-fluorophenyl)amino]-1H-pyrazol-1-yl}-3-cyanopiperidine-1-carboxylate, 1-cyclopropylethyl (3S,4S)-4-{4-carbamoyl-3-[(4-fluorophenyl)amino]-1H-pyrazol-1-yl}-3-cyanopiperidine-1-carboxylate, 2-phenylethyl-4-{4-carbamoyl-3-[(4-fluorophenyl)amino]-1H-pyrazol-1-yl}-3-cyanopiperidine-1-carboxylate, 2-phenylethyl (3R,4R)-4-{4-carbamoyl-3-[(4-fluorophenyl)amino]-1H-pyrazol-1-yl}-3-cyanopiperidine-1-carboxylate, 2-phenylethyl (3S,4S)-4-{4-carbamoyl-3-[(4-fluorophenyl)amino]-1H-pyrazol-1-yl}-3-cyanopiperidine-1-carboxylate, 2,3-dihydro-1H-inden-2-yl-4-{4-carbamoyl-3-[(4-fluorophenyl)amino]-1H-pyrazol-1-yl}-3-cyanopiperidine-1-carboxylate, 2,3-dihydro-1H-inden-2-yl (3R,4R)-4-{4-carbamoyl-3-[(4-fluorophenyl)amino]-1H-pyrazol-1-yl}-3-cyanopiperidine-1-carboxylate, 2,3-dihydro-1H-inden-2-yl (3S,4S)-4-{4-carbamoyl-3-[(4-fluorophenyl)amino]-1H-pyrazol-1-yl}-3-cyanopiperidine-1-carboxylate, 2-ethoxy-2-oxoethyl-4-{4-carbamoyl-3-[(4-fluorophenyl)amino]-1H-pyrazol-1-yl}-3-cyanopiperidine-1-carboxylate, 2-ethoxy-2-oxoethyl (3S,4S)-4-{4-carbamoyl-3-[(4-fluorophenyl)amino]-1H-pyrazol-1-yl}-3-cyanopiperidine-1-carboxylate, 2-ethoxy-2-oxoethyl (3R,4R)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl-4-{4-carbamoyl-3-[(4-fluorophenyl)amino]-1H-pyrazol-1-yl}-3-cyanopiperidine-1-carboxylate,

[1-(cyanomethyl)cyclopropyl]methyl (3R,4R)-4-{4-carbamoyl-3-[(4-fluorophenyl)amino]-1H-pyrazol-1-yl}-3-cyanopiperidine-1-carboxylate,

[1-(cyanomethyl)cyclopropyl]methyl (3S,4S)-4-{4-carbamoyl-3-[(4-fluorophenyl)amino]-1H-pyrazol-1-yl}-3-cyanopiperidine-1-carboxylate, but-3-yn-1-yl-4-{4-carbamoyl-3-[(4-fluorophenyl)amino]-1H-pyrazol-1-yl}-3-cyanopiperidine-1-carboxylate, but-3-yn-1-yl (3R,4S)-4-{4-carbamoyl-3-[(4-fluorophenyl)amino]-1H-pyrazol-1-yl}-3-cyanopiperidine-1-carboxylate, but-3-yn-1-yl (3S,4R)-4-{4-carbamoyl-3-[(4-fluorophenyl)amino]-1H-pyrazol-1-yl}-3-cyanopiperidine-1-carboxylate, 2-cyclopropylethyl-4-{4-carbamoyl-3-[(4-fluorophenyl)amino]-1H-pyrazol-1-yl}-3-cyanopiperidine-1-carboxylate, 2-cyclopropylethyl (3R,4S)-4-{4-carbamoyl-3-[(4-fluorophenyl)amino]-1H-pyrazol-1-yl}-3-cyanopiperidine-1-carboxylate, 2-cyclopropylethyl (3S,4R)-4-{4-carbamoyl-3-[(4-fluorophenyl)amino]-1H-pyrazol-1-yl}-3-cyanopiperidine-1-carboxylate, 2,3-dihydro-1H-inden-2-yl-4-{4-carbamoyl-3-[(4-fluorophenyl)amino]-1H-pyrazol-1-yl}-3-cyanopiperidine-1-carboxylate, 2,3-dihydro-1H-inden-2-yl (3R,4S)-4-{4-carbamoyl-3-[(4-fluorophenyl)amino]-1H-pyrazol-1-yl}-3-cyanopiperidine-1-carboxylate, 2,3-dihydro-1H-inden-2-yl (3S,4R)-4-{4-carbamoyl-3-[(4-fluorophenyl)amino]-1H-pyrazol-1-yl}-3-cyanopiperidine-1-carboxylate, 2,2,2-trifluoro-1-methylethyl-4-{4-carbamoyl-3-[(4-fluorophenyl)amino]-1H-pyrazol-1-yl}-3-cyanopiperidine-1-carboxylate, 2,2,2-trifluoro-1-methylethyl (3R,4S)-4-{4-carbamoyl-3-[(4-fluorophenyl)amino]-1H-pyrazol-1-yl}-3-cyanopiperidine-1-carboxylate,
2,2,2-trifluoro-1-methylethyl (3S,4R)-4-{4-carbamoyl-3-[(4-fluorophenyl)amino]-1H-pyrazol-1-yl}-3-cyanopiperidine-1-carboxylate,
ethyl-4-{4-carbamoyl-3-[(4-fluorophenyl)amino]-1H-pyrazol-yl}-3-cyanopiperidine-1-carboxylate,
ethyl (3S,4R)-4-{4-carbamoyl-3-[(4-fluorophenyl)amino]-1H-pyrazol-1-yl}-3-cyanopiperidine-1-carboxylate,
ethyl (3R,4S)-4-{4-carbamoyl-3-[(4-fluorophenyl)amino]-1H-pyrazol-1-yl}-3-cyanopiperidine-1-carboxylate,
(3-methyloxetan-3-yl)methyl-4-{4-carbamoyl-3-[(4-fluorophenyl)amino]-1H-pyrazol-1-yl}-3-cyanopiperidine-1-carboxylate,
(3-methyloxetan-3-yl)methyl (3R,4S)-4-{4-carbamoyl-3-[(4-fluorophenyl)amino]-1H-pyrazol-1-yl}-3-cyanopiperidine-1-carboxylate,
(3-methyloxetan-3-yl)methyl (3S,4R)-4-{4-carbamoyl-3-[(4-fluorophenyl)amino]-1H-pyrazol-1-yl}-3-cyanopiperidine-1-carboxylate,
cyclopropylmethyl-4-{4-carbamoyl-3-[(4-fluorophenyl)amino]-1H-pyrazol-1-yl}-3-cyanopiperidine-1-carboxylate,
cyclopropylmethyl (3R,4S)-4-{4-carbamoyl-3-[(4-fluorophenyl)amino]-1H-pyrazol-1-yl}-3-cyanopiperidine-1-carboxylate,
cyclopropylmethyl (3S,4R)-4-{4-carbamoyl-3-[(4-fluorophenyl)amino]-1H-pyrazol-1-yl}-3-cyanopiperidine-1-carboxylate,
2-fluoro-1-(fluoromethyl)ethyl-4-{4-carbamoyl-3-[(4-fluorophenyl)amino]-1H-pyrazol-1-yl}-3-cyanopiperidine-1-carboxylate,
2-fluoro-1-(fluoromethyl)ethyl (3R,4S)-4-{4-carbamoyl-3-[(4-fluorophenyl)amino]-1H-pyrazol-1-yl}-3-cyanopiperidine-1-carboxylate,
2-fluoro-1-(fluoromethyl)ethyl (3S,4R)-4-{4-carbamoyl-3-[(4-fluorophenyl)amino]-1H-pyrazol-1-yl}-3-cyanopiperidine-1-carboxylate,
2-phenylethyl-4-{4-carbamoyl-3-[(4-fluorophenyl)amino]-1H-pyrazol-1-yl}-3-cyanopiperidine-1-carboxylate,
2-phenylethyl (3R,4S)-4-{4-carbamoyl-3-[(4-fluorophenyl)amino]-1H-pyrazol-1-yl}-3-cyanopiperidine-1-carboxylate,
2-phenylethyl (3S,4R)-4-{4-carbamoyl-3-[(4-fluorophenyl)amino]-1H-pyrazol-1-yl}-3-cyanopiperidine-1-carboxylate,
cyclopentyl-4-{4-carbamoyl-3-[(4-fluorophenyl)amino]-1H-pyrazol-1-yl}-3-cyanopiperidine-1-carboxylate,
cyclopentyl (3R,4S)-4-{4-carbamoyl-3-[(4-fluorophenyl)amino]-1H-pyrazol-1-yl}-3-cyanopiperidine-1-carboxylate,
cyclopentyl (3S,4R)-4-{4-carbamoyl-3-[(4-fluorophenyl)amino]-1H-pyrazol-1-yl}-3-cyanopiperidine-1-carboxylate,
2,2-dimethylpropyl-4-{4-carbamoyl-3-[(4-fluorophenyl)amino]-1H-pyrazol-1-yl}-3-cyanopiperidine-1-carboxylate,
2,2-dimethylpropyl (3R,4S)-4-{4-carbamoyl-3-[(4-fluorophenyl)amino]-1H-pyrazol-1-yl}-3-cyanopiperidine-1-carboxylate,
2,2-dimethylpropyl (3S,4R)-4-{4-carbamoyl-3-[(4-fluorophenyl)amino]-1H-pyrazol-1-yl}-3-cyanopiperidine-1-carboxylate,
tetrahydrofuran-3-yl-4-{4-carbamoyl-3-[(4-fluorophenyl)amino]-1H-pyrazol-1-yl}-3-cyanopiperidine-1-carboxylate,
tetrahydrofuran-3-yl (3R,4S)-4-{4-carbamoyl-3-[(4-fluorophenyl)amino]-1H-pyrazol-1-yl}-3-cyanopiperidine-1-carboxylate,
tetrahydrofuran-3-yl (3S,4R)-4-{4-carbamoyl-3-[(4-fluorophenyl)amino]-1H-pyrazol-1-yl}-3-cyanopiperidine-1-carboxylate,
benzyl-4-{4-carbamoyl-3-[(4-fluorophenyl)amino]-1H-pyrazol-1-yl}-3-cyanopiperidine-1-carboxylate,
benzyl (3R,4S)-4-{4-carbamoyl-3-[(4-fluorophenyl)amino]-1H-pyrazol-1-yl}-3-cyanopiperidine-1-carboxylate,
benzyl (3S,4R)-4-{4-carbamoyl-3-[(4-fluorophenyl)amino]-1H-pyrazol-1-yl}-3-cyanopiperidine-1-carboxylate,
2-methyl-2-(1H-pyrazol-1-yl)propyl-4-{4-carbamoyl-3-[(4-fluorophenyl)amino]-1H-pyrazol-1-yl}-3-cyanopiperidine-1-carboxylate,
2-methyl-2-(1H-pyrazol-1-yl)propyl (3R,4S)-4-{4-carbamoyl-3-[(4-fluorophenyl)amino]-1H-pyrazol-1-yl}-3-cyanopiperidine-1-carboxylate,
2-methyl-2-(1H-pyrazol-1-yl)propyl (3S,4R)-4-{4-carbamoyl-3-[(4-fluorophenyl)amino]-1H-pyrazol-1-yl}-3-cyanopiperidine-1-carboxylate,
2-methoxyethyl-4-{4-carbamoyl-3-[(4-fluorophenyl)amino]-1H-pyrazol-1-yl}-3-cyanopiperidine-1-carboxylate,
2-methoxyethyl (3R,4S)-4-{4-carbamoyl-3-[(4-fluorophenyl)amino]-1H-pyrazol-1-yl}-3-cyanopiperidine-1-carboxylate,
2-methoxyethyl (3S,4R)-4-{4-carbamoyl-3-[(4-fluorophenyl)amino]-1H-pyrazol-1-yl}-3-cyanopiperidine-1-carboxylate,
3-phenylpropyl-4-{4-carbamoyl-3-[(4-fluorophenyl)amino]-1H-pyrazol-1-yl}-3-cyanopiperidine-1-carboxylate,
3-phenylpropyl (3R,4S)-4-{4-carbamoyl-3-[(4-fluorophenyl)amino]-1H-pyrazol-1-yl}-3-cyanopiperidine-1-carboxylate,
3-phenylpropyl (3S,4R)-4-{4-carbamoyl-3-[(4-fluorophenyl)amino]-1H-pyrazol-1-yl}-3-cyanopiperidine-1-carboxylate,
2-methylpropyl-4-{4-carbamoyl-3-[(4-fluorophenyl)amino]-1H-pyrazol-1-yl}-3-cyanopiperidine-1-carboxylate,
2-methylpropyl (3R,4S)-4-{4-carbamoyl-3-[(4-fluorophenyl)amino]-1H-pyrazol-1-yl}-3-cyanopiperidine-1-carboxylate,
2-methylpropyl (3S,4R)-4-{4-carbamoyl-3-[(4-fluorophenyl)amino]-1H-pyrazol-1-yl}-3-cyanopiperidine-1-carboxylate,
oxetan-3-yl-4-{4-carbamoyl-3-[(4-fluorophenyl)amino]-1H-pyrazol-1-yl}-3-cyanopiperidine-1-carboxylate,
oxetan-3-yl (3R,4S)-4-{4-carbamoyl-3-[(4-fluorophenyl)amino]-1H-pyrazol-1-yl}-3-cyanopiperidine-1-carboxylate,
oxetan-3-yl (3S,4R)-4-{4-carbamoyl-3-[(4-fluorophenyl)amino]-1H-pyrazol-1-yl}-3-cyanopiperidine-1-carboxylate,
2-fluoroethyl-4-{4-carbamoyl-3-[(4-fluorophenyl)amino]-1H-pyrazol-yl}-3-cyanopiperidine-1-carboxylate,
2-fluoroethyl (3R,4S)-4-{4-carbamoyl-3-[(4-fluorophenyl)amino]-1H-pyrazol-1-yl}-3-cyanopiperidine-1-carboxylate, 2-fluoroethyl (3S,4R)-4-{4-carbamoyl-3-[(4-fluorophenyl)amino]-1H-pyrazol-1-yl}-3-cyanopiperidine-1-carboxylate,
2-ethoxy-2-oxoethyl-4-{4-carbamoyl-3-[(4-fluorophenyl)amino]-1H-pyrazol-1-yl}-3-cyanopiperidine-1-carboxylate,
2-ethoxy-2-oxoethyl (3R,4S)-4-{4-carbamoyl-3-[(4-fluorophenyl)amino]-1H-pyrazol-1-yl}-3-cyanopiperidine-1-carboxylate,
2-ethoxy-2-oxoethyl (3S,4R)-4-{4-carbamoyl-3-[(4-fluorophenyl)amino]-1H-pyrazol-1-yl}-3-cyanopiperidine-1-carboxylate,
tetrahydro-2H-pyran-4-yl-4-{4-carbamoyl-3-[(4-fluorophenyl)amino]-1H-pyrazol-yl}-3-cyanopiperidine-1-carboxylate,
tetrahydro-2H-pyran-4-yl (3R,4S)-4-{4-carbamoyl-3-[(4-fluorophenyl)amino]-1H-pyrazol-1-yl}-3-cyanopiperidine-1-carboxylate,
tetrahydro-2H-pyran-4-yl (3S,4R)-4-{4-carbamoyl-3-[(4-fluorophenyl)amino]-1H-pyrazol-1-yl}-3-cyanopiperidine-1-carboxylate,
cyclohexyl-4-{4-carbamoyl-3-[(4-fluorophenyl)amino]-1H-pyrazol-1-yl}-3-cyanopiperidine-1-carboxylate,
cyclohexyl (3R,4S)-4-{4-carbamoyl-3-[(4-fluorophenyl)amino]-1H-pyrazol-1-yl}-3-cyanopiperidine-1-carboxylate,
cyclohexyl (3S,4R)-4-{4-carbamoyl-3-[(4-fluorophenyl)amino]-1H-pyrazol-1-yl}-3-cyanopiperidine-1-carboxylate,
(1-methylcyclopropyl)methyl-4-{4-carbamoyl-3-[(4-fluorophenyl)amino]-1H-pyrazol-1-yl}-3-cyanopiperidine-1-carboxylate,
(1-methylcyclopropyl)methyl (3R,4S)-4-{4-carbamoyl-3-[(4-fluorophenyl)amino]-1H-pyrazol-1-yl}-3-cyanopiperidine-1-carboxylate,
(1-methylcyclopropyl)methyl (3S,4R)-4-{4-carbamoyl-3-[(4-fluorophenyl)amino]-1H-pyrazol-1-yl}-3-cyanopiperidine-1-carboxylate,
3-methoxypropyl-4-{4-carbamoyl-3-[(4-fluorophenyl)amino]-1H-pyrazol-1-yl}-3-cyanopiperidine-1-carboxylate,
3-methoxypropyl (3R,4S)-4-{4-carbamoyl-3-[(4-fluorophenyl)amino]-1H-pyrazol-1-yl}-3-cyanopiperidine-1-carboxylate,
3-methoxypropyl (3S,4R)-4-{4-carbamoyl-3-[(4-fluorophenyl)amino]-1H-pyrazol-1-yl}-3-cyanopiperidine-1-carboxylate,
[1-(cyanomethyl)cyclopropyl]methyl-4-{4-carbamoyl-3-[(4-fluorophenyl)amino]-1H-pyrazol-1-yl}-3-cyanopiperidine-1-carboxylate,
[1-(cyanomethyl)cyclopropyl]methyl (3R,4S)-4-{4-carbamoyl-3-[(4-fluorophenyl)amino]-1H-pyrazol-1-yl}-3-cyanopiperidine-1-carboxylate,
[1-(cyanomethyl)cyclopropyl]methyl (3S,4R)-4-{4-carbamoyl-3-[(4-fluorophenyl)amino]-1H-pyrazol-1-yl}-3-cyanopiperidine-1-carboxylate,
2,2-difluoroethyl-4-{4-carbamoyl-3-[(4-fluorophenyl)amino]-1H-pyrazol-1-yl}-3-cyanopiperidine-1-carboxylate,
2,2-difluoroethyl (3R,4S)-4-{4-carbamoyl-3-[(4-fluorophenyl)amino]-1H-pyrazol-1-yl}-3-cyanopiperidine-1-carboxylate,
2,2-difluoroethyl (3S,4R)-4-{4-carbamoyl-3-[(4-fluorophenyl)amino]-1H-pyrazol-1-yl}-3-cyanopiperidine-1-carboxylate,
2,2,2-trifluoroethyl-4-{4-carbamoyl-3-[(4-fluorophenyl)amino]-1H-pyrazol-1-yl}-3-cyanopiperidine-1-carboxylate,
2,2,2-trifluoroethyl (3R,4S)-4-{4-carbamoyl-3-[(4-fluorophenyl)amino]-1H-pyrazol-1-yl}-3-cyanopiperidine-1-carboxylate,
2,2,2-trifluoroethyl (3S,4R)-4-{4-carbamoyl-3-[(4-fluorophenyl)amino]-1H-pyrazol-1-yl}-3-cyanopiperidine-1-carboxylate,
2,2-difluoro-3-hydroxypropyl-4-{4-carbamoyl-3-[(4-fluorophenyl)amino]-1H-pyrazol-yl}-3-cyanopiperidine-1-carboxylate,
2,2-difluoro-3-hydroxypropyl (3R,4S)-4-{4-carbamoyl-3-[(4-fluorophenyl)amino]-1H-pyrazol-1-yl}-3-cyanopiperidine-1-carboxylate,
2,2-difluoro-3-hydroxypropyl (3S,4R)-4-{4-carbamoyl-3-[(4-fluorophenyl)amino]-1H-pyrazol-1-yl}-3-cyanopiperidine-1-carboxylate,
1-cyclopropylethyl-4-{4-carbamoyl-3-[(4-fluorophenyl)amino]-1H-pyrazol-1-yl}-3-cyanopiperidine-1-carboxylate,
1-cyclopropylethyl (3R,4S)-4-{4-carbamoyl-3-[(4-fluorophenyl)amino]-1H-pyrazol-1-yl}-3-cyanopiperidine-1-carboxylate,
1-cyclopropylethyl (3S,4R)-4-{4-carbamoyl-3-[(4-fluorophenyl)amino]-1H-pyrazol-1-yl}-3-cyanopiperidine-1-carboxylate,
2-Cyano-2-methylpropyl-3-{4-carbamoyl-3-[(4-fluorophenyl)amino]-1H-pyrazol-1-yl}-4-cyanopiperidine-1-carboxylate,
2-Cyano-2-methylpropyl (3S,4R)-3-{4-carbamoyl-3-[(4-fluorophenyl)amino]-1H-pyrazol-1-yl}-4-cyanopiperidine-1-carboxylate,
2-Cyano-2-methylpropyl (3R,4S)-3-{4-carbamoyl-3-[(4-fluorophenyl)amino]-1H-pyrazol-1-yl}-4-cyanopiperidine-1-carboxylate,
2,2,2-trifluoro-1-methylethyl-3-{4-carbamoyl-3-[(4-fluorophenyl)amino]-1H-pyrazol-1-yl}-4-cyanopiperidine-1-carboxylate,
2,2,2-trifluoro-1-methylethyl (3S,4R)-3-{4-carbamoyl-3-[(4-fluorophenyl)amino]-1H-pyrazol-1-yl}-4-cyanopiperidine-1-carboxylate,
2,2,2-trifluoro-1-methylethyl (3R,4S)-3-{4-carbamoyl-3-[(4-fluorophenyl)amino]-1H-pyrazol-1-yl}-4-cyanopiperidine-1-carboxylate,
2-fluoro-1-(fluoromethyl)ethyl-3-{4-carbamoyl-3-[(4-fluorophenyl)amino]-1H-pyrazol-1-yl}-4-cyanopiperidine-1-carboxylate,
2-fluoro-1-(fluoromethyl)ethyl (3S,4R)-3-{4-carbamoyl-3-[(4-fluorophenyl)amino]-1H-pyrazol-1-yl}-4-cyanopiperidine-1-carboxylate,
2-fluoro-1-(fluoromethyl)ethyl (3R,4S)-3-{4-carbamoyl-3-[(4-fluorophenyl)amino]-1H-pyrazol-1-yl}-4-cyanopiperidine-1-carboxylate,
(1-methylcyclopropyl)methyl-3-{4-carbamoyl-3-[(4-fluorophenyl)amino]-1H-pyrazol-1-yl}-4-cyanopiperidine-1-carboxylate,
(1-methylcyclopropyl)methyl (3R,4S)-3-{4-carbamoyl-3-[(4-fluorophenyl)amino]-1H-pyrazol-1-yl}-4-cyanopiperidine-1-carboxylate,
(1-methylcyclopropyl)methyl (3S,4R)-3-{4-carbamoyl-3-[(4-fluorophenyl)amino]-1H-pyrazol-1-yl}-4-cyanopiperidine-1-carboxylate,
1-cyclopropylethyl-3-{4-carbamoyl-3-[(4-fluorophenyl)amino]-1H-pyrazol-1-yl}-4-cyanopiperidine-1-carboxylate, 1-cyclopropylethyl (3S,4R)-3-{4-carbamoyl-3-[(4-fluorophenyl)amino]-1H-pyrazol-1-yl}-4-cyanopiperidine-1-carboxylate,
1-cyclopropylethyl (3R,4S)-3-{4-carbamoyl-3-[(4-fluorophenyl)amino]-1H-pyrazol-1-yl}-4-cyanopiperidine-1-carboxylate,
2,2-difluoro-3-hydroxypropyl-3-{4-carbamoyl-3-[(4-fluorophenyl)amino]-1H-pyrazol-1-yl}-4-cyanopiperidine-1-carboxylate,
2,2-difluoro-3-hydroxypropyl (3S,4R)-3-{4-carbamoyl-3-[(4-fluorophenyl)amino]-1H-pyrazol-1-yl}-4-cyanopiperidine-1-carboxylate,
2,2-difluoro-3-hydroxypropyl (3R,4S)-3-{4-carbamoyl-3-[(4-fluorophenyl)amino]-1H-pyrazol-1-yl}-4-cyanopiperidine-1-carboxylate,
3-(dimethylamino)-2,2-dimethylpropyl-3-{4-carbamoyl-3-[(4-fluorophenyl)amino]-1H-pyrazol-1-yl}-4-cyanopiperidine-1-carboxylate,
3-(dimethylamino)-2,2-dimethylpropyl (3S,4R)-3-{4-carbamoyl-3-[(4-fluorophenyl)amino]-1H-pyrazol-1-yl}-4-cyanopiperidine-1-carboxylate,
3-(dimethylamino)-2,2-dimethylpropyl (3R,4S)-3-{4-carbamoyl-3-[(4-fluorophenyl)amino]-1H-pyrazol-1-yl}-4-cyanopiperidine-1-carboxylate,
ethyl-3-{4-carbamoyl-3-[(4-fluorophenyl)amino]-1H-pyrazol-yl}-4-cyanopiperidine-1-carboxylate,
ethyl (3S,4R)-3-{4-carbamoyl-3-[(4-fluorophenyl)amino]-1H-pyrazol-1-yl}-4-cyanopiperidine-1-carboxylate,
ethyl (3R,4S)-3-{4-carbamoyl-3-[(4-fluorophenyl)amino]-1H-pyrazol-1-yl}-4-cyanopiperidine-1-carboxylate,
2-methylpropyl-3-{4-carbamoyl-3-[(4-fluorophenyl)amino]-1H-pyrazol-1-yl}-4-cyanopiperidine-1-carboxylate,
2-methylpropyl (3S,4R)-3-{4-carbamoyl-3-[(4-fluorophenyl)amino]-1H-pyrazol-1-yl}-4-cyanopiperidine-1-carboxylate,
2-methylpropyl (3R,4S)-3-{4-carbamoyl-3-[(4-fluorophenyl)amino]-1H-pyrazol-1-yl}-4-cyanopiperidine-1-carboxylate,
2,2,2-trifluoroethyl-3-{4-carbamoyl-3-[(4-fluorophenyl)amino]-1H-pyrazol-1-yl}-4-cyanopiperidine-1-carboxylate,
2,2,2-trifluoroethyl (3S,4R)-3-{4-carbamoyl-3-[(4-fluorophenyl)amino]-1H-pyrazol-1-yl}-4-cyanopiperidine-1-carboxylate,
2,2,2-trifluoroethyl (3R,4S)-3-{4-carbamoyl-3-[(4-fluorophenyl)amino]-1H-pyrazol-1-yl}-4-cyanopiperidine-1-carboxylate,
2-fluoroethyl-3-{4-carbamoyl-3-[(4-fluorophenyl)amino]-1H-pyrazol-1-yl}-4-cyanopiperidine-1-carboxylate,
2-fluoroethyl (3S,4R)-3-{4-carbamoyl-3-[(4-fluorophenyl)amino]-1H-pyrazol-1-yl}-4-cyanopiperidine-1-carboxylate,
2-fluoroethyl (3R,4S)-3-{4-carbamoyl-3-[(4-fluorophenyl)amino]-1H-pyrazol-1-yl}-4-cyanopiperidine-1-carboxylate,
2,2-dimethylpropyl-3-{4-carbamoyl-3-[(4-fluorophenyl)amino]-1H-pyrazol-1-yl}-4-cyanopiperidine-1-carboxylate,
2,2-dimethylpropyl (3S,4R)-3-{4-carbamoyl-3-[(4-fluorophenyl)amino]-1H-pyrazol-1-yl}-4-cyanopiperidine-1-carboxylate,
2,2-dimethylpropyl (3R,4S)-3-{4-carbamoyl-3-[(4-fluorophenyl)amino]-1H-pyrazol-1-yl}-4-cyanopiperidine-1-carboxylate,
cyclopropylmethyl-3-{4-carbamoyl-3-[(4-fluorophenyl)amino]-1H-pyrazol-1-yl}-4-cyanopiperidine-1-carboxylate,
cyclopropylmethyl (3S,4R)-3-{4-carbamoyl-3-[(4-fluorophenyl)amino]-1H-pyrazol-1-yl}-4-cyanopiperidine-1-carboxylate,
cyclopropylmethyl (3R,4S)-3-{4-carbamoyl-3-[(4-fluorophenyl)amino]-1H-pyrazol-1-yl}-4-cyanopiperidine-1-carboxylate,
benzyl-3-{4-carbamoyl-3-[(4-fluorophenyl)amino]-1H-pyrazol-1-yl}-4-cyanopiperidine-1-carboxylate,
benzyl (3S,4R)-3-{4-carbamoyl-3-[(4-fluorophenyl)amino]-1H-pyrazol-1-yl}-4-cyanopiperidine-1-carboxylate,
benzyl (3R,4S)-3-{4-carbamoyl-3-[(4-fluorophenyl)amino]-1H-pyrazol-1-yl}-4-cyanopiperidine-1-carboxylate,
2-methoxyethyl-3-{4-carbamoyl-3-[(4-fluorophenyl)amino]-1H-pyrazol-1-yl}-4-cyanopiperidine-1-carboxylate,
2-methoxyethyl (3S,4R)-3-{4-carbamoyl-3-[(4-fluorophenyl)amino]-1H-pyrazol-1-yl}-4-cyanopiperidine-1-carboxylate,
2-methoxyethyl (3R,4S)-3-{4-carbamoyl-3-[(4-fluorophenyl)amino]-1H-pyrazol-1-yl}-4-cyanopiperidine-1-carboxylate,
2-ethoxy-2-oxoethyl-3-{4-carbamoyl-3-[(4-fluorophenyl)amino]-1H-pyrazol-yl}-4-cyanopiperidine-1-carboxylate,
2-ethoxy-2-oxoethyl (3S,4R)-3-{4-carbamoyl-3-[(4-fluorophenyl)amino]-1H-pyrazol-1-yl}-4-cyanopiperidine-1-carboxylate,
2-ethoxy-2-oxoethyl (3R,4S)-3-{4-carbamoyl-3-[(4-fluorophenyl)amino]-1H-pyrazol-1-yl}-4-cyanopiperidine-1-carboxylate,
tetrahydro-2H-pyran-4-yl-3-{4-carbamoyl-3-[(4-fluorophenyl)amino]-1H-pyrazol-1-yl}-4-cyanopiperidine-1-carboxylate,
tetrahydro-2H-pyran-4-yl (3S,4R)-3-{4-carbamoyl-3-[(4-fluorophenyl)amino]-1H-pyrazol-1-yl}-4-cyanopiperidine-1-carboxylate,
tetrahydro-2H-pyran-4-yl (3R,4S)-3-{4-carbamoyl-3-[(4-fluorophenyl)amino]-1H-pyrazol-1-yl}-4-cyanopiperidine-1-carboxylate,
2-(dimethylamino)ethyl-3-{4-carbamoyl-3-[(4-fluorophenyl)amino]-1H-pyrazol-1-yl}-4-cyanopiperidine-1-carboxylate,
2-(dimethylamino)ethyl (3S,4R)-3-{4-carbamoyl-3-[(4-fluorophenyl)amino]-1H-pyrazol-1-yl}-4-cyanopiperidine-1-carboxylate,
2-(dimethylamino)ethyl (3R,4S)-3-{4-carbamoyl-3-[(4-fluorophenyl)amino]-1H-pyrazol-1-yl}-4-cyanopiperidine-1-carboxylate,
2-morpholin-4-ylethyl-3-{4-carbamoyl-3-[(4-fluorophenyl)amino]-1H-pyrazol-yl}-4-cyanopiperidine-1-carboxylate,
2-morpholin-4-ylethyl (3S,4R)-3-{4-carbamoyl-3-[(4-fluorophenyl)amino]-1H-pyrazol-1-yl}-4-cyanopiperidine-1-carboxylate,
2-morpholin-4-ylethyl (3R,4S)-3-{4-carbamoyl-3-[(4-fluorophenyl)amino]-1H-pyrazol-1-yl}-4-cyanopiperidine-1-carboxylate,

[1-(cyanomethyl)cyclopropyl]methyl-3-{4-carbamoyl-3-[(4-fluorophenyl)amino]-1H-pyrazol-1-yl}-4-cyanopiperidine-1-carboxylate,
[1-(cyanomethyl)cyclopropyl]methyl (3S,4R)-3-{4-carbamoyl-3-[(4-fluorophenyl)amino]-1H-pyrazol-1-yl}-4-cyanopiperidine-1-carboxylate,
[1-(cyanomethyl)cyclopropyl]methyl (3R,4S)-3-{4-carbamoyl-3-[(4-fluorophenyl)amino]-1H-pyrazol-1-yl}-4-cyanopiperidine-1-carboxylate,
oxetan-3-yl-3-{4-carbamoyl-3-[(4-fluorophenyl)amino]-1H-pyrazol-1-yl}-4-cyanopiperidine-1-carboxylate,
oxetan-3-yl (3S,4R)-3-{4-carbamoyl-3-[(4-fluorophenyl)amino]-1H-pyrazol-1-yl}-4-cyanopiperidine-1-carboxylate,
oxetan-3-yl (3R,4S)-3-{4-carbamoyl-3-[(4-fluorophenyl)amino]-1H-pyrazol-1-yl}-4-cyanopiperidine-1-carboxylate,
(3-methyloxetan-3-yl)methyl-3-{4-carbamoyl-3-[(4-fluorophenyl)amino]-1H-pyrazol-1-yl}-4-cyanopiperidine-1-carboxylate,
(3-methyloxetan-3-yl)methyl (3S,4R)-3-{4-carbamoyl-3-[(4-fluorophenyl)amino]-1H-pyrazol-1-yl}-4-cyanopiperidine-1-carboxylate,
(3-methyloxetan-3-yl)methyl (3R,4S)-3-{4-carbamoyl-3-[(4-fluorophenyl)amino]-1H-pyrazol-1-yl}-4-cyanopiperidine-1-carboxylate,
2-cyclopropylethyl-3-{4-carbamoyl-3-[(4-fluorophenyl)amino]-1H-pyrazol-1-yl}-4-cyanopiperidine-1-carboxylate,
2-cyclopropylethyl (3S,4R)-3-{4-carbamoyl-3-[(4-fluorophenyl)amino]-1H-pyrazol-1-yl}-4-cyanopiperidine-1-carboxylate,
2-cyclopropylethyl (3R,4S)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl (3S,4R)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl (3R,4S)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl (3S,4R)-3-{4-carbamoyl-3-[(4-fluorophenyl)amino]-1H-pyrazol-1-yl}-4-cyanopiperidine-1-carboxylate,
2-methyl-2-(1H-pyrazol-1-yl)propyl (3R,4S)-3-{4-carbamoyl-3-[(4-fluorophenyl)amino]-1H-pyrazol-1-yl}-4-cyanopiperidine-1-carboxylate,
2,2-difluoro-3-hydroxypropyl-3-{4-carbamoyl-3-[(4-fluorophenyl)amino]-1H-pyrazol-1-yl}-4-cyanopiperidine-1-carboxylate,
2,2-difluoro-3-hydroxypropyl (3S,4R)-3-{4-carbamoyl-3-[(4-fluorophenyl)amino]-1H-pyrazol-1-yl}-4-cyanopiperidine-1-carboxylate,
2,2-difluoro-3-hydroxypropyl (3R,4S)-3-{4-carbamoyl-3-[(4-fluorophenyl)amino]-1H-pyrazol-1-yl}-4-cyanopiperidine-1-carboxylate,
2,2,2-trifluoro-1-methylethyl-4-{4-carbamoyl-3-[(4-fluorophenyl)amino]-1H-pyrazol-1-yl}-3-cyanopiperidine-1-carboxylate,
2,2,2-trifluoro-1-methylethyl (3R,4R)-4-{4-carbamoyl-3-[(4-fluorophenyl)amino]-1H-pyrazol-1-yl}-3-cyanopiperidine-1-carboxylate,
2,2,2-trifluoro-1-methylethyl (3S,4S)-4-{4-carbamoyl-3-[(4-fluorophenyl)amino]-1H-pyrazol-1-yl}-3-cyanopiperidine-1-carboxylate,
1-[4-cyano-1-(pyridazin-3-ylmethyl)piperidin-3-yl]-3-[(4-fluorophenyl)amino]-1H-pyrazole-4-carboxamide,
1-[(3S,4R)-4-cyano-1-(pyridazin-3-ylmethyl)piperidin-3-yl]-3-[(4-fluorophenyl)amino]-1H-pyrazole-4-carboxamide,
1-[(3R,4S)-4-cyano-1-(pyridazin-3-ylmethyl)piperidin-3-yl]-3-[(4-fluorophenyl)amino]-1H-pyrazole-4-carboxamide,
1-[4-cyano-1-(pyrazin-2-ylmethyl)piperidin-3-yl]-3-[(4-fluorophenyl)amino]-1H-pyrazole-4-carboxamide,
1-[(3S,4R)-4-cyano-1-(pyrazin-2-ylmethyl)piperidin-3-yl]-3-[(4-fluorophenyl)amino]-1H-pyrazole-4-carboxamide,
1-[(3R,4S)-4-cyano-1-(pyrazin-2-ylmethyl)piperidin-3-yl]-3-[(4-fluorophenyl)amino]-1H-pyrazole-4-carboxamide,
1-[4-cyano-1-(isoxazol-3-ylmethyl)piperidin-3-yl]-3-[(4-fluorophenyl)amino]-1H-pyrazole-4-carboxamide,
1-[(3S,4R)-4-cyano-1-(isoxazol-3-ylmethyl)piperidin-3-yl]-3-[(4-fluorophenyl)amino]-1H-pyrazole-4-carboxamide,
1-[(3R,4S)-4-cyano-1-(isoxazol-3-ylmethyl)piperidin-3-yl]-3-[(4-fluorophenyl)amino]-1H-pyrazole-4-carboxamide,
1-[4-cyano-1-(1,3-oxazol-4-ylmethyl)piperidin-3-yl]-3-[(4-fluorophenyl)amino]-1H-pyrazole-4-carboxamide,
1-[(3S,4R)-4-cyano-1-(1,3-oxazol-4-ylmethyl)piperidin-3-yl]-3-[(4-fluorophenyl)amino]-1H-pyrazole-4-carboxamide,
1-[(3R,4S)-4-cyano-1-(1,3-oxazol-4-ylmethyl)piperidin-3-yl]-3-[(4-fluorophenyl)amino]-1H-pyrazole-4-carboxamide,
1-{4-cyano-1-[(1-methyl-1H-pyrazol-3-yl)methyl]piperidin-3-yl}-3-[(4-fluorophenyl)amino]-1H-pyrazole-4-carboxamide,
1-{(3S,4R)-4-cyano-1-[(1-methyl-1H-pyrazol-3-yl)methyl]piperidin-3-yl}-3-[(4-fluorophenyl)amino]-1H-pyrazole-4-carboxamide,
1-{(3R,4S)-4-cyano-1-[(1-methyl-1H-pyrazol-3-yl)methyl]piperidin-3-yl}-3-[(4-fluorophenyl)amino]-1H-pyrazole-4-carboxamide,
1-[4-cyano-1-(1,3-thiazol-4-ylmethyl)piperidin-3-yl]-3-[(4-fluorophenyl)amino]-1H-pyrazole-4-carboxamide,
1-[(3S,4R)-4-cyano-1-(1,3-thiazol-4-ylmethyl)piperidin-3-yl]-3-[(4-fluorophenyl)amino]-1H-pyrazole-4-carboxamide,
1-[(3R,4S)-4-cyano-1-(1,3-thiazol-4-ylmethyl)piperidin-3-yl]-3-[(4-fluorophenyl)amino]-1H-pyrazole-4-carboxamide,
1-{4-cyano-1-[(4-fluoropyridin-2-yl)methyl]piperidin-3-yl}-3-[(4-fluorophenyl)amino]-1H-pyrazole-4-carboxamide,
1-{(3S,4R)-4-cyano-1-[(4-fluoropyridin-2-yl)methyl]piperidin-3-yl}-3-[(4-fluorophenyl)amino]-1H-pyrazole-4-carboxamide,
1-{(3R,4S)-4-cyano-1-[(4-fluoropyridin-2-yl)methyl]piperidin-3-yl}-3-[(4-fluorophenyl)amino]-1H-pyrazole-4-carboxamide,
1-[4-cyano-1-(1,3-oxazol-2-ylmethyl)piperidin-3-yl]-3-[(4-fluorophenyl)amino]-1H-pyrazole-4-carboxamide, 1-[(3S,4R)-4-cyano-1-(1,3-oxazol-2-ylmethyl)piperidin-3-yl]-3-[(4-fluorophenyl)amino]-1H-pyrazole-4-carboxamide,
1-[(3R,4S)-4-cyano-1-(1,3-oxazol-2-ylmethyl)piperidin-3-yl]-3-[(4-fluorophenyl)amino]-1H-pyrazole-4-carboxamide,
1-{4-cyano-1-[(3-methoxycyclobutyl)methyl]piperidin-3-yl}-3-[(4-fluorophenyl)amino]-1H-pyrazole-4-carboxamide,
1-{(3S,4R)-4-cyano-1-[(3-methoxycyclobutyl)methyl]piperidin-3-yl}-3-[(4-fluorophenyl)amino]-1H-pyrazole-4-carboxamide,
1-{(3R,4S)-4-cyano-1-[(3-methoxycyclobutyl)methyl]piperidin-3-yl}-3-[(4-fluorophenyl)amino]-1H-pyrazole-4-carboxamide,
1-{4-cyano-1-[2-(tetrahydro-2H-pyran-4-yl)ethyl]piperidin-3-yl}-3-[(4-fluorophenyl)amino]-1H-pyrazole-4-carboxamide,
1-{(3S,4R)-4-cyano-1-[2-(tetrahydro-2H-pyran-4-yl)ethyl]piperidin-3-yl}-3-[(4-fluorophenyl)amino]-1H-pyrazole-4-carboxamide,
1-{(3R,4S)-4-cyano-1-[2-(tetrahydro-2H-pyran-4-yl)ethyl]piperidin-3-yl}-3-[(4-fluorophenyl)amino]-1H-pyrazole-4-carboxamide,
1-[4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[(3S,4R)-4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[(3R,4S)-4-cyano-1-{[3-(1-hydroxy-1-methylethyl)cyclobutyl]methyl}piperidin-3-yl]-3-[(4-fluorophenyl)amino]-1H-pyrazole-4-carboxamide,
1-[4-cyano-1-(cyclobutylmethyl)piperidin-3-yl]-3-[(4-fluorophenyl)amino]-1H-pyrazole-4-carboxamide,
1-[(3S,4R)-4-cyano-1-(cyclobutylmethyl)piperidin-3-yl]-3-[(4-fluorophenyl)amino]-1H-pyrazole-4-carboxamide,
1-[(3R,4S)-4-cyano-1-(cyclobutylmethyl)piperidin-3-yl]-3-[(4-fluorophenyl)amino]-1H-pyrazole-4-carboxamide,
1-{(4-cyano-1-[(1-methyl-1H-pyrazol-5-yl)methyl]piperidin-3-yl}-3-[(4-fluorophenyl)amino]-1H-pyrazole-4-carboxamide,
1-{(3S,4R)-4-cyano-1-[(1-methyl-1H-pyrazol-5-yl)methyl]piperidin-3-yl}-3-[(4-fluorophenyl)amino]-1H-pyrazole-4-carboxamide,
1-{(3R,4S)-4-cyano-1-[(1-methyl-1H-pyrazol-5-yl)methyl]piperidin-3-yl}-3-[(4-fluorophenyl)amino]-1H-pyrazole-4-carboxamide,
1-{(4-cyano-1-[(5-methylisoxazol-3-yl)methyl]piperidin-3-yl}-3-[(4-fluorophenyl)amino]-1H-pyrazole-4-carboxamide,
1-{(3S,4R)-4-cyano-1-[(5-methylisoxazol-3-yl)methyl]piperidin-3-yl}-3-[(4-fluorophenyl)amino]-1H-pyrazole-4-carboxamide,
1-{(3R,4S)-4-cyano-1-[(5-methylisoxazol-3-yl)methyl]piperidin-3-yl}-3-[(4-fluorophenyl)amino]-1H-pyrazole-4-carboxamide,
1-{4-cyano-1-[(1,5-dimethyl-1H-pyrazol-4-yl)methyl]piperidin-3-yl}-3-[(4-fluorophenyl)amino]-1H-pyrazole-4-carboxamide,
1-{(3S,4R)-4-cyano-1-[(1,5-dimethyl-1H-pyrazol-4-yl)methyl]piperidin-3-yl}-3-[(4-fluorophenyl)amino]-1H-pyrazole-4-carboxamide,
1-{(3R,4S)-4-cyano-1-[(1,5-dimethyl-1H-pyrazol-4-yl)methyl]piperidin-3-yl}-3-[(4-fluorophenyl)amino]-1H-pyrazole-4-carboxamide,
1-{4-cyano-1-[(5-fluoropyridin-2-yl)methyl]piperidin-3-yl}-3-[(4-fluorophenyl)amino]-1H-pyrazole-4-carboxamide,
1-{(3S,4R)-4-cyano-1-[(5-fluoropyridin-2-yl)methyl]piperidin-3-yl}-3-[(4-fluorophenyl)amino]-1H-pyrazole-4-carboxamide,
1-{(3R,4S)-4-cyano-1-[(5-fluoropyridin-2-yl)methyl]piperidin-3-yl}-3-[(4-fluorophenyl)amino]-1H-pyrazole-4-carboxamide,
1-{4-cyano-1-[(2-fluoropyridin-3-yl)methyl]piperidin-3-yl}-3-[(4-fluorophenyl)amino]-1H-pyrazole-4-carboxamide,
1-{(3S,4R)-4-cyano-1-[(2-fluoropyridin-3-yl)methyl]piperidin-3-yl}-3-[(4-fluorophenyl)amino]-1H-pyrazole-4-carboxamide,
1-{(3R,4S)-4-cyano-1-[(2-fluoropyridin-3-yl)methyl]piperidin-3-yl}-3-[(4-fluorophenyl)amino]-1H-pyrazole-4-carboxamide,
1-{4-cyano-1-[(2-methyl-1,3-thiazol-5-yl)methyl]piperidin-3-yl}-3-[(4-fluorophenyl)amino]-1H-pyrazole-4-carboxamide,
1-{(3S,4R)-4-cyano-1-[(2-methyl-1,3-thiazol-5-yl)methyl]piperidin-3-yl}-3-[(4-fluorophenyl)amino]-1H-pyrazole-4-carboxamide,
1-{(3R,4S)-4-cyano-1-[(2-methyl-1,3-thiazol-5-yl)methyl]piperidin-3-yl}-3-[(4-fluorophenyl)amino]-1H-pyrazole-4-carboxamide,
1-{4-cyano-1-[(1-ethyl-1H-imidazol-2-yl)methyl]piperidin-3-yl}-3-[(4-fluorophenyl)amino]-1H-pyrazole-4-carboxamide,
1-{(3S,4R)-4-cyano-1-[(1-ethyl-1H-imidazol-2-yl)methyl]piperidin-3-yl}-3-[(4-fluorophenyl)amino]-1H-pyrazole-4-carboxamide,
1-{(3R,4S)-4-cyano-1-[(1-ethyl-1H-imidazol-2-yl)methyl]piperidin-3-yl}-3-[(4-fluorophenyl)amino]-1H-pyrazole-4-carboxamide,
1-{4-cyano-1-[(3-methyl-4,5-dihydroisoxazol-5-yl)methyl]piperidin-3-yl}-3-[(4-fluorophenyl)amino]-1H-pyrazole-4-carboxamide,
1-{(3S,4R)-4-cyano-1-[(3-methyl-4,5-dihydroisoxazol-5-yl)methyl]piperidin-3-yl}-3-[(4-fluorophenyl)amino]-1H-pyrazole-4-carboxamide,
1-{(3R,4S)-4-cyano-1-[(3-methyl-4,5-dihydroisoxazol-5-yl)methyl]piperidin-3-yl}-3-[(4-fluorophenyl)amino]-1H-pyrazole-4-carboxamide,
1-[4-cyano-1-(tetrahydrofuran-3-ylmethyl)piperidin-3-yl]-3-[(4-fluorophenyl)amino]-1H-pyrazole-4-carboxamide,
1-[(3S,4R)-4-cyano-1-(tetrahydrofuran-3-ylmethyl)piperidin-3-yl]-3-[(4-fluorophenyl)amino]-1H-pyrazole-4-carboxamide,
1-[(3R,4S)-4-cyano-1-(tetrahydrofuran-3-ylmethyl)piperidin-3-yl]-3-[(4-fluorophenyl)amino]-1H-pyrazole-4-carboxamide,
1-[3-cyano-1-(pyridazin-3-ylmethyl)piperidin-4-yl]-3-[(4-fluorophenyl)amino]-1H-pyrazole-4-carboxamide,
1-[(3R,4R)-3-cyano-1-(pyridazin-3-ylmethyl)piperidin-4-yl]-3-[(4-fluorophenyl)amino]-1H-pyrazole-4-carboxamide,
1-[(3S,4S)-3-cyano-1-(pyridazin-3-ylmethyl)piperidin-4-yl]-3-[(4-fluorophenyl)amino]-1H-pyrazole-4-carboxamide,
1-[3-cyano-1-(pyrazin-2-ylmethyl)piperidin-4-yl]-3-[(4-fluorophenyl)amino]-1H-pyrazole-4-carboxamide, 1-[(3R,4R)-3-cyano-1-(pyrazin-2-ylmethyl)piperidin-4-yl]-3-[(4-fluorophenyl)amino]-1H-pyrazole-4-carboxamide,
1-[(3S,4S)-3-cyano-1-(pyrazin-2-ylmethyl)piperidin-4-yl]-3-[(4-fluorophenyl)amino]-1H-pyrazole-4-carboxamide,
1-[3-cyano-1-(isoxazol-3-ylmethyl)piperidin-4-yl]-3-[(4-fluorophenyl)amino]-1H-pyrazole-4-carboxamide,
1-[(3R,4R)-3-cyano-1-(isoxazol-3-ylmethyl)piperidin-4-yl]-3-[(4-fluorophenyl)amino]-1H-pyrazole-4-carboxamide,
1-[(3S,4S)-3-cyano-1-(isoxazol-3-ylmethyl)piperidin-4-yl]-3-[(4-fluorophenyl)amino]-1H-pyrazole-4-carboxamide,
1-[3-cyano-1-(1,3-oxazol-4-ylmethyl)piperidin-4-yl]-3-[(4-fluorophenyl)amino]-1H-pyrazole-4-carboxamide,
1-[(3R,4R)-3-cyano-1-(1,3-oxazol-4-ylmethyl)piperidin-4-yl]-3-[(4-fluorophenyl)amino]-1H-pyrazole-4-carboxamide,
1-[(3S,4S)-3-cyano-1-(1,3-oxazol-4-ylmethyl)piperidin-4-yl]-3-[(4-fluorophenyl)amino]-1H-pyrazole-4-carboxamide,
1-{3-cyano-1-[(1-methyl-1H-pyrazol-3-yl)methyl]piperidin-4-yl}-3-[(4-fluorophenyl)amino]-1H-pyrazole-4-carboxamide,
1-{(3R,4R)-3-cyano-1-[(1-methyl-1H-pyrazol-3-yl)methyl]piperidin-4-yl}-3-[(4-fluorophenyl)amino]-1H-pyrazole-4-carboxamide,
1-{(3S,4S)-3-cyano-1-[(1-methyl-1H-pyrazol-3-yl)methyl]piperidin-4-yl}-3-[(4-fluorophenyl)amino]-1H-pyrazole-4-carboxamide,
1-[3-cyano-1-(1,3-thiazol-4-ylmethyl)piperidin-4-yl]-3-[(4-fluorophenyl)amino]-1H-pyrazole-4-carboxamide,
1-[(3R,4R)-3-cyano-1-(1,3-thiazol-4-ylmethyl)piperidin-4-yl]-3-[(4-fluorophenyl)amino]-1H-pyrazole-4-carboxamide,
1-[(3S,4S)-3-cyano-1-(1,3-thiazol-4-ylmethyl)piperidin-4-yl]-3-[(4-fluorophenyl)amino]-1H-pyrazole-4-carboxamide,
1-{3-cyano-1-[(5-fluoropyridin-3-yl)methyl]piperidin-4-yl}-3-[(4-fluorophenyl)amino]-1H-pyrazole-4-carboxamide,
1-{(3R,4R)-3-cyano-1-[(5-fluoropyridin-3-yl)methyl]piperidin-4-yl}-3-[(4-fluorophenyl)amino]-1H-pyrazole-4-carboxamide,
1-{(3S,4S)-3-cyano-1-[(5-fluoropyridin-3-yl)methyl]piperidin-4-yl}-3-[(4-fluorophenyl)amino]-1H-pyrazole-4-carboxamide,
1-[3-cyano-1-(1,3-oxazol-2-ylmethyl)piperidin-4-yl]-3-[(4-fluorophenyl)amino]-1H-pyrazole-4-carboxamide,
1-[(3R,4R)-3-cyano-1-(1,3-oxazol-2-ylmethyl)piperidin-4-yl]-3-[(4-fluorophenyl)amino]-1H-pyrazole-4-carboxamide,
1-[(3S,4S)-3-cyano-1-(1,3-oxazol-2-ylmethyl)piperidin-4-yl]-3-[(4-fluorophenyl)amino]-1H-pyrazole-4-carboxamide,
1-{3-cyano-1-[(3-methoxycyclobutyl)methyl]piperidin-4-yl}-3-[(4-fluorophenyl)amino]-1H-pyrazole-4-carboxamide,
1-{(3R,4R)-3-cyano-1-[(3-methoxycyclobutyl)methyl]piperidin-4-yl}-3-[(4-fluorophenyl)amino]-1H-pyrazole-4-carboxamide,
1-{(3S,4S)-3-cyano-1-[(3-methoxycyclobutyl)methyl]piperidin-4-yl}-3-[(4-fluorophenyl)amino]-1H-pyrazole-4-carboxamide,
1-{3-cyano-1-[2-(tetrahydro-2H-pyran-4-yl)ethyl]piperidin-4-yl}-3-[(4-fluorophenyl)amino]-1H-pyrazole-4-carboxamide,
1-{(3R,4R)-3-cyano-1-[2-(tetrahydro-2H-pyran-4-yl)ethyl]piperidin-4-yl}-3-[(4-fluorophenyl)amino]-1H-pyrazole-4-carboxamide,
1-{(3S,4S)-3-cyano-1-[2-(tetrahydro-2H-pyran-4-yl)ethyl]piperidin-4-yl}-3-[(4-fluorophenyl)amino]-1H-pyrazole-4-carboxamide,
1-{3-cyano-1-[(1-methyl-1H-pyrazol-5-yl)methyl]piperidin-4-yl}-3-[(4-fluorophenyl)amino]-1H-pyrazole-4-carboxamide,
1-{(3R,4R)-3-cyano-1-[(1-methyl-1H-pyrazol-5-yl)methyl]piperidin-4-yl}-3-[(4-fluorophenyl)amino]-1H-pyrazole-4-carboxamide,
1-{(3S,4S)-3-cyano-1-[(1-methyl-1H-pyrazol-5-yl)methyl]piperidin-4-yl}-3-[(4-fluorophenyl)amino]-1H-pyrazole-4-carboxamide,
1-{3-cyano-1-[(5-methylisoxazol-3-yl)methyl]piperidin-4-yl}-3-[(4-fluorophenyl)amino]-1H-pyrazole-4-carboxamide,
1-{(3R,4R)-3-cyano-1-[(5-methylisoxazol-3-yl)methyl]piperidin-4-yl}-3-[(4-fluorophenyl)amino]-1H-pyrazole-4-carboxamide,
1-{(3S,4S)-3-cyano-1-[(5-methylisoxazol-3-yl)methyl]piperidin-4-yl}-3-[(4-fluorophenyl)amino]-1H-pyrazole-4-carboxamide,
1-{3-cyano-1-[(1,5-dimethyl-1H-pyrazol-4-yl)methyl]piperidin-4-yl}-3-[(4-fluorophenyl)amino]-1H-pyrazole-4-carboxamide,
1-{(3R,4R)-3-cyano-1-[(1,5-dimethyl-1H-pyrazol-4-yl)methyl]piperidin-4-yl}-3-[(4-fluorophenyl)amino]-1H-pyrazole-4-carboxamide,
1-{(3S,4S)-3-cyano-1-[(1,5-dimethyl-1H-pyrazol-4-yl)methyl]piperidin-4-yl}-3-[(4-fluorophenyl)amino]-1H-pyrazole-4-carboxamide,
1-{3-cyano-1-[(2-fluoropyridin-3-yl)methyl]piperidin-4-yl}-3-[(4-fluorophenyl)amino]-1H-pyrazole-4-carboxamide,
1-{(3R,4R)-3-cyano-1-[(2-fluoropyridin-3-yl)methyl]piperidin-4-yl}-3-[(4-fluorophenyl)amino]-1H-pyrazole-4-carboxamide,
1-{(3S,4S)-3-cyano-1-[(2-fluoropyridin-3-yl)methyl]piperidin-4-yl}-3-[(4-fluorophenyl)amino]-1H-pyrazole-4-carboxamide,
1-{3-cyano-1-[(6-fluoropyridin-2-yl)methyl]piperidin-4-yl}-3-[(4-fluorophenyl)amino]-1H-pyrazole-4-carboxamide,
1-{(3S,4S)-3-cyano-1-[(6-fluoropyridin-2-yl)methyl]piperidin-4-yl}-3-[(4-fluorophenyl)amino]-1H-pyrazole-4-carboxamide,
1-{(3R,4R)-3-cyano-1-[(6-fluoropyridin-2-yl)methyl]piperidin-4-yl}-3-[(4-fluorophenyl)amino]-1H-pyrazole-4-carboxamide,
1-{3-cyano-1-[(2-methyl-1,3-thiazol-5-yl)methyl]piperidin-4-yl}-3-[(4-fluorophenyl)amino]-1H-pyrazole-4-carboxamide,
1-{(3R,4R)-3-cyano-1-[(2-methyl-1,3-thiazol-5-yl)methyl]piperidin-4-yl}-3-[(4-fluorophenyl)amino]-1H-pyrazole-4-carboxamide,
1-{(3S,4S)-3-cyano-1-[(2-methyl-1,3-thiazol-5-yl)methyl]piperidin-4-yl}-3-[(4-fluorophenyl)amino]-1H-pyrazole-4-carboxamide,
1-{3-cyano-1-[(1-ethyl-1H-imidazol-2-yl)methyl]piperidin-4-yl}-3-[(4-fluorophenyl)amino]-1H-pyrazole-4-carboxamide, 1-{(3R,4R)-3-cyano-1-[(1-ethyl-1H-imidazol-2-yl)methyl]piperidin-4-yl}-3-[(4-fluorophenyl)amino]-1H-pyrazole-4-carboxamide,
1-{(3S,4S)-3-cyano-1-[(1-ethyl-1H-imidazol-2-yl)methyl]piperidin-4-yl}-3-[(4-fluorophenyl)amino]-1H-pyrazole-4-carboxamide,
1-{3-cyano-1-[(3-methyl-4,5-dihydroisoxazol-5-yl)methyl]piperidin-4-yl}-3-[(4-fluorophenyl)amino]-1H-pyrazole-4-carboxamide,
1-{(3R,4R)-3-cyano-1-[(3-methyl-4,5-dihydroisoxazol-5-yl)methyl]piperidin-4-yl}-3-[(4-fluorophenyl)amino]-1H-pyrazole-4-carboxamide,
1-{(3S,4S)-3-cyano-1-[(3-methyl-4,5-dihydroisoxazol-5-yl)methyl]piperidin-4-yl}-3-[(4-fluorophenyl)amino]-1H-pyrazole-4-carboxamide,
1-[3-cyano-1-(cyclobutylmethyl)piperidin-4-yl]-3-[(4-fluorophenyl)amino]-1H-pyrazole-4-carboxamide,
1-[(3R,4R)-3-cyano-1-(cyclobutylmethyl)piperidin-4-yl]-3-[(4-fluorophenyl)amino]-1H-pyrazole-4-carboxamide,
1-[4-cyano-1-(1,3-thiazol-5-ylmethyl)piperidin-3-yl]-3-[(4-fluorophenyl)amino]-1H-pyrazole-4-carboxamide,
1-[(3S,4R)-4-cyano-1-(1,3-thiazol-5-ylmethyl)piperidin-3-yl]-3-[(4-fluorophenyl)amino]-1H-pyrazole-4-carboxamide,
1-[(3R,4S)-4-cyano-1-(1,3-thiazol-5-ylmethyl)piperidin-3-yl]-3-[(4-fluorophenyl)amino]-1H-pyrazole-4-carboxamide,
1-{4-cyano-1-[(4-methyl-1,3-oxazol-5-yl)methyl]piperidin-3-yl}-3-[(4-fluorophenyl)amino]-1H-pyrazole-4-carboxamide,
1-{(3S,4R)-4-cyano-1-[(4-methyl-1,3-oxazol-5-yl)methyl]piperidin-3-yl}-3-[(4-fluorophenyl)amino]-1H-pyrazole-4-carboxamide,
1-{(3S,4R,3R,4S)-4-cyano-1-[(4-methyl-1,3-oxazol-5-yl)methyl]piperidin-3-yl}-3-[(4-fluorophenyl)amino]-1H-pyrazole-4-carboxamide,
1-(3-cyano-1,1-dioxidotetrahydro-2H-thiopyran-4-yl)-3-((4-fluorophenyl)amino)-1H-pyrazole-4-carboxamide,
1-((3R,4S)-3-cyano-1,1-dioxidotetrahydro-2H-thiopyran-4-yl)-3-((4-fluorophenyl)amino)-1H-pyrazole-4-carboxamide,
1-((3S,4R)-3-cyano-1,1-dioxidotetrahydro-2H-thiopyran-4-yl)-3-((4-fluorophenyl)amino)-1H-pyrazole-4-carboxamide,
1-(3-cyano-1,1-dioxidotetrahydro-2H-thiopyran-4-yl)-3-((4-fluorophenyl)amino)-1H-pyrazole-4-carboxamide,
1-((3R,4S)-3-cyano-1,1-dioxidotetrahydro-2H-thiopyran-4-yl)-3-((4-fluorophenyl)amino)-1H-pyrazole-4-carboxamide,
1-((3S,4R)-3-cyano-1,1-dioxidotetrahydro-2H-thiopyran-4-yl)-3-((4-fluorophenyl)amino)-1H-pyrazole-4-carboxamide,
1-(3-cyano-1,1-dioxidotetrahydro-2H-thiopyran-4-yl)-3-((4-(trifluoromethyl)phenyl)amino)-1H-pyrazole-4-carboxamide,
1-((3R,4R)-3-cyano-1,1-dioxidotetrahydro-2H-thiopyran-4-yl)-3-((4-(trifluoromethyl)phenyl)amino)-1H-pyrazole-4-carboxamide,
1-((3S,4S)-3-cyano-1,1-dioxidotetrahydro-2H-thiopyran-4-yl)-3-((4-(trifluoromethyl)phenyl)amino)-1H-pyrazole-4-carboxamide,
1-(3-cyano-1,1-dioxidotetrahydro-2H-thiopyran-4-yl)-3-((4-(trifluoromethyl)phenyl)amino)-1H-pyrazole-4-carboxamide,
1-((3R,4S)-3-cyano-1,1-dioxidotetrahydro-2H-thiopyran-4-yl)-3-((4-(trifluoromethyl)phenyl)amino)-1H-pyrazole-4-carboxamide,
1-((3S,4R)-3-cyano-1,1-dioxidotetrahydro-2H-thiopyran-4-yl)-3-((4-(trifluoromethyl)phenyl)amino)-1H-pyrazole-4-carboxamide,
1-(4-cyano-1,1-dioxidotetrahydrothiophen-3-yl)-3-((4-fluorophenyl)amino)-1H-pyrazole-4-carboxamide,
1-((3S,4S)-4-cyano-1,1-dioxidotetrahydrothiophen-3-yl)-3-((4-fluorophenyl)amino)-1H-pyrazole-4-carboxamide,
1-((3R,4R)-4-cyano-1,1-dioxidotetrahydrothiophen-3-yl)-3-((4-fluorophenyl)amino)-1H-pyrazole-4-carboxamide,
1-(4-cyano-1,1-dioxidotetrahydrothiophen-3-yl)-3-((4-fluorophenyl)amino)-1H-pyrazole-4-carboxamide,
1-((3S,4R)-4-cyano-1,1-dioxidotetrahydrothiophen-3-yl)-3-((4-fluorophenyl)amino)-1H-pyrazole-4-carboxamide,
1-((3R,4S)-4-cyano-1,1-dioxidotetrahydrothiophen-3-yl)-3-((4-fluorophenyl)amino)-1H-pyrazole-4-carboxamide,
1-(4-cyano-1,1-dioxidotetrahydrothiophen-3-yl)-3-((4-((trifluoromethyl)sulfonyl)phenyl)amino)-1H-pyrazole-4-carboxamide,
1-((3S,4R)-4-cyano-1,1-dioxidotetrahydrothiophen-3-yl)-3-((4-((trifluoromethyl)sulfonyl)phenyl)amino)-1H-pyrazole-4-carboxamide,
1-((3R,4S)-4-cyano-1,1-dioxidotetrahydrothiophen-3-yl)-3-((4-((trifluoromethyl)sulfonyl)phenyl)amino)-1H-pyrazole-4-carboxamide,
1-(4-cyano-1,1-dioxidotetrahydrothiophen-3-yl)-3-((2-fluoropyridin-4-yl)amino)-1H-pyrazole-4-carboxamide,
1-((3S,4S)-4-cyano-1,1-dioxidotetrahydrothiophen-3-yl)-3-((2-fluoropyridin-4-yl)amino)-1H-pyrazole-4-carboxamide,
1-((3R,4R)-4-cyano-1,1-dioxidotetrahydrothiophen-3-yl)-3-((2-fluoropyridin-4-yl)amino)-1H-pyrazole-4-carboxamide,
1-(4-cyano-4-methyl-1,1-dioxidotetrahydrothiophen-3-yl)-3-((4-fluorophenyl)amino)-1H-pyrazole-4-carboxamide,
1-((3S,4R)-4-cyano-4-methyl-1,1-dioxidotetrahydrothiophen-3-yl)-3-((4-fluorophenyl)amino)-1H-pyrazole-4-carboxamide,
1-((3R,4S)-4-cyano-4-methyl-1,1-dioxidotetrahydrothiophen-3-yl)-3-((4-fluorophenyl)amino)-1H-pyrazole-4-carboxamide,
1-(4-cyano-4-methyl-1,1-dioxidotetrahydrothiophen-3-yl)-3-((4-fluorophenyl)amino)-1H-pyrazole-4-carboxamide,
1-((3S,4S)-4-cyano-4-methyl-1,1-dioxidotetrahydrothiophen-3-yl)-3-((4-fluorophenyl)amino)-1H-pyrazole-4-carboxamide,
1-((3R,4R)-4-cyano-4-methyl-1,1-dioxidotetrahydrothiophen-3-yl)-3-((4-fluorophenyl)amino)-1H-pyrazole-4-carboxamide,
1-(4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-((3S,4R)-4-cyano-tetrahydro-2H-pyran-3-yl)-3-(2-fluoropyridin-4-ylamino)-1H-pyrazole-4-carboxamide,
1-(4-cyano-tetrahydro-2H-pyran-3-yl)-3-(2-fluoropyridin-4-ylamino)-1H-pyrazole-4-carboxamide, 1-((3S,4R)-4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-(4-cyano-tetrahydro-2H-pyran-3-yl)-3-(2-fluoropyridin-4-ylamino)-1H-pyrazole-4-carboxamide,
1-((3R,4S)-4-cyano-tetrahydro-2H-pyran-3-yl)-3-(2-fluoropyridin-4-ylamino)-1H-pyrazole-4-carboxamide,
1-((3S,4R)-4-cyano-tetrahydro-2H-pyran-3-yl)-3-(2-fluoropyridin-4-ylamino)-1H-pyrazole-4-carboxamide,
1-(4-cyanotetrahydro-2H-pyran-3-yl)-3-((4-(trifluoromethoxy)phenyl)amino)-1H-pyrazole-4-carboxamide,
1-((3R,4S)-4-cyanotetrahydro-2H-pyran-3-yl)-3-((4-(trifluoromethoxy)phenyl)amino)-1H-pyrazole-4-carboxamide,
1-((3S,4R)-4-cyanotetrahydro-2H-pyran-3-yl)-3-((4-(trifluoromethoxy)phenyl)amino)-1H-pyrazole-4-carboxamide,
3-[(4-chlorophenyl)amino]-1-[4-cyanotetrahydro-2H-pyran-3-yl]-1H-pyrazole-4-carboxamide,
3-[(4-chlorophenyl)amino]-1-[(3R,4S)-4-cyanotetrahydro-2H-pyran-3-yl]-1H-pyrazole-4-carboxamide,
3-[(4-chlorophenyl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-[(2-fluoropyridin-4-yl)amino]-1H-pyrazole-4-carboxamide,
1-[(3S,4R)-4-cyanotetrahydro-2H-pyran-3-yl]-3-[(2-fluoropyridin-4-yl)amino]-1H-pyrazole-4-carboxamide,
1-[(3R,4S)-4-cyanotetrahydro-2H-pyran-3-yl]-3-[(2-fluoropyridin-4-yl)amino]-1H-pyrazole-4-carboxamide,
1-[4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[(3R,4S)-4-cyanotetrahydro-2H-pyran-3-yl]-3-({4-[(1R or 1S)-2,2,2-trifluoro-1-hydroxyethyl]phenyl}amino)-1H-pyrazole-4-carboxamide,
1-[4-cyanotetrahydro-2H-pyran-3-yl]-3-({4-[2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1S)-2,2,2-trifluoro-1-hydroxyethyl]phenyl}amino)-1H-pyrazole-4-carboxamide,
1-[(3R,4S)-4-cyanotetrahydro-2H-pyran-3-yl]-3-({4-[(1S)-2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1R)-2,2,2-trifluoro-1-hydroxyethyl]phenyl}amino)-1H-pyrazole-4-carboxamide,
1-[(3S,4R)-4-cyanotetrahydro-2H-pyran-3-yl]-3-({4-[(1R)-2,2,2-trifluoro-1-hydroxyethyl]phenyl}amino)-1H-pyrazole-4-carboxamide,
1-[(4-cyanotetrahydro-2H-pyran-3-yl)-3-[(3,4-dichlorophenyl)amino]-1H-pyrazole-4-carboxamide,
1-[(3S,4R)-4-cyanotetrahydro-2H-pyran-3-yl]-3-[(3,4-dichlorophenyl)amino]-1H-pyrazole-4-carboxamide,
1-[(3R,4S)-4-cyanotetrahydro-2H-pyran-3-yl]-3-[(3,4-dichlorophenyl)amino]-1H-pyrazole-4-carboxamide,
3-[(4-chloro-3-fluorophenyl)amino]-1-[(4-cyanotetrahydro-2H-pyran-3-yl]-1H-pyrazole-4-carboxamide,
3-[(4-chloro-3-fluorophenyl)amino]-1-[(3S,4R)-4-cyanotetrahydro-2H-pyran-3-yl]-1H-pyrazole-4-carboxamide,
3-[(4-chloro-3-fluorophenyl)amino]-1-[(3R,4S)-4-cyanotetrahydro-2H-pyran-3-yl]-1H-pyrazole-4-carboxamide,
1-[4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[4-cyanotetrahydro-2H-pyran-3-yl]-3-({4-[2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(4-cyanotetrahydro-2H-pyran-3-yl)-3-{[4-(trifluoromethoxy)phenyl]amino}-1H-pyrazole-4-carboxamide,
1-[(3R,4S)-4-cyanotetrahydro-2H-pyran-3-yl]-3-{[4-(trifluoromethoxy)phenyl]amino}-1H-pyrazole-4-carboxamide,
1-[(3S,4R)-4-cyanotetrahydro-2H-pyran-3-yl]-3-{[4-(trifluoromethoxy)phenyl]amino}-1H-pyrazole-4-carboxamide,
3-[(7-chloroquinolin-3-yl)amino]-1-[4-cyanotetrahydro-2H-pyran-3-yl]-1H-pyrazole-4-carboxamide,
3-[(7-chloroquinolin-3-yl)amino]-1-[(3R,4S)-4-cyanotetrahydro-2H-pyran-3-yl]-1H-pyrazole-4-carboxamide,
3-[(7-chloroquinolin-3-yl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-{[4-(trifluoromethoxy)phenyl]amino}-1H-pyrazole-4-carboxamide,
1-[(3S,4R)-4-cyanotetrahydro-2H-pyran-3-yl]-3-{[4-(trifluoromethoxy)phenyl]amino}-1H-pyrazole-4-carboxamide,
1-[(3R,4S)-4-cyanotetrahydro-2H-pyran-3-yl]-3-{[4-(trifluoromethoxy)phenyl]amino}-1H-pyrazole-4-carboxamide,
3-[(4-chloro-3-fluorophenyl)amino]-1-[4-cyanotetrahydro-2H-pyran-3-yl]-1H-pyrazole-4-carboxamide,
3-[(4-chloro-3-fluorophenyl)amino]-1-[(3R,4S)-4-cyanotetrahydro-2H-pyran-3-yl]-1H-pyrazole-4-carboxamide,
3-[(4-chloro-3-fluorophenyl)amino]-1-[(3S,4R)-4-cyanotetrahydro-2H-pyran-3-yl]-1H-pyrazole-4-carboxamide,
1-[(4-cyanotetrahydro-2H-pyran-3-yl)-3-{[4-(1-methoxy-1-methylethyl)phenyl]amino}-1H-pyrazole-4-carboxamide,
1-[(3R,4S)-4-cyanotetrahydro-2H-pyran-3-yl]-3-{[4-(3-methyloxetan-3-yl)phenyl]amino}-1H-pyrazole-4-carboxamide, 1-[(3S,4R)-4-cyanotetrahydro-2H-pyran-3-yl]-3-{[4-(3-methyloxetan-3-yl)phenyl]amino}-1H-pyrazole-4-carboxamide,
1-[4-cyanotetrahydro-2H-pyran-3-yl]-3-{[4-(1-methoxy-1-methylethyl)phenyl]amino}-1H-pyrazole-4-carboxamide,
1-[(3S,4R)-4-cyanotetrahydro-2H-pyran-3-yl]-3-{[4-(3-methyloxetan-3-yl)phenyl]amino}-1H-pyrazole-4-carboxamide,
1-[(3R,4R)-4-cyanotetrahydro-2H-pyran-3-yl]-3-{[4-(1-methoxy-1-methylethyl)phenyl]amino}-1H-pyrazole-4-carboxamide,
1-[(3R,4S)-4-cyanotetrahydro-2H-pyran-3-yl]-3-{[4-(3-methyloxetan-3-yl)phenyl]amino}-1H-pyrazole-4-carboxamide,
3-[(6-chloropyridin-3-yl)amino]-1-[(4-cyanotetrahydro-2H-pyran-3-yl]-1H-pyrazole-4-carboxamide,
3-[(6-chloropyridin-3-yl)amino]-1-[(3S,4R)-4-cyanotetrahydro-2H-pyran-3-yl]-1H-pyrazole-4-carboxamide,
3-[(6-chloropyridin-3-yl)amino]-1-[(3R,4S)-4-cyanotetrahydro-2H-pyran-3-yl]-1H-pyrazole-4-carboxamide,
1-[(4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[(4-cyanotetrahydro-2H-pyran-3-yl]-3-[(6-fluoropyridin-3-yl)amino]-1H-pyrazole-4-carboxamide,
1-[(3R,4S)-4-cyanotetrahydro-2H-pyran-3-yl]-3-[(6-fluoropyridin-3-yl)amino]-1H-pyrazole-4-carboxamide,
1-[(3S,4R)-4-cyanotetrahydro-2H-pyran-3-yl]-3-[(6-fluoropyridin-3-yl)amino]-1H-pyrazole-4-carboxamide,
1-[(4-cyanotetrahydro-2H-pyran-3-yl]-3-[(5-fluoropyridin-3-yl)amino]-1H-pyrazole-4-carboxamide,
1-[(3S,4R)-4-cyanotetrahydro-2H-pyran-3-yl]-3-[(5-fluoropyridin-3-yl)amino]-1H-pyrazole-4-carboxamide,
1-[(3R,4S)-4-cyanotetrahydro-2H-pyran-3-yl]-3-[(5-fluoropyridin-3-yl)amino]-1H-pyrazole-4-carboxamide,
1-[4-cyanotetrahydro-2H-pyran-3-yl]-3-{[6-(difluoromethyl)pyridin-3-yl]amino}-1H-pyrazole-4-carboxamide,
1-[(3S,4R)-4-cyanotetrahydro-2H-pyran-3-yl]-3-{[6-(difluoromethyl)pyridin-3-yl]amino}-1H-pyrazole-4-carboxamide,
1-[(3R,4S)-4-cyanotetrahydro-2H-pyran-3-yl]-3-{[6-(difluoromethyl)pyridin-3-yl]amino}-1H-pyrazole-4-carboxamide,
1-[4-cyanotetrahydro-2H-pyran-3-yl]-3-{[4-(dimethylcarbamoyl)phenyl]amino}-1H-pyrazole-4-carboxamide,
1-[(3R,4S)-4-cyanotetrahydro-2H-pyran-3-yl]-3-{[4-(dimethylcarbamoyl)phenyl]amino}-1H-pyrazole-4-carboxamide,
1-[(3S,4R)-4-cyanotetrahydro-2H-pyran-3-yl]-3-{[4-(dimethylcarbamoyl)phenyl]amino}-1H-pyrazole-4-carboxamide,
3-[(4-cyanophenyl)amino]-1-[4-cyanotetrahydro-2H-pyran-3-yl]-1H-pyrazole-4-carboxamide,
3-[(4-cyanophenyl)amino]-1-[(3R,4S)-4-cyanotetrahydro-2H-pyran-3-yl]-1H-pyrazole-4-carboxamide,
3-[(4-cyanophenyl)amino]-1-[(3S,4R)-4-cyanotetrahydro-2H-pyran-3-yl]-1H-pyrazole-4-carboxamide,
1-[4-cyanotetrahydro-2H-pyran-3-yl]-3-{[6-(2,2,2-trifluoroethoxy)pyridin-3-yl]amino}-1H-pyrazole-4-carboxamide,
1-[(3R,4S)-4-cyanotetrahydro-2H-pyran-3-yl]-3-{[6-(2,2,2-trifluoroethoxy)pyridin-3-yl]amino}-1H-pyrazole-4-carboxamide,
1-[(3S,4R)-4-cyanotetrahydro-2H-pyran-3-yl]-3-{[6-(2,2,2-trifluoroethoxy)pyridin-3-yl]amino}-1H-pyrazole-4-carboxamide,
1-[4-cyanotetrahydro-2H-pyran-3-yl]-3-(phenylamino)-1H-pyrazole-4-carboxamide,
1-[(3R,4S)-4-cyanotetrahydro-2H-pyran-3-yl]-3-(phenylamino)-1H-pyrazole-4-carboxamide,
1-[(3S,4R)-4-cyanotetrahydro-2H-pyran-3-yl]-3-(phenylamino)-1H-pyrazole-4-carboxamide,
1-[4-cyanotetrahydro-2H-pyran-3-yl]-3-[(2-fluoropyridin-4-yl)amino]-1H-pyrazole-4-carboxamide,
1-[(3R,4S)-4-cyanotetrahydro-2H-pyran-3-yl]-3-[(2-fluoropyridin-4-yl)amino]-1H-pyrazole-4-carboxamide,
1-[(3S,4R)-4-cyanotetrahydro-2H-pyran-3-yl]-3-[(2-fluoropyridin-4-yl)amino]-1H-pyrazole-4-carboxamide,
1-[4-cyanotetrahydro-2H-pyran-3-yl]-3-{[6-(trifluoromethyl)pyridin-3-yl]amino}-1H-pyrazole-4-carboxamide,
1-[(3S,4R)-4-cyanotetrahydro-2H-pyran-3-yl]-3-{[6-(trifluoromethyl)pyridin-3-yl]amino}-1H-pyrazole-4-carboxamide,
1-[(3R,4S)-4-cyanotetrahydro-2H-pyran-3-yl]-3-{[6-(trifluoromethyl)pyridin-3-yl]amino}-1H-pyrazole-4-carboxamide,
1-[4-cyanotetrahydro-2H-pyran-3-yl]-3-({4-[2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1R)-2,2-difluoro-1-hydroxy-1-methylethyl]phenyl}amino)-1H-pyrazole-4-carboxamide,
1-[(3S,4R)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-[(3R,4S)-4-cyanotetrahydro-2H-pyran-3-yl]-3-({4-[(1S)-2,2-difluoro-1-hydroxy-1-methylethyl]phenyl}amino)-1H-pyrazole-4-carboxamide,
1-(4-Cyano-6-methyltetrahydro-2H-pyran-3-yl)-3-((2-fluoropyridin-4-yl)amino)-1H-pyrazole-4-carboxamide,
1-((3R,4S,6R)-4-Cyano-6-methyltetrahydro-2H-pyran-3-yl)-3-((2-fluoropyridin-4-yl)amino)-1H-pyrazole-4-carboxamide,
1-((3R,4R,6R)-4-Cyano-6-methyltetrahydro-2H-pyran-3-yl)-3-((2-fluoropyridin-4-yl)amino)-1H-pyrazole-4-carboxamide,
1-((3R,4R,6S)-4-Cyano-6-methyltetrahydro-2H-pyran-3-yl)-3-((2-fluoropyridin-4-yl)amino)-1H-pyrazole-4-carboxamide,
1-((3R,4S,6R)-4-Cyano-6-methyltetrahydro-2H-pyran-3-yl)-3-((2-fluoropyridin-4-yl)amino)-1H-pyrazole-4-carboxamide,
1-((3S,4S,6R)-4-Cyano-6-methyltetrahydro-2H-pyran-3-yl)-3-((2-fluoropyridin-4-yl)amino)-1H-pyrazole-4-carboxamide,
1-((3S,4S,6S)-4-Cyano-6-methyltetrahydro-2H-pyran-3-yl)-3-((2-fluoropyridin-4-yl)amino)-1H-pyrazole-4-carboxamide, 1-((3S,4R,6R)-4-Cyano-6-methyltetrahydro-2H-pyran-3-yl)-3-((2-fluoropyridin-4-yl)amino)-1H-pyrazole-4-carboxamide, 1-((3S,4R,6S)-4-Cyano-6-methyltetrahydro-2H-pyran-3-yl)-3-((2-fluoropyridin-4-yl)amino)-1H-pyrazole-4-carboxamide, 1-(3-cyano-tetrahydro-2H-pyran-4-yl)-3-(2-fluoropyridin-4-ylamino)-1H-pyrazole-4-carboxamide, 1-((3R,4R)-3-cyano-tetrahydro-2H-pyran-4-yl)-3-(2-fluoropyridin-4-ylamino)-1H-pyrazole-4-carboxamide, 1-((3S,4S)-3-cyano-tetrahydro-2H-pyran-4-yl)-3-(2-fluoropyridin-4-ylamino)-1H-pyrazole-4-carboxamide, 1-(3-cyano-1,1-dioxidotetrahydro-2H-thiopyran-4-yl)-3-((4-fluorophenyl)amino)-1H-pyrazole-4-carboxamide, 1-((3R,4R)-3-cyano-1,1-dioxidotetrahydro-2H-thiopyran-4-yl)-3-((4-fluorophenyl)amino)-1H-pyrazole-4-carboxamide, 1-((3S,4S)-3-cyano-1,1-dioxidotetrahydro-2H-thiopyran-4-yl)-3-((4-fluorophenyl)amino)-1H-pyrazole-4-carboxamide, 1-((3-cyano-1,1-dioxidotetrahydro-2H-thiopyran-4-yl)-3-((4-(trifluoromethyl)phenyl)amino)-1H-pyrazole-4-carboxamide, 1-((3R,4S)-3-cyano-1,1-dioxidotetrahydro-2H-thiopyran-4-yl)-3-((4-(trifluoromethyl)phenyl)amino)-1H-pyrazole-4-carboxamide, 1-((3S,4R)-3-cyano-1,1-dioxidotetrahydro-2H-thiopyran-4-yl)-3-((4-(trifluoromethyl)phenyl)amino)-1H-pyrazole-4-carboxamide, 1-(4-cyano-4-methyl-1,1-dioxidotetrahydrothiophen-3-yl)-3-((4-fluorophenyl)amino)-1H-pyrazole-4-carboxamide, 1-((3S,4R)-4-cyano-4-methyl-1,1-dioxidotetrahydrothiophen-3-yl)-3-((4-fluorophenyl)amino)-1H-pyrazole-4-carboxamide, 1-((3R,4S)-4-cyano-4-methyl-1,1-dioxidotetrahydrothiophen-3-yl)-3-((4-fluorophenyl)amino)-1H-pyrazole-4-carboxamide, 1-(4-Cyano-4-methyl-1,1-dioxidotetrahydrothiophen-3-yl)-3-((4-fluorophenyl)amino)-1H-pyrazole-4-carboxamide, 1-((3R,4R)-4-Cyano-4-methyl-1,1-dioxidotetrahydrothiophen-3-yl)-3-((4-fluorophenyl)amino)-1H-pyrazole-4-carboxamide, 1-((3S,4S)-4-Cyano-4-methyl-1,1-dioxidotetrahydrothiophen-3-yl)-3-((4-fluorophenyl)amino)-1H-pyrazole-4-carboxamide; or a pharmaceutically acceptable salt or stereoisomer thereof.

11. A pharmaceutical composition comprising a compound of claim 1 or a pharmaceutically acceptable salt, or a stereoisomer thereof and a pharmaceutically acceptable carrier.

12. A method for the treatment of a JAK-mediated disease comprising administering to a patient in need thereof a therapeutically effective amount of a compound of claim 1 or a stereoisomer, or a pharmaceutically acceptable thereof.

13. A method of treating a condition in a mammal that can be ameliorated by the selective inhibition of a Janus kinase JAK1 relative to JAK 2 and JAK 3 which condition is selected from arthritis, asthma, and obstructive airways diseases, autoimmune diseases or disorders, and cancer comprising administering to the mammal in need of such treatment, a therapeutically effective amount of a compound according to claim 1 or a pharmaceutically acceptable salt or a stereoisomer thereof.

14. A method according to claim 13, wherein said condition is arthritis.

15. A method according to claim 14, wherein said condition is selected from rheumatoid arthritis, juvenile arthritis, and psoriatic arthritis.

16. A method according to claim 13, wherein said condition is asthma or obstructive airways diseases.

17. A method according to claim 13, wherein said condition is selected from: chronic asthma, late asthma, airway hyper-responsiveness, bronchitis, bronchial asthma, allergic asthma, intrinsic asthma, extrinsic asthma, dust asthma, recurrent airway obstruction, chronic obstruction pulmonary disease (COPD), and emphysema.

18. A method according to claim 13, wherein said condition is autoimmune diseases or disorders.

19. A method of treating asthma in a mammal in need thereof, comprising administering a therapeutically effective amount of a compound according to claim 1 or a pharmaceutically acceptable salt or a stereoisomer, thereof.

20. A method of treating arthritis in a mammal in need thereof, comprising administering a therapeutically effective amount of a compound according to claim 1 or a pharmaceutically acceptable salt or stereoisomer, thereof.

* * * * *